(12) United States Patent
Glazko et al.

(10) Patent No.: US 11,236,398 B2
(45) Date of Patent: Feb. 1, 2022

(54) COMPOSITIONS AND METHODS FOR DETECTING SESSILE SERRATED ADENOMAS/POLYPS

(71) Applicants: BioVentures, LLC, Little Rock, AR (US); The United States As Represented By The Department of Veterans Affairs, Washington, DC (US)

(72) Inventors: Galina Glazko, Little Rock, AR (US); Curt H. Hagedorn, Little Rock, AR (US); Yasir Rahmatallah, Little Rock, AR (US)

(73) Assignees: BioVentures, LLC, Little Rock, AR (US); The United States As Represented By The Department of Veterans Affairs, Washington, DC (US)

( * ) Notice: Subject to any disclaimer, the term of this patent is extended or adjusted under 35 U.S.C. 154(b) by 168 days.

(21) Appl. No.: 16/489,604

(22) PCT Filed: Mar. 1, 2018

(86) PCT No.: PCT/US2018/020517
§ 371 (c)(1),
(2) Date: Aug. 28, 2019

(87) PCT Pub. No.: WO2018/160880
PCT Pub. Date: Sep. 7, 2018

(65) Prior Publication Data
US 2020/0131583 A1 Apr. 30, 2020

Related U.S. Application Data

(60) Provisional application No. 62/465,588, filed on Mar. 1, 2017.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 6,566,495 | B1 | 5/2003 | Fodor et al. |
| 2011/0287957 | A1 | 11/2011 | Rosenthal et al. |
| 2012/0315216 | A1 | 12/2012 | Clarke et al. |
| 2013/0065228 | A1 | 3/2013 | Hinoue et al. |
| 2013/0345077 | A1 | 12/2013 | Kalady et al. |
| 2015/0275307 | A1 | 10/2015 | Hagedorn et al. |

FOREIGN PATENT DOCUMENTS

| | | | |
|---|---|---|---|
| WO | 2016183487 A1 | 11/2016 | |
| WO | WO-2016183487 A1 * | 11/2016 | ......... C07K 16/3092 |
| WO | 2018160880 A1 | 9/2018 | |

OTHER PUBLICATIONS

Gonzalo et al. J Pathol 2013; 230: 420-429.*
Liberzon, A. et al., "Molecular signatures database (MSigDB) 3.0," Bioinformatics, 2011, pp. 1739-1740, vol. 27, No. 12.
Lieberman, D. et al., "Use of Colonoscopy to Screen Asymptomatic Adults for Colorectal Cancer," N. Engl. J. Med., Jul. 2000, pp. 162-168, vol. 343, No. 3.
Limketkai, B. et al., "The cutting edge of serrated polyps: a practical guide to approaching and managing serrated colon polyps," Gastrointest. Endosc., 2013, pp. 360-375, vol. 77, No. 3.
Manning, S. et al., "The Role of Gut Hormone Peptide YY in Energy and Glucose Homeostasis: Twelve Years on," Annu. Rev. Physiol., 2014, pp. 11.1-11.24, vol. 76.
Marioni, J. et al., "RNA-seq: An assessment of technical reproducibility and comparison with gene expression arrays," Genome Res., 2008, pp. 1509-1517, vol. 18, Cold Spring Harbor Laboratory Press.
McVey, M. et al., "MMEJ repair of double-strand breaks (director's cut): deleted sequences and alternative endings," Trends Genet., 2008, pp. 529-538, vol. 24, No. 11.
Mestdagh, P. et al., "A novel and universal method for microRNA RT-qPCR data normalization," Genome Biol., 2009, pp. R64.1-R64.10, vol. 10, No. 6, Article R64.
Opitz, C. et al., "The Indoleamine-2,3-Dioxygenase (IDO) Inhibitor 1-Methyl-D-tryptophan Upregulates IDO1 in Human Cancer Cells," PLoS One, May 2011, pp. 1-11, vol. 6, No. 5, e19823.
Oshimori, N. et al., "The Plk1 target Kizuna stabilizes mitotic centrosomes to ensure spindle bipolarity," Nat. Cell Biol., Oct. 2006, pp. 1095-1101, vol. 8, No. 10, with Supplementary Information, pp. 1-4.
Owens, S. et al., "Selective expression of gastric mucin MUC6 in colonic sessile serrated adenoma but not in hyperplastic polyp aids in morphological diagnosis of serrated polyps," Mod. Pathol., 2008, pp. 660-669, vol. 21.
Paveliiz, T. et al., "MRE11-deficiency associated with improved long-term disease free survival and overall survival in a subset of stage III colon cancer patients in randomized CALGB 89803 trial," PLoS One, Oct. 2014, pp. 1-10, vol. 9, No. 10, e108483.
Payne, S. et al., "Endoscopic Detection of Proximal Serrated Lesions and Pathologic Identification of Sessile Serrated Adenomas/Polyps Vary on the Basis of Center," Clin. Gastroenterol. Hepatol., 2014, pp. 1119-1126, vol. 12, No. 7.

(Continued)

*Primary Examiner* — Juliet C Switzer
(74) *Attorney, Agent, or Firm* — Polsinelli PC

(57) ABSTRACT

The disclosure provides a method to detect sessile serrated adenomas/polyps (SSA/Ps) and to differentiate SSA/Ps from hyperplastic polyps (HPs). The method uses a molecular signature that is platform-independent and could be used with multiple platforms such as microarray, RNA-seq or real-time quantitative platforms.

4 Claims, 31 Drawing Sheets
(25 of 31 Drawing Sheet(s) Filed in Color)

(56) References Cited

OTHER PUBLICATIONS

Pope, J. et al., "Claudin-1 overexpression in intestinal epithelial cells enhances susceptibility to adenamatous polyposis coli-mediated colon tumorigenesis," Mol. Cancer, 2014, pp. 1-13, vol. 13, No. 167.

Prendergast, G. et al., "Towards a Genetic Definition of Cancer-Associated Inflammation: Role of the IDO Pathway," Am. J. Pathol., May 2010, pp. 2082-2087, vol. 176, No. 5.

Prendergast, G. et al., "Indoleamine 2,3-dioxygenase pathways of pathogenic inflammation and immune escape in cancer," Cancer Immunol. Immunother., 2014, pp. 721-735, vol. 63.

Quintero, E. et al., "Colonoscopy versus Fecal Immunochemical Testing in Colorectal-Cancer Screening," N. Engl. J. Med., Feb. 2012, pp. 697-706, vol. 366, No. 8, with Correction, May 2016, pp. 1898, vol. 374, No. 19.

Rahmatallah, Y. et al., "Gene Sets Net Correlations Analysis (GSNCA): a multivariate differential coexpression test for gene sets," Bioinformatics, 2014, pp. 360-368, vol. 30, No. 3.

Rahmatallah, Y. et al., "Platform-independent gene expression signature differentiates sessile serrated adenomas/polyps and hyperplastic polyps of the colon," BMC Med. Genomics, 2017, pp. 1-18, vol. 10, No. 81.

Rex, D. et al., "Serrated Lesions of the Colorectum: Review and Recommendations From an Expert Panel," NIH Public Access Author Manuscript, Sep. 1, 2013, pp. 1-39, published in final edited form as: Am. J. Gastroenterol., Sep. 2012, pp. 1315-1330, vol. 107, No. 9.

Rockett, J. et al., "DNA arrays: technology, options and toxicological applications," Xenobiotica, 2000, pp. 155-177, vol. 30, No. 2, Taylor & Francis Ltd.

Saeys, Y. et al., "A review of feature selection techniques in bioinformatics," Bioinformatics, 2007, pp. 2507-2517, vol. 23, No. 19.

Salazar, R. et al., "Gene Expression Signature to Improve Prognosis Prediction of Stage II and III Colorectal Cancer," J. Clin. Oncol., Jan. 2011, pp. 17-24, vol. 29, No. 1.

Samarajiwa, S. et al., "INTERFEROME: the database of interferon regulated genes," Nucleic Acids Res., 2009, pp. D852-D857, vol. 37, Database Issue.

Savage, R., "Probability Inequalities of the Tchebycheff Type," J. Res. National Bureau of Standards—B. Mathematics and Mathematical Physics, Jul.-Sep. 1961, pp. 211-226, vol. 65B, No. 3.

Scolnick, D. et al., "Chfr defines a mitotic stress checkpoint that delays entry into metaphase," Nature, Jul. 2000, pp. 430-435, vol. 406.

Shalka, N. et al., "Carboxypeptidase E: a negative regulator of the canonical Wnt signaling pathway," NIH Public Access Author Manuscript, Jun. 7, 2013, pp. 1-20, published in final edited form as: Oncogene, Jun. 6, 2013, pp. 2836-2847, vol. 32, No. 23.

Shan, Z-Z. et al., "Overexpression of Tbx3 is correlated with Epithelial-Mesenchymal Transition phenotype and predicts poor prognosis of colorectal cancer," Am. J. Cancer Res., 2015, pp. 344-353, vol. 5, No. 1.

Shi, W. et al., "Functional analysis of multiple genomic signatures demonstrates that classification algorithms choose phenotype-related genes," Pharmacogenomics J., 2010, pp. 310-323, vol. 10.

Shon, W-J. et al., "Severity of DSS-induced colitis is reduced in Ido1-deficient mice with down-regulation of TLR-MyD88-NF-kB transcriptional networks," Sci. Rep., 2015, pp. 1-12, vol. 5, No. 17305.

Simon, R., "Roadmap for Developing and Validating Therapeutically Relevant Genomic Classifiers," J. Clin. Oncol., Oct. 2005, pp. 7332-7341, vol. 23, No. 29.

Starodub, A. et al., "First-in-Human Trial of a Novel Anti-Trop-2 Antibody-SN-38 Conjugate, Sacituzumab Govitecan, for the Treatment of Diverse Metastatic Solid Tumors," Clin. Cancer Res., 2015, pp. 3870-3878, vol. 21, No. 17.

Su, Z. et al., "An investigation of biomarkers derived from legacy microarray data for their utility in the RNA-seq era," Genome Biol., 2014, pp. 1-25, vol. 15, No. 523.

Tarca, A. et al., "Strengths and limitations of microarray-based phenotype prediction: lessons learned from the IMPROVER Diagnostic Signature Challenge," Bioinformatics, 2013, pp. 2892-2899, vol. 29, No. 22.

Tibshirani, R. et al., "Diagnosis of multiple cancer types by shrunken centroids of gene expression," PNAS, May 2002, pp. 6567-6572, vol. 99, No. 10.

Tinmouth, J. et al., "Sessile Serrated Polyps at Screening Colonoscopy: Have They Been Under Diagnosed?," Am. J. Gastroenterol., Jul. 2014, advance online publication, pp. 1-7.

Torlakovic, E. et al., "Serrated Adenomatous Polyposis in Humans," Gastroenterol., Mar. 1996, pp. 748-755, vol. 110, No. 3.

Torlakovic, E. et al., "Morphologic Reappraisal of Serrated Colorectal Polyps," Am. J. Surg. Pathol., 2003, pp. 65-81, vol. 27, No. 1, Lippincott Williams & Wilkins, Inc.

Torlakovic, E. et al., "Sessile Serrated Adenoma (SSA) vs. Traditional Serrated Adenoma (TSA)," Am. J. Surg. Pathol., Jan. 2008, pp. 21-29, vol. 32, No. 1, Lippincott Williams & Wilkins.

Trapnell, C. et al., "Differential gene and transcript expression analysis of RNA-seq experiments with TopHat and Cufflinks," Nat. Protoc., 2012, pp. 562-578, vol. 7, No. 3.

Trapnell, C. et al., "Differential analysis of gene regulation at transcript resolution with RNA-seq," Nat. Biotechnol., Jan. 2013, pp. 46-53, vol. 31, No. 1, with Online Methods, 1 pg.

Uyttenhove, C. et al., "Evidence for a tumoral immune resistance mechanism based on tryptophan degradation by indoleamine 2,3-dioxygenase," Nat. Med., Oct. 2003, pp. 1269-1274, vol. 9, No. 10.

Wang, G. et al., "PIK3R3 Induces Epithelial-to-Mesenchymal Transition and Promotes Metastasis in Colorectal Cancer," Mol. Cancer Ther., 2014, pp. 1837-1847, vol. 13, No. 7.

Wang, C. et al., "The concordance between RNA-seq and microarray data depends on chemical treatment and transcript abundance," Nat. Biotechnol., Sep. 2014, pp. 926-932, vol. 32, No. 9, with Online Methods, 3 pgs.

Weiss, A. et al., "The TGFbeta Superfamily Signaling Pathway," WIREs Dev. Biol., Jan./Feb. 2013, pp. 47-63, vol. 2, Wiley Periodicals, Inc.

Wu, D. et al., "ROAST: rotation gene set tests for complex microarray experiments," Bioinformatics, 2010, pp. 2176-2182, vol. 26, No. 17.

Xiong, S. et al., "Pla2g16 phospholipase mediates gain-of-function activities of mutant p53," PNAS, Jul. 2014, pp. 11145-11150, vol. 111, No. 30.

Yamanami, H. et al., "Down-regulation of sialidase NEU4 may contribute to invasive properties of human colon cancers," Cancer Sci., Mar. 2007, pp. 299-307, vol. 98, No. 3.

Yu, X. et al., "Chfr is required for tumor suppression and Aurora A regulation," Nat. Genet., Apr. 2005, pp. 401-406, vol. 37, No. 4.

Zauber, A. et al., "Colonoscopic Polypectomy and Long-Term Prevention of Colorectal-Cancer Deaths," N. Engl. J. Med., Feb. 2012, pp. 687-696, vol. 366, No. 8.

Zhang, J-X. et al., "Overexpression of the secretory small GTPase Rab27B in human breast cancer correlates closely with lymph node metastasis and predicts poor prognosis," J. Transl. Med., 2012, pp. 1-10, vol. 10, No. 242.

Alizadeh, A. et al., "Distinct types of diffuse large B-cell lymphoma identified by gene expression profiling," Nature, Feb. 3, 2000, pp. 503-511, vol. 403.

Ambroise, C. et al., "Selection bias in gene extraction on the basis of microarray gene-expression data," PNAS, May 14, 2002, pp. 6562-6566, vol. 99, No. 10.

Ashburner, M. et al., "Gene Ontology: tool for the unification of biology," Nat. Genet., May 2000, pp. 25-29, vol. 25.

Ball, H. et al., "Indoleamine 2,3-dioxygenase-2; a new enzyme in the kynurenine pathway," Int. J. Biochem. Cell Biol., 2009, pp. 467-471, vol. 41, No. 3, Elsevier Ltd.

Bao, J. et al., "Rab27b Is a Potential Predictor for Metastasis and Prognosis in Colorectal Cancer," Gastroenterol. Res. Pract., 2014, pp. 1-7, vol. 2014, No. 913106.

(56) References Cited

OTHER PUBLICATIONS

Baron, K. et al., "Recruitment and activation of SLK at the leading edge of migrating cells requires Src family kinase activity and the LIM-only protein 4," Biochim. Biophys. Acta, 2015, pp. 1683-1692, vol. 1853.

Bartley, A. et al., "Expression of Gastric Pyloric Mucin MUC6 in Colorectal Serrated Polyps," NIH Public Access Author Manuscript, Aug. 1, 2010, pp. 1-14, published in final edited form as: Mod. Pathol., Feb. 2010, pp. 169-176, vol. 23, No. 2.

Beggs, A. et al., "Loss of Expression and Promoter Methylation of SLIT2 Are Associated with Sessile Serrated Adenoma Formation," PLOS Genet., May 2013, pp. 1-10, vol. 9, No. 5, e1003488.

Bettington, M. et al., "The serrated pathway to colorectal carcinoma: current concepts and challenges," Histopathology, 2013, pp. 367-386, vol. 62.

Byrne, J. et al., "Tumor protein D52 (TPD52) and cancer—oncogene understudy or understudied oncogene?," Tumour Biol., 2014, pp. 7369-7382, vol. 35.

Carrega, P. et al., "The Yin and Yang of Innate Lymphoid Cells in Cancer," Immunol. Lett., 2016, pp. 29-35, vol. 179.

Caruso, M. et al., "Over-expression of cathepsin E and trefoil factor 1 in sessile serrated adenomas of the colorectum identified by gene expression analysis," Virchows Arch., 2009, pp. 291-302, vol. 454.

Castaldi, P. et al., "An empirical assessment of validation practices for molecular classifiers," Brief. Bioinform., 2011, pp. 189-202, vol. 12, No. 3.

Chang, C. et al., "An overview of recommendations and translational milestones for genomic tests in cancer," Genet. Med., Oct. 2014, pp. 1-10, vol. 17, No. 6.

Chen, J. et al., "Feed-Forward Reciprocal Activation of PAFR and STAT3 Regulates Epithelial-Mesenchymal Transition in Non-Small Cell Lung Cancer," Cancer Res., Oct. 2015, pp. 4198-4210, vol. 75, No. 19.

Chibon, F., "Cancer gene expression signatures—The rise and fall?," Eur. J. Cancer, 2013, pp. 2000-2009, vol. 49.

Cleven, A. et al., "CHFR Promoter Methylation Indicates Poor Prognosis in Stage II Microsatellite Stable Colorectal Cancer," Clin. Cancer Res., 2014, pp. 3261-3271, vol. 20, No. 12.

Dave, S. et al., "Prediction of Survival in Follicular Lymphoma Based on Molecular Features of Tumor-Infiltrating Immune Cells," N. Engl. J. Med., Nov. 2004, pp. 2159-2169, vol. 351, No. 21.

De Sousa, F. "Poor-prognosis colon cancer is defined by a molecularly distinct subtype and develops from serrated precursor lesions," Nat. Med, 2013, pp. 614-618, vol. 19, No. 5.

De Veer, M. et al., "Functional classification of interferon-stimulated genes identified using microarrays," J. Leukoc. Biol., Jun. 2001, pp. 912-920, vol. 69.

Delker, D. et al., "RNA Sequencing of Sessile Serrated Colon Polyps Identifies Differentially Expressed Genes and Immunohistochemical Markers," PLoS One, Feb. 2014, pp. 1-12, vol. 9, No. 2, e88367.

El-Salhy, M. et al., "The role of peptide YY in gastrointestinal diseases and disorders (Review)," Int. J. Mol. Med., 2013, pp. 275-282, vol. 31.

Fallarino, F. et al., "T Cell Apoptosis by Kynurenines," In: Allegri et al. (eds), Developments in Tryptophan and Serotonin Metabolism, Adv. Exp. Med. Biol., 2003, pp. 183-190, vol. 527, Kluwer Academic/Plenum Publishers.

Fang, Y. et al., "Elevated expressions of MMP7, TROP2, and survivin are associated with survival, disease recurrence, and liver metastasis of colon cancer," Int. J. Colorectal Dis., 2009, pp. 875-884, vol. 24.

Fumagalli, D. et al., "Transfer of clinically relevant gene expression signatures in breast cancer: from Affymetrix microarray to Illumina RNA-Sequencing technology," BMC Genomics, 2014, pp. 1-12, vol. 15, No. 1008.

Galamb, O. et al., "Diagnostic mRNA expression patterns of inflamed, benign,and malignant colorectal biopsy specimen and their correlation with peripheral blood results," Cancer Epidemiol Biomarkers Prev., 2008, pp. 2835-2845, vol. 17, No. 10.

Gibson, J. et al., "MUC Expression in Hyperplastic and Serrated Colonic Polyps: Lack of Specificity of MUC6," Am. J. Surg. Pathol., May 2011, pp. 742-749, vol. 35, No. 5, Lippincott Williams & Wilkins.

Glebov, O. et al., "Distinguishing Right from Left Colon by the Pattern of Gene Expression," Cancer Epidemiol Biomarkers Prev, Aug. 2003, pp. 755-762, vol. 12.

Gonzalo, D. et al., "Gene expression profiling of serrated polyps identifies annexin A10 as a marker of a sessile serrated adenoma/polyp," J. Pathol., 2013, pp. 420-429, vol. 230.

Gray, R. et al., "Validation Study of a Quantitative Multigene Reverse Transcriptase-Polymerase Chain Reaction Assay for Assessment of Recurrence Risk in Patients With Stage II Colon Cancer," J. Clin. Oncol., Dec. 2011, pp. 1611-4619, vol. 29, No. 35.

Hamada, S. et al., "Regulators of epithelial mesenchymal transition in pancreatic cancer," Front. Physiol., Jul. 2012, pp. 1-5, vol. 3, No. 254.

Hanahan, D. et al., "Hallmarks of Cancer: The Next Generation," Cell, Mar. 2011, pp. 646-674, vol. 144.

Hendrix, A. et al., "Effect of the Secretory Small GTPase Rab27B on Breast Cancer Growth, Invasion, and Metastasis," J. Natl. Cancer Inst., Jun. 2010, pp. 866-880, vol. 102, No. 12.

Hewish, M. et al., "Mismatch repair deficient colorectal cancer in the era of personalized treatment," Nat. Rev. Clin. Oncol., Apr. 2010, pp. 197-208, vol. 7.

Higuchi, T. et al., "My approach to serrated polyps of the colorectum," J. Clin. Pathol., 2004, pp. 682-686, vol. 57.

Iansante, V. et al., "PARP14 promotes the Warburg effect in hepatocellular carcinoma by inhibiting JNK1-dependent PKM2 phosphorylation and activation," Nat. Commun., 2015, pp. 1-15, vol. 6, No. 7882.

International Search Report and Written Opinion dated Jun. 18, 2018 from related Patent Application No. PCT/US2018/020517; 14 pgs.

Irizarry, R. et al., "Exploration, normalization, and summaries of high density oligonucleotide array probe level data," Biostatistics, 2003, pp. 249-264, vol. 4, No. 2, Oxford University Press, Great Britain.

Ishigooka, S. et al., "Evaluation of magnifying colonoscopy in the diagnosis of serrated polyps," World J. Gastroenterol., Aug. 2012, pp. 4308-4316, vol. 18, No. 32.

Kahi, C. et al., "Prevalence and Variable Detection of Proximal Colon Serrated Polyps During Screening Colonoscopy," Clin Gastroenterol. Hepatol., Jan. 2011, pp. 42-46, vol. 9, No. 1.

Kahi, C. et al., "High colonoscopic prevalence of proximal colon serrated polyps in average-risk men and women," Gastrointest. Endosc., Mar. 2012, pp. 515-520, vol. 75, No. 3.

Kanth, P. et al., "Gene Signature in Sessile Serrated Polyps Identifies Colon Cancer Subtype," HHS Public Access Author Manuscript, Jun. 1, 2017, pp. 1-24, published in final edited form as: Cancer Prev. Res., Jun. 2016, pp. 456-465, vol. 9, No. 6.

Kim, J. et al., "Complex Behavior of ALDH1A1 and IGFBP1 in Liver Metastasis from a Colorectal Cancer," PLoS One, May 2016, pp. 1-15, vol. 11, No. 5, e0155160.

Lagal, V. et al., "Spire-1 contributes to the invadosome and its associated invasive properties," J. Cell Sci., 2014, pp. 328-340, vol. 127.

Langmead, B. et al., "Ultrafast and memory-efficient alignment of short DNA sequences to the human genome," Genome Biol., 2009, pp. 1-10, vol. 10, No. 3, Article R25.

Lascorz, J. et al., "Consensus Pathways Implicated in Prognosis of Colorectal Cancer Identified Through Systematic Enrichment Analysis of Gene Expression Profiling Studies," PLoS One, Apr. 2011, pp. 1-9, vol. 6, No. 4, e18867.

Lash, R. et al., "Sessile serrated adenomas: prevalence of dysplasia and carcinoma in 2139 patients," J. Clin. Pathol., 2010, pp. 681-686, vol. 63.

Levin, B. et al., "Screening and Surveillance for the Early Detection of Colorectal Cancer and Adenomatous Polyps, 2008: A Joint Guideline From the American Cancer Society, the US Multi-Society Task Force on Colorectal Cancer, and the American College of Radiology," Gastroenterology, May 2008, pp. 1570-1595, vol. 134, No. 5.

(56) References Cited

OTHER PUBLICATIONS

Li, H. et al., "Basic helix-loop-helix transcription factors and enteroendocrine cell differentiation," Diabetes Obes. Metab., 2011, pp. 5-12, vol. 13, Suppl. 1, Blackwell Publishing Ltd.

Li, J. et al., "The oncogenic TBX3 is a downstream target and mediator of the TGF-beta1 signaling pathway," Mol. Biol. Cell, Nov. 15, 2013, pp. 3569-3576, vol. 24.

Zhao, P. et al., "Clinical investigation of TROP-2 as an independent biomarker and potential therapeutic target in colon cancer," Mol. Med. Rep., 2015, pp. 4364-4369, vol. 12.

\* cited by examiner

COMPOSITIONS AND METHODS FOR DETECTING SESSILE SERRATED ADENOMAS/POLYPS

CROSS REFERENCE TO RELATED APPLICATIONS

This application claims the benefit of International application number PCT/US2018/020517, filed Mar. 1, 2018, which claims the benefit of U.S. Provisional Application No. 62/465,588, filed Mar. 1, 2017, the disclosures of which are hereby incorporated by reference in their entirety.

GOVERNMENTAL RIGHTS

This invention was made with government support under CA176130 awarded by the National Institutes of Health. The government has certain rights in the invention.

FIELD OF THE INVENTION

The disclosure provides a method to detect sessile serrated adenomas/polyps (SSA/Ps) and to differentiate SSA/Ps from hyperplastic polyps (HPs). The method uses a molecular signature that is platform-independent and could be used with multiple platforms such as microarray, RNA-seq or real-time qPCR platforms.

BACKGROUND OF THE INVENTION

Colon cancer is the second largest cause of cancer-related deaths in the United States. Colonic neoplasms originate primarily from colon polyps, and develop via partially overlapping but mechanistically distinct pathways that have been designated as the adenomatous and serrated pathways. Accumulating evidence indicates that the majority of other colon adenocarcinomas, possibly 20-30%, arise from a subset of serrated polyps, designated sessile serrated adenomas/polyps (SSA/Ps), which were previously classified as hyperplastic polyps and thought to have little or no tumorigenic potential.

Sessile serrated adenomas/polyps (SSA/Ps) have been distinguished from hyperplastic polyps (HPs) on the basis of their endoscopic appearance (larger, flat and hypermucinous) and histologic characteristics (dilatated crypts, horizontal crypts, and boot shaped deformities). However, because HPs may often have overlapping similar features, including serrated crypt architecture, borderline phenotypes can be difficult to assign. This has been highlighted by a number of studies documenting the frequent misclassification of SSA/Ps as HPs, resulting in inadequate follow-up. Conversely, misclassifying an HP as an SSA/P may result in unnecessary cancer screening in these patients. SSA/Ps account for 20-30% of colon cancers whereas HPs have little or no risk of progressing to colon cancer.

Thus, there is a need in the art for reliable diagnostic assays that could aid in the distinction between these lesions. Such an assay would be helpful for both diagnosis and surveillance stratification of patients.

SUMMARY OF THE INVENTION

In an aspect, the disclosure provides a method of detecting sessile serrated adenomas/polyps (SSA/Ps) in a subject. The method comprises: (a) determining the level of expression of the nucleic acids in the molecular signature in a biological sample obtained from the subject, wherein the molecular signature is selected from the group consisting of CHFR, CHGA, CLDN1, KIZ, MEGF6, NTRK2, PLA2G16, PTAFR, SBSPON, SEMG1, SLC7A9, SPIRE1, TACSTD2, FOXD1, PIK3R3, PRUNE2, TPD52L1, TRIB2, C4BPA, CPE, DPP10, GRAMD1B, GRIN2D, KLK7, MYCN, and TM4SF4; (b) comparing the level of expression of each nucleic acid in the molecular signature to a reference value; and (c) detecting SSA/Ps in the subject based on the level of expression of each nucleic acid in the molecular signature relative to the reference value.

In another aspect, the disclosure provides a method of differentiating sessile serrated adenomas/polyps (SSA/Ps) from hyperplastic polyps (HPs) in a subject. The method comprises: (a) determining the level of expression of the nucleic acids in the molecular signature in a biological sample obtained from the subject, wherein the molecular signature is selected from the group consisting of CHFR, CHGA, CLDN1, KIZ, MEGF6, NTRK2, PLA2G16, PTAFR, SBSPON, SEMG1, SLC7A9, SPIRE1, TACSTD2, FOXD1, PIK3R3, PRUNE2, TPD52L1, TRIB2, C4BPA, CPE, DPP10, GRAMD1B, GRIN2D, KLK7, MYCN, and TM4SF4; (b) comparing the level of expression of each nucleic acid in the molecular signature to a reference value; and (c) detecting SSA/Ps or HPs in the subject based on the level of expression of each nucleic acid in the molecular signature relative to the reference value.

In still another aspect, the disclosure provides a method of predicting the likelihood that a colorectal polyp in a subject will develop into colorectal cancer. The method comprises: (a) determining the level of expression of the nucleic acids in the molecular signature in a biological sample obtained from the subject, wherein the molecular signature is selected from the group consisting of CHFR, CHGA, CLDN1, KIZ, MEGF6, NTRK2, PLA2G16, PTAFR, SBSPON, SEMG1, SLC7A9, SPIRE1, TACSTD2, FOXD1, PIK3R3, PRUNE2, TPD52L1, TRIB2, C4BPA, CPE, DPP10, GRAMD1B, GRIN2D, KLK7, MYCN, and TM4SF4; (b) comparing the level of expression of each nucleic acid in the molecular signature to a reference value; and (c) detecting SSA/Ps in the subject based on the level of expression of each nucleic acid in the molecular signature relative to the reference value, wherein the detection of SSA/Ps in the subject indicates an increased likelihood of developing colorectal cancer.

In still yet another aspect, the disclosure provides a method of determining treatment of a subject diagnosed with serrated polyps or suspected of having serrated polyps. The method comprises: (a) determining the level of expression of the nucleic acids in the molecular signature in a biological sample obtained from the subject, wherein the molecular signature is selected from the group consisting of CHFR, CHGA, CLDN1, KIZ, MEGF6, NTRK2, PLA2G16, PTAFR, SBSPON, SEMG1, SLC7A9, SPIRE1, TACSTD2, FOXD1, PIK3R3, PRUNE2, TPD52L1, TRIB2, C4BPA, CPE, DPP10, GRAMD1B, GRIN2D, KLK7, MYCN, and TM4SF4; (b) comparing the level of expression of each nucleic acid in the molecular signature to a reference value; (c) detecting SSA/Ps in the subject based on the level of expression of each nucleic acid in the molecular signature relative to the reference value; and (d) treating the subject more aggressively if SSA/Ps are detected.

Additionally, the disclosure provides a kit to differentiate SSA/Ps and HPs in a subject. The kit comprises detection agents that can detect the expression products of a molecular signature in a biological sample obtained from the subject, wherein the molecular signature is selected from the group consisting of CHFR, CHGA, CLDN1, KIZ, MEGF6, NTRK2, PLA2G16, PTAFR, SBSPON, SEMG1, SLC7A9, SPIRE1, TACSTD2, FOXD1, PIK3R3, PRUNE2, TPD52L1, TRIB2, C4BPA, CPE, DPP10, GRAMD1B, GRIN2D, KLK7, MYCN, and TM4SF4.

BRIEF DESCRIPTION OF THE FIGURES

The application file contains at least one drawing executed in color. Copies of this patent application publication with color drawing(s) will be provided by the Office upon request and payment of the necessary fee.

(FIG. 2A) SSA/P and HP samples are not well-separated when all the expressed genes are considered; (FIG. 2B) control right (CR) and control left (CL) samples are well-separated when all the expressed genes are considered; (FIG. 2C) SSA/P and HP samples are well-separated when only the genes differentially expressed between SSA/Ps and HPs with the exclusion of genes, DE between CR and CL are considered (139 genes); (FIG. 2D) CR and CL samples are well-separated when only the 152 genes in (FIG. 2C) are considered.

(FIG. 5A) The fold change in both platforms was larger than the within-phenotype variability and the correlation coefficient between platforms ($\rho_{true}$) was high; (FIG. 5B) when phenotypic labels in part A were randomly resampled, the fold change in both platforms became negligible as compared to the within-phenotype variability and the correlation coefficient between platforms ($\rho_{random}$) became low. (FIG. 5C) The fold change in both platforms was smaller than the within-phenotype variability and the correlation coefficient between platforms ($\rho_{true}$) was low; (FIG. 5D) when phenotypic labels in FIG. 5C were randomly resampled, the correlation coefficient ($\rho_{random}$) was low.

(FIG. 13A) correlation between the RNA-seq and the Illumina platforms when phenotypic labels are preserved; (FIG. 13B) correlation between the RNA-seq and the Illumina platforms when phenotypic labels are randomly resampled; (FIG. 13C) correlation between the RNA-seq and the Affymetrix platforms when phenotypic labels are preserved; (FIG. 13D) correlation between the RNA-seq and the Affymetrix platforms when phenotypic labels are randomly resampled.

(FIG. 14A) RNA-seq dataset (17243 genes and 31 samples); (FIG. 14B) Illumina dataset (17123 genes and 12 samples); (FIG. 14C) Affymetrix dataset (19090 genes and 17 samples).

(FIG. 15A) RNA-seq data set; (FIG. 15B) Illumina data set; (FIG. 15C) Affymetrix data set.

(FIG. 18A) raw expression levels centered around zero; (FIG. 18B) normalized expression levels by first subtracting sample medians and then by subtracting gene-wise medians from each individual gene.

DETAILED DESCRIPTION OF THE INVENTION

Figure 1:
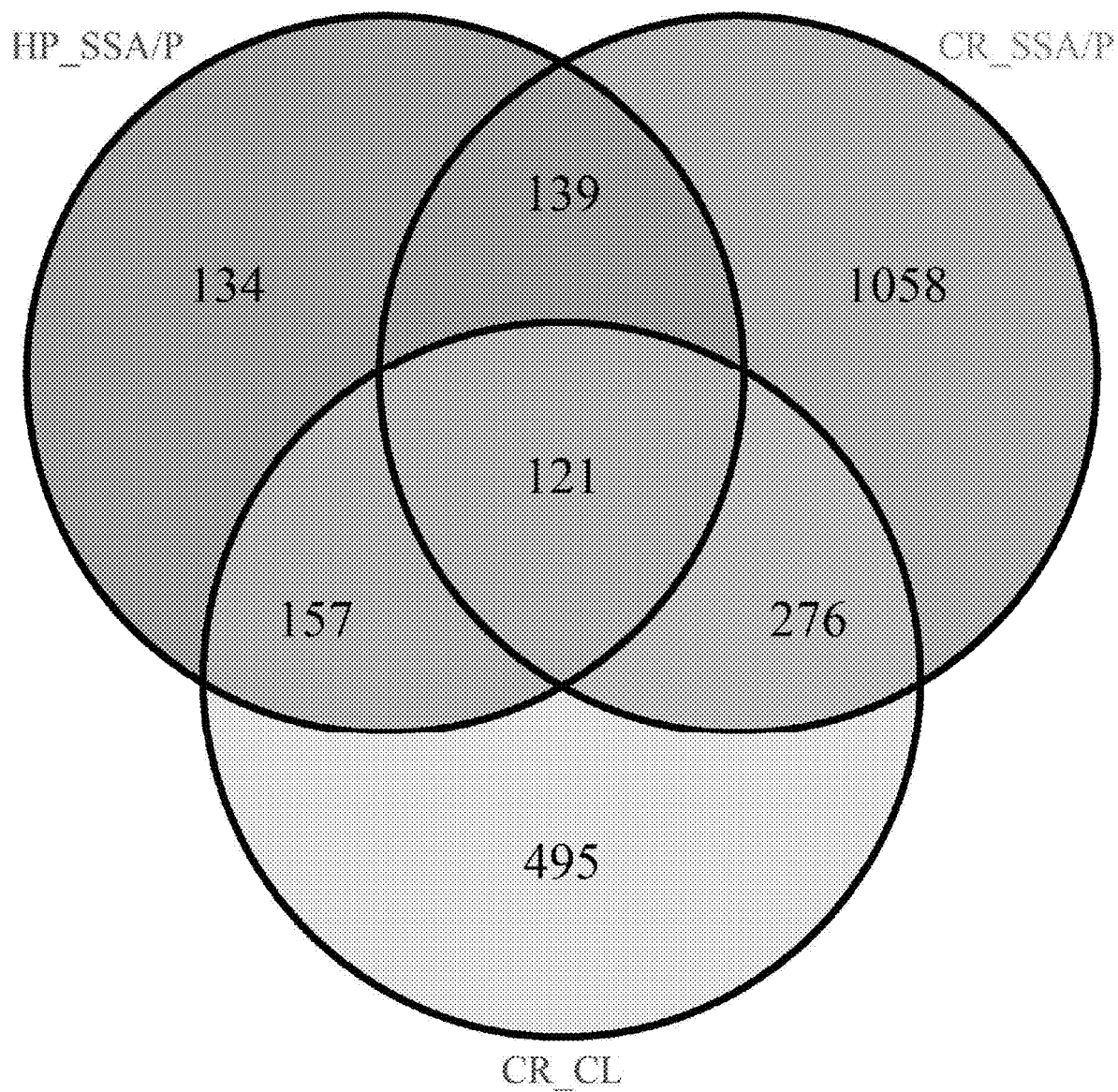
FIG. 1 depicts a Venn diagram summarizing the differentially expressed (DE) genes in three comparisons.
Figure 2A:
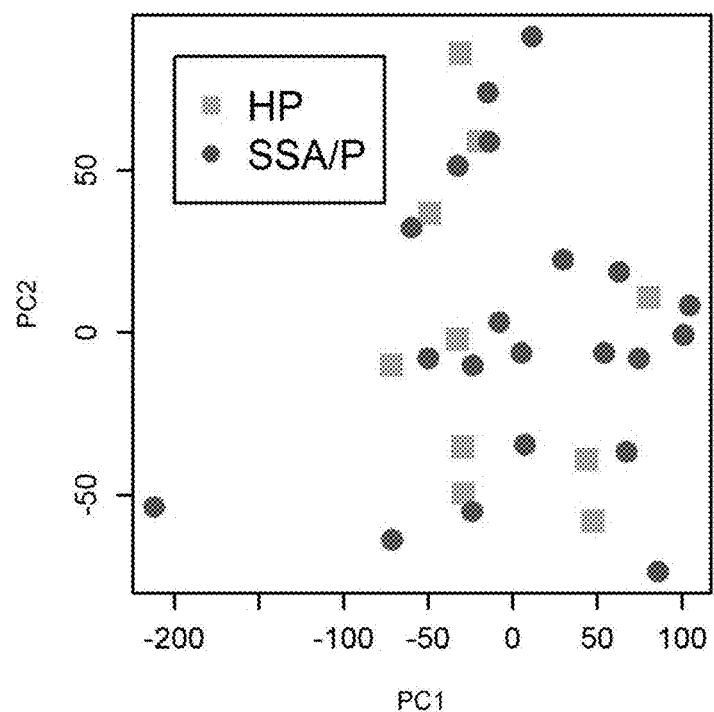
FIG. 2A, FIG. 2B, FIG. 2C, and FIG. 2D depicts principle component analysis (PCA) scatter plots.
Figure 2B:
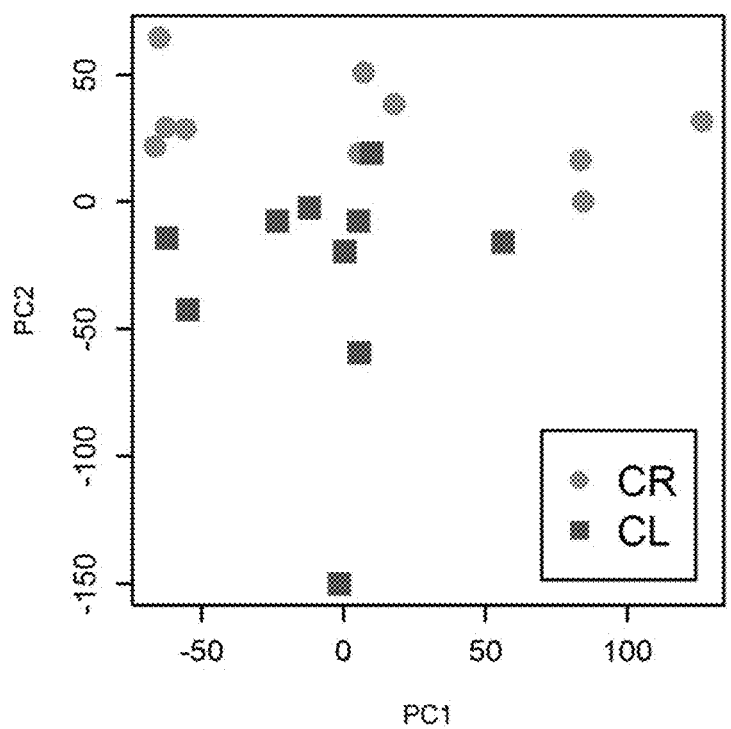
Figure 2C:
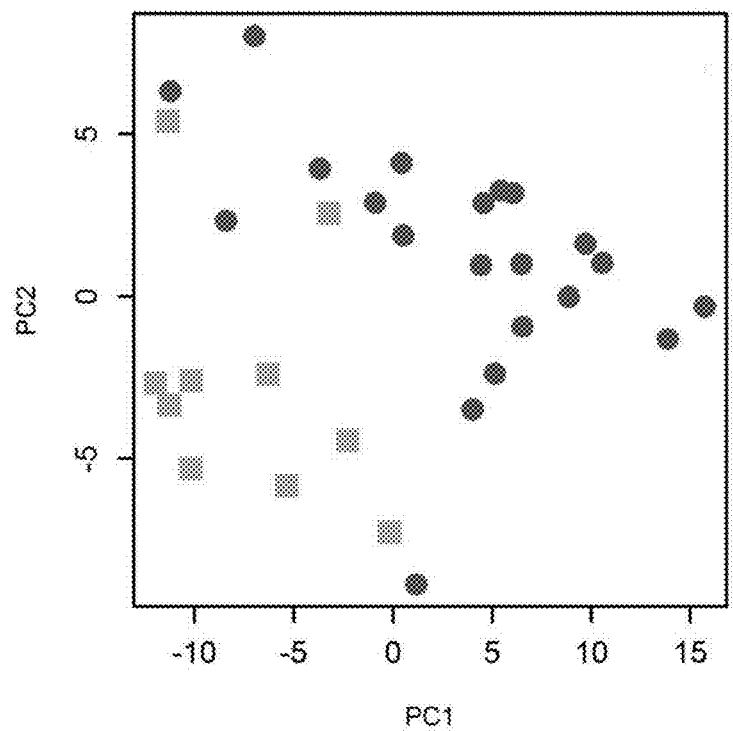
Figure 2D:
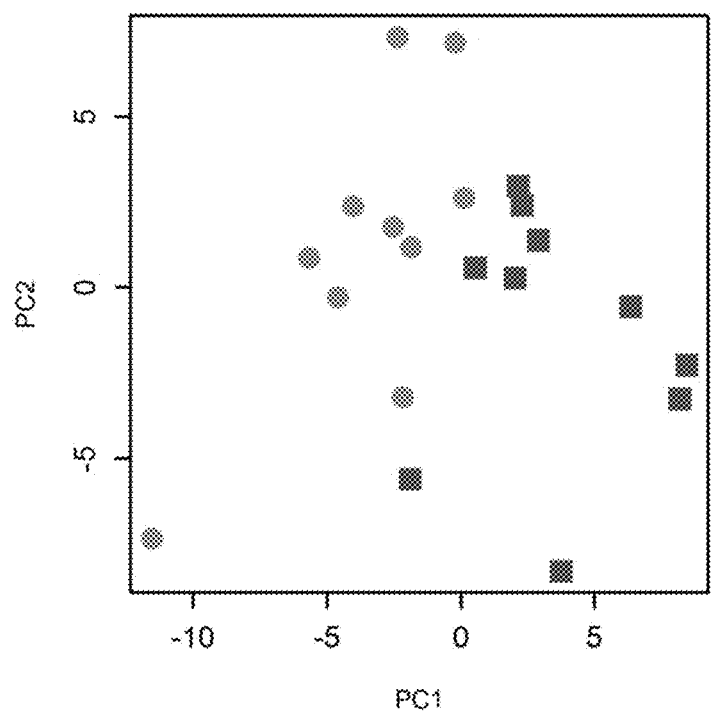

Provided herein are methods to detect sessile serrated adenomas/polyps (SSA/Ps) and to distinguish SSA/Ps from hyperplastic polyps (HPs). Prior to the disclosure, there has been difficulty in distinguishing SSA/Ps from HPs. Current histopathological methods have about 60-70% accuracy in distinguishing SSA/Ps from HPs. However, the methodology disclosed herein has an impressive 90% accuracy at correctly distinguishing SSA/Ps from HPs. Notably, the molecular signature disclosed herein was able to achieve this accuracy on preserved FFPE tissues. Further, the molecular signature was developed such that it is platform-independent and could be used with multiple platforms such as microarray, RNA-seq or real-time qPCR platforms to effectively distinguish SSA/Ps from HPs. As SSA/Ps have a higher risk of progressing to cancer, it is important that SSA/Ps are accurately diagnosed such that the subject is treated properly. By accurately detecting SSA/Ps, the subject may be treated more aggressively or monitored more frequently. Thus, the method disclosed herein may be used to determine the risk of progression to colorectal cancer and also decrease the risk of progression to colorectal cancer by allowing for earlier interventions.

Details of the methods are described in more detail below.

I. Molecular Signature

In an aspect, the disclosure provides a molecular signature for differentiating sessile serrated adenomas/polyps (SSA/Ps) and hyperplastic polyps (HPs) in a subject. As used herein, the term "molecular signature" refers to a set of nucleic acids that are differentially expressed in a subject. For example, serrated polyps may be classified into hyperplastic polyps (HPs), sessile serrated adenomas/polyps (SSA/Ps), and traditional serrated adenomas (TSAs) and the expression levels of the nucleic acids in the molecular signature may be used to differentiate SSA/Ps and HPs. Accordingly, the molecular signature may also be used to predict prognosis, predict development of colorectal cancer, develop a treatment strategy, develop a follow-up/monitoring strategy, determine response to treatment, monitor progression of disease, etc.

In one embodiment, the molecular signature comprises at least 3, at least 4, at least 5, at least 6, at least 7, at least 8, at least 9, at least 10, at least 11, at least 12, at least 13, at least 14, at least 15, at least 16, or at least 17 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4. Specifically, the molecular signature comprises 18 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4.

In another embodiment, the molecular signature comprises at least 3, at least 4, at least 5, at least 6, at least 7, at least 8, at least 9, at least 10, at least 11, at least 12, at least 13, at least 14, or at least 15 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. Specifically, the molecular signature comprises 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2.

In still another embodiment, the molecular signature comprises at least 3, at least 4, at least 5, at least 6, at least 7, at least 8, at least 9, at least 10, at least 11, or at least 12 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2. Specifically, the molecular signature comprises 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2.

Alternatively, a molecular signature of the disclosure may comprise 3 to 10, 10 to 20, 20 to 30, 30 to 50, 50 to 100, 100 to 200, 200 to 300, 300 to 400 and more than 400 nucleic acids. In one embodiment, a molecular signature of the disclosure may comprise at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all 26 nucleic acids from Table A. In addition, other nucleic acids not herein described may be combined with any of the presently disclosed nucleic acids to aid in the differentiation of sessile serrated adenomas/polyps (SSA/Ps) and hyperplastic polyps (HPs). A skilled artisan would be able to determine the various sequences of the nucleic acids listed in Table A. Nucleic acids have transcript variants due to alternative splicing. A skilled artisan would be able to determine various transcript variants from the accession numbers provided.

TABLE A

Nucleic acids for molecular signature.

| Gene Name | Description | Homo sapiens Accession Number |
|---|---|---|
| C4BPA | complement component 4 binding protein alpha | NM_000715.3 |
| CHFR | checkpoint with forkhead and ring finger domains, E3 ubiquitin protein ligase | NM_001161344.1 |
| CHGA | chromogranin A | NM_001275.3 |
| CLDN1 | claudin 1 | NM_021101.4 |

TABLE A-continued

Nucleic acids for molecular signature.

| Gene Name | Description | Homo sapiens Accession Number |
|---|---|---|
| CPE | carboxypeptidase E | NM_001873.3 |
| DPP10 | dipeptidyl peptidase like 10 | NM_020868.4 |
| FOXD1 | forkhead box D1 | NM_004472.2 |
| GRAMD1B | GRAM domain containing 1B | NM_001286563.1 |
| GRIN2D | glutamate ionotropic receptor NMDA type subunit 2D | NM_000836.2 |
| KIZ | kizuna centrosomal protein | NM_018474.4 |
| KLK7 | kallikrein related peptidase 7 | NM_005046.3 |
| MEGF6 | multiple EGF like domains 6 | NM_001409.3 |
| MYCN | v-myc avian myelocytomatosis viral oncogene neuroblastoma derived homolog | NM_001293228.1 |
| NTRK2 | neurotrophic tyrosine kinase, receptor, type 2 | NM_006180.4 |
| PIK3R3 | phosphoinositide-3-kinase regulatory subunit 3 | NM_003629.3 |
| PLA2G16 | phospholipase A2 group XVI | NM_007069.3 |
| PRUNE2 | prune homolog 2 | NM_015225.2 |
| PTAFR | platelet activating factor receptor | NM_001164721.1 |
| SBSPON | somatomedin B and thrombospondin type 1 domain containing | NM_153225.3 |
| SEMG1 | semenogelin I | NM_003007.4 |
| SLC7A9 | solute carrier family 7 member 9 | NM_014270.4 |
| SPIRE1 | spire type actin nucleation factor 1 | NM_001128626.1 |
| TACSTD2 | tumor-associated calcium signal transducer 2 | NM_002353.2 |
| TM4SF4 | transmembrane 4 L six family member 4 | NM_004617.3 |
| TPD52L1 | tumor protein D52-like 1 | NM_003287.3 |
| TRIB2 | tribbles pseudokinase 2 | NM_021643.3 |

The molecular signature may further comprise one or more nucleic acids used as a normalization control. A normalization control compensates for systemic technical differences between experiments, to see more clearly the systemic biological differences between samples. A normalization control is a nucleic acid whose expression is not expected to be different across samples. Generally, these nucleic acids may be known as 'housekeeping' nucleic acids which are required for basic cell processes. Non-limiting examples of housekeeping nucleic acids commonly used as normalization controls include GAPDH, ACTB, B2M, TUBA, G6PD, LDHA, HPRT, ALDOA, PFKP, PGK1, PGAM1, VIM and UBC.

II. Methods

In an aspect, the disclosure provides a method to classify a subject based on the level of expression of the nucleic acids in a molecular signature of the disclosure. The method generally comprises: (a) determining the level of expression of the nucleic acids in a molecular signature of the disclosure in a biological sample obtained from the subject; (b) comparing the level of expression of each nucleic acid in the molecular signature to a reference value; and (c) classifying the subject based on the level of expression of each nucleic acid in the molecular signature relative to the reference value. In an embodiment, the molecular signature comprises 18 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4. In another embodiment, the molecular signature comprises 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. In still another embodiment, the molecular signature comprises 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2.

In another aspect, the disclosure provides a method of detecting sessile serrated adenomas/polyps (SSA/Ps) in a subject. The method comprises: (a) determining the level of expression of the nucleic acids in a molecular signature of the disclosure in a biological sample obtained from the subject; (b) comparing the level of expression of each nucleic acid in the molecular signature to a reference value; and (c) detecting SSA/Ps in the subject based on the level of expression of each nucleic acid in the molecular signature relative to the reference value. In an embodiment, the molecular signature comprises 18 nucleic acids selected from the group consisting of C4BPA, CHGA, CLDN1, CPE, DPP10, GRAMD1B, GRIN2D, KIZ, KLK7, MEGF6, MYON, NTRK2, PLA2G16, SBSPON, SEMG1, SLC7A9, SPIRE1, and TM4SF4. In another embodiment, the molecular signature comprises 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. In still another embodiment, the molecular signature comprises 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2. Specifically, step (c) comprises detecting SSA/Ps in the subject when CHFR, CHGA, and NTRK2 are decreased relative to the reference value and when CLDN1, KIZ, MEGF6, PLA2G16, PTAFR, SBSPON, SEMG1, SLC7A9, SPIRE1, and TACSTD2 are increased relative to the reference value, wherein the reference value is the level of expression of each nucleic acid in the molecular signature in a non-diseased or HP sample. Additionally, step (c) comprises detecting SSA/Ps in the subject when NTRK2 is decreased relative to the reference value and when CLDN1, FOXD1, KIZ, MEGF6, PIK3R3, PLA2G16, PRUNE2, PTAFR, SBSPON, SEMG1, SLC7A9, SPIRE1, TPD52L1, and TRIB2 are increased relative to the reference value, wherein the reference value is the level of expression of each nucleic acid in the molecular signature in a non-diseased or HP sample. Further, step (c) comprises detecting SSA/Ps in the subject when CHGA, CPE, DPP10, and NTRK2 are decreased relative to the reference value and when C4BPA, CLDN1, GRAMD1B, GRIN2D, KIZ, KLK7, MEGF6, MYCN, PLA2G16, SBSPON, SEMG1, SLC7A9, SPIRE1, and TM4SF4 are increased relative to the reference value, wherein the reference value is the level of expression of each nucleic acid in the molecular signature in a non-diseased or HP sample.

In still another aspect, the disclosure provides a method of differentiating sessile serrated adenomas/polyps (SSA/Ps) from hyperplastic polyps (HPs) in a subject. The method comprises: (a) determining the level of expression of the nucleic acids in a molecular signature of the disclosure in a biological sample obtained from the subject; (b) comparing the level of expression of each nucleic acid in the molecular signature to a reference value; and (c) detecting SSA/Ps or HPs in the subject based on the level of expression of each nucleic acid in the molecular signature relative to the reference value. In an embodiment, the molecular signature comprises 18 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4. In another embodiment, the molecular signature comprises 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. In still another embodiment, the molecular signature comprises 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2. Specifically, step (c) comprises detecting SSA/Ps in the subject when CHFR, CHGA, and NTRK2 are decreased relative to the reference value and when CLDN1, KIZ, MEGF6, PLA2G16, PTAFR, SBSPON, SEMG1, SLC7A9, SPIRE1, and TACSTD2 are increased relative to the reference value, wherein the reference value is the level of expression of each nucleic acid in the molecular signature in a non-diseased or HP sample. Additionally, step (c) comprises detecting SSA/Ps in the subject when NTRK2 is decreased relative to the reference value and when CLDN1, FOXD1, KIZ, MEGF6, PIK3R3, PLA2G16, PRUNE2, PTAFR, SBSPON, SEMG1, SLC7A9, SPIRE1, TACSTD2, TPD52L1, and TRIB2 are increased relative to the reference value, wherein the reference value is the level of expression of each nucleic acid in the molecular signature in a non-diseased or HP sample. Further, step (c) comprises detecting SSA/Ps in the subject when CHGA, CPE, DPP10, and NTRK2 are decreased relative to the reference value and when C4BPA, CLDN1, GRAMD1B, GRIN2D, KIZ, KLK7, MEGF6, MYCN, PLA2G16, SBSPON, SEMG1, SLC7A9, SPIRE1, and TM4SF4 are increased relative to the reference value, wherein the reference value is the level of expression of each nucleic acid in the molecular signature in a non-diseased or HP sample.

In still yet another aspect, the disclosure provides a method of predicting the likelihood that a colorectal polyp in a subject will develop into colorectal cancer. The method comprises: (a) determining the level of expression of the nucleic acids in a molecular signature of the disclosure in a biological sample obtained from the subject; (b) comparing the level of expression of each nucleic acid in the molecular signature to a reference value; and (c) detecting SSA/Ps in the subject based on the level of expression of each nucleic acid in the molecular signature relative to the reference value, wherein the detection of SSA/Ps in the subject indicates an increased likelihood of developing colorectal cancer. Treatment decisions may then be made based on the detection of SSA/Ps. In an embodiment, the molecular signature comprises 18 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4. In another embodiment, the molecular signature comprises 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. In still another embodiment, the molecular signature comprises 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2. Specifically, step (c) comprises detecting SSA/Ps in the subject when CHFR, CHGA, and NTRK2 are decreased relative to the reference value and when CLDN1, KIZ, MEGF6, PLA2G16, PTAFR, SBSPON, SEMG1, SLC7A9, SPIRE1, and TACSTD2 are increased relative to the reference value, wherein the reference value is the level of expression of each nucleic acid in the molecular signature in a non-diseased or HP sample. Additionally, step (c) comprises detecting SSA/Ps in the subject when NTRK2 is decreased relative to the reference value and when CLDN1, FOXD1, KIZ, MEGF6, PIK3R3, PLA2G16, PRUNE2, PTAFR, SBSPON, SEMG1, SLC7A9, SPIRE1, TACSTD2, TPD52L1, and TRIB2 are increased relative to the reference value, wherein the reference value is the level of expression of each nucleic acid in the molecular signature in a non-diseased or HP sample. Further, step (c) comprises detecting SSA/Ps in the subject when CHGA, CPE, DPP10, and NTRK2 are decreased relative to the reference value and when C4BPA, CLDN1, GRAMD1B, GRIN2D, KIZ, KLK7, MEGF6, MYCN, PLA2G16, SBSPON, SEMG1, SLC7A9, SPIRE1, and TM4SF4 are increased relative to the reference value, wherein the reference value is the level of expression of each nucleic acid in the molecular signature in a non-diseased or HP sample.

In other aspects, the disclosure provides a method of determining treatment of a subject diagnosed with serrated polyps or suspected of having serrated polyps. The method generally comprises: (a) determining the level of expression of the nucleic acids in a molecular signature of the disclosure in a biological sample obtained from the subject; (b) comparing the level of expression of each nucleic acid in the molecular signature to a reference value; (c) detecting SSA/Ps in the subject based on the level of expression of each nucleic acid in the molecular signature relative to the reference value; and (d) treating the subject more aggressively if SSA/Ps are detected. Serrated polyps may be classified into hyperplastic polyps (HPs), sessile serrated adenomas/polyps (SSA/Ps), and traditional serrated adenomas (TSAs). SSA/Ps have the strongest association with an increased risk for colon cancer. Accordingly, if SSA/Ps are detected, the subject may be more aggressively treated relative to treatment for HPs. Non-limiting examples of treatment for SSA/Ps include polypectomy, endoscopic resection, and surgical resection, all followed with surveillance. Additionally or alternatively, if SSA/Ps are detected, the subject may be subjected to an increased frequency of surveillance, such as colonoscopy. For example, the subject may receive a colonoscopy about every 1 to about every 6 years. Accordingly, if SSA/Ps are detected, the subject may receive a colonoscopy about every 1 year, about every 2 years, about every 3 years, about every 4 years, about every 5 years, or about every 6 years. For example, a subject having a polyp classified as an SSA/P according to the methods detailed herein and the polyp having diameter of at least about 10 mm would have a subsequent colonoscopy in about 2 years to about 4 years, or about 3 years. For example, a subject having a polyp classified as an SSA/P according to the methods detailed herein and the polyp having of diameter of less than about 5 mm would have a subsequent colonoscopy in about 4 years to about 6 years, or about 5 years. A subject having a polyp classified as an SSA/P according to the methods detailed herein and being of diameter of about 5 mm to about 10 mm would have a subsequent colonoscopy in about 2 years to about 6 years, about 3 to about 5 years, or about 4 years. More frequent colonoscopies may be suggested for subjects having multiple SSA/P polyps. By more accurately diagnosing a polyp as a SSA/P instead of as a hyperplastic polyp, a subject may be more frequently screened by colonoscopy, leading to a reduced incidence of colon cancer and deaths due to colon cancer. In an embodiment, the molecular signature comprises 18 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4. In another embodiment, the molecular signature comprises 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. In still another embodiment, the molecular signature comprises 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2. Specifically, step (c) comprises detecting SSA/Ps in the subject when CHFR, CHGA, and NTRK2 are decreased relative to the reference value and when CLDN1, KIZ, MEGF6, PLA2G16, PTAFR, SBSPON, SEMG1, SLC7A9, SPIRE1, and TACSTD2 are increased relative to the reference value, wherein the reference value is the level of expression of each nucleic acid in the molecular signature in a non-diseased or HP sample. Additionally, step (c) comprises detecting SSA/Ps in the subject when NTRK2 is decreased relative to the reference value and when CLDN1, FOXD1, KIZ, MEGF6, PIK3R3, PLA2G16, PRUNE2, PTAFR, SBSPON, SEMG1, SLC7A9, SPIRE1, TACSTD2, TPD52L1, and TRIB2 are increased relative to the reference value, wherein the reference value is the level of expression of each nucleic acid in the molecular signature in a non-diseased or HP sample. Further, step (c) comprises detecting SSA/Ps in the subject when CHGA, CPE, DPP10, and NTRK2 are decreased relative to the reference value and when C4BPA, CLDN1, GRAMD1B, GRIN2D, KIZ, KLK7, MEGF6, MYCN, PLA2G16, SBSPON, SEMG1, SLC7A9, SPIRE1, and TM4SF4 are increased relative to the reference value, wherein the reference value is the level of expression of each nucleic acid in the molecular signature in a non-diseased or HP sample.

In other aspects, the disclosure provides a method for monitoring serrated polyps in a subject. In such an embodiment, a method of detecting sessile serrated adenomas/polyps (SSA/Ps) in a subject is performed at one point in time. Then, at a later time, the method of detecting sessile serrated adenomas/polyps (SSA/Ps) in the subject may be performed to determine the change in serrated polyps over time. For example, the method of detecting sessile serrated adenomas/polyps (SSA/Ps) may be performed on the same subject days, weeks, months, or years following the initial use of the method to detect sessile serrated adenomas/polyps (SSA/Ps). Accordingly, the method of detecting SSA/Ps may be used to follow a subject over time to determine when the risk of progressing to more severe disease is high thereby requiring treatment. Additionally, the method of detecting SSA/Ps may be used to measure the rate of disease progression. For example, an increased level of CLDN1, KIZ, MEGF6, PLA2G16, PTAFR, SBSPON, SEMG1, SLC7A9, SPIRE1, and TACSTD2 and decreased level of CHFR, CHGA, and NTRK2 may indicate disease progression. Early assessment of the risk of colorectal cancer in the subject may reduce the development and/or progression of symptoms associated with colorectal cancer by enabling improved interventions or enabling earlier interventions. The term "risk" as used herein refers to the probability that an event will occur over a specific time period, for example, as in the development of colorectal cancer (CRC) and can mean a subject's "absolute" risk or "relative" risk. Absolute risk can be measured with reference to either actual observation, post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary depending on how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

Additionally, a method for monitoring serrated polyps in a subject may be used to determine the response to treatment. As used herein, subjects who respond to treatment are said to have benefited from treatment. For example, a method of detecting SSA/Ps may be performed on the biological sample of the subject prior to initiation of treatment. Then, at a later time, a method of detecting SSA/Ps may be used to determine the response to treatment over time. For example, a method of detecting SSA/Ps may be performed on the biological sample of the same subject days, weeks, months, or years following initiation of treatment. Accordingly, a method of detecting SSA/Ps may be used to follow a subject receiving treatment to determine if the subject is responding to treatment. If the level of expression of the nucleic acids in a molecular signature of the disclosure remains the same, then the subject may not be responding to treatment. If the level of expression of the nucleic acids in a molecular signature of the disclosure changes, then the subject may be responding to treatment. These steps may be repeated to determine the response to therapy over time.

In any of the foregoing embodiments, the subject may or may not be diagnosed with serrated polyps or SSA/Ps. In certain embodiments, the subject may not be diagnosed with serrated polyps or SSA/Ps but is suspected of having serrated polyps or SSA/Ps based on symptoms. Non-limiting examples of symptoms of serrated polyps or SSA/Ps that may lead to a diagnosis include bleeding and iron deficiency anemia. In other embodiments, the subject may not be diagnosed with serrated polyps or SSA/Ps but is at risk of having serrated polyps or SSA/Ps. Non-limiting examples of risk factors for serrated polyps or SSA/Ps include smoking, diabetes, obesity, age, sex, diet, and family history. In other embodiment, the subject has no symptoms and/or no risk factors for serrated polyps or SSA/Ps. Methods of diagnosing serrated polyps or SSA/Ps are known in the art. Non-limiting examples of methods of diagnosing serrated polyps or SSA/Ps include histological pathology.

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas, and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an embodiment, the animal is a laboratory animal. Non-limiting examples of a laboratory animal may include rodents, canines, felines, and non-human primates. In certain embodiments, the animal is a rodent. In a preferred embodiment, the subject is human.

(a) Biological Sample

As used herein, the term "biological sample" refers to a sample obtained from a subject. Any biological sample which may be assayed for nucleic acid expression products may be used. Numerous types of biological samples are known in the art. Suitable biological sample may include, but are not limited to, tissue samples or bodily fluids. In some embodiments, the biological sample is a tissue sample such as a tissue biopsy from the gastrointestinal tract. The biopsy may be taken during a colonoscopy, prior to surgical resection, during surgical resection or following surgical resection. The biopsied tissue may be fixed, embedded in paraffin or plastic, and sectioned, or the biopsied tissue may be frozen and cryosectioned. In an embodiment, the biological sample is a formalin-fixed paraffin-embedded (FFPE) tissue sample. Alternatively, the biopsied tissue may be processed into individual cells or an explant, or processed into a homogenate, a cell extract, a membranous fraction, or a protein extract. In a specific embodiment, the biopsied tissue is from a colorectal polyp. In other embodiments, the sample may be a bodily fluid. Non-limiting examples of suitable bodily fluids include blood, plasma, serum, or feces. The fluid may be used "as is", the cellular components may be isolated from the fluid, or a protein fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the nucleic acids of a molecular signature of the disclosure can be accurately detected and the level of expression measured according to the disclosure.

In some embodiments, a single sample is obtained from a subject to detect the molecular signature in the sample. Alternatively, the molecular signature may be detected in samples obtained over time from a subject. As such, more than one sample may be collected from a subject over time. For instance, 2, 3, 4, 5, 6, 7, 8, 9, 10, 11, 12, 13, 14, 15, 16, or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16, or more samples are collected from a subject over time.

When more than one sample is collected from a subject over time, samples may be collected every 1, 2, 3, 4, 5, 6, 7, 8, 9, 10, 11, 12, or more days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12, or more days. In still other embodiments, samples are collected a month apart, 3 months apart, 6 months apart, 1 year apart, 2 years apart, 5 years apart, 10 years apart, or more.

(b) Determining the Level of Nucleic Acid Expression

Once a sample is obtained, it is processed in vitro to detect and measure the level of expression of the nucleic acids in a molecular signature of the disclosure. Methods for assessing the level of nucleic acid expression are well known in the art and all suitable methods for detecting and measuring the level of expression of nucleic acids known to one of skill in the art are contemplated within the scope of the invention. The term "amount of nucleic acid expression" or "level of nucleic acid expression" or "expression level" as used herein refers to a measurable level of expression of the nucleic acids, such as, without limitation, the level of messenger RNA transcript expressed or a specific exon or other portion of a transcript, the level of proteins or portions thereof expressed from the nucleic acids, the number or presence of DNA polymorphisms of the nucleic acids, the enzymatic or other activities of the proteins codec by the nucleic acids, and the level of a specific metabolite. The term "nucleic acid" includes DNA and RNA and can be either double stranded or single stranded. In a specific embodiment, determining the level of expression of a nucleic acid of the molecular signature comprises, in part, measuring the level of RNA expression. The term "RNA" includes mRNA transcripts, and/or specific spliced or other alternative variants of mRNA, including anti-sense products. The term "RNA product of the nucleic acid" as used herein refers to RNA transcripts transcribed from the nucleic acids and/or specific spliced or alternative variants. Non-limiting examples of suitable methods to assess a level of nucleic acid expression may include arrays, such as microarrays, RNA-seq, PCR, such as RT-PCR (including quantitative RT-PCR), nuclease protection assays and Northern blot analyses. In an embodiment, the method to assess the level of nucleic acid expression is microarray, RNA-seq or real-time qPCR.

In one embodiment, the level of nucleic acid expression may be determined by using an array, such as a microarray. Methods of using a nucleic acid microarray are well and widely known in the art. For example, a plurality of nucleic acid probes that are complementary or hybridizable to an expression product of each nucleic acid of the molecular signature are used on the array. Accordingly, 3 to 10, 10 to 20, 20 to 30, 30 to 50, 50 to 100, 100 to 200, 200 to 300, 300 to 400, and more than 400 nucleic acids may be used on the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500, or more nucleotides in length.

In another embodiment, the level of nucleic acid expression may be determined using PCR. Methods of PCR are well and widely known in the art, and may include quantitative PCR, semi-quantitative PCR, multiplex PCR, or any combination thereof. Specifically, the level of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The level of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. This allows comparisons between assays that are performed on different occasions.

(c) Comparing the Level of Nucleic Acid Expression and Detecting SSA/Ps

The level of expression of each nucleic acid of the molecular signature may be compared to a reference expression level for each nucleic acid of the molecular signature. The subject expression levels of the nucleic acids in the molecular signature in a biological sample are compared to the corresponding reference expression levels of the nucleic acids of the molecular signature to detect SSA/Ps. Accordingly, a reference expression level may comprise 3 to 10, 10 to 20, 20 to 30, 30 to 50, 50 to 100, 100 to 200, 200 to 300, 300 to 400, and more than 400 expression levels based on the number of nucleic acids in the molecular signature. Any suitable reference value known in the art may be used. For example, a suitable reference value may be the level of molecular signature in a biological sample obtained from a subject or group of subjects of the same species that have no signs or symptoms of disease (i.e. serrated polyps). In another example, a suitable reference value may be the level of molecular signature in a biological sample obtained from a subject or group of subjects of the same species that have not been diagnosed with disease (i.e. serrated polyps). In still another example, a suitable reference value may be the level of molecular signature in a biological sample obtained from a subject or group of subjects of the same species that have been diagnosed with SSA/Ps. In yet still another example, a suitable reference value may be the level of molecular signature in a biological sample obtained from a subject or group of subjects of the same species that been diagnosed with HPs. In a different example, a suitable reference value may be the background signal of the assay as determined by methods known in the art. In another different example, a suitable reference value may be the level of molecular signature in a non-diseased or HP sample stored on a computer readable medium. In still another different example, a suitable reference value may be the level of molecular signature in a SSA/Ps sample stored on a computer readable medium. Common forms of computer-readable media include, for example, a floppy disk, a flexible disk, hard disk, magnetic tape, or other magnetic medium, a CD-ROM, CDRW, DVD, or other optical medium, punch cards, paper tape, optical mark sheets, or other physical medium with patterns of holes or other optically recognizable indicia, a RAM, a PROM, and EPROM, a FLASH-EPROM, or other memory chip or cartridge, a carrier wave, or other medium from which a computer can read.

In other examples, a suitable reference value may be the level of the molecular signature in a reference sample obtained from the same subject. The reference sample may or may not have been obtained from the subject when serrated polyps or SSA/Ps were not suspected. A skilled artisan will appreciate that that is not always possible or desirable to obtain a reference sample from a subject when the subject is otherwise healthy. For example, in an acute setting, a reference sample may be the first sample obtained from the subject at presentation. In another example, when monitoring effectiveness of a therapy, a reference sample may be a sample obtained from a subject before therapy began. In a specific embodiment, a reference value may be the level of expression of each nucleic acid of the molecular signature in a non-diseased portion of the subject. Such a reference expression level may be used to create a control value that is used in testing diseased samples from the subject.

The expression level of each nucleic acid of the molecular signature is compared to the reference expression level of each nucleic acid of the molecular signature to determine if the nucleic acids of the molecular signature in the test sample are differentially expressed relative to the reference expression level of the corresponding nucleic acid. The term "differentially expressed" or "differential expression" as used herein refers to a difference in the level of expression of the nucleic acids that can be assayed by measuring the level of expression of the products of the nucleic acids, such as the difference in level of messenger RNA transcript or a portion thereof expression or of proteins expressed of the nucleic acids.

The term "difference in the level of expression" refers to an increase or decrease in the measurable expression levels of a given nucleic acid, for example as measured by the amount of messenger RNA transcript and/or the amount of protein in a biological sample as compared with the measureable expression level of a given nucleic acid in a reference sample (i.e. non-diseased or HP sample). In one embodiment, the differential expression can be compared using the ratio of the level of expression of a given nucleic acid or nucleic acids as compared with the expression level of the given nucleic acid or nucleic acids of a reference sample, wherein the ratio is not equal to 1.0. For example, an RNA or protein is differentially expressed if the ratio of the level of expression of a first sample as compared with a second sample is greater than or less than 1.0. For example, a ratio of greater than 1, 1.2, 1.5, 1.7, 2, 3, 4, 5, 10, 15, 20 or more, or a ratio less than 1, 0.8, 0.6, 0.4, 0.2, 0.1, 0.05, 0.001, or less. In another embodiment, the differential expression is measured using p-value. For instance, when using p-value, a nucleic acid is identified as being differentially expressed between a first sample and a second sample when the p-value is less than 0.1, preferably less than 0.05, more preferably less than 0.01, even more preferably less than 0.005, the most preferably less than 0.0001.

Depending on the sample used for reference expression levels, the difference in the level of expression may or may not be statistically significant. For example, if the sample used for reference expression levels is from a subject or subjects diagnosed with SSA/Ps, then when the difference in the level of expression is not significantly different, the subject has SSA/Ps. However, when the difference in the level of expression is significantly different, the subject has HPs. Alternatively, if the sample used for reference expression levels is from a subject or subjects diagnosed with no disease or HP, then when the difference in the level of expression is not significantly different, the subject does not have SSA/Ps. However, when the difference in the level of expression is significantly different, the subject has SSA/Ps.

(d) Treatment

The determination of SSA/Ps may be used to select treatment for subjects. As explained herein, a molecular signature disclosed herein can classify a subject as having HPs or SSA/Ps and into groups that might benefit from more aggressive therapy or determine the appropriate treatment for the subject. In an embodiment, a subject classified as having SSA/Ps may be treated. A skilled artisan would be able to determine standard treatment for SSA/Ps. Accordingly, the methods disclosed herein may be used to select treatment for serrated polyp subjects. In an embodiment, the subject is treated based on the level of expression of the nucleic acids in a molecular signature of the disclosure measured in the sample. This classification may be used to identify groups that are in need of treatment or not or in need of more aggressive treatment. The term "treatment" or "therapy" as used herein means any treatment suitable for the treatment of SSA/Ps. Treatment may consist of standard treatments for SSA/Ps. Non-limiting examples of standard treatment for SSA/Ps include increased surveillance, polypectomy, endoscopic resection, and surgical resection. Additionally, the treatment decision may be made based on evidence of progression from SSA/Ps to cancer.

III. Kit

In an aspect, there is provided a kit to differentiate SSA/Ps and HPs in a subject, comprising detection agents that can detect the expression products of a molecular signature of the disclosure, and instructions for use. The kit may further comprise one or more nucleic acids used as a normalization control. The kit may comprise detection agents that can detect the expression products of 3 to 10, 10 to 20, 20 to 30, 30 to 50, 50 to 100, 100 to 200, 200 to 300, 300 to 400, and more than 400 nucleic acids described herein.

In another aspect, there is provided a kit to select a therapy for a subject with serrated polyps, comprising detection agents that can detect the expression products of a molecular signature of the disclosure, and instructions for use. The kit may further comprise one or more nucleic acids used as a normalization control. The kit may comprise detection agents that can detect the expression products of 3 to 10, 10 to 20, 20 to 30, 30 to 50, 50 to 100, 100 to 200, 200 to 300, 300 to 400, and more than 400 nucleic acids described herein.

A person skilled in the art will appreciate that a number of detection agents can be used to determine the expression of the nucleic acids. For example, to detect RNA products of the biomarkers, probes, primers, complementary nucleotide sequences or nucleotide sequences that hybridize to the RNA products can be used.

Accordingly, in one embodiment, the detection agents are probes that hybridize to the nucleic acids in the molecular signature. A person skilled in the art will appreciate that the detection agents can be labeled. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The kit can also include a control or reference standard and/or instructions for use thereof. In addition, the kit can include ancillary agents such as vessels for storing or transporting the detection agents and/or buffers or stabilizers.

In some embodiments, the kit is a nucleic acid array, a multiplex RNA, a chip based array, and the like.

In certain embodiments, the kit is a nucleic acid array. Such an array may be used to determine the expression level of the nucleic acids in a biological sample. An array may be comprised of a substrate having disposed thereon nucleic acid sequences capable of hybridizing to the nucleic acid sequences of a molecular signature of the disclosure. For instance, the array may comprise nucleic acid sequences capable of hybridizing to 18 nucleic acids selected from the group consisting of C4BPA, CHGA, CLDN1, CPE, DPP10, GRAMD1B, GRIN2D, KIZ, KLK7, MEGF6, MYCN, NTRK2, PLA2G16, SBSPON, SEMG1, SLC7A9, SPIRE1, and TM4SF4. In another embodiment, the array may comprise nucleic acid sequences capable of hybridizing to 16 nucleic acids selected from the group consisting of CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, and TRIB2. In still another embodiment, the array may comprise nucleic acid sequences capable of hybridizing to 13 nucleic acids selected from the group consisting of CHFR, CHGA, CLDN1, KIZ, MEGF6, NTRK2, PLA2G16, PTAFR, SBSPON, SEMG1, SLC7A9, SPIRE1, and TACSTD2.

In certain embodiments, the kit is a chip based array. Such an array may be used to determine the expression level of the proteins in a biological sample. The proteins may be the transcription products from the nucleic acid sequences disclosed herein.

A person skilled in the art will appreciate that a number of detection agents can be used to determine the expression level of the transcription products of the nucleic acid sequences disclosed herein.

Several substrates suitable for the construction of arrays are known in the art. The substrate may be a material that may be modified to contain discrete individual sites appropriate for the attachment or association of the nucleic acid and is amenable to at least one detection method. Alternatively, the substrate may be a material that may be modified for the bulk attachment or association of the nucleic acid and is amenable to at least one detection method. Non-limiting examples of substrate materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. In an embodiment, the substrates may allow optical detection without appreciably fluorescing.

A substrate may be planar, a substrate may be a well, i.e. a 1534-, 384-, or 96-well plate, or alternatively, a substrate may be a bead. Additionally, the substrate may be the inner surface of a tube for flow-through sample analysis to minimize sample volume. Similarly, the substrate may be flexible, such as a flexible foam, including closed cell foams made of particular plastics. Other suitable substrates are known in the art.

The nucleic acid or biomolecules may be attached to the substrate in a wide variety of ways, as will be appreciated by those in the art. The nucleic acid may either be synthesized first, with subsequent attachment to the substrate, or may be directly synthesized on the substrate. The substrate and the nucleic acid may both be derivatized with chemical functional groups for subsequent attachment of the two. For example, the substrate may be derivatized with a chemical functional group including, but not limited to, amino groups, carboxyl groups, oxo groups or thiol groups. Using these functional groups, the nucleic acid may be attached using functional groups on the biomolecule either directly or indirectly using linkers.

The nucleic acid may also be attached to the substrate non-covalently. For example, a biotinylated nucleic acid can be prepared, which may bind to surfaces covalently coated with streptavidin, resulting in attachment. Alternatively, a nucleic acid or nucleic acids may be synthesized on the surface using techniques such as photopolymerization and photolithography. Additional methods of attaching biomolecules to arrays and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, each of which is hereby incorporated by reference in its entirety).

In one embodiment, the nucleic acid or nucleic acids attached to the substrate are located at a spatially defined address of the array. Arrays may comprise from about 1 to about several hundred thousand addresses. A nucleic acid may be represented more than once on a given array. In other words, more than one address of an array may be comprised of the same nucleic acid. In some embodiments, two, three, or more than three addresses of the array may be comprised of the same nucleic acid. In certain embodiments, the array may comprise control nucleic acids and/or control addresses. The controls may be internal controls, positive controls, negative controls, or background controls.

Furthermore, the nucleic acids used for the array may be labeled. One skilled in the art understands that the type of label selected depends in part on how the array is being used. Suitable labels may include fluorescent labels, chromagraphic labels, chemi-luminescent labels, FRET labels, etc. Such labels are well known in the art.

As various changes could be made in the above compounds, products and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.
Introduction.

Screening programs have resulted in significant reduction of colorectal cancer (CRC) related deaths. Key to the improvement of clinical outcomes is the appropriate follow-up using colonoscopy and removal of premalignant polyps. However, different types of colonic polyps have different malignant potentials and recommendations for removal and follow-up vary depending on their type. The most common polyps include the conventional adenomas and serrated polyps, and until approximately 1996 the hyperplastic polyp was the only recognized type of serrated polyp. The term sessile serrated adenoma/polyp was introduced to define serrated lesions which were generally considered to be preneoplastic, usually lack cytological dysplasia and have been reported in 5% of average-risk patients undergoing screening colonoscopy. Currently, serrated polyps are divided into three main categories: typical hyperplastic polyps (HPs), sessile serrated adenoma polyps (SSA/Ps) and traditional serrated adenomas (relatively rare). However, SSA/Ps and HPs share significant histological similarities, as serrated crypt architecture is the principal microscopic feature in both polyps. Dilated or boot-shaped crypt bases are diagnostic features of SSA/Ps. In general, SSA/Ps are larger than HPs and are more commonly located in proximal (right) colon. However, given the significant histologic overlap between the two polyp types, biopsy specimens are frequently equivocal in cases lacking the diagnostic hallmarks of SSA/Ps. In addition, several studies have pointed out significant observer-to-observer variability, even among expert pathologists. Because SSA/Ps have the potential to progress into colon cancer, reliable biomarkers that aid in this differential diagnosis are needed. It is estimated that SSA/Ps account for 15-30% of colon cancers by progression through the serrated neoplasia pathway. However, this pathway remains relatively uncharacterized as compared to the adenoma-carcinoma pathway. Genetic and epigenetic mechanisms operating in the serrated pathway can include BRAF mutations, KRAS mutations, CpG island methylator high (CIMP-H) and microsatellite instability high (MSI-H) phenotypes which often predict a poor clinical outcome. However, the serrated neoplasia pathway remains to be defined by a characteristic set of genetic and epigenetic lesions.

Since the advent of high-throughput gene expression technologies (microarrays, RNA sequencing) molecular signatures that accurately diagnose or predict disease outcome based on expression of sets of genes have been developed. In many cases gene expression signatures can be associated with biological mechanisms, subtypes of cancer that look histologically similar, tumor stages, as well as the ability to metastasize, relapse or respond to specific therapies. Expression-based classifiers were also developed to identify patients with a poor prognosis for stage II colon cancers. Recently, a subgroup of colon cancers with a very poor prognosis was identified and this subgroup has several up-regulated pathways in common with sessile serrated adenomas. However, there is no molecular classifier, differentiating between SSA/Ps and HPs.

Several recent studies used transcriptome analyses to gain insights into the biology of SSA/Ps. For example, in a gene array study SSA/Ps were compared to tubular adenomas (TAs) and control samples. Among 67 differentially expressed (DE) genes the two most up-regulated genes (Cathepsin E and Trefoil Factor 1) were verified in QRT-PCR and immunohistochemistry experiments that showed that these genes were overexpressed in SSA/Ps. In another gene array study 162 DE genes were identified in SSA/Ps as compared to microvesicular hyperplastic polyps (MVHP, HP subtype). Validation by QRT-PCR and immunohistochemistry identified annexin A10 as a potential diagnostic marker of SSA/Ps. Another study used RNA sequencing (RNA-seq) to analyze the SSA/P transcriptomes and identified 1,294 genes, differentially expressed in SSA/Ps as compared to HPs. This analysis provided evidence that molecular pathways involved in colonic mucosal integrity and cell adhesion were overrepresented in SSA/Ps.

The goals of this study were two-fold. First, to gain insights into the biological processes underlying the differences between SSA/Ps and HPs. Data from HPs and SSA/Ps matched with control samples was analyzed. Importantly, the right and left colon have a different embryological origin and it was shown that more than 1,000 genes are differentially expressed in adult right versus left colon. SSA/Ps occur predominantly in the right colon and HPs occur predominantly in the left colon. Consequently, some genes that are DE between SSA/Ps and HPs are likely to be due to their different anatomical location (right versus left). Therefore, to find genes and pathways that are DE specifically between SSA/Ps and HPs, it is first necessary to exclude genes that are DE between the right and left colon. As such, in addition to SSA/Ps and HPs, control samples obtained from the right colon (CR) and left colon (CL) were also included in the study. The analysis of differentially expressed genes and pathways revealed several differentially expressed and differentially co-expressed pathways between SSA/Ps and HP, CR samples. The pathways found here are generally considered hallmarks of cancer: they were associated with the ability to escape apoptotic signals, the inflammatory state of premalignant lesions and uncontrolled proliferation.

Second, to develop an expression-based classifier that reliably differentiates between HPs and SSA/Ps and is platform-independent (it works for RNA-seq as well as for microarrays). For that independent microarray data sets were collected: an Illumina gene array data set (six HPs and six SSA/Ps) and subsets of samples from two Affymetrix data sets (eleven HPs from GSE10714 and six SSA/Ps from GSE45270). Typically, the most ambiguous step in classifier development is the step of feature selection because of the 'large p small n' problem of omics data. Omics data have at most only hundreds of samples (n) and thousands of features (p), and using all features will lead to model over-fitting and poor generalizability. Feature selection techniques differ in the way they combine feature selection with the construction of the classification model and usually are classified into three categories: filter, wrapper, and embedded algorithms. Filter algorithms preselect features before using classifier based, for example, on the results of significance testing. Wrapper algorithms combine the search of optimal features with the model selection and evaluate features by training and testing classification model. For example, the Shrunken Centroid Classifier (SCC) first finds a centroid for each class and selects features to shrink the gene centroid toward the overall class centroid. Here is presented a new way to combine filter and wrapper algorithms that fitted best to the goal, i.e. building platform independent classifier. First, the feature space was reduced by selecting only those features (genes) that were concordantly expressed over all three platforms. Second, SCC (using all genes left after filtering) was applied on RNA-seq data for further reducing the feature space and selecting features with optimal classification performance. The classifier, developed based on RNA-seq data identified SSA/P and HP subtypes in independent microarray data sets with low classification errors. The molecular signature that correctly classifies SSA/Ps and HPs consists of thirteen genes and is a first platform-independent signature that is applicable as diagnostic tool for distinguishing SSA/Ps from HPs. The molecular signature achieved an impressive correct classification rate (90%) when expression levels obtained by real-time quantitative polymerase chain reaction (qPCR) from 45 independent formalin-fixed paraffin-embedded (FFPE) SSA/P and HP samples were used for validation. These results demonstrate the clinical value of the molecular signature.

Expression Analysis.

Filtering Steps.

Genes were called DE if two conditions were met: $|\log_2 FC|>0.5$ and adjusted p-values $P_{adj}<0.05$ (see Methods for more detail). The intersections of the three comparisons: (1) Control Right (CR) versus Control Left (CL) samples (CR_CL), (2) HP versus SSA/P samples (HP_SSA/P) and (3) CR versus SSA/P samples (CR_SSA/P) are shown in FIG. 1. There were 1049 genes DE between CR and CL samples, and among these genes 157 were also DE between HPs and SSA/Ps and 276 were DE between CR and SSA/P samples. There were 121 genes in the intersection of all three comparisons. With the aim of identifying only genes that reliably differentiate between HPs and SSA/Ps as well as between SSA/Ps and CR samples, the three aforementioned groups were excluded from the further study. The following groups were considered for further analysis: (1) 139 genes that were DE between SSA/Ps and both HP and CR samples (Table 4), (2) 134 genes, exclusively DE between HPs and SSA/Ps (Table 5) and (3) 1058 genes, exclusively DE between CR and SSA/P samples (Table 6). The 121 genes in the intersection of all three comparisons (Table 7) were excluded for the sake of rigor, i.e. for considering only genes that were DE between different polyp types, without referring to the anatomical location. Although these 121 genes were excluded here, further investigation is needed to assess their importance in differentiating between HPs and SSA/Ps.

FIG. 2 presents PCA plot illustrating the difficulties in differentiating between SSA/P and HP samples even at the molecular level. The two groups are clearly intermingled when all expressed genes are included (FIG. 2A) and the separation is much better when genes DE between HPs and SSA/Ps as well as between SSA/Ps and CR samples are included with the exclusion of genes DE between CR and CL samples (FIG. 2C). Thus, the filtering step allows more detailed characterization of the differences between HPs and SSA/Ps (so the better separation).

Characteristic Differences Between SSA/Ps and Other Samples.

To understand more clearly the biological differences between SSA/Ps and other samples, only genes expressed at the same level in HP and CR samples and significantly up- or down-regulated in SSA/Ps were first considered. At this step only genes satisfying the following conditions: (1) gene expression level (e) satisfied an equation: $e=|(CR-HP)|/(CR+HP+0.01)<0.1$ and (2) gene was significantly DE in CR_SSA/P and HP_SSA/P comparisons were considered.

Figure 3:
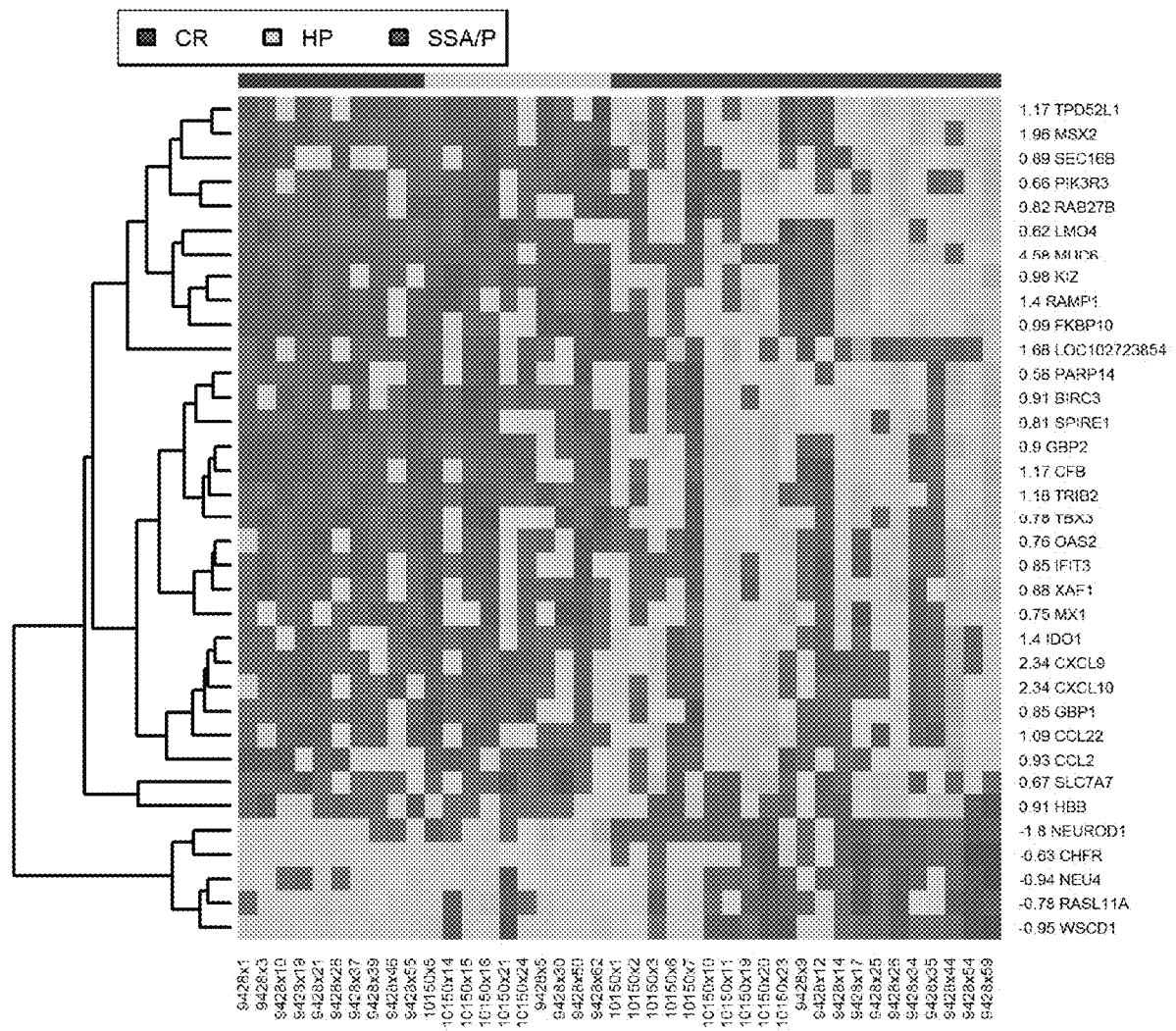
FIG. 3 depicts a heatmap of RNA-seq expression data. Hierarchical clustering of CR (green), HP (yellow) and SSA/Ps (blue) biopsies (columns) and differentially expressed genes (rows). Only genes that were expressed at the same level in HP and CR samples but significantly up- or down-regulated in SSA/Ps are shown. Down-regulated and up-regulated genes in SSA/P are indicated in blue and orange colors, respectively. The $\log_2(SSA/P/HP)$ is shown next to gene names on the right side.

There were only five genes down-regulated in SSA/Ps and expressed at the same level in HPs and CRs (FIG. 3). Two of them regulate cell differentiation and proliferation: NEUROD1 (neuronal differentiation 1) is involved in enteroendocrine cell differentiation and CHFR (checkpoint with forkhead associated and RING Finger) is an early mitotic checkpoint regulator that delays transition to metaphase in response to mitotic stress. CHFR has been found to be frequently inactivated in many malignancies by promoter methylation, in particular, in microsatellite stable and BRAF wild-type CRCs stage II. NEU4, another down-regulated gene, maintains normal mucosa and its down-regulation was suggested to contribute to invasive properties of colon cancers. Other down-regulated genes are RASL11A (regulates translation and transcription) and WSCD1 (WSC domain containing 1, poorly characterized).

Twenty out of thirty genes up-regulated in SSA/Ps and expressed at the same level in CR and HP samples, were found to be interferon-regulated (IR). In addition to modulating innate immune response, interferons regulate a large variety of cellular functions, such as cell proliferation, differentiation, as well as play important roles in inflammatory diseases and anti-tumor response. These twenty genes were represented by (1) genes, involved in the epithelial-mesenchymal transition (EMT): PIK3R3, RAB27B, and MSX2; (2) classical IR genes: GBP2, CFB, TRIB2, TBX3, OAS2, IFIT3, XAF1, MX1, IDO1, CXCL9, CXCL10, GBP1, CCL22, CCL2; (3) genes, not conventionally considered IR: RAMP1, PARP14, and TPD52L1.

Among these twenty genes there were three especially interesting in the context of SSA/Ps progression toward cancer. Indoleamine 2,3-dioxygenase 1 (IDO1) has attracted considerable attention recently because of its immunemodulatory role besides the degradation of tryptophan. IDO regulates T cell activity by reducing the local concentration of tryptophan and increasing the production of its metabolites that suppress T lymphocytes proliferation and induce apoptosis. Because most human tumors constitutively express IDO, the idea that IDO inhibitors may reverse immune suppression, associated with tumor growth, is very attractive for immunotherapy and a competitive inhibitor for IDO (I-mT) is currently in clinical trials. 001 was 2.7 times up-regulated in SSA/Ps as compared to HP, CR samples. PIK3R3, an isoform of class IA phosphoinositide 3-kinase (PI3K), that specifically interacts with cell proliferation regulators and promotes metastasis and EMT in colorectal cancer, was also up-regulated in SSA/Ps. PARP14 promotes aerobic glycolysis or the Warburg effect, used by the majority of tumor cells, by inhibiting pro-apoptotic kinase JNK1. Immunosuppressive state, the shift toward aerobic glycolysis and the EMT, are all considered the major hallmarks of cancer. While these three genes are only infinitesimal parts of the invasive cascades, their up-regulation points toward how SSA/Ps may progress to cancer.

Several IR genes reported here have been also found to be up-regulated in a number of malignancies (including CRCs). For example, RAB27B was expressed at a high level and is a special member of the small GTPase Rab family regulating exocytosis which has been associated with a poor prognosis in patients with CRC. Increased expression of RAB27B has been shown to predict a poor outcome in patients with breast cancer. The suggested mechanism by which Rab27b stimulates invasive tumor growth includes regulation of the heat shock HSP90a protein and the indirect induction of MMP-2, a protease that requires an association with extracellular HSP90a for its activity to accelerate the degradation of extracellular matrix. The transcription factor TBX3 (T-box 3), which plays an important role in embryonic development, was also up-regulated in SSA/Ps. Previously it was suggested that TBX3 promotes an invasive cancer phenotype and more recently it was also shown that increased expression of TBX3 was associated with a poor prognosis in CRC patients. The transcriptional co-regulator LIM-only protein 4 (LMO4) has been associated with poor prognosis and is overexpressed in about 60% of all human breast tumors and has been shown to increase cell proliferation and migration. LMO4 was up-regulated in SSA/Ps. Tumor protein D52-like proteins (TPD52) are small proteins that were first identified in breast cancer, are overexpressed in many other cancers, but remain poorly characterized. TPD52L1, member of the family, was upregulated in SSA/Ps.

Besides the twenty IR genes, there were other interesting genes up-regulated in SSA/Ps and expressed at the same level in CR and HP samples. MUC6 (mucin 6) was the most highly up-regulated gene and has been previously suggested as a candidate biomarker for SSA/Ps but later was found to be not specific enough to reliably differentiate SSA/Ps form HPs. KIZ (kizuna centrosomal protein) is a gene that is critical for the establishment of robust mitotic centrosome architecture and proper chromosome segregation at mitosis. While depletion of KIZ results in multipolar spindles, how up-regulation of KIZ affects mitosis is unknown. SPIRE1, an actin organizer, was recently found to contribute to invadosome functions by speeding up extracellular matrix lysis while overexpressed.

One of the limitations of studying differentially expressed genes one gene at a time is that it does not allow a systems-level view of global changes in expression and co-expression patterns between phenotypes. Thus, the inventors sought to identify all pathways that were significantly up- or down-regulated, as well as differentially co-expressed between SSA/Ps and HP, CR samples. Pathways were presented by all gene ontology (GO) terms from C5 collection of gene sets in MSigDB.

Pathways, Differentially Expressed Between SSA/Ps and HP, CR Samples.

To find pathways, significantly up- or down-regulated ROAST, a parametric multivariate rotation gene set test, was applied. ROAST uses the framework of linear models and tests whether for all genes in a pathway, a particular contrast of the coefficients is non-zero. It can account for correlations between genes and has the flexibility of using different alternative hypotheses, testing whether the direction of changes for a gene in a pathway is up, down or mixed (up or down). Only pathways where genes were significantly up- or down-regulated (FDR<0.05) were selected. There were fifteen pathways, significantly up-regulated in SSA/Ps as compared to HP, CR samples (Table 1). In agreement with the pattern found for individual genes, two out of the fifteen pathways were 'Inflammatory response' and 'Immunological synapse' (Table 1). GO term 'Extracellular structure organization and biogenesis' overlaps with two KEGG pathways: 'KEGG focal adhesion' and 'KEGG ECM receptor interaction'. Overexpression of these pathways as well as 'Cell adhesion' (two pathways) category might indicate changes in cell motility and migration ability in SSA/Ps phenotype as compared to HP, CR samples. Up-regulation of 'Cell growth and death' (two pathways) category suggests increased cellular proliferation in SSA/Ps phenotype.

There was only one pathway down-regulated in SSA/Ps as compared to HP, CR samples, namely 'Transmembrane receptor protein serine threonine kinase signaling pathways' (FDR<0.05). The pathway generates a series of molecular signals as a consequence of a transmembrane receptor serine/threonine kinase binding to its ligand and regulates fundamental cell processes such as proliferation, differentiation, death, cytoskeletal organization, adhesion and migration. For this pathway, one of the most significantly down-regulated genes was HIPK2 (homeodomain interacting protein kinase 2). HIPK2 interacts with many transcription factors including p53 and is a tumor suppressor that regulates cell-cycle checkpoint activation and apoptosis. Therefore, its down-regulation may contribute to up-regulation of 'Positive regulation of cell proliferation' pathway. However, given that Transmembrane receptor protein serine threonine kinase signaling pathways' regulates many fundamental cellular processes, its main downstream targets in the case of SSA/Ps require further study.

Pathways, Differentially Co-Expressed Between SSA/Ps and HP, Cr Samples.

To find pathways that were differentially co-expressed, an approach that assesses multivariate changes in the gene co-expression network between two conditions, the Gene Sets Net Correlations Analysis (GSNCA), was applied. GSNCA tests the hypothesis that the co-expression network of a pathway did not change between two conditions. In addition, for each condition it builds a core of co-expression network, using the most highly correlated genes, and finds a 'hub' gene, defined as the one, with the highest correlations with the other genes in a pathway (see Rahmatallah et al., *Bioinformatics* 2014; 30(3): 360-8, the disclosure of which is hereby incorporated by reference in its entirety, for more detail). In other words, hub genes are the most 'influential' genes in a pathway. When hub genes in a pathway are different between phenotypes, it points toward regulatory changes in a pathway dynamic.

There were seven pathways significantly differentially co-expressed between SSA/Ps and CR, HP samples (P<0.05). Five out of seven were pathways regulating homologous and non-homologous recombination, DNA replication, GTPase activities and proteins targeting towards a membrane using signals contained within the protein (FIG. 7, FIG. 8, FIG. 9, FIG. 10, and FIG. 11). For all five pathways, hub genes were different between HPs and SSA/Ps, with a shift in SSA/Ps toward hub genes related to genomic instability. For example, for 'Meiosis I' and 'Meiotic recombination' pathways, hub genes were RAD51 and MRE11A in HPs and SSA/Ps, respectively. Both proteins are involved in the homologous recombination and repair of DNA double strand breaks. MRE11A also participates in alternative end-joining (A-EJ), an important pathway in the formation of chromosomal translocations. The shift from RAD51 to MRE11A in SSA/P phenotype might indicate an increased genomic instability, the key change in all cancer cells.

Figure 4A:
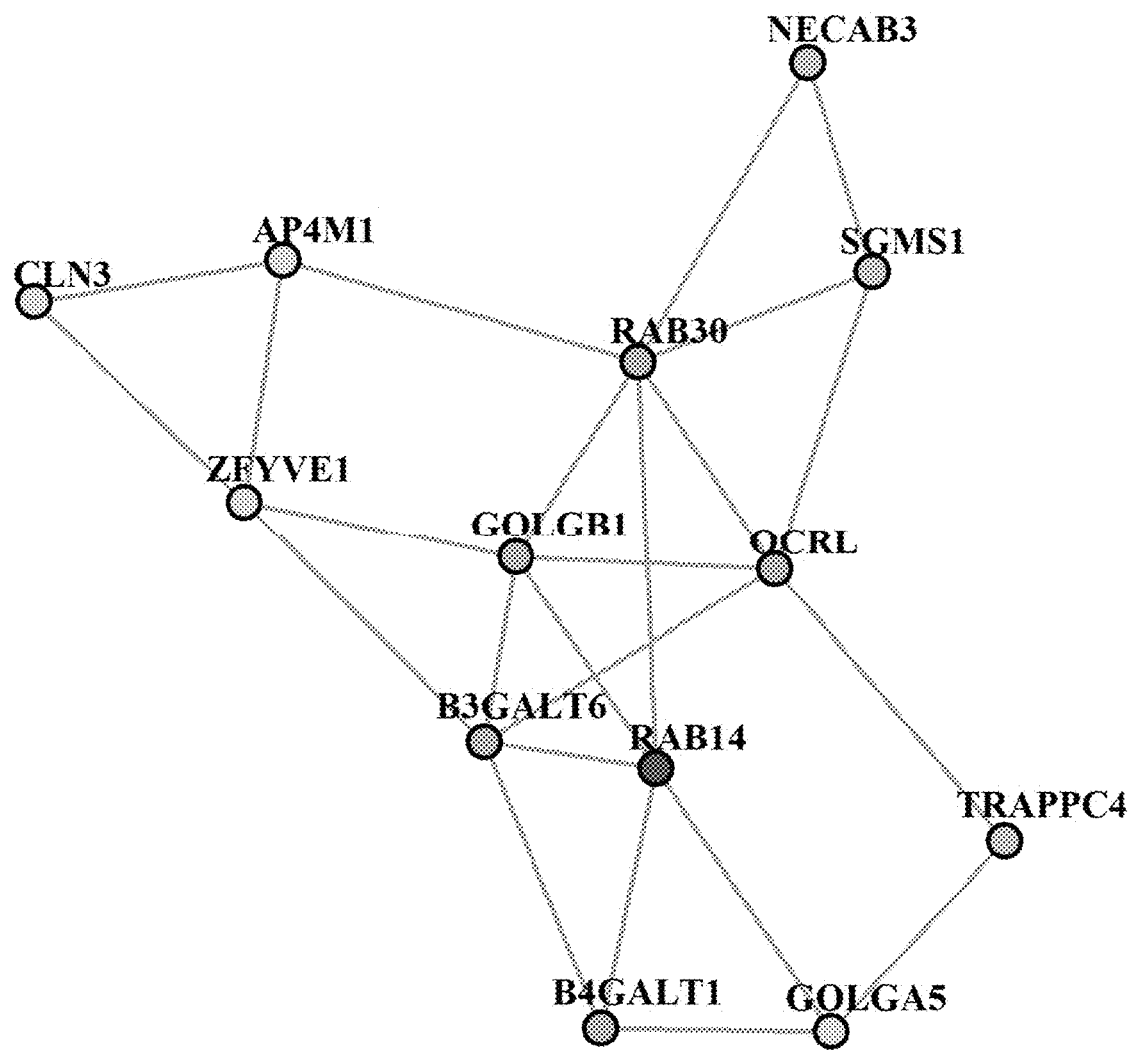
FIG. 4 depicts MST2 of the 'Golgi stack' gene set from the C5 collection of MSigDB. This gene set was detected by GSNCA ($P<0.05$) in both comparisons: HPs versus SSA/Ps (FIG. 4A) and CRs versus SSA/Ps (FIG. 4B).
Figure 4B:
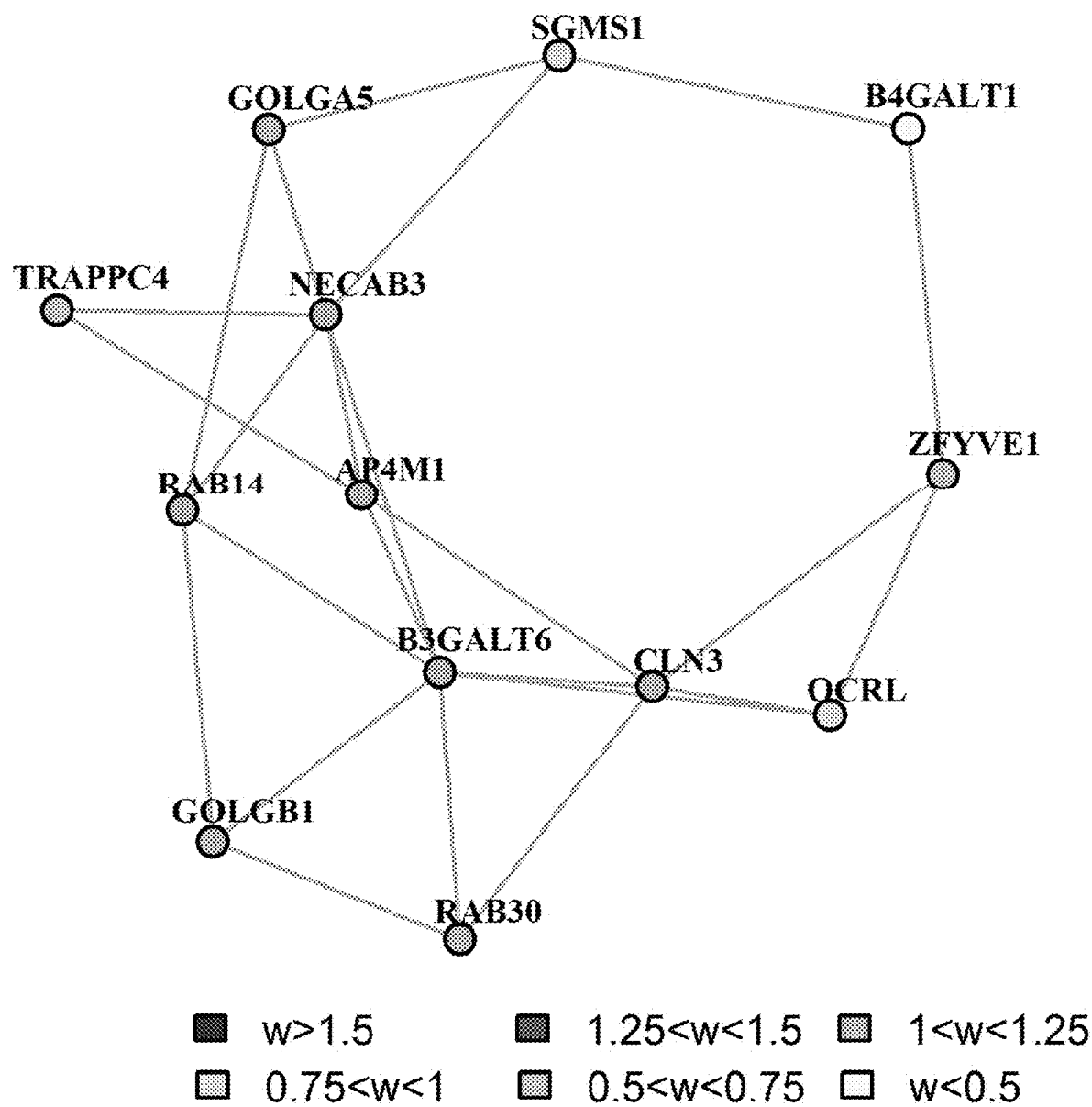
Figure 5A:
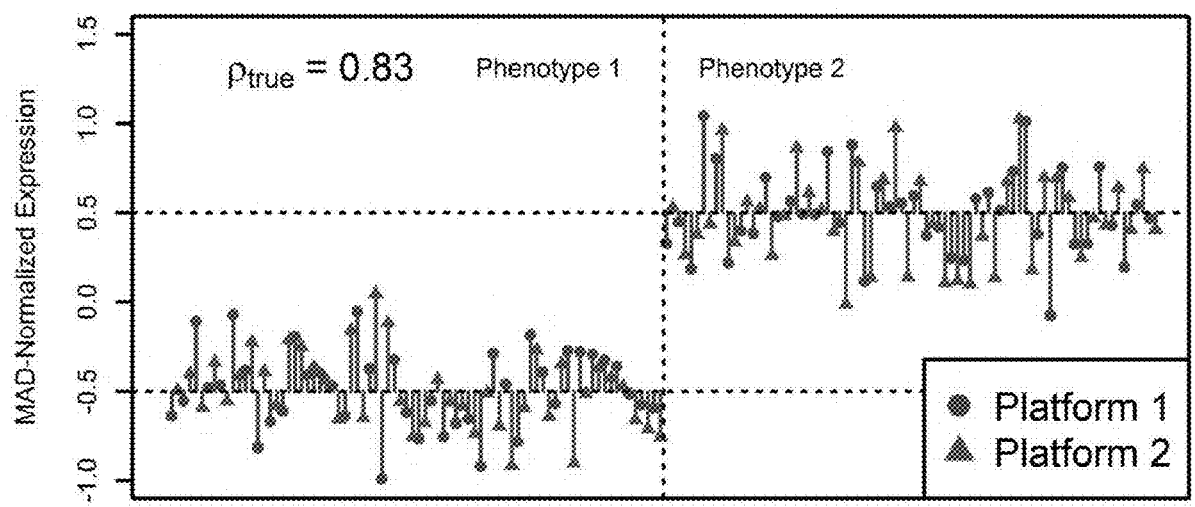
FIG. 5A, FIG. 5B, FIG. 5C, and FIG. 5D depicts examples, illustrating the new feature selection step.
Figure 5B:
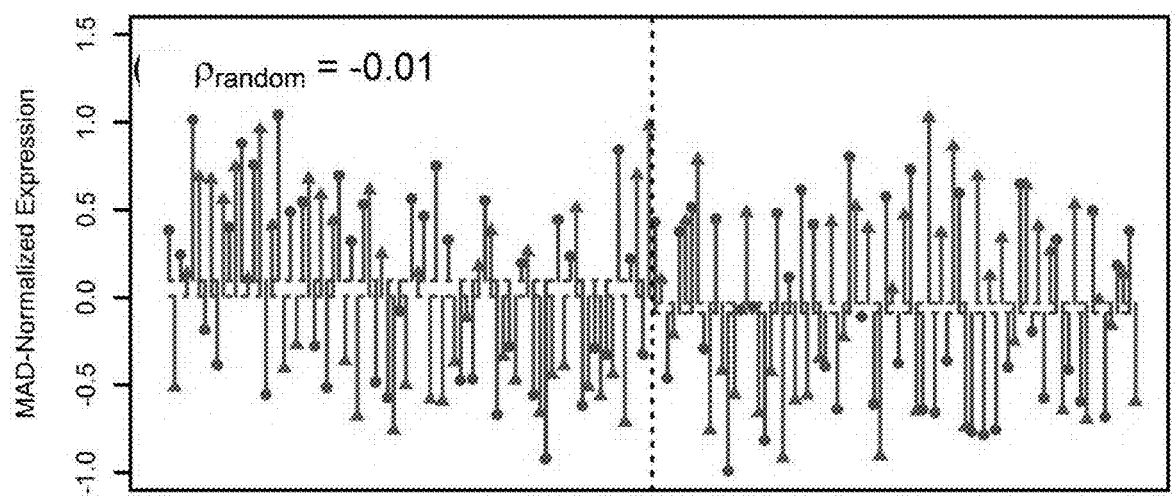
Figure 5C:
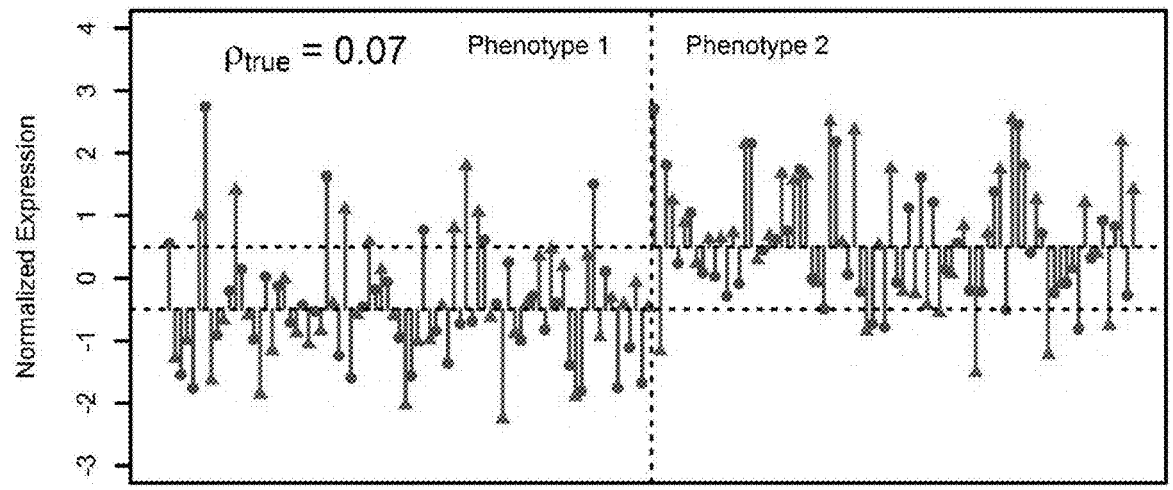
Figure 5D:
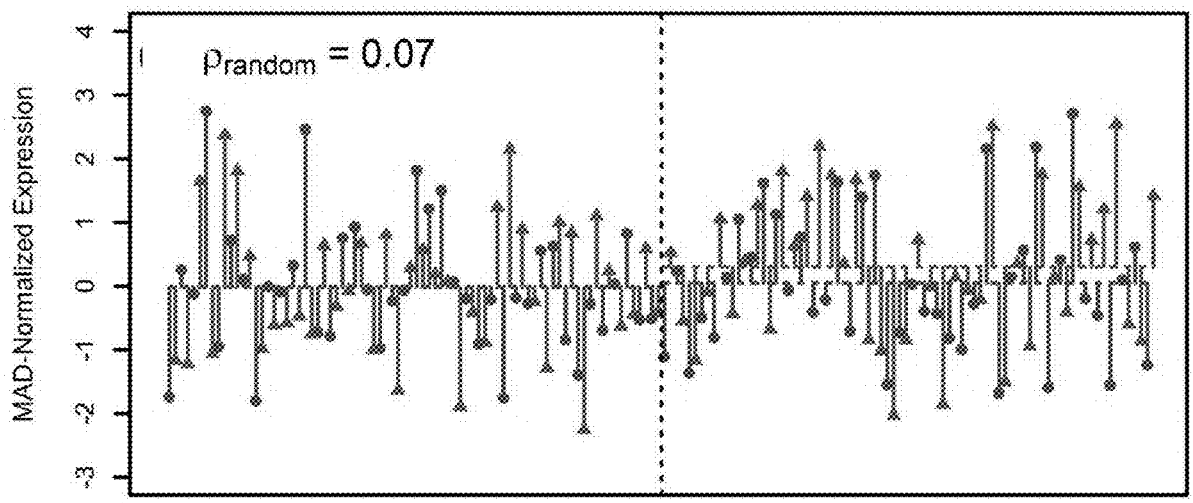
Figure 12A:
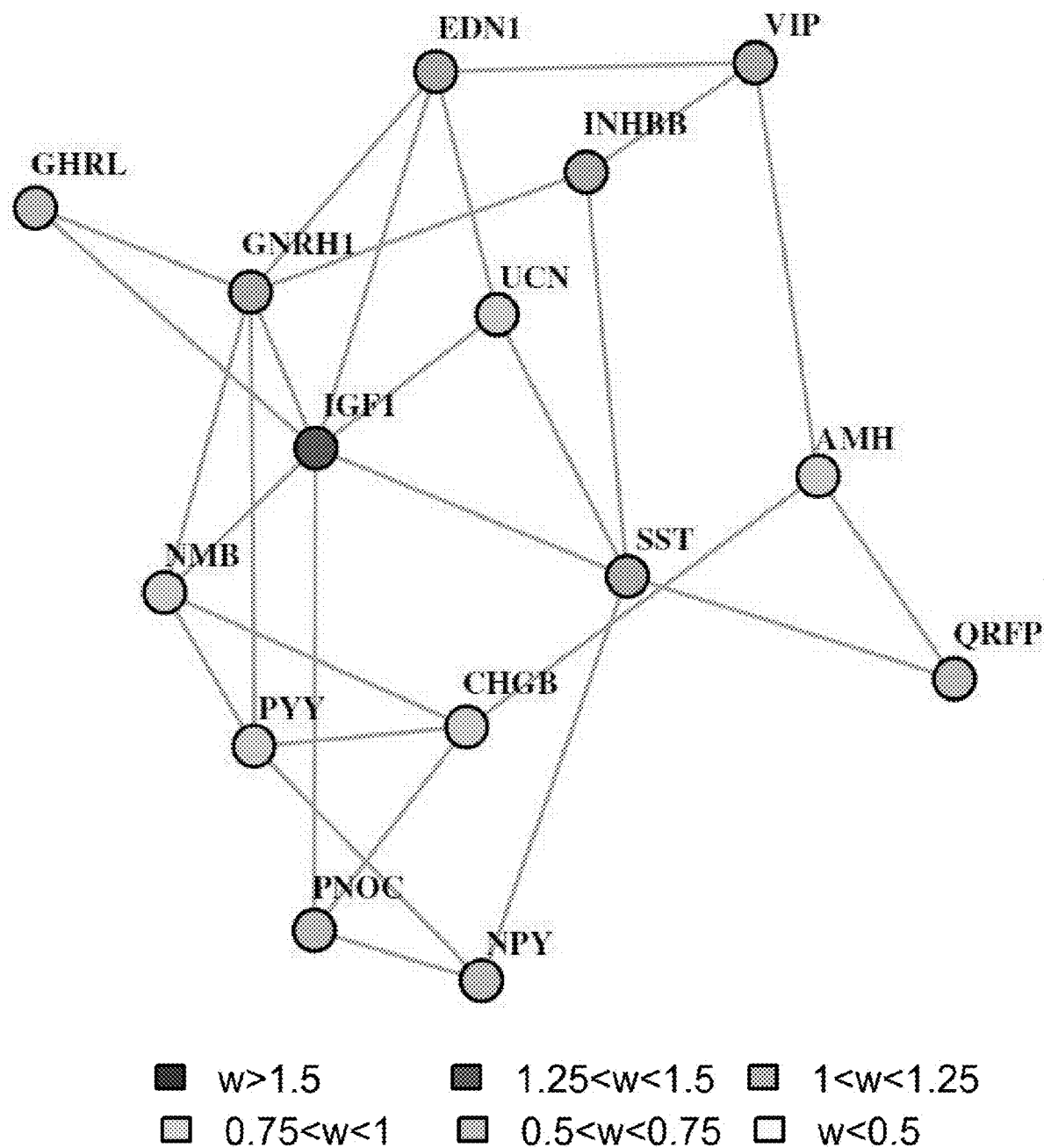
FIG. 12 depicts MST2 of the HORMONE ACTIVITY gene set from the C5 collection obtained from MSigDB. This gene set is detected by GSNCA ($P<0.05$) in both comparisons: HP versus SSA/P (FIG. 12A) and CR versus SSA/P (FIG. 12B).
Figure 12B:
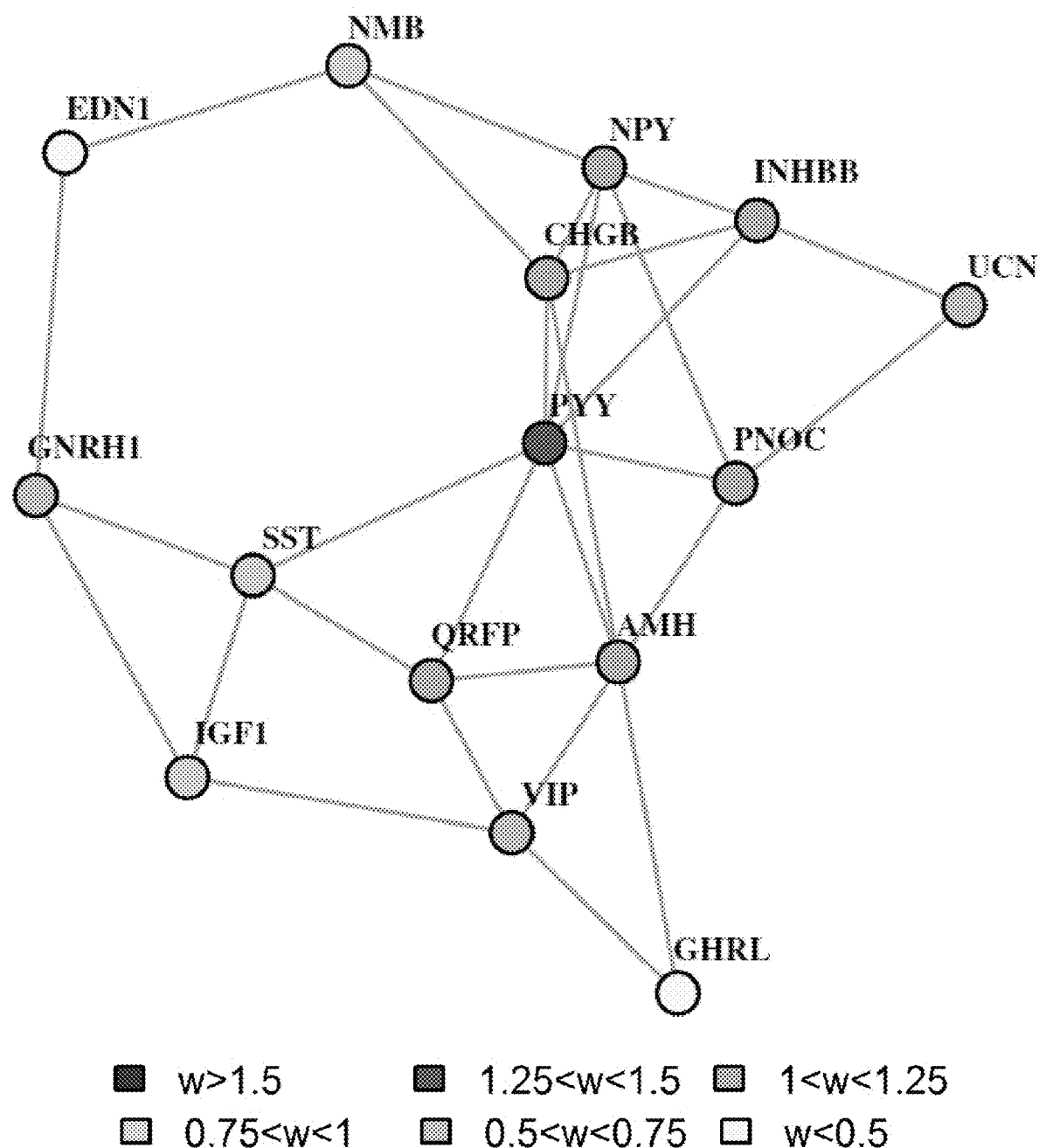
Figure 13A:
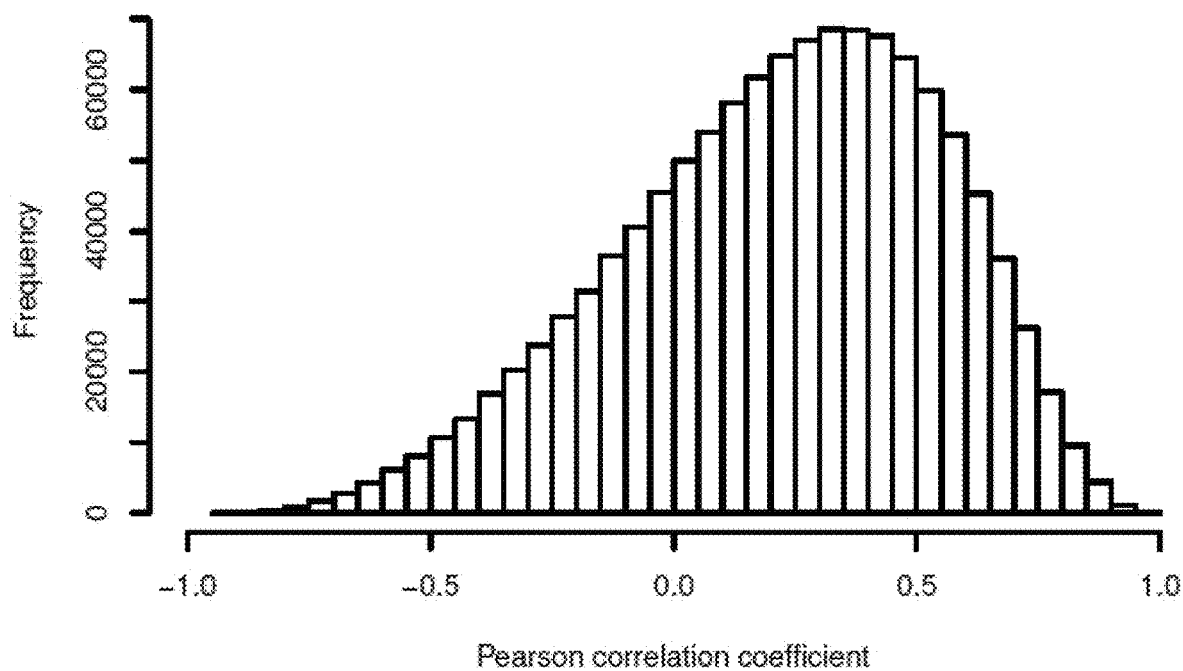
FIG. 13A, FIG. 13B, FIG. 13C, and FIG. 13D depict histograms of the Pearson correlation coefficient between two platforms obtained in 10000 iterations. Only 117 genes expressed in all three platforms (RNA-seq, Illumina, and Affymetrix) and found to be differentially expressed between SSA/Ps and both HPs and CRs are considered.
Figure 13B:
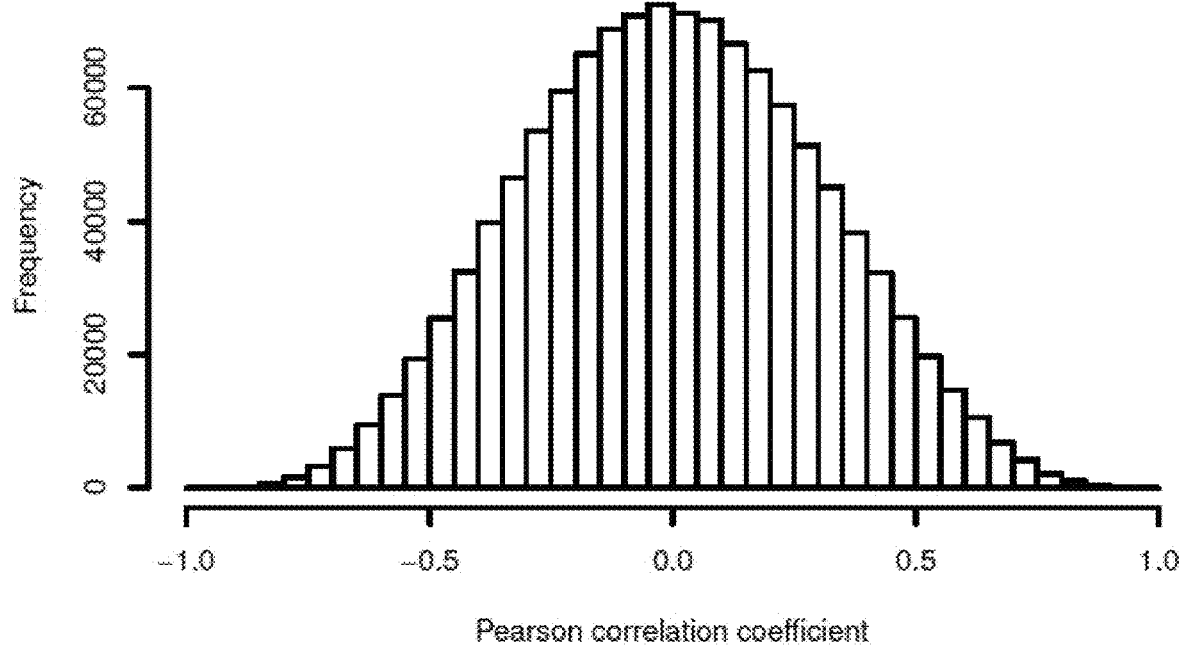
Figure 13C:
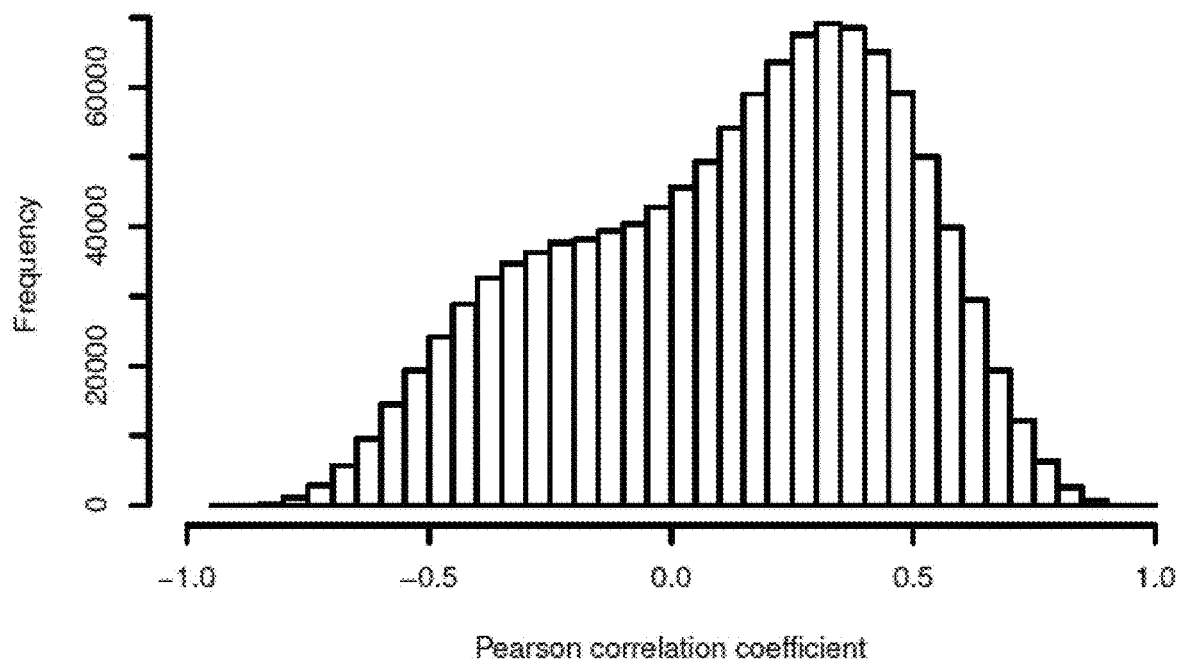
Figure 13D:
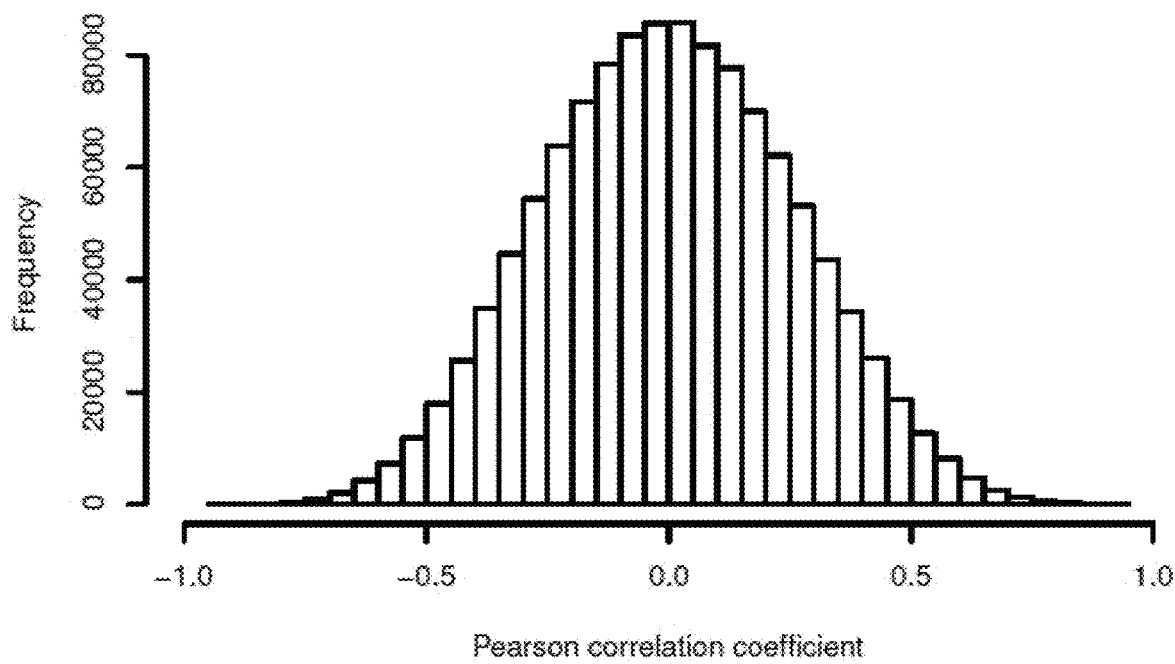

For 'Golgi stack' pathway, the shift of hub genes was associated with the well-known phenotypic difference between HPs and SSA/Ps (FIG. 4). The hub gene in HP phenotype was RAB14, low molecular mass GTPase that is involved in intracellular membrane trafficking and cell-cell adhesion. The hub gene in SSA/P phenotype was B3GALT6, a beta-1,3-galactosyltransferase, required for glycosaminoglycan (mucopolysaccharides) synthesis, including mucin. The presence of abundant surface mucin is the conventional colonoscopic characteristic of SSA/Ps. For 'Hormone activity' in HP phenotype the hub gene was IGF1, the insulin-like growth factor that promotes cell proliferation and inhibits apoptosis, stimulates glucose transport in cells and enhances glucose uptake (FIG. 12). In SSA/P phenotype, the hub gene was PYY, encoding a member of the neuropeptide Y (NPY) family of peptides. This gut peptide plays important roles in energy and glucose homeostasis, in regulating gastrointestinal motility and absorption of water and electrolytes and has been associated with several gastrointestinal diseases. Its role in SSA/P phenotype, if any, remains to be defined.

These cases illustrate the ability of GSNCA to confirm existing knowledge, generate new testable hypotheses and raise interesting questions. For 'Golgi stack' pathway, the shift from RAB14 toward B3GALT6, essential for the mucopolysaccharides synthesis corresponded to known phenotypic differences between HPs and SSA/Ps. The involvement of deficient mismatch repair (dMMR) pathway (that includes MRE11) in CRC is well documented. Recently, the truncated MRE11 polypeptide was found to be a significant prognostic marker for long-term survival and response to treatment of patients with CRC stage III. GSNCA highlighted MRE11A as a new hub gene in 'Meiosis I' and 'Meiotic recombination' pathways, and it would be worth investigating its mutational status and prognostic potential in the context of SSA/Ps.

Based on the analysis of individual genes and differentially expressed and co-expressed pathways SSA/Ps difference from HP, CR samples involves: (1) up-regulation of IR genes, EMT genes and genes previously associated with the invasive cancer phenotype; (2) up-regulation of pathways, implicated in proliferation, inflammation, cell-cell adhesion and down-regulation of serine threonine kinase signaling pathway; and (3) de-regulation of a set of pathways regulating cell division, protein trafficking and kinase activities.

Given the complexity of the molecular processes underlying SSA/P phenotype, involving hundreds of differentially expressed genes and many pathways, for the practical purpose of readily distinguishing SSA/Ps from HPs, the inventors developed a platform-independent molecular classifier with low classification error rate (see below).

Molecular Classifiers.

Typically, the development of molecular classifiers consists of the following steps: feature selection, model selection, training, estimation of the classification error rate, with every step potentially leading to an inflated performance estimate. The systematic errors in classifier development, such as inappropriate applications of cross-validation for classifiers' training and testing, are usually the first to blame for poor generalizability (high error rate on independent data sets). Poor generalizability is further emphasized when the training and independent test data are obtained using different platforms, e.g. different microarray platforms, or microarrays and RNA-seq. To avoid such errors, the inventors developed a new feature selection step identifying the genes, most concordant between different platforms. After the new feature selection step was implemented, a classifier was trained on RNA-seq data and further tested on two independent microarray data sets (testing sets, see Methods for more details). Identifiers from different platforms were mapped to gene symbols and only genes that were expressed in RNA-seq data and present on both microarray platforms were considered (Table 8).

Feature Normalization.

For classifier development, 139 genes DE between SSA/Ps and HP, CR samples (Table 4) were considered. Gene expressions for both RNA-seq and microarray platforms were normalized to a common range by subtracting the median absolute deviation (MAD) from each gene's expression. Hence, gene expressions were centered around zero and genes with large fold changes between two phenotypes had positive expressions under one phenotype and negative expressions under the other. Genes with the small variability were filtered out (MAD<0.1). Finally, only the genes expressed in all three platforms (117 genes) were considered for further classifier design steps.

Feature Selection Step.

Selecting only genes (features) with high concordance between platforms is crucial to design a platform-independent classifier. Platform-independent classifier, trained using one platform, should have low classification error rate while being tested using other platform. Here, to assess genes concordance between platforms, a new non-parametric test was developed (see Methods for details). The test identified genes, robustly differentiating two phenotypes under different platforms, the best candidates for an inter-platform signature. Previously, the concordance between platforms has been measured by the correlation between mean expressions or fold changes or by intersection between lists of DE genes.

The idea behind the new test is simple: identify genes with expression levels highly correlated between platforms. The practical difficulty of implementing the idea is that the numbers of samples, as well as the samples identities, are different between platforms. Consider two distributions: (1) correlation coefficients for all genes between two platforms, preserving phenotypic labels (0) and (2) correlation coefficients for all genes between two platforms, randomly resampling phenotypic labels ($\rho_{random}$). FIG. 13 presents the distributions of $\rho_{true}$ $\rho_{random}$ when the HP and SSA/P samples from the RNA-seq training data were compared with the Illumina and Affymetrix data sets. Some genes had higher correlations when phenotypic labels were preserved, compared to when they were randomly resampled, introducing negative skewness to the distribution of $\rho_{true}$ (see FIG. 13). In other words, these genes correlations between platforms were higher than by chance, illustrated by the case when phenotypic labels were randomly resampled. These genes were our candidate concordant genes. More formally, to identify concordant genes, the null hypothesis $H_0$: $\bar{\rho}_{true} \leq \bar{\rho}_{random} + \max(SD(\rho_{true} \cup \rho_{random}))$ was tested.

FIG. 5 illustrates how the test works using two examples of typical MAD-normalized gene expressions in two platforms. In one example, forty observations were sampled from two normal distributions N(0.5, 0.25) and N(−0.5, 0.25), representing different phenotypes. In this example, the fold change in both platforms was larger than the within-phenotype variability (FIG. 5A) and the correlation coefficient between platforms ($\rho_{true}$) was high. When phenotypic labels were randomly resampled, the fold change in both platforms became negligible as compared to the within-phenotype variability (FIG. 5B) and the correlation coefficient between platforms ($\rho_{random}$) became low. In another example, forty observations were sampled from two normal distributions N(0.5, 1) and N(−0.5, 1), again representing different phenotypes. However, in this example, the fold change in both platforms was smaller than the within-phenotype variability (FIG. 5C and FIG. 5D) and the correlation coefficient between platforms was low when phenotypic labels were either preserved or randomly resampled. Although the fold change between phenotypes was the same in both examples ($\log_2 FC=1$), Pearson correlation coefficient between expressions in two platforms preserving phenotypic labels ($\rho_{true}$) was higher in case A compared to case C because of the lower within-phenotype variability. Randomly resampling phenotypic labels led, expectedly, to much lower correlations between two platforms ($\rho_{random}$) (FIG. 5B and FIG. 5D). Accordingly, $\rho_{true} > \rho_{random}$ in the first example (FIG. 5A and FIG. 5B) but not in the second (FIG. 5B, FIG. 5D). Taking average correlation between platforms, for a large number of iterations, $H_0$ will be rejected for the first example (FIG. 5A and FIG. 5B) but not for the second (FIG. 5C and FIG. 5D). The Methods summarizes the steps of the proposed test.

The test was used to find genes with high concordance between RNA-seq and Illumina platforms (23 genes detected), RNA-seq and Affymetrix platforms (20 genes detected), and between RNA-seq and both Illumina and Affymetrix platforms (16 genes detected). Only genes, detected by the Wilcoxon's test at P<0.05 were considered. The values of the term $\max(SD(\rho_{true} \cup \rho_{random})$ were 0.41 and 0.39 when RNA-seq data were compared with Illumina and Affymetrix data sets, respectively.

Classifier Design and Gene Signatures.

The model selection step provides a great flexibility because there are many machine learning algorithms available for classification purposes. The nearest shrunken centroid classifier (SCC) was selected because it was successfully used before for developing many microarray-based classifiers, in particular a prognostic classifier in CRCs. To select the threshold value that returns the minimum mean error with the least number of genes, a 3-fold cross-validation was performed over a range of threshold values for 100 iterations.

Training the classifier using the RNA-seq data set and considering only the genes with high concordance with the Illumina, Affymetrix, and both platforms yielded three signatures of 18, 16, and 13 genes (see Table 2). The 18 and 16 gene signatures resulted in zero (out of 12 Illumina samples) and three (out of 17 Affymetrix samples) errors. Classification errors did not change when the 13 genes signature was used instead. Hence we considered these 13 genes as the smallest successful signature for both Illumina and Affymetrix platforms. The samples in the Illumina data set were identified as belonging to SSA/Ps or HPs phenotypes by gastrointestinal pathologists based on a higher stringency criterion than what has been done for the samples in the Affymetrix data set. It is therefore no surprise that there was less ambiguity in classifying the Illumina samples. Although the Illumina samples were acquired by a different platform compared to the training RNA-seq data set, they were classified without errors. Aside from the stringent criterion in assigning phenotype labels for Illumina samples, this result could be due to the higher resolution in quantifying gene expression by the RNA-seq platform.

In conclusion, the independent validation (i.e. using different platforms) results have shown the feasibility of building molecular classifiers using RNA-seq training data. Moreover, classifiers built using one platform (RNA-seq) were applicable to other platforms (Affymetrix, Illumina) and had low classification error rates in predicting HP or SSA/P phenotypes as long as only concordant features were considered.

Smallest Successful Signature.

The genes included in the smallest signature (13 genes) were on the average approximately four folds up-(down-) regulated between SSA/Ps and HPs (Table 3). The average absolute fold change considering all the 14006 expressed genes in the RNA-seq training data set was 1.27. There were three down- and ten up-regulated genes in SSA/Ps, involved in several molecular processes that have been discussed earlier. Down-regulated genes included NTRK2 (neurotrophic tyrosine kinase receptor, type 2), CHFR (negative regulator of cell cycle checkpoint) and CHGA (chromogranin A, endocrine marker). NTRK2 controls the signaling cascade that mainly regulates cells growth and survival.

Up-regulated genes included several genes (SLC7A9, SEMG1, SBSPON and MEGF6) that were not well functionally characterized (except SLC7A9, a marker for cystinuria) and are not discussed here. Two genes (KIZ and SPIRE1) were among the genes up-regulated in SSA/Ps and equally down-regulated in HP, CR samples (FIG. 3). TROP-2 (TACSTD2, tumor-associated calcium signal transducer 2) is a cell-surface transmembrane glycoprotein overexpressed in many epithelial tumors. TROP-2 was suggested as a biomarker to determine the clinical prognosis and as a potential therapeutic target in colon cancer and an antibody-drug conjugate targeting TROP-2 is currently in phase II clinical trials. Claudin-1 (CLDN1, tight junction protein) was also up-regulated. Specifically, Claudin-1 has been suggested to be involved in the regulation of colorectal cancer progression by up-regulating Notch- and Wnt-signaling and mucosal inflammation. In addition, CLDN1 was also associated with liver metastasis of CRC. PLA2G16 phospholipase was also up-regulated and its up-regulation may be a signal of gain-of-function activities of mutant p53 that is required for metastasis. Finally, PTAFR, platelet activating factor receptor, was found to stimulate EMT by activating STAT3 cascade.

In sum, the up-regulated signature genes included those previously associated with invasive cell activities (CLDN1, PLA2G16, PTAFR, SPIRE1), spindle formation (KIZ) while down-regulated genes included checkpoints controlling cell growth (CHFR, NTRK2).

Summary Metric with Class Probability.

The ultimate goal of building a classifier and finding gene signatures is to use the signature in clinical practice for diagnostic and prognostic purposes. Here, a simple procedure that uses the signatures in Table 2 was developed to classify new samples as either HP or SSA/P and provides a class probability for the decision. The mean of the MAD-normalized expression of the genes in the signature was used as a summary metric (SM). Since most of the genes in the signatures in Table 2 were over-expressed in SSA/P, SM>0 for SSA/P samples and SM<0 for HP samples. Before calculating the mean expression, the signs of the expressions of the few genes that were over-expressed in HP were inverted. This step increased the magnitude of the mean regardless of its sign. There were only three genes over-expressed in HP in the 13-gene signature (CHFR, CHGA and NTRK2), one in the 16-gene Affymetrix signature (NTRK2), and four in the 18-gene Illumina signature (CHGA, CPE, DPP10, and NTRK2). The class assignment (HP or SSA/P) depends simply on the sign of the mean expression.

Figure 6:
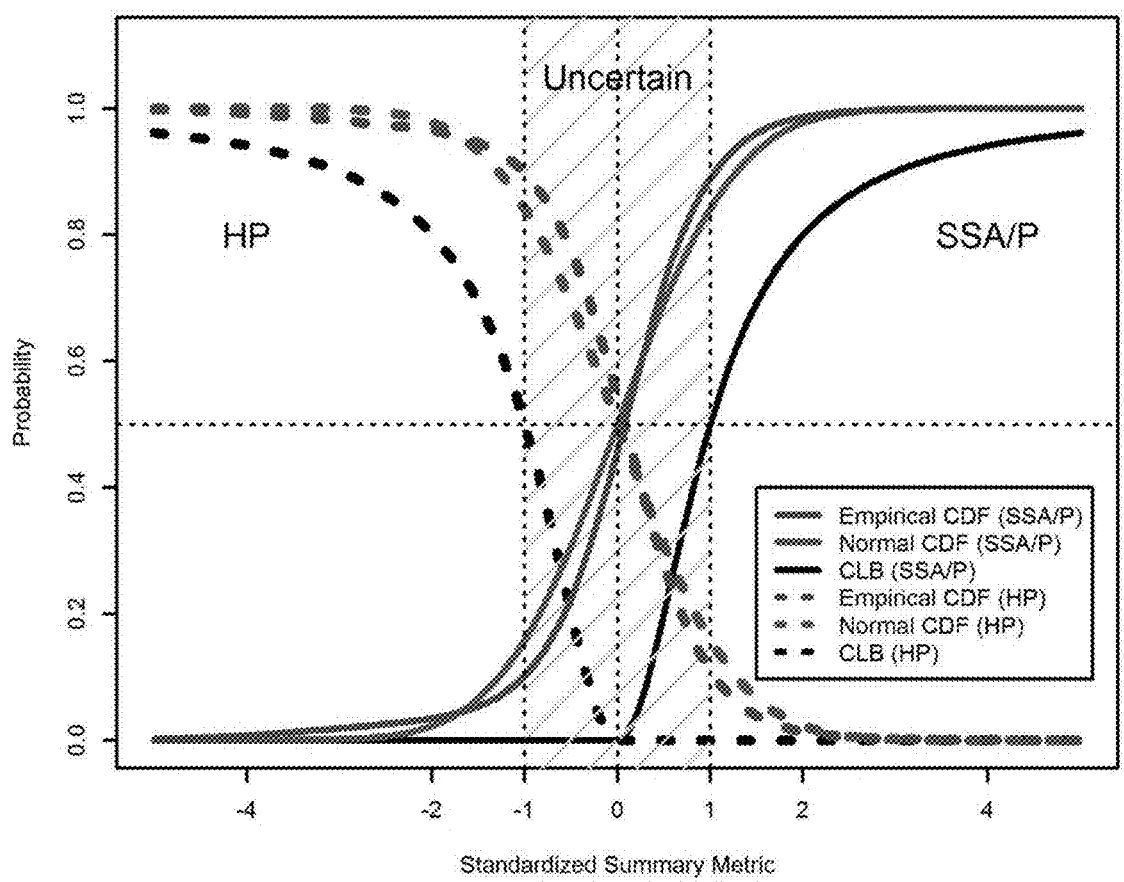
FIG. 6 depicts the probability of an assigned SSA/P (HP) class is the cumulative distribution function CDF(SM) (1-CDF(SM)) of the empirical distribution of SM after standardization. The empirical approach can also be substituted by the normal approximation of SM. Since both approaches have limitations, the Cantelli lower bound (CLB) is used as a conservative probability assignment for the SM score.
Figure 7A:
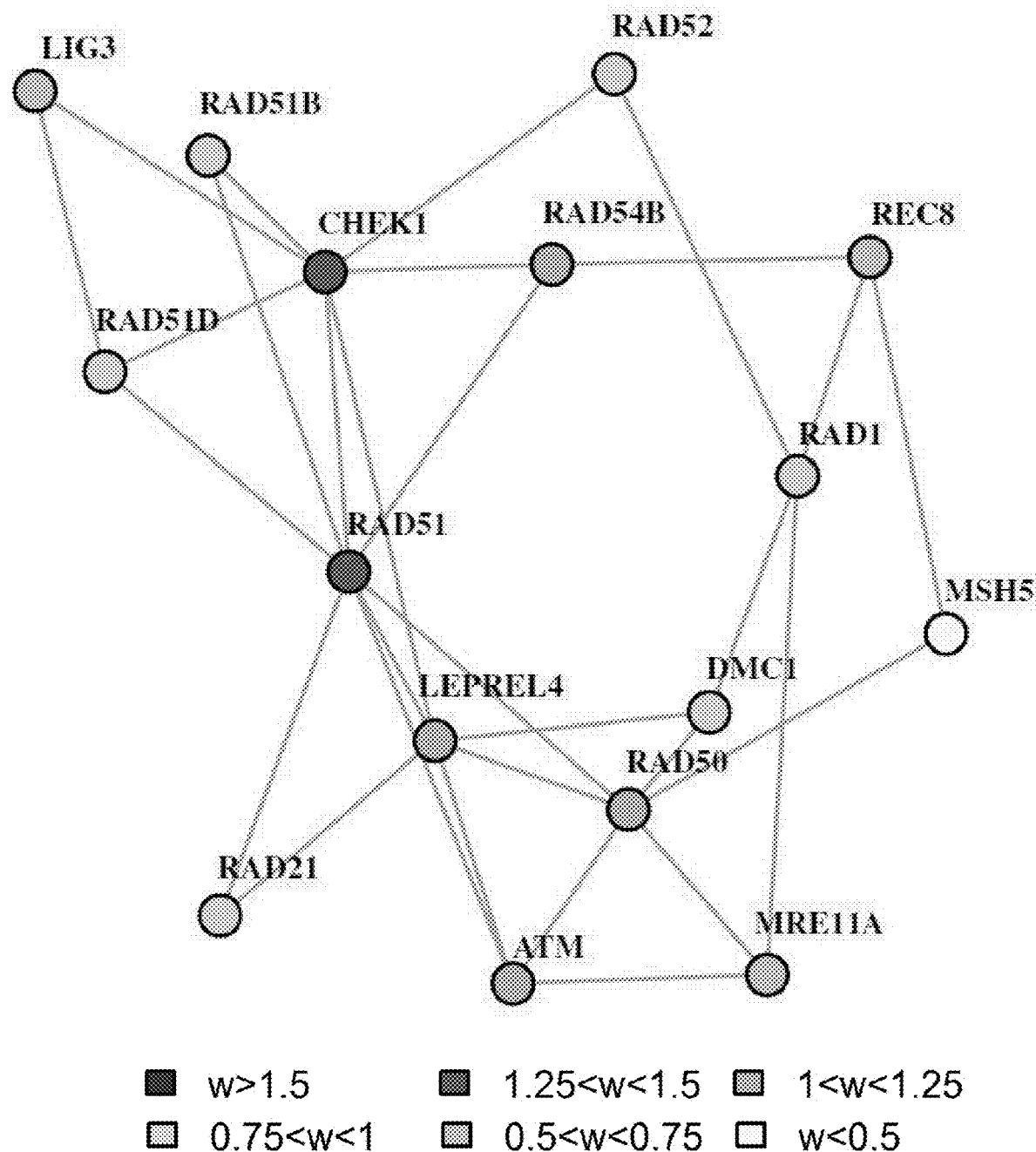
FIG. 7 depicts MST2 of the MEIOSIS gene set of the C5 collection obtained from MSigDB. This gene set is detected by GSNCA ($P<0.05$) in both comparisons: HP versus SSA/P (FIG. 7A) and CR versus SSA/P (FIG. 7B).
Figure 7B:
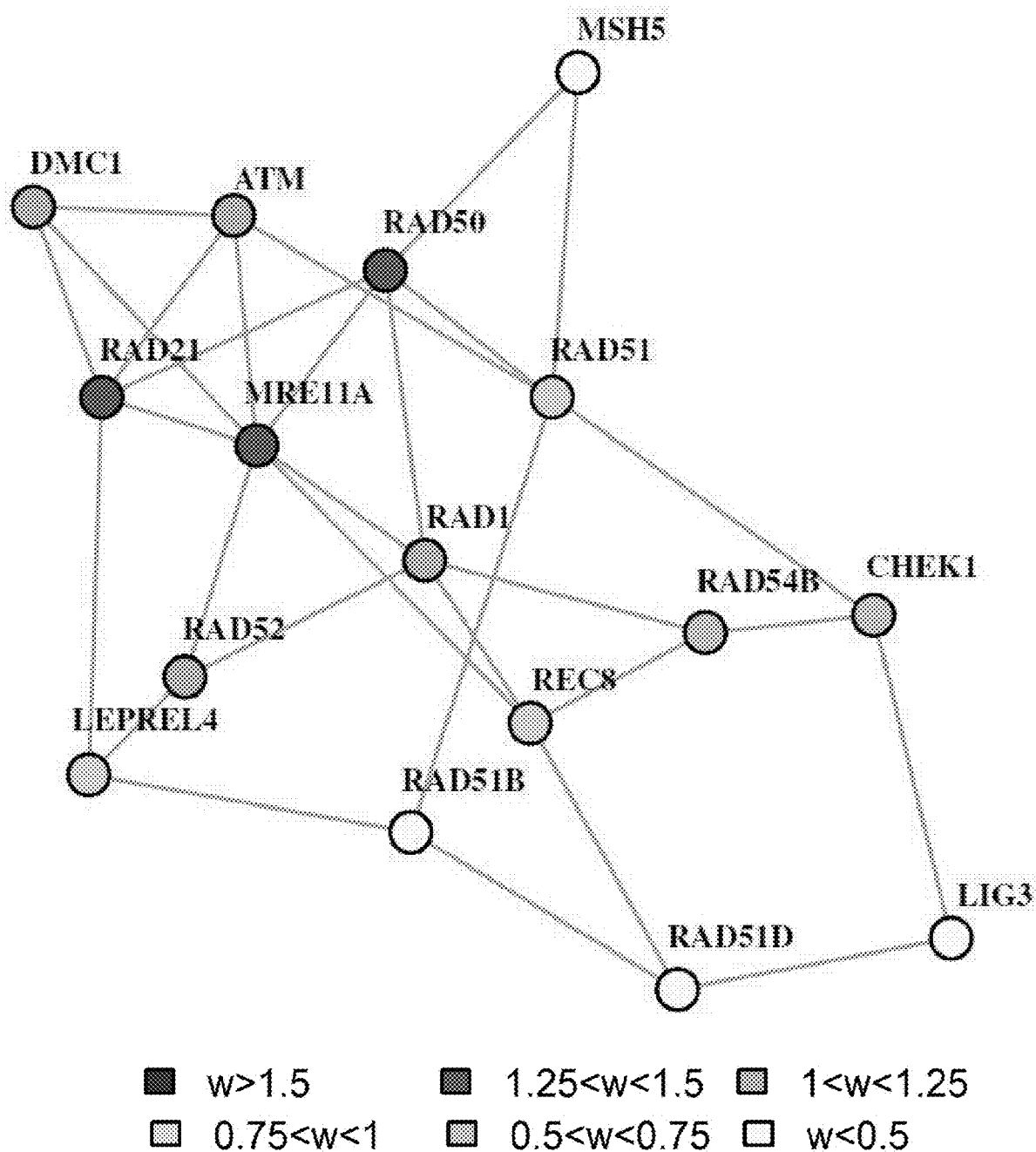
Figure 8A:
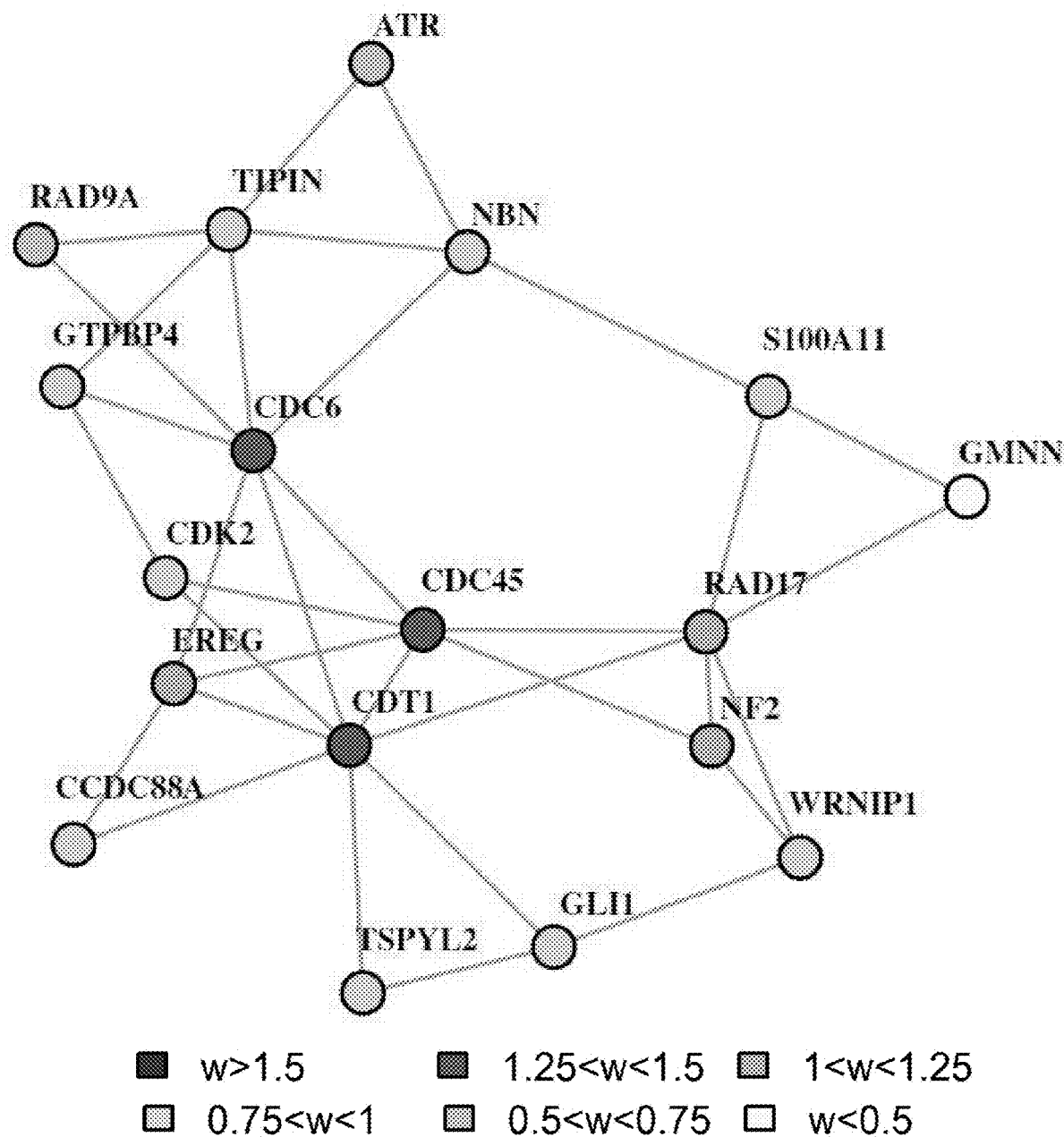
FIG. 8 depicts MST2 of the REGULATION OF DNA REPLICATION gene set of the C5 collection obtained from MSigDB. This gene set is detected by GSNCA ($P<0.05$) in both comparisons: HP versus SSA/P (FIG. 8A) and CR versus SSA/P (FIG. 8B).
Figure 8B:
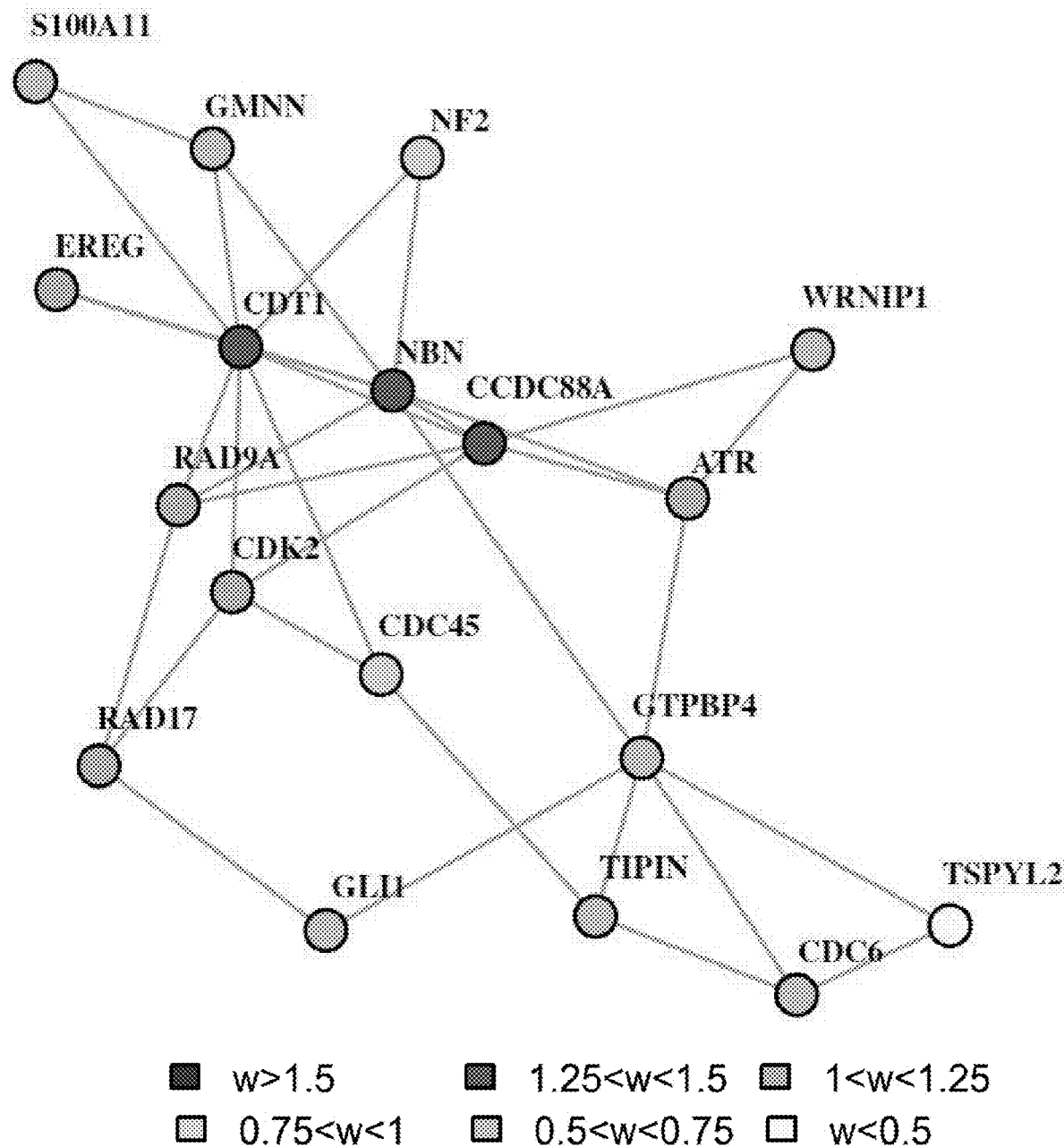
Figure 9A:
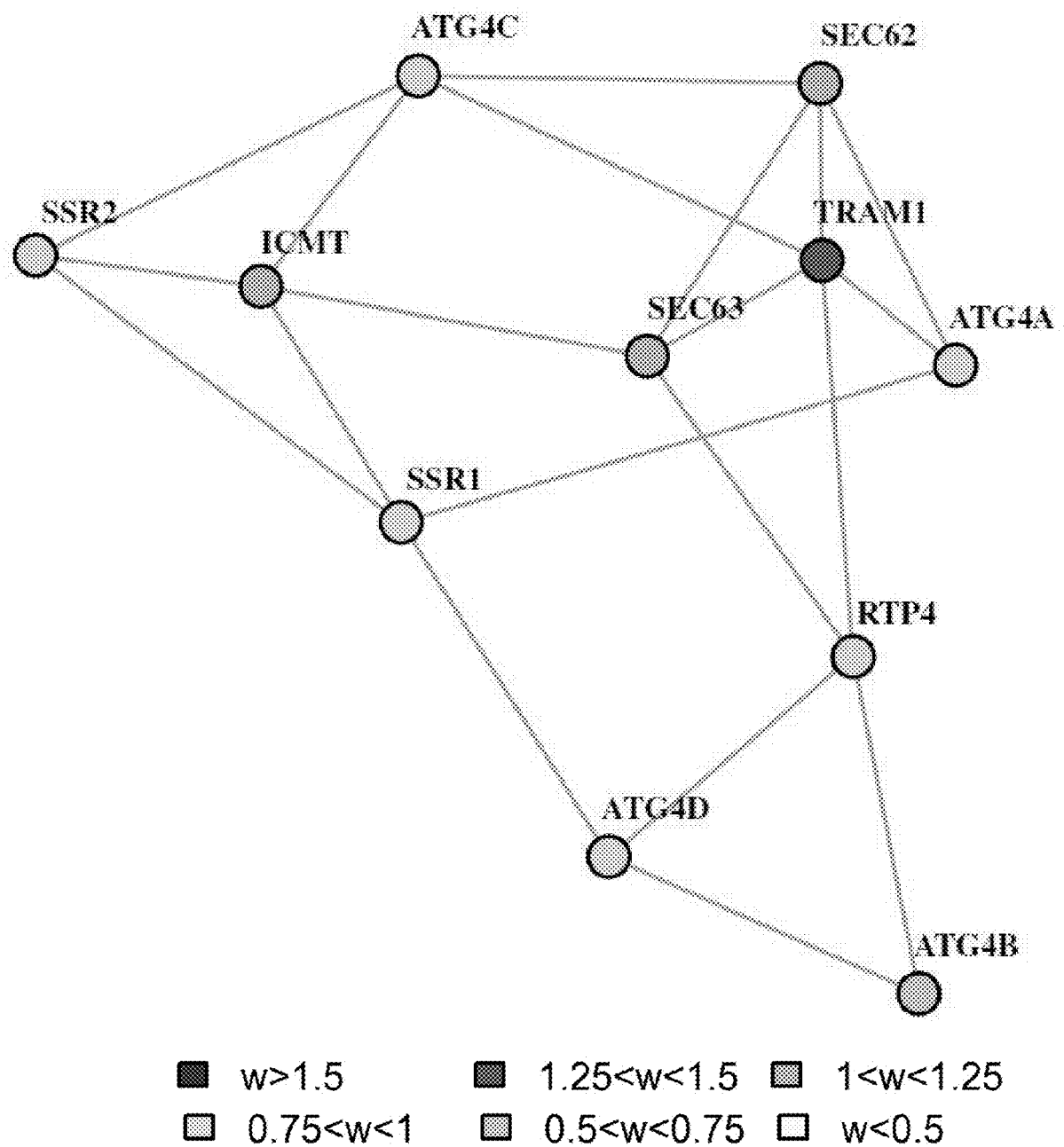
FIG. 9 depicts MST2 of the PROTEIN TARGETING TO MEMBRANE gene set of the C5 collection obtained from MSigDB. This gene set is detected by GSNCA ($P<0.05$) in both comparisons: HP versus SSA/P (FIG. 9A) and CR versus SSA/P (FIG. 9B).
Figure 9B:
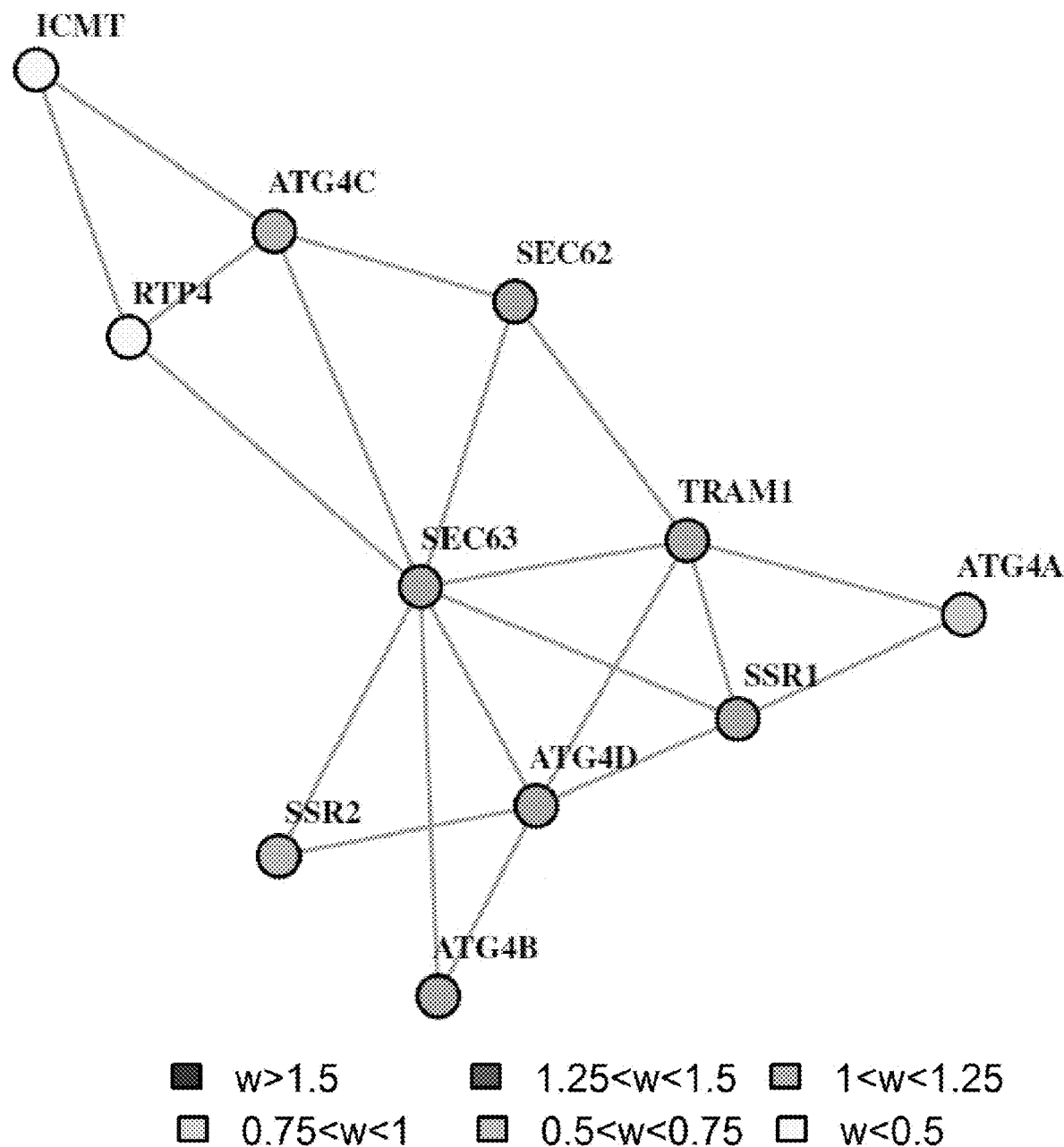
Figure 10A:
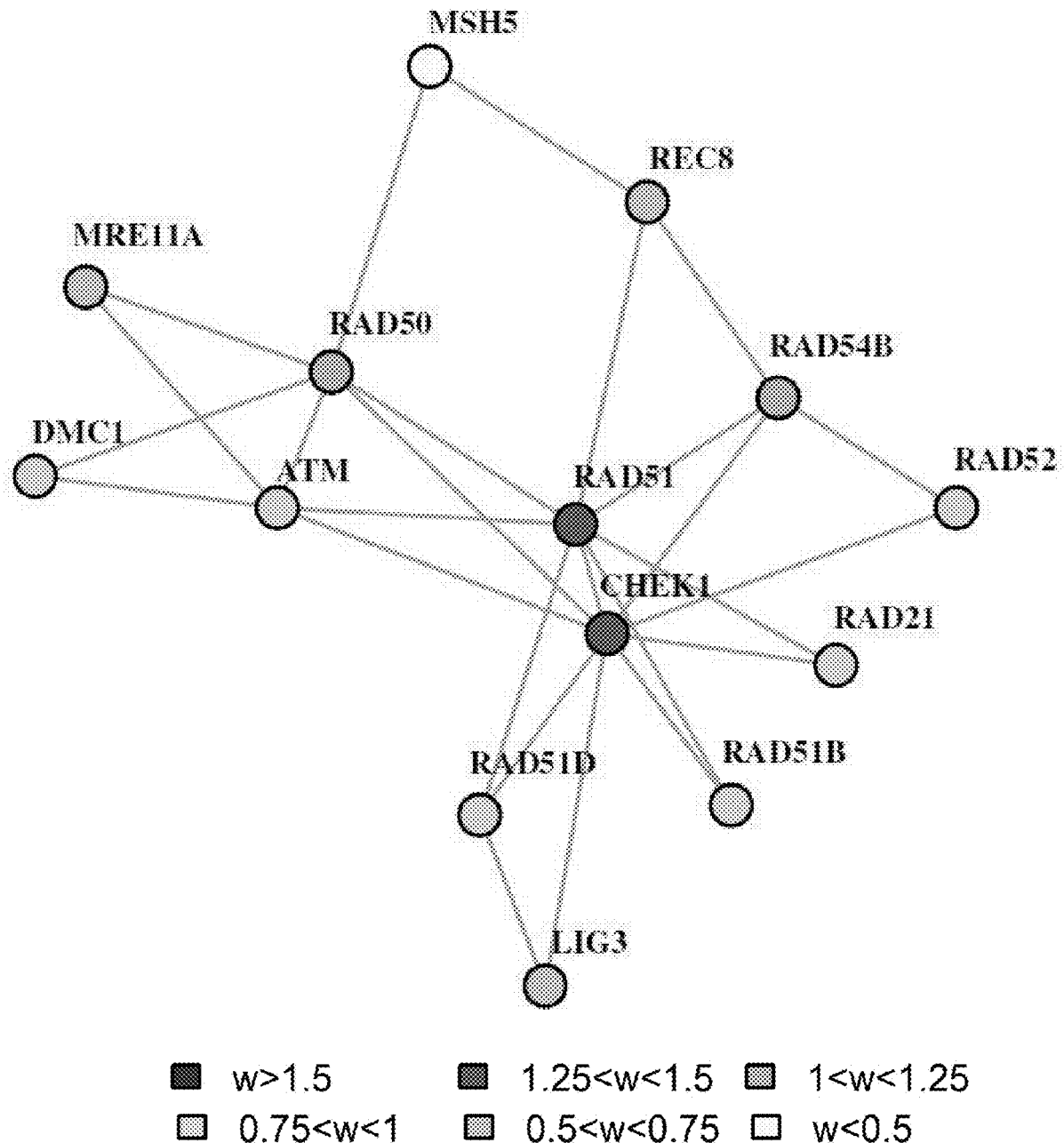
FIG. 10 depicts MST2 of the MEIOTIC RECOMBINATION gene set from the C5 collection obtained from MSigDB. This gene set is detected by GSNCA ($P<0.05$) in both comparisons: HP versus SSA/P (FIG. 10A) and CR versus SSA/P (FIG. 10B).
Figure 10B:
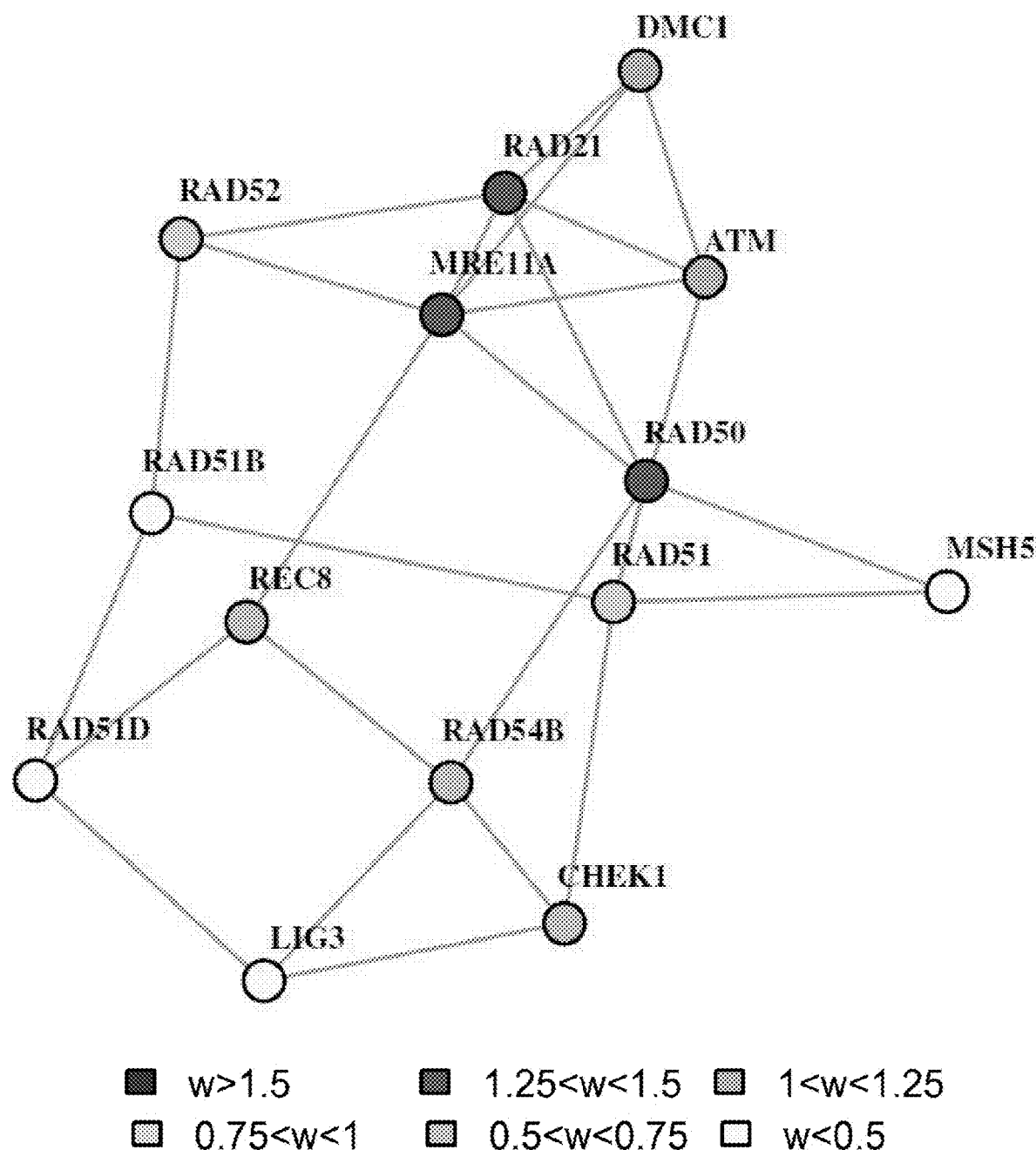
Figure 11A:
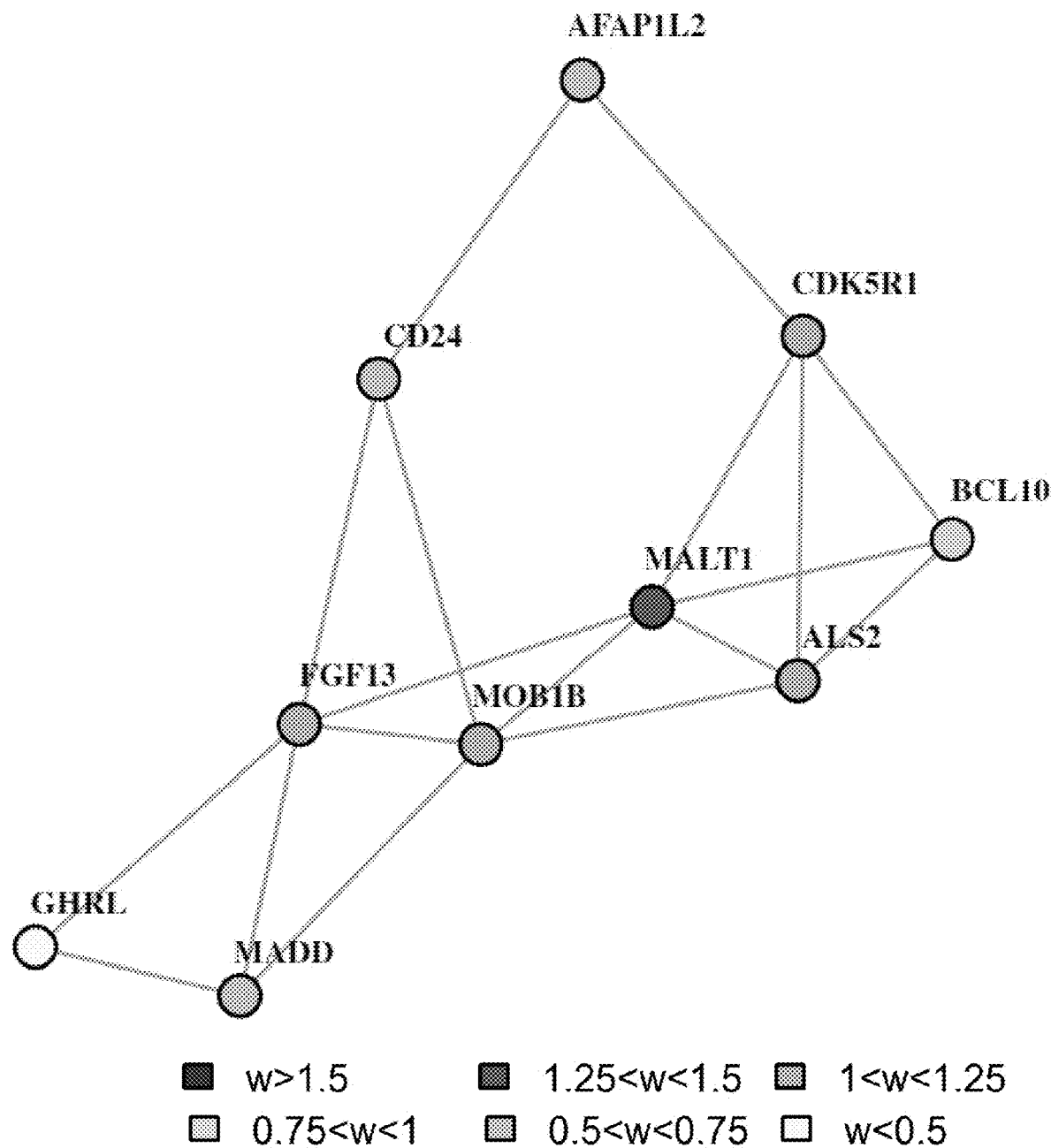
FIG. 11 depicts MST2 of the KINASE ACTIVATOR ACTIVITY gene set from the C5 collection obtained from MSigDB. This gene set is detected by GSNCA ($P<0.05$) in both comparisons: HP versus SSA/P (FIG. 11A) and CR versus SSA/P (FIG. 11B).
Figure 11B:
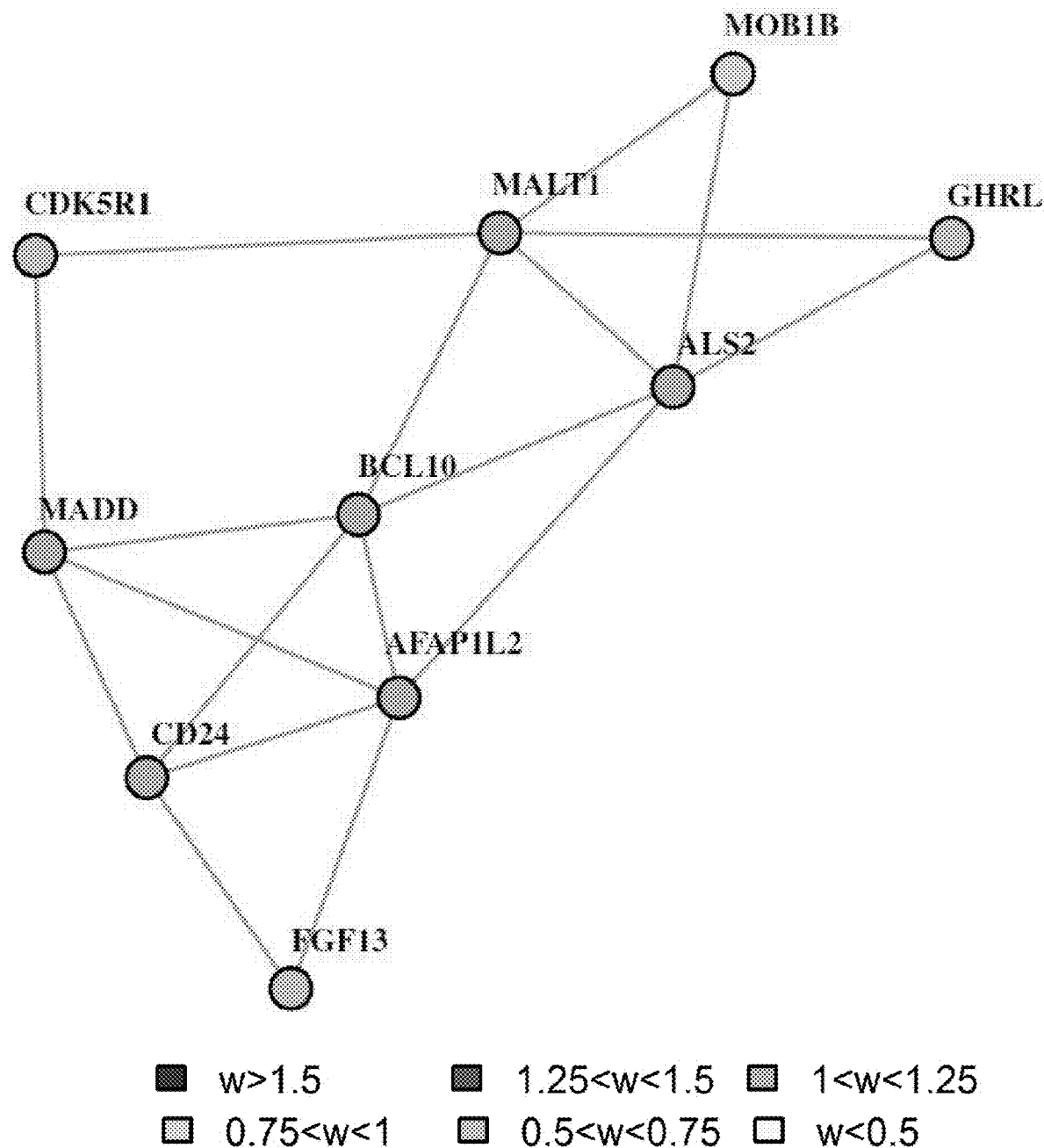
Figure 14A:
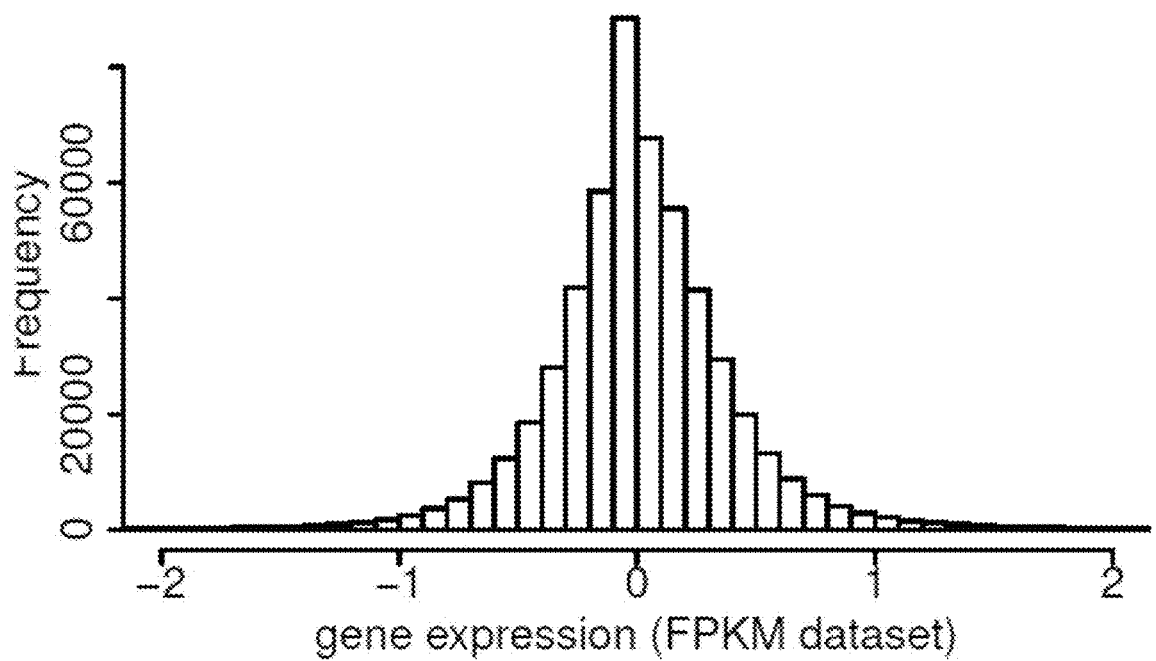
FIG. 14A, FIG. 14B, and FIG. 14C depict histograms of the MAD-normalized log-scale gene expression data in all three platforms approximately follows a Laplace-like distribution centered around zero.
Figure 14B:
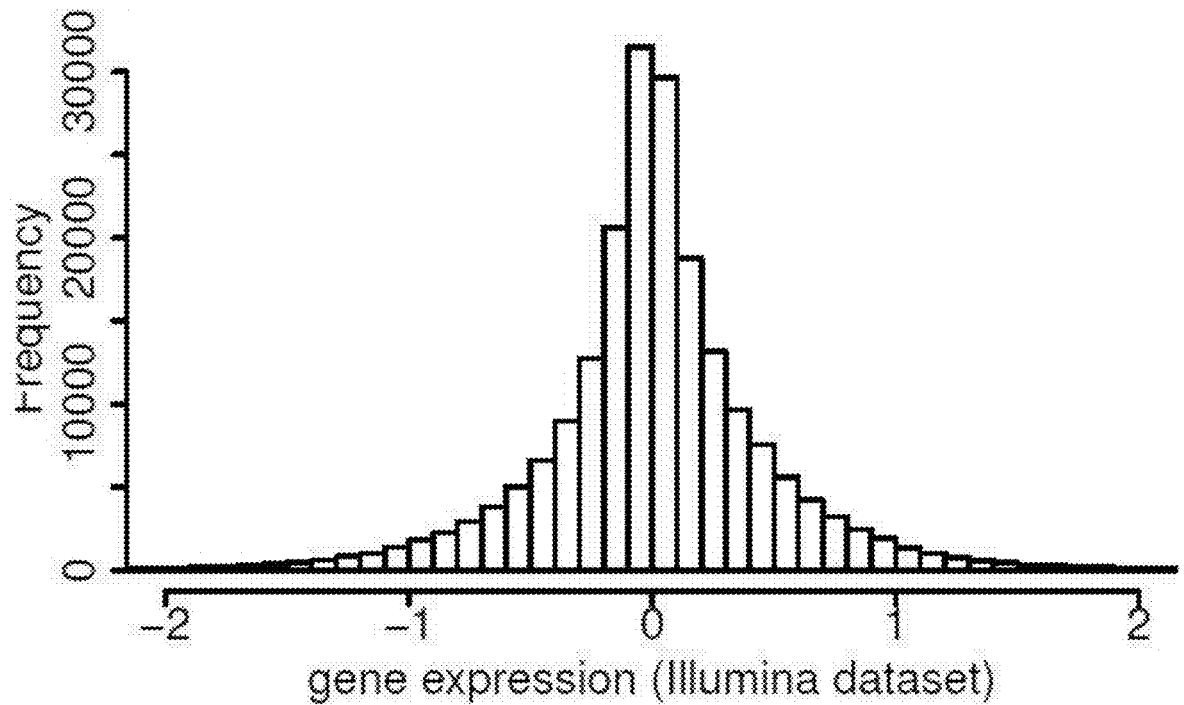
Figure 14C:
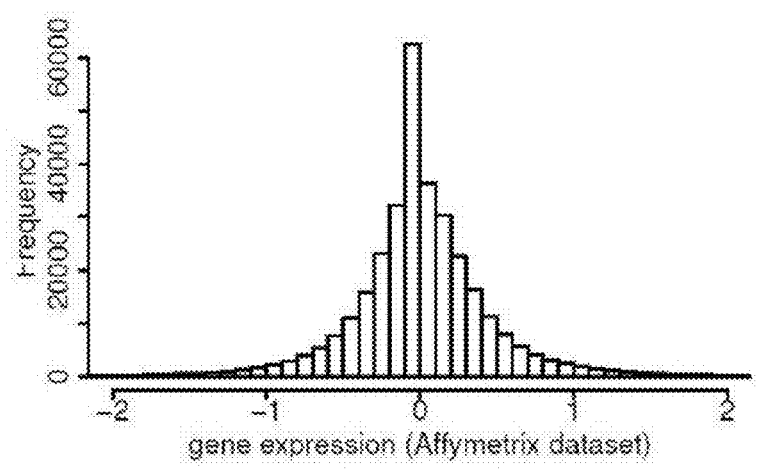
Figure 15A:
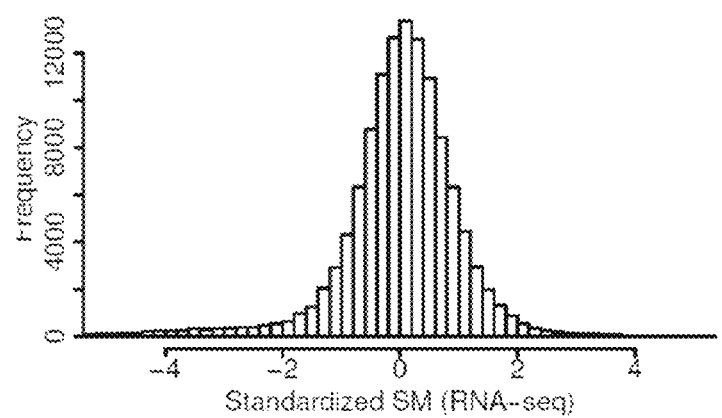
FIG. 15A, FIG. 15B, and FIG. 15C depict histograms of the summary metric (SM) obtained by summing the MAD-normalized expressions of a random signature of 15 genes in all three platforms. Six HP and six SSA/P samples were randomly selected from each platform in each iteration and a total of 10000 iterations were used to generate the histogram of SM. The SM approximately follows a normal-like distribution that is centered around zero and has a higher kurtosis than the standard normal distribution.
Figure 15B:
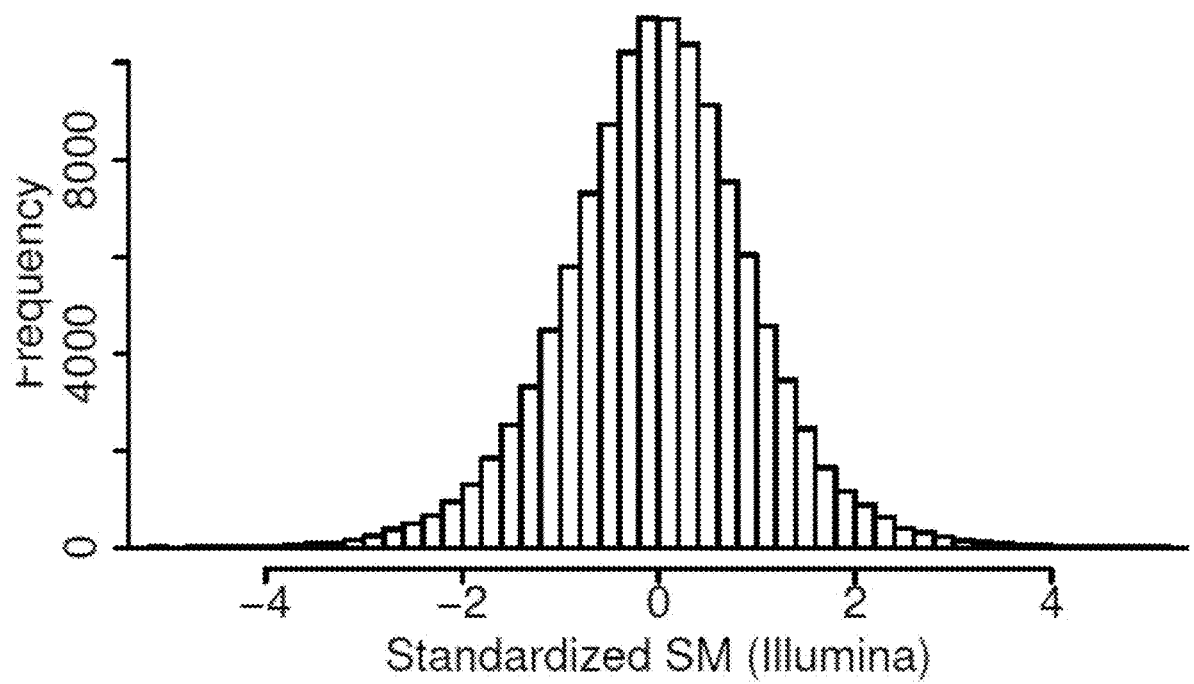
Figure 15C:
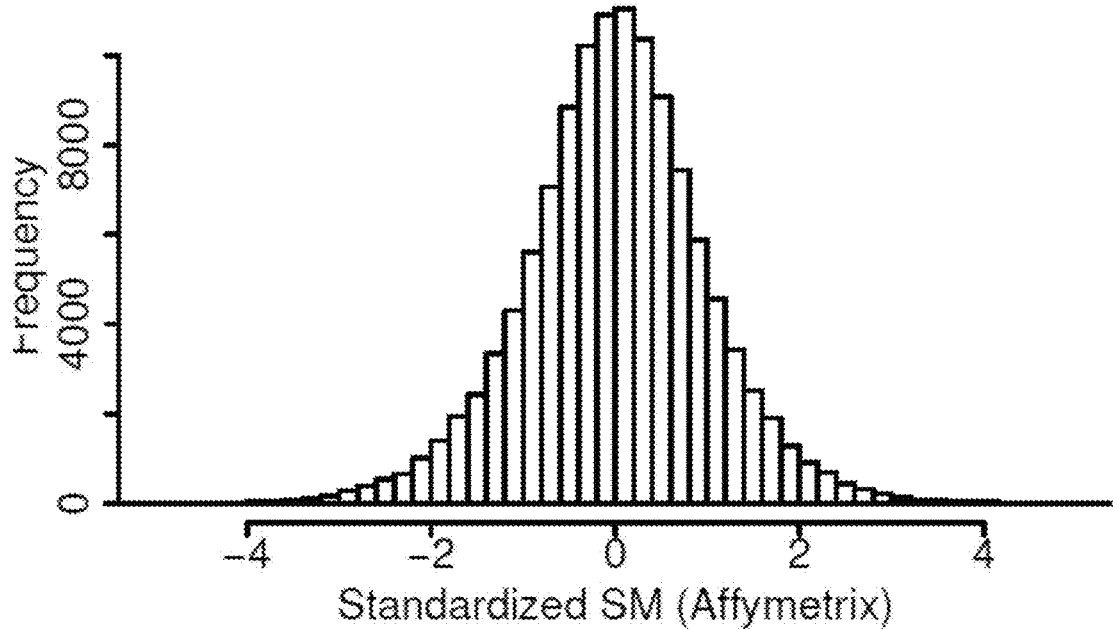

MAD-normalized gene expressions had approximately Laplace-like distribution (FIG. 14) and SM distributions were approximately normal (FIG. 15). According to the central-limit theorem, the SM distributions should be normal, especially for signatures with a large number of genes p≥30 (FIG. 15). The normal approximation is still valid when the signature size p<30 if the population is not too different from a normal distribution. There are several ways of assigning a class probability to a new sample using training RNA-seq data set as a reference. The distribution of SM can be estimated by calculating SMs for many random signatures of the same size as the signature in use. The probability of an assigned SSA/P (HP) class is the cumulative distribution function CDF(SM) (1−CDF(SM)) of the empirical distribution of SM after standardization (FIG. 6). Another possibility is to use the normal approximation of SM (FIG. 6). The first approach is impaired by the possible differences in the distribution of SM between different platforms. For example, applying MAD normalization to the $\log_e$-scale FPKM RNA-seq data yielded SM with negative tail that extended beyond the corresponding tail in microarray data (FIG. 15). The second approach is impaired by deviation from normality especially for very small signatures. Generally, the distribution of SM was normal-like with higher kurtosis for small signatures. While the distribution of SM had kurtosis ≈8 and 4 for RNA-seq and microarray data, respectively (using 15 genes in a signature), the kurtosis of a standard normal distribution is 3.

Due to the potential difficulties in fitting an exact distribution to SM another solution was found. A lower bound for P(X≥SM) as the probability for an assigned SSA/P class and P(X≤−SM) as the probability for an assigned HP can be estimated using Cantelli's inequality (also known as one-sided Tchebycheff's inequality). Cantelli's inequality estimates an upper bound for the probability that observations from some distribution are bigger than or smaller than their average:

$$P(X - \mu \leq a) = CDF(\mu + a) \geq 1 - \frac{\sigma^2}{\sigma^2 + a^2}, a \geq 0$$

$$P(X - \mu \leq a) = CDF(\mu + a) \leq \frac{\sigma^2}{\sigma^2 + a^2}, a < 0$$

We either choose a=SM and σ=0.14 (which happened to be a standard deviation of SM in all three platforms when the number of genes is 15), or choose a=standardized SM and σ=1. FIG. 6 presents Cantelli lower bound (CLB) SSA/P (HP) probabilities. When SM∈[−σ, σ] (or $SM_{standardized} \in [-1,1]$) the probability of class assignment is zero for one class and <50% for the other, therefore no probability was assigned (Uncertain zone, FIG. 6). To avoid false positive the probability was assigned if and only if Cantelli lower bound of SM was >0.5. The results of classifying samples in the Illumina and Affymetrix data sets using the summary metric and the class probability assigned to each decision are presented in Table 9, Table 10, and Table 11. For comparison, the class probabilities obtained using the empirical approach, normal approximation, and the SCC (independent of SM) are also shown. Standardized SM and σ=1 were used. When the Affymetrix samples were classified using the 16-gene signature, 2 of the 3 misclassified HP samples by SCC are deemed uncertain by CLB while assigned P(SSA/P) of 75% and 94% by SCC (Table 10).

Independent Validation and Clinical Diagnostic Tool.

Figure 16:
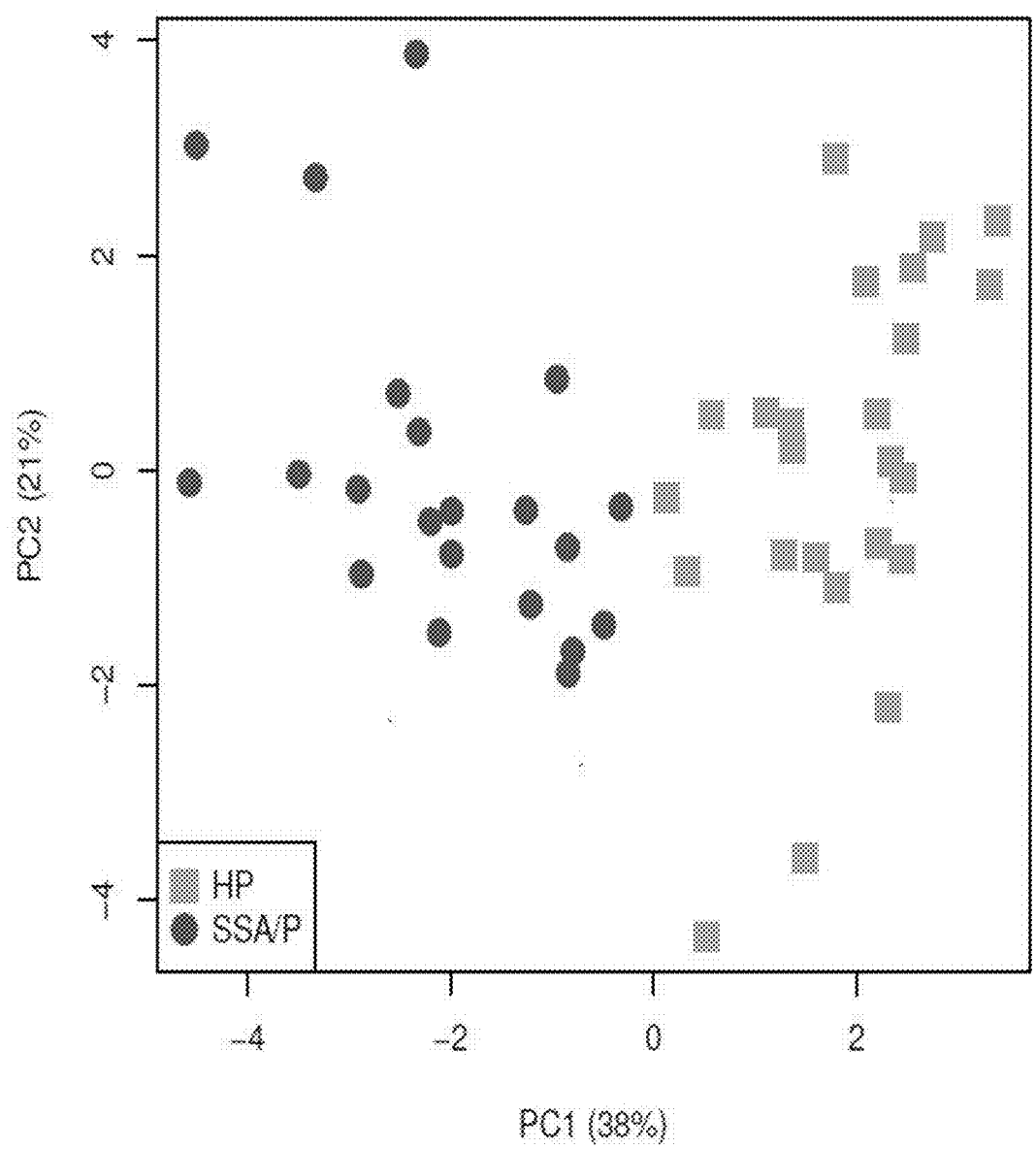
FIG. 16 depicts a principle component analysis (PCA) scatter plot showing the first and second components for normalized expression levels by first subtracting sample medians and then by subtracting gene-wise medians from each individual gene.

To further validate the accuracy of the 13 genes molecular signature and demonstrate its diagnostic value in clinically relevant settings, expression levels were obtained from 45 (24 HPs and 21 SSA/Ps) independent FFPE SSA/P and HP samples with real-time qPCR (see Methods). By simply applying proper normalization and summarizing expression levels using the summary metric (see Methods), the 13 genes molecular signature correctly classified 90% of the independent FFPE samples (Table 12). FIG. 16 shows the scatter plot of the first and second principle components of normalized expression levels. The 13 genes molecular signature indeed placed HP and SSA/P independent FFPE samples in two well-separated clusters. This approach is simple and relies on the ability of the combined 13 genes to properly distinguish between HP and SSA/P, rather than relying on a complex classifier. The steps required to apply this simple approach as a clinical diagnostic tool to new qPCR samples are summarized in Methods. It is worth mentioning here that the signature that was found using RNA-seq data from fresh tissue samples achieved a remarkable correct classification rate despite any possible RNA degradation in preserved FFPE tissues.

Discussion.

Conventionally, SSA/Ps are distinguished from HPs on the basis of histopathological features. Because HPs have similar histopathological features, a significant error rate of classifying SSA/P as HP can occur, especially if expert gastrointestinal pathologists are not available. This clinical challenge was the driver of this study, which aimed to develop biomarker-based test to distinguish between SSA/Ps and HPs. Another challenge was to elucidate molecular mechanisms, contributing to the differences between SSA/P and HP phenotypes.

Previously, the differences between phenotypes were considered mostly at the level of individual genes. The genes DE between SSA/Ps and CR (or HP) samples (MUC17, TFF1 and CTSE, SLIT2) were also found in the present analysis. In addition, these genes were also DE between CR and CL samples, so their association with HP and SSA/P phenotypes is uncertain. Among other SSA/Ps potential biomarkers (ANXA10, FABP6 and TTF2), ANXA10 was found to be significantly DE between HP and SSA/P samples (Table 5) and TFF2 was found to be significantly DE between SSA/Ps and HP, CR samples (Table 4). FABP6 was not significantly DE.

To get the systems-level view of the differences between HP and SSA/P phenotypes the data were analyzed employing different functional units (genes and pathways) as well as different regulatory relationships (differential expression, co-expression). At the level of individual genes, only genes expressed at the same level in HP and CR samples and significantly up- or down-regulated in SSA/Ps were considered. Most interestingly, two third of the up-regulated genes were interferon-regulated genes, including IDO1. In addition, at the pathway level, 'Inflammatory response' and 'Immunological synapse' were also up-regulated in SSA/Ps as compared to HP, CR samples. IDO has been implicated in inflammatory processes; for example, in the mouse model of DSS induced colitis, it has been shown that IDO1 stimulates an inflammatory response (elevated levels of pro-inflammatory chemokines and cytokines), the same pathway that was found up-regulated here. However, generally IDO is known as being immunosuppressive: its activity promotes apoptosis of T-cells, NK cells and induces the differentiation of T regulatory cells ($T_{regs}$). The mechanism by which IDO mediates inflammation is not well understood but the connection between IDO-mediated inflammation and immunosuppression in tumor cells has been discussed. It could be that IDO1 also plays a role in potentiating SSA/Ps into tumor progression by increasing inflammatory state and facilitating immune escape, but whether there is a link requires further study. Other important up-regulated genes and pathways differentiating SSA/P from HP phenotypes involve cell motility, migration ability, EMT and ECM interaction (FIG. 3 and Table 1) that impact cell invasive and metastatic behavior, another important hallmark of cancer. Considering pathways differentially co-expressed between SSA/Ps and HP phenotypes, it was found that hub genes were always different between two phenotypes (R code). For two differentially co-expressed meiosis-related pathways, the shift was from RAD51 to MRE11A, a gene involved in non-homologous recombination and mismatch repair pathway. One of the most studied genotypic subtypes of CRC is that characterized by a deficient mismatch repair pathway (dMMR), usually found in combination with microsatellite instability (MSI). Whether SSA/Ps indeed result in dMMR CRC subtype remains to be studied. For now, as evidenced by up-regulation of pathways and genes found, it appears that SSA/Ps are prone to neoplastic changes most probably because of inflammatory and immune escape state, as well as an increased cell motility and migration ability.

While the computational analysis indeed elucidated genes and pathways DE between SSA/Ps and HPs, indicated plausible directions toward tumor progression and even pointed to existing preventive/treatment options (suppressors of IDO1 and TROP-2), the major goal was more practical: to build a molecular classifier accurately differentiating between SSA/Ps and HPs. Using RNA-seq data set and the new feature selection strategy suggested here in combination with popular SCC, a molecular classifier that is applicable to microarray data was developed. The classifier was tested on two independent data sets and resulted in zero (out of 12 Illumina samples) and three (out of 17 Affymetrix samples) errors. The smallest successful signature for both platforms (13 genes, Table 3) included up-regulated genes previously associated with invasive cell activities (CLD1, PLA2G16, PTAFR, SPIRE1) and down-regulated checkpoints controlling cell growth (CHFR, NTRK2). In addition, a simple procedure was developed that uses the MAD-normalized signatures in Table 2 to classify new samples as either HP or SSA/P and provides a class probability for the decision, estimated using Cantelli's inequality. The median expression for any gene in any new platform can also be calculated reliably given that enough samples are available. Any new sample from the same platform is then added to re-calculate the median and perform the MAD normalization. For high throughput platforms where thousands of genes are profiled, it is possible to calculate the Cantelli lower bound for SSA/P and HP probabilities. For other clinical settings that profile a few genes (such as real-time qPCR), accurate classification is also possible (results demonstrated herein) but without class assignment probabilities (see Methods). The proposed molecular classifier demonstrates clinical diagnostic value and it could be used to classify future samples profiled with microarray, RNA-seq, or real-time qPCR platforms. The more accurate diagnosis of patients with SSA/Ps will enable future studies that better define the risk of colon cancer in patients with SSA/Ps, determine if subsets of patients have stratified risks for colon cancer and refine the recommendations for follow up care of patients with SSA/Ps.

Methods.

RNA-Seq Training Data Set.

The RNA-seq data set used in this study consists of a subset of the NCBI gene expression omnibus (GEO) series with the accession number GSE76987. Ten (10) control left (CL), 10 control right (CR), 10 microvesicular hyperplastic polyps (MVHPs), and 21 sessile serrated adenoma/polyps (SSA/Ps) samples were included. Raw single-end (SE) RNA-seq reads of 50 base pairs were provided in FASTQ file format from the ILLUMINA HiSeq 2000 platform. To insure high quality reads, the fastX-toolkit (version 0.0.13) was employed to discard any read with median Phred score<30. The surviving sequence reads were aligned to the UCSC hg19 human reference genome using Tophat (version 2.0.12). Tophat aligns RNA-seq reads to mammalian-sized genomes using the high-throughput short read aligner Bowtie (version 2.2.1) and then analyzes the mapping results to identify splice junctions between exons. Cufflinks was used to quantify the abundances of genes, taking into account biases in library preparation protocols. Cufflinks implements a linear statistical model to estimate the assigned abundance to each transcript that explains the observed reads (especially reads originating from a common exon in several isoforms of the same gene) with maximum likelihood. The normalized gene expression values are provided in fragments per kilobase per millions (FPKM) of mapped reads. The $\log_2(1+FPKM)$ transformation was applied to FPKM values in all analyses.

Illumine Testing Data Set.

This data set consists of 6 normal colon samples, 6 microvesicular hyperplastic polyps (MVHPs) and 6 sessile serrated adenomas/polyps (SSA/Ps). The total RNA was converted to cDNA and modified using the Illumina DASL-HT assay and hybridized to the Illumina HumanHT-12 WG-DASL V4.0 R2 expression beadchip. The biopsies were classified by seven gastrointestinal pathologists who reviewed 109 serrated polyps and identified 60 polyps with consensus. The $\log_e$-scale of the expression measurements provided under the gene expression omnibus (GEO) accession number GSE43841 was used. Only MVHP and SSA/P samples were considered for the analyses. Illumina probe identifiers were mapped to gene symbol identifiers using the Bioconductor annotation package illuminaHumanWGDASLv4.db. Whenever multiple probes were mapped to the same gene, the probe with the largest t-statistic between MVHP and SSA/P was selected.

Affymetrix Testing Data Set.

Subsets of samples from two GEO data sets, GSE10714 and GSE45270, were considered. The total RNA was extracted from 11 patients with hyperplastic polyps (HPs) from GSE10714 and from 6 patients with sessile serrated adenoma/polyps (SSPs) from GSE45270. Genome-wide gene expression profile was evaluated by the HGU133plus2 microarrays from Affymetrix. The background correction, normalization, and probe summarization steps were implemented using the robust multi-array (RMA) method for the combined samples. Probe identifiers were mapped to gene symbol identifiers using the Bioconductor annotation package hgu133plus2.db. When multiple probes were mapped to the same gene, the probe with the largest t-statistic between the 11 HP samples and the 6 SSA/P samples was selected.

Biospecimens for Independent Validation Studies.

Formalin-fixed paraffin embedded (FFPE) specimens of SSA/Ps (n=21, size range 0.3-3 cm) and HPs (n=24, size range 0.3-0.5 cm) with an unequivocal diagnosis based on the review of at least two independent expert GI pathologists were analyzed. SSA/Ps were from the right colon (sigmoid flexure to cecum) and HPs were from both the left and transverse colon. All samples represented unused de-identified pathologic specimens that were obtained under IRB approval. Total RNA was extracted from six to seven 10 µm slices of FFPE tissues using a RNeasy FFPE kit (Qiagen, Germany) according to the manufacturer's instructions. The concentration of extracted RNA was determined by Qubit RNA HS assays. Reverse transcription reactions were performed utilizing high capacity RNA-to-cDNA kit (Applied Biosystems, Carlsbad, Calif.) in 20 µL reactions containing 1 µg of RNA, in compliance with the manufacturer's protocol.

qPCR was performed with an ABI 7900HT Fast Real-Time PCR System (Applied Biosystems, Carlsbad, Calif.). With the exception of SBSPON all primers were selected from the PrimerBank database[101], and specific primers for SBSPON were purchased from OriGene Technologies (Rockville, Md.) (Table S11). As a control we utilized human 18S ribosomal RNA (Qiagen, Germany). 15 µL reaction mixtures contained 7.5 µL of PowerUp SYBR green 2× master mix (Applied Biosystems, Carlsbad, Calif.), 0.75 µL of each primer pair (10 µM), and 20 ng of cDNA. The reaction involved initial denaturing for 2 minutes at 95° C., followed by 40 cycles of 95° C. for 15 seconds and 60° C. for 60 seconds. All analyses were carried out in triplicates.

Differential Expression Analysis.

Differentially expressed (DE) genes were detected using the returned values from the Cuffdiff2 algorithm. Expressed genes with adjusted p-values $P_{adj}<0.05$ and absolute $\log_2$ fold change>0.5 were considered DE. P-values were controlled for multiple testing using the Benjamini-Hochberg false discovery rate (FDR) method.

Feature Selection Step (Concordant Genes).

The following algorithm for selecting genes, concordant between platforms, was developed:

1. Let matrices $X=[X_1, \ldots, X_n]$ and $Y=[Y_1, \ldots, Y_m]$ represent n(m) p-dimensional measurements of gene expression from two platforms. Let $n=n_1+n_2$, $m=m_1+m_2$ where X(Y) has $n_1(m_1)$ samples that belong to phenotype 1 and $n_2(m_2)$ samples that belong to phenotype 2.
2. Sample without replacement from each platform selecting $\min(n_1, m_1)$ random samples that belong to phenotype 1 and $\min(n_2, m_2)$ random samples that belong to phenotype 2. Find the Pearson correlation coefficient between the two platforms for each of the p genes. These correlations are calculated with actual phenotype labels ($\rho_{true}$).
3. Sample without replacement from each platform selecting $\min(n_1, m_1)$ and $\min(n_2, m_2)$ random samples that belong to any phenotype. Find the Pearson correlation coefficient between the two platforms for each of the p genes. These correlations are calculated when samples from both phenotypes are randomly sampled ($\rho_{random}$).
4. Repeat steps 2 and 3 for a large number of times (we use $10^4$ times) and record the p (number of genes) correlation values in each step to estimate the distribution of $\rho_{true}$ and $\rho_{random}$ (see FIG. 13). Calculate pooled standard deviation for each gene from the two estimated distributions of $\rho_{sep}$ and $\rho_{mix}$ and use the maximum value $\max(SD(\rho_{true} \cup \rho_{random}))$ for step 5.
5. Use the non-parametric Wilcoxon's test of means to test the one-sided hypothesis $H_0$: $\bar{\rho}_{true} \leq \bar{\rho}_{random}+\max(SD(\rho_{true} \cup \rho_{random}))$ against the alternative $H_1$: $\bar{\rho}_{true} > \bar{\rho}_{random}+\max(SD(\rho_{true} \cup \rho_{random}))$. This test rejects the null hypothesis for genes that are consistently over-expressed in one phenotype under both platforms, especially when the within-phenotype variability is negligible compared to the fold change (see FIG. 5). The term $\max(SD(\rho_{true} \cup \rho_{random}))$ can optionally be multiplied by a constant to increase or decrease the number of genes that rejects the null hypothesis.

Building the Classifier.

The shrunken centroid classifier (SCC) works as follows: First, it shrinks each phenotype gene centroids towards the overall centroids and standardizes by the within-phenotype standard deviation of each gene, giving higher weights to genes with stable within-phenotype expression. The centroids of each phenotype deviate from the overall centroids and the deviation is quantified by the absolute standardized deviation. The absolute standardized deviation is compared to a shrinkage threshold and any value smaller than the threshold leads to discarding the corresponding gene from the classification process.

To select the threshold for the centroid shrinkage, a 3-fold cross-validation over a range of 30 threshold values for 100 iterations was performed (R package pamr version 1.55). The threshold returning the minimum mean error with the least number of genes was selected. Within every iteration, genes' ability to separate between HP and SSA/P samples was assessed by calculating the area under the ROC curve (R package ROCR version 1.0-7) and only genes with AUC>0.8 were left in the signature. The signature was employed with the SCC to classify independent validation samples as either HPs or SSA/Ps. For a p-dimensional validation sample X, the classifier calculates a discriminant score $\delta_k(X')$ for class k and assigns the class with $\min_k(\delta_k(X'))$ as the classification decision. Discriminant scores are used to estimate class probabilities (posterior probabilities) as a measure of the certainty of classification decision $$p_k(X^*) = \frac{e^{-\frac{1}{2}\delta_k(X^*)}}{\sum_{m=1}^{M} e^{-\frac{1}{2}\delta_m(X^*)}}$$

where M is the number of classes.

Classification of Independent FFPE Samples.

Figure 17:
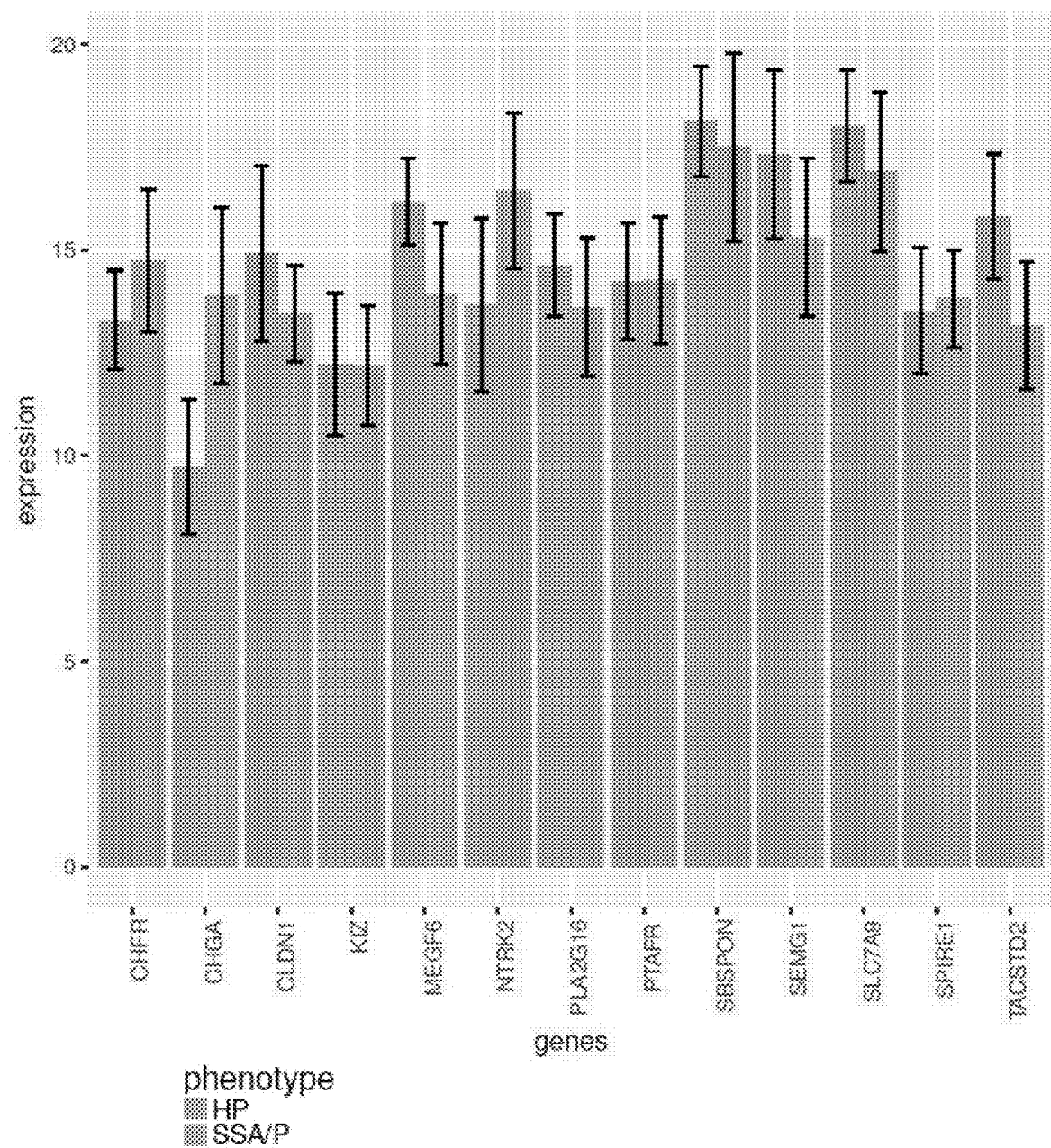
FIG. 17 depicts a barplot of the average raw expression levels of 13 genes obtained by qPCR from 45 FFPE tissue samples. For each gene, samples are grouped according to their phenotype (HP or SSA/P). Error bars extend to ±one standard deviation. Raw expression levels are relative to the housekeeping genes, hence higher levels here refer to lower values.
Figure 18A:
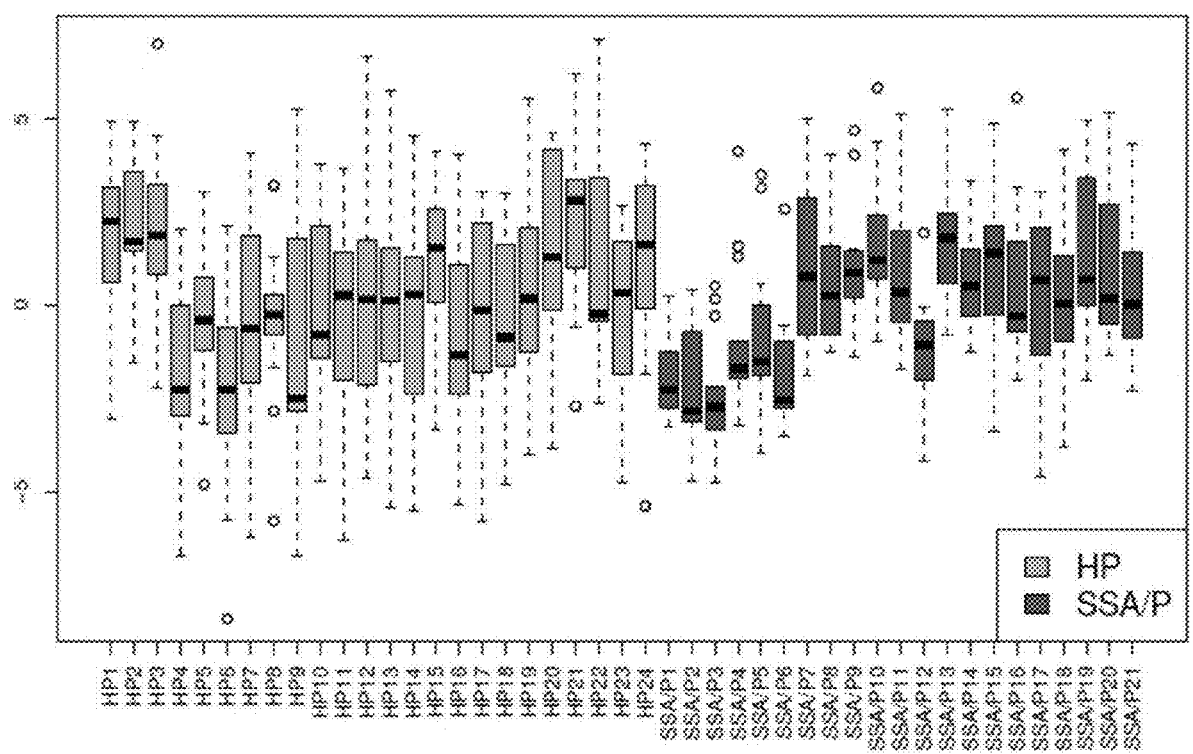
FIG. 18A and FIG. 18B depict boxplots for the expression levels of 13 genes obtained by qPCR from 45 FFPE tissue samples.
Figure 18B:
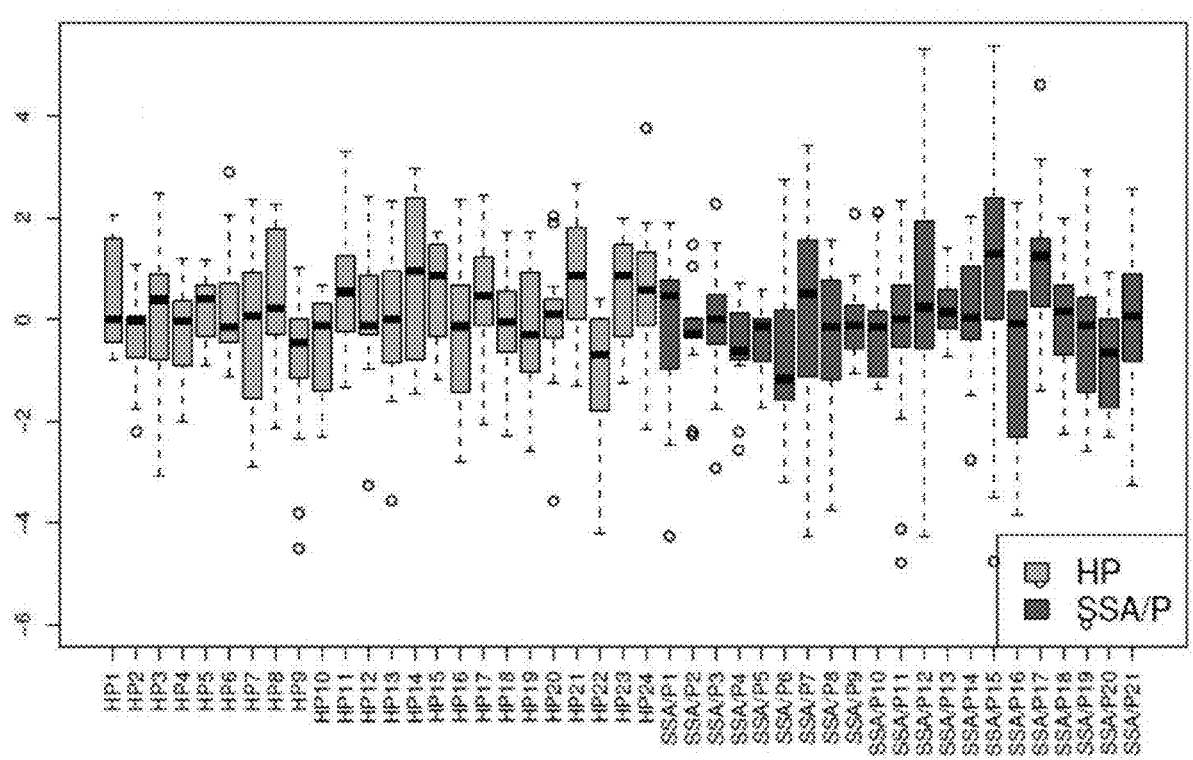

Expression levels of 13 genes were estimated relative to a reference level of a housekeeping gene, such that larger values represent lower expression levels and smaller values represent higher expression levels (see FIG. 17). Some samples were positively or negatively biased relative to each other (see FIG. 18A). Therefore, raw expression levels were normalized using two steps. First, raw expressions were shifted by their respective sample means or medians to remove any possible positive or negative biases between samples and center expression levels around zero. This step is crucial to reduce technical variation between samples. Three options that keep gene ranks in each sample unchanged (arithmetic mean, geometric mean, and median) were tried and no significant difference in the classification results was noticed (see Table 12). It was also found that the quantile normalization which forces all samples to have similar quantiles yielded lower performance (data not shown). Although subtracting the arithmetic or geometric mean showed minor improvement in Table 12, subtracting the median is recommended when outliers are present in some samples. Expression levels are then multiplied by −1 to let higher expression levels be represented by larger values. Second, the gene-wise MAD normalization was applied such that genes with large fold changes between HP and SSA/P are likely to have positive values under one phenotype and negative values under the other. The normalized expression levels are shown in FIG. 18B. The summary metric (SM) is used to score each sample and each sample is then labeled as HP if SM<0 and as SSA/P if SM>0.

FIG. 14 and FIG. 15 have shown that the distribution of the MAD-normalized expression and the distribution of SM in one RNA-seq and two microarray data sets were comparable hence the shrunken centroid classifier trained with RNA-seq data can be applied successfully to classify microarray samples. Accurate estimates of the summary metric distribution for each platform allowed proper standardization of the summary metric and hence proper phenotype assignment probability using CLB. While this approach works for high throughput platforms that profile thousands of genes, it is not applicable under typical clinical settings when qPCR is used to profile only a few genes because the distribution of SM is unknown. This is why phenotype assignment probabilities are not available when platforms that profile a few genes (such as small-scale qPCR) are used.

To classify new qPCR samples using our simple approach, the two normalization steps above must be applied. R code implementing the two normalization steps and classifying samples using the summary metric of 13 genes is provided in R code below. To apply MAD normalization to real-time qPCR expression levels, multiple samples are necessary to estimate the median expression level for each gene accurately. Therefore the raw qPCR expression levels for the FFPE data set (24 HPs and 21 SSA/Ps) in Table S10 was provided to allow the normalization of any new qPCR samples. The first normalization step resolves any potential shift biases between the new samples and the samples in Table 13.

Software Availability.

The nearest shrunken centroid classifier implementation in R is available in the CRAN package pamr. Below provides R code and instructions on how to apply the simple 13 genes signature to classify new qPCR samples into either HP or SSA/P.

R Code and Instructions.

```
# save a copy of Supplementary Table S10 in you working directory
setwd("working directory here")
# choose "mean", "geometricMean", or "median" for sample normalization
sample.nor <- "median"
# read Table 13
FFPEtab <- read.csv("Table_13.csv")
class.labels <- as.character(FFPEtab[,2])
FFPEmat <- as.matrix(FFPEtab[,3:15])
rownames(FFPEmat) <- as.character(FFPEtab[,1])
colnames(FFPEmat) <- colnames(FFPEtab)[3:15]
FFPEmat <- t(FFPEmat)
# read you new samples from a comma-delimited file
# expression levels should occupy one or more columns
# gene names must be in the first column and sample names can be used
new.samples <- read.csv("new_samples.csv")
new.mat <- as.matrix(new.samples)
rownames(new.mat) <- as.character(new.samples[,1])
```

```
new.mat <- new.mat[rownames(FFPEmat),]
# append new samples to Table 13
FFPEmat <- cbind(FFPEmat, new.mat)
# subtract the mean/median from each sample
if(sample.nor == "median") mm <- apply(FFPEmat, 2, "median")
if(sample.nor == "mean") mm <- apply(FFPEmat, 2, "mean")
if(sample.nor == "geometricMean") mm <- apply(FFPEmat, 2,
function(x){prod(x)^length(x)})
mat <- matrix(mm, 13, 45, byrow=TRUE)
FFPEmat <- FFPEmat - mat
# center each gene's expression around zero
# multiply by -1 to let higher values represent higher expression levels
FFPEmat.nor <- -sweep(FFPEmat, 1, apply(FFPEmat, 1, "median"))
# calculate the summary metric (SM)
# expression of genes "CHFR", "CHGA", and "NTRK2" is multiplied by -1
sig <-
c("CHFR","CHGA","CLDN1","KIZ","MEGF6","NTRK2","PLA2G16","PTAFR","SBSPO
N","SEMG1","SLC7A9","SPIRE1","TACSTD2")
signature.size <- length(sig)
mask <- matrix(1, signature.size, ncol(FFPEmat.nor), byrow=FALSE)
mask[c(1,2,6),] <- -1
SM <- colMeans(FFPEmat.nor[sig,]*mask)
# if SM>0 then sample is classified as SSA/P
# else if SM<0 then sample is classified as HP
```

REFERENCES

1. Zauber, A. G., S. J. Winawer, M. J. O'Brien, I. Lansdorp-Vogelaar, M. van Ballegooijen, B. F. Hankey, W. Shi, J. H. Bond, M. Schapiro, J. F. Panish, E. T. Stewart, and J. D. Waye, *Colonoscopic polypectomy and long-term prevention of colorectal-cancer deaths.* N Engl J Med, 2012. 366(8): p. 687-96.
2. Lieberman, D. A., D. G. Weiss, J. H. Bond, D. J. Ahnen, H. Garewal, and G. Chejfec, *Use of colonoscopy to screen asymptomatic adults for colorectal cancer. Veterans Affairs Cooperative Study Group 380.* N Engl J Med, 2000. 343(3): p. 162-8.
3. Levin, B., D. A. Lieberman, B. McFarland, R. A. Smith, D. Brooks, K. S. Andrews, C. Dash, F. M. Giardiello, S. Glick, T. R. Levin, P. Pickhardt, D. K. Rex, A. Thorson, S. J. Winawer, G. American Cancer Society Colorectal Cancer Advisory, U. S. M.-S. T. Force, and C. American College of Radiology Colon Cancer, *Screening and surveillance for the early detection of colorectal cancer and adenomatous polyps, 2008: a joint guideline from the American Cancer Society, the US Multi-Society Task Force on Colorectal Cancer, and the American College of Radiology.* CA Cancer J Clin, 2008. 58(3): p. 130-60.
4. Quintero, E., A. Castells, L. Bujanda, J. Cubiella, D. Salas, A. Lanas, M. Andreu, F. Carballo, J. D. Morillas, C. Hernandez, R. Jover, I. Montalvo, J. Arenas, E. Laredo, V. Hernandez, F. Iglesias, E. Cid, R. Zubizarreta, T. Sala, M. Ponce, M. Andres, G. Teruel, A. Perls, M. P. Roncales, M. Polo-Tomas, X. Bessa, O. Ferrer-Armengou, J. Grau, A. Serradesanferm, A. Ono, J. Cruzado, F. Perez-Riquelme, I. Alonso-Abreu, M. de la Vega-Prieto, J. M. Reyes-Melian, G. Cacho, J. Diaz-Tasende, A. Herreros-de-Tejada, C. Poves, C. Santander, A. Gonzalez-Navarro, and C. S. Investigators, Colonoscopy versus fecal immunochemical testing in colorectal-cancer screening. N Engl J Med, 2012. 366(8): p. 697-706.
5. Limketkai, B. N., D. Lam-Himlin, M. A. Arnold, and C. A. Arnold, *The cutting edge of serrated polyps: a practical guide to approaching and managing serrated colon polyps.* Gastrointest Endosc, 2013. 77(3): p. 360-75.
6. Kahi, C. J., D. G. Hewett, D. L. Norton, G. J. Eckert, and D. K. Rex, *Prevalence and variable detection of proximal colon serrated polyps during screening colonoscopy.* Clin Gastroenterol Hepatol, 2011. 9(1): p. 42-6.
7. Torlakovic, E. and D. C. Snover, Serrated adenomatous polyposis in humans. Gastroenterology, 1996. 110(3): p. 748-55.
8. Kahi, C. J., X. Li, G. J. Eckert, and D. K. Rex, *High colonoscopic prevalence of proximal colon serrated polyps in average-risk men and women.* Gastrointest Endosc, 2012. 75(3): p. 515-20.
9. Torlakovic, E., E. Skovlund, D. C. Snover, G. Torlakovic, and J. M. Nesland, *Morphologic reappraisal of serrated colorectal polyps.* Am J Surg Pathol, 2003. 27(1): p. 65-81.
10. Torlakovic, E. E., J. D. Gomez, D. K. Driman, J. R. Parfitt, C. Wang, T. Benerjee, and D. C. Snover, *Sessile serrated adenoma (SSA) vs. traditional serrated adenoma (TSA).* Am J Surg Pathol, 2008. 32(1): p. 21-9.
11. Lash, R. H., R. M. Genta, and C. M. Schuler, *Sessile serrated adenomas: prevalence of dysplasia and carcinoma in 2139 patients.* J Clin Pathol, 2010. 63(8): p. 681-6.
12. Rex, D. K., D. J. Ahnen, J. A. Baron, K. P. Batts, C. A. Burke, R. W. Burt, J. R. Goldblum, J. G. Guillem, C. J. Kahi, M. F. Kalady, M. J. O'Brien, R. D. Odze, S. Ogino, S. Parry, D. C. Snover, E. E. Torlakovic, P. E. Wise, J. Young, and J. Church, *Serrated lesions of the colorectum: review and recommendations from an expert panel.* Am J Gastroenterol, 2012. 107(9): p. 1315-29; quiz 1314, 1330.
13. Payne, S. R., T. R. Church, M. Wandell, T. Rosch, N. Osborn, D. Snover, R. W. Day, D. F. Ransohoff, and D. K. Rex, *Endoscopic detection of proximal serrated lesions and pathologic identification of sessile serrated adenomas/polyps vary on the basis of center.* Clin Gastroenterol Hepatol, 2014. 12(7): p. 1119-26.
14. Tinmouth, J., P. Henry, E. Hsieh, N. N. Baxter, R. J. Hilsden, S. Elizabeth McGregor, L. F. Paszat, A. Ruco, R. Saskin, A. J. Schell, E. E. Torlakovic, and L. Rabeneck, *Sessile serrated polyps at screening colonoscopy: have they been under diagnosed?* Am J Gastroenterol, 2014. 109(11): p. 1698-704.
15. Bettington, M., N. Walker, A. Clouston, I. Brown, B. Leggett, and V. Whitehall, *The serrated pathway to col-*

*orectal carcinoma: current concepts and challenges.* Histopathology, 2013. 62(3): p. 367-86.
16. De Sousa, E. M. F., X. Wang, M. Jansen, E. Fessler, A. Trinh, L. P. de Rooij, J. H. de Jong, O. J. de Boer, R. van Leersum, M. F. Bijlsma, H. Rodermond, M. van der Heijden, C. J. van Noesel, J. B. Tuynman, E. Dekker, F. Markowetz, J. P. Medema, and L. Vermeulen, *Poor-prognosis colon cancer is defined by a molecularly distinct subtype and develops from serrated precursor lesions.* Nat Med, 2013. 19(5): p. 614-8.
17. Castaldi, P. J., I. J. Dahabreh, and J. P. Ioannidis, *An empirical assessment of validation practices for molecular classifiers.* Brief Bioinform, 2011. 12(3): p. 189-202.
18. Chang, C. Q., S. R. Tingle, K. K. Filipski, M. J. Khoury, T. K. Lam, S. D. Schully, and J. P. Ioannidis, *An overview of recommendations and translational milestones for genomic tests in cancer.* Genet Med, 2014.
19. Chibon, F., *Cancer gene expression signatures—the rise and fall?* Eur J Cancer, 2013. 49(8): p. 2000-9.
20. Shi, W., M. Bessarabova, D. Dosymbekov, Z. Derso, T. Nikolskaya, M. Dudoladova, T. Serebryiskaya, A. Bugrim, A. Guryanov, R. J. Brennan, R. Shah, J. Dopazo, M. Chen, Y. Deng, T. Shi, G. Jurman, C. Furlanello, R. S. Thomas, J. C. Corton, W. Tong, L. Shi, and Y. Nikolsky, *Functional analysis of multiple genomic signatures demonstrates that classification algorithms choose phenotype-related genes.* Pharmacogenomics J, 2010. 10(4): p. 310-23.
21. Su, Z., H. Fang, H. Hong, L. Shi, W. Zhang, W. Zhang, Y. Zhang, Z. Dong, L. J. Lancashire, M. Bessarabova, X. Yang, B. Ning, B. Gong, J. Meehan, J. Xu, W. Ge, R. Perkins, M. Fischer, and W. Tong, *An investigation of biomarkers derived from legacy microarray data for their utility in the RNA-seq era.* Genome Biol, 2014. 15(12): p. 523.
22. Tarca, A. L., M. Lauria, M. Unger, E. Bilal, S. Boue, K. Kumar Dey, J. Hoeng, H. Koeppl, F. Martin, P. Meyer, P. Nandy, R. Norel, M. Peitsch, J. J. Rice, R. Romero, G. Stolovitzky, M. Talikka, Y. Xiang, C. Zechner, and I. D. Collaborators, *Strengths and limitations of microarray-based phenotype prediction: lessons learned from the IMPROVER Diagnostic Signature Challenge.* Bioinformatics, 2013. 29(22): p. 2892-9.
23. Alizadeh, A. A., M. B. Eisen, R. E. Davis, C. Ma, I. S. Lossos, A. Rosenwald, J. C. Boldrick, H. Sabet, T. Tran, X. Yu, J. I. Powell, L. Yang, G. E. Marti, T. Moore, J. Hudson, Jr., L. Lu, D. B. Lewis, R. Tibshirani, G. Sherlock, W. C. Chan, T. C. Greiner, D. D. Weisenburger, J. O. Armitage, R. Warnke, R. Levy, W. Wilson, M. R. Greyer, J. C. Byrd, D. Botstein, P. O. Brown, and L. M. Staudt, *Distinct types of diffuse large B-cell lymphoma identified by gene expression profiling.* Nature, 2000. 403(6769): p. 503-11.
24. Dave, S. S., G. Wright, B. Tan, A. Rosenwald, R. D. Gascoyne, W. C. Chan, R. I. Fisher, R. M. Braziel, L. M. Rimsza, T. M. Grogan, T. P. Miller, M. LeBlanc, T. C. Greiner, D. D. Weisenburger, J. C. Lynch, J. Vose, J. O. Armitage, E. B. Smeland, S. Kvaloy, H. Nolte, J. Delabie, J. M. Connors, P. M. Lansdorp, Q. Ouyang, T. A. Lister, A. J. Davies, A. J. Norton, H. K. Muller-Hermelink, G. Ott, E. Campo, E. Montserrat, W. H. Wilson, E. S. Jaffe, R. Simon, L. Yang, J. Powell, H. Zhao, N. Goldschmidt, M. Chiorazzi, and L. M. Staudt, *Prediction of survival in follicular lymphoma based on molecular features of tumor-infiltrating immune cells.* N Engl J Med, 2004. 351(21): p. 2159-69.
25. Lascorz, J., B. Chen, K. Hemminki, and A. Forsti, *Consensus pathways implicated in prognosis of colorectal cancer identified through systematic enrichment analysis of gene expression profiling studies.* PLoS One, 2011. 6(4): p. e18867.
26. Salazar, R., P. Roepman, G. Capella, V. Moreno, I. Simon, C. Dreezen, A. Lopez-Doriga, C. Santos, C. Marijnen, J. Westerga, S. Bruin, D. Kerr, P. Kuppen, C. van de Velde, H. Morreau, L. Van Velthuysen, A. M. Glas, L. J. Van't Veer, and R. Tollenaar, *Gene expression signature to improve prognosis prediction of stage II and III colorectal cancer.* J Clin Oncol, 2011. 29(1): p. 17-24.
27. Gray, R. G., P. Quirke, K. Handley, M. Lopatin, L. Magill, F. L. Baehner, C. Beaumont, K. M. Clark-Langone, C. N. Yoshizawa, M. Lee, D. Watson, S. Shak, and D. J. Kerr, *Validation study of a quantitative multigene reverse transcriptase-polymerase chain reaction assay for assessment of recurrence risk in patients with stage II colon cancer.* J Clin Oncol, 2011. 29(35): p. 4611-9.
28. Caruso, M., J. Moore, G. J. Goodall, M. Thomas, S. Phillis, A. Tyskin, G. Cheetham, N. Lerda, H. Takahashi, and A. Ruszkiewicz, *Over-expression of cathepsin E and trefoil factor 1 in sessile serrated adenomas of the colorectum identified by gene expression analysis.* Virchows Arch, 2009. 454(3): p. 291-302.
29. Gonzalo, D. H., K. K. Lai, B. Shadrach, J. R. Goldblum, A. E. Bennett, E. Downs-Kelly, X. Liu, W. Henricks, D. T. Patil, P. Carver, J. Na, B. Gopalan, L. Rybicki, and R. K. Pai, *Gene expression profiling of serrated polyps identifies annexin A10 as a marker of a sessile serrated adenoma/polyp.* J Pathol, 2013. 230(4): p. 420-9.
30. Delker, D. A., B. M. McGettigan, P. Kanth, S. Pop, D. W. Neklason, M. P. Bronner, R. W. Burt, and C. H. Hagedorn, *RNA sequencing of sessile serrated colon polyps identifies differentially expressed genes and immunohistochemical markers.* PLoS One, 2014. 9(2): p. e88367.
31. Glebov, O. K., L. M. Rodriguez, K. Nakahara, J. Jenkins, J. Cliatt, C. J. Humbyrd, J. DeNobile, P. Soballe, R. Simon, G. Wright, P. Lynch, S. Patterson, H. Lynch, S. Gallinger, A. Buchbinder, G. Gordon, E. Hawk, and I. R. Kirsch, *Distinguishing right from left colon by the pattern of gene expression.* Cancer Epidemiol Biomarkers Prev, 2003. 12(8): p. 755-62.
32. Hanahan, D. and R. A. Weinberg, *Hallmarks of cancer: the next generation. Cell,* 2011. 144(5): p. 646-74.
33. Galamb, O., F. Sipos, N. Solymosi, S. Spisak, T. Krenacs, K. Toth, Z. Tulassay, and B. Molnar, *Diagnostic mRNA expression patterns of inflamed, benign, and malignant colorectal biopsy specimen and their correlation with peripheral blood results.* Cancer Epidemiol Biomarkers Prev, 2008. 17(10): p. 2835-45.
34. Saeys, Y., I. Inza, and P. Larranaga, *A review of feature selection techniques in bioinformatics.* Bioinformatics, 2007. 23(19): p. 2507-17.
35. Tibshirani, R., T. Hastie, B. Narasimhan, and G. Chu, *Diagnosis of multiple cancer types by shrunken centroids of gene expression.* Proc Natl Acad Sci USA, 2002. 99(10): p. 6567-72.
36. Li, H. J., S. K. Ray, N. K. Singh, B. Johnston, and A. B. Leiter, *Basic helix-loop—helix transcription factors and enteroendocrine cell differentiation.* Diabetes Obes Metab, 2011. 13 Suppl 1: p. 5-12.
37. Scolnick, D. M. and T. D. Halazonetis, *Chfr defines a mitotic stress checkpoint that delays entry into metaphase.* Nature, 2000. 406(6794): p. 430-5.

38. Yu, X., K. Minter-Dykhouse, L. Malureanu, W. M. Zhao, D. Zhang, C. J. Merkle, I. M. Ward, H. Saya, G. Fang, J. van Deursen, and J. Chen, *Chfr is required for tumor suppression and Aurora A regulation.* Nat Genet, 2005. 37(4): p. 401-6.

39. Cleven, A. H., S. Derks, M. X. Draht, K. M. Smits, V. Melotte, L. Van Neste, B. Tournier, V. Jooste, C. Chapusot, M. P. Weijenberg, J. G. Herman, A. P. de Bruine, and M. van Engeland, *CHFR promoter methylation indicates poor prognosis in stage II microsatellite stable colorectal cancer.* Clin Cancer Res, 2014. 20(12): p. 3261-71.

40. Yamanami, H., K. Shiozaki, T. Wada, K. Yamaguchi, T. Uemura, Y. Kakugawa, T. Hujiya, and T. Miyagi, *Downregulation of sialidase NEU4 may contribute to invasive properties of human colon cancers.* Cancer Sci, 2007. 98(3): p. 299-307.

41. Samarajiwa, S. A., S. Forster, K. Auchettl, and P. J. Hertzog, *INTERFEROME: the database of interferon regulated genes.* Nucleic Acids Res, 2009. 37(Database issue): p. D852-7.

42. de Veer, M. J., M. Holko, M. Frevel, E. Walker, S. Der, J. M. Paranjape, R. H. Silverman, and B. R. Williams, *Functional classification of interferon-stimulated genes identified using microarrays.* J Leukoc Biol, 2001. 69(6): p. 912-20.

43. Carrega, P., S. Campana, I. Bonaccorsi, and G. Ferlazzo, *The Yin and Yang of Innate Lymphoid Cells in Cancer.* Immunol Lett, 2016.

44. Wang, G., X. Yang, C. Li, X. Cao, X. Luo, and J. Hu, *PIK3R3 induces epithelial-to-mesenchymal transition and promotes metastasis in colorectal cancer.* Mol Cancer Ther, 2014. 13(7): p. 1837-47.

45. Zhang, J. X., X. X. Huang, M. B. Cai, Z. T. Tong, J. W. Chen, D. Qian, Y. J. Liao, H. X. Deng, D. Z. Liao, M. Y. Huang, Y. X. Zeng, D. Xie, and S. J. Mai, *Overexpression of the secretory small GTPase Rab27B in human breast cancer correlates closely with lymph node metastasis and predicts poor prognosis.* J Transl Med, 2012. 10: p. 242.

46. Hamada, S., K. Satoh, A. Masamune, and T. Shimosegawa, *Regulators of epithelial mesenchymal transition in pancreatic cancer.* Front Physiol, 2012. 3: p. 254.

47. Ball, H. J., H. J. Yuasa, C. J. Austin, S. Weiser, and N. H. Hunt, *Indoleamine 2,3-dioxygenase-2; a new enzyme in the kynurenine pathway.* Int J Biochem Cell Biol, 2009. 41(3): p. 467-71.

48. Fallarino, F., U. Grohmann, C. Vacca, C. Orabona, A. Spreca, M. C. Fioretti, and P. Puccetti, *T cell apoptosis by kynurenines.* Adv Exp Med Biol, 2003. 527: p. 183-90.

49. Uyttenhove, C., L. Pilotte, I. Theate, V. Stroobant, D. Colau, N. Parmentier, T. Boon, and B. J. Van den Eynde, *Evidence for a tumoral immune resistance mechanism based on tryptophan degradation by indoleamine 2,3-dioxygenase.* Nat Med, 2003. 9(10): p. 1269-74.

50. Opitz, C. A., U. M. Litzenburger, U. Opitz, F. Sahm, K. Ochs, C. Lutz, W. Wick, and M. Platten, *The indoleamine-2,3-dioxygenase (IDO) inhibitor 1-methyl-D-tryptophan upregulates IDO1 in human cancer cells.* PLoS One, 2011. 6(5): p. e19823.

51. Iansante, V., P. M. Choy, S. W. Fung, Y. Liu, J. G. Chai, J. Dyson, A. Del Rio, C. D'Santos, R. Williams, S. Chokshi, R. A. Anders, C. Bubici, and S. Papa, *PARP14 promotes the Warburg effect in hepatocellular carcinoma by inhibiting JNK1-dependent PKM2 phosphorylation and activation.* Nat Commun, 2015. 6: p. 7882.

52. Bao, J., Y. Ni, H. Qin, L. Xu, Z. Ge, F. Zhan, H. Zhu, J. Zhao, X. Zhou, X. Tang, and L. Tang, *Rab27b is a potential predictor for metastasis and prognosis in colorectal cancer.* Gastroenterol Res Pract, 2014. 2014: p. 913106.

53. Hendrix, A., D. Maynard, P. Pauwels, G. Braems, H. Denys, R. Van den Broecke, J. Lambert, S. Van Belle, V. Cocquyt, C. Gespach, M. Bracke, M. C. Seabra, W. A. Gahl, O. De Wever, and W. Westbroek, *Effect of the secretory small GTPase Rab27B on breast cancer growth, invasion, and metastasis.* J Natl Cancer Inst, 2010. 102 (12): p. 866-80.

54. Li, J., M. S. Weinberg, L. Zerbini, and S. Prince, *The oncogenic TBX3 is a downstream target and mediator of the TGF-beta 1 signaling pathway.* Mol Biol Cell, 2013. 24(22): p. 3569-76.

55. Shan, Z. Z., X. B. Yan, L. L. Yan, Y. Tian, Q. C. Meng, W. W. Qiu, Z. Zhang, and Z. M. Jin, *Overexpression of Tbx3 is correlated with Epithelial-Mesenchymal Transition phenotype and predicts poor prognosis of colorectal cancer.* Am J Cancer Res, 2015. 5(1): p. 344-53.

56. Baron, K. D., K. Al-Zahrani, J. Conway, C. Labreche, C. J. Storbeck, J. E. Visvader, and L. A. Sabourin, *Recruitment and activation of SLK at the leading edge of migrating cells requires Src family kinase activity and the LIM-only protein 4.* Biochim Biophys Acta, 2015. 1853 (7): p. 1683-92.

57. Byrne, J. A., S. Frost, Y. Chen, and R. K. Bright, *Tumor protein D52 (TPD52) and cancer-oncogene understudy or understudied oncogene?* Tumour Biol, 2014. 35(8): p. 7369-82.

58. Owens, S. R., S. I. Chiosea, and S. F. Kuan, *Selective expression of gastric mucin MUC6 in colonic sessile serrated adenoma but not in hyperplastic polyp aids in morphological diagnosis of serrated polyps.* Mod Pathol, 2008. 21(6): p. 660-9.

59. Bartley, A. N., P. A. Thompson, J. A. Buckmeier, C. Y. Kepler, C. H. Hsu, M. S. Snyder, P. Lance, A. Bhattacharyya, and S. R. Hamilton, *Expression of gastric pyloric mucin, MUC6, in colorectal serrated polyps.* Mod Pathol, 2010. 23(2): p. 169-76.

60. Gibson, J. A., H. P. Hahn, A. Shahsafaei, and R. D. Odze, *MUC expression in hyperplastic and serrated colonic polyps: lack of specificity of MUC6.* Am J Surg Pathol, 2011. 35(5): p. 742-9.

61. Oshimori, N., M. Ohsugi, and T. Yamamoto, *The Plk1 target Kizuna stabilizes mitotic centrosomes to ensure spindle bipolarity.* Nat Cell Biol, 2006. 8(10): p. 1095-101.

62. Lagal, V., M. Abrivard, V. Gonzalez, A. Perazzi, S. Popli, E. Verzeroli, and I. Tardieux, *Spire-1 contributes to the invadosome and its associated invasive properties.* J Cell Sci, 2014. 127(Pt 2): p. 328-40.

63. Ashburner, M., C. A. Ball, J. A. Blake, D. Botstein, H. Butler, J. M. Cherry, A. P. Davis, K. Dolinski, S. S. Dwight, J. T. Eppig, M. A. Harris, D. P. Hill, L. Issel-Tarver, A. Kasarskis, S. Lewis, J. C. Matese, J. E. Richardson, M. Ringwald, G. M. Rubin, and G. Sherlock, *Gene ontology: tool for the unification of biology. The Gene Ontology Consortium.* Nat Genet, 2000. 25(1): p. 25-9.

64. Liberzon, A., A. Subramanian, R. Pinchback, H. Thorvaldsdottir, P. Tamayo, and J. P. Mesirov, *Molecular signatures database (MSigDB) 3.0.* Bioinformatics, 2011. 27(12): p. 1739-40.

65. Wu, D., E. Lim, F. Vaillant, M. L. Asselin-Labat, J. E. Visvader, and G. K. Smyth, *ROAST: rotation gene set tests for complex microarray experiments.* Bioinformatics, 2010. 26(17): p. 2176-82.

66. Weiss, A. and L. Attisano, *The TGFbeta superfamily signaling pathway*. Wiley Interdiscip Rev Dev Biol, 2013. 2(1): p. 47-63.
67. Rahmatallah, Y., F. Emmert-Streib, and G. Glazko, *Gene Sets Net Correlations Analysis (GSNCA): a multivariate differential coexpression test for gene sets*. Bioinformatics, 2014. 30(3): p. 360-8.
68. McVey, M. and S. E. Lee, *MMEJ repair of double-strand breaks (director's cut): deleted sequences and alternative endings*. Trends Genet, 2008. 24(11): p. 529-38.
69. Ishigooka, S., M. Nomoto, N. Obinata, Y. Oishi, Y. Sato, S. Nakatsu, M. Suzuki, Y. Ikeda, T. Maehata, T. Kimura, Y. Watanabe, T. Nakajima, H. O. Yamano, H. Yasuda, and F. Itoh, *Evaluation of magnifying colonoscopy in the diagnosis of serrated polyps*. World J Gastroenterol, 2012. 18(32): p. 4308-16.
70. Manning, S. and R. L. Batterham, *The role of gut hormone peptide YY in energy and glucose homeostasis: twelve years on*. Annu Rev Physiol, 2014. 76: p. 585-608.
71. El-Salhy, M., T. Mazzawi, D. Gundersen, J. G. Hatlebakk, and T. Hausken, *The role of peptide YY in gastrointestinal diseases and disorders (review)*. Int J Mol Med, 2013. 31(2): p. 275-82.
72. Newish, M., C. J. Lord, S. A. Martin, D. Cunningham, and A. Ashworth, *Mismatch repair deficient colorectal cancer in the era of personalized treatment*. Nat Rev Clin Oncol, 2010. 7(4): p. 197-208.
73. Pavelitz, T., L. Renfro, N. R. Foster, A. Caracol, P. Welsch, V. V. Lao, W. B. Grady, D. Niedzwiecki, L. B. Saltz, M. M. Bertagnolli, R. M. Goldberg, P. S. Rabinovitch, M. Emond, R. J. Monnat, Jr., and N. Maizels, *MRE11-deficiency associated with improved long-term disease free survival and overall survival in a subset of stage III colon cancer patients in randomized CALGB 89803 trial*. PLoS One, 2014. 9(10): p. e108483.
74. Ambroise, C. and G. J. McLachlan, *Selection bias in gene extraction on the basis of microarray gene-expression data*. Proc Natl Acad Sci USA, 2002. 99(10): p. 6562-6.
75. Simon, R., *Roadmap for developing and validating therapeutically relevant genomic classifiers*. J Clin Oncol, 2005. 23(29): p. 7332-41.
76. Trapnell, C., D. G. Hendrickson, M. Sauvageau, L. Goff, J. L. Rinn, and L. Pachter, *Differential analysis of gene regulation at transcript resolution with RNA-seq*. Nat Biotechnol, 2013. 31(1): p. 46-53.
77. Fumagalli, D., A. Blanchet-Cohen, D. Brown, C. Desmedt, D. Gacquer, S. Michiels, F. Rothe, S. Majjaj, R. Salgado, D. Larsimont, M. Ignatiadis, M. Maetens, M. Piccart, V. Detours, C. Sotiriou, and B. Haibe-Kains, *Transfer of clinically relevant gene expression signatures in breast cancer: from Affymetrix microarray to Illumina RNA-Sequencing technology*. BMC Genomics, 2014. 15: p. 1008.
78. Marioni, J. C., C. E. Mason, S. M. Mane, M. Stephens, and Y. Gilad, *RNA-seq: an assessment of technical reproducibility and comparison with gene expression arrays*. Genome Res, 2008. 18(9): p. 1509-17.
79. Wang, C., B. Gong, P. R. Bushel, J. Thierry-Mieg, D. Thierry-Mieg, J. Xu, H. Fang, H. Hong, J. Shen, Z. Su, J. Meehan, X. Li, L. Yang, H. Li, P. P. Labaj, D. P. Kreil, D. Megherbi, S. Gaj, F. Caiment, J. van Delft, J. Kleinjans, A. Scherer, V. Devanarayan, J. Wang, Y. Yang, H. R. Qian, L. J. Lancashire, M. Bessarabova, Y. Nikolsky, C. Furlanello, M. Chierici, D. Albanese, G. Jurman, S. Riccadonna, M. Filosi, R. Visintainer, K. K. Zhang, J. Li, J. H. Hsieh, D. L. Svoboda, J. C. Fuscoe, Y. Deng, L. Shi, R. S. Paules, S. S. Auerbach, and W. Tong, *The concordance between RNA-seq and microarray data depends on chemical treatment and transcript abundance*. Nat Biotechnol, 2014. 32(9): p. 926-32.
80. Zhao, P., H. Z. Yu, and J. H. Cai, *Clinical investigation of TROP-2 as an independent biomarker and potential therapeutic target in colon cancer*. Mol Med Rep, 2015. 12(3): p. 4364-9.
81. Fang, Y. J., Z. H. Lu, G. Q. Wang, Z. Z. Pan, Z. W. Zhou, J. P. Yun, M. F. Zhang, and D. S. Wan, *Elevated expressions of MMP7, TROP2, and survivin are associated with survival, disease recurrence, and liver metastasis of colon cancer*. Int J Colorectal Dis, 2009. 24(8): p. 875-84.
82. Starodub, A. N., A. J. Ocean, M. A. Shah, M. J. Guarino, V. J. Picozzi, Jr., L. T. Vandat, S. S. Thomas, S. V. Govindan, P. P. Maliakal, W. A. Wegener, S. A. Hamburger, R. M. Sharkey, and D. M. Goldenberg, *First-in-Human Trial of a Novel Anti-Trop-2 Antibody-SN-38 Conjugate, Sacituzumab Govitecan, for the Treatment of Diverse Metastatic Solid Tumors*. Clin Cancer Res, 2015. 21(17): p. 3870-8.
83. Pope, J. L., R. Ahmad, A. A. Bhat, M. K. Washington, A. B. Singh, and P. Dhawan, *Claudin-1 overexpression in intestinal epithelial cells enhances susceptibility to adenomatous polyposis coli-mediated colon tumorigenesis*. Mol Cancer, 2014. 13: p. 167.
84. Kim, J. C., Y. J. Ha, K. H. Tak, S. A. Roh, C. W. Kim, T. W. Kim, S. K. Kim, S. Y. Kim, D. H. Cho, and Y. S. Kim, *Complex Behavior of ALDH1A1 and IGFBP1 in Liver Metastasis from a Colorectal Cancer*. PLoS One, 2016. 11(5): p. e0155160.
85. Xiong, S., H. Tu, M. Kollareddy, V. Pant, Q. Li, Y. Zhang, J. G. Jackson, Y. A. Suh, A. C. Elizondo-Fraire, P. Yang, G. Chau, M. Tashakori, A. R. Wasylishen, Z. Ju, H. Solomon, V. Rotter, B. Liu, A. K. El-Naggar, L. A. Donehower, L. A. Martinez, and G. Lozano, *Pla2g16 phospholipase mediates gain-of-function activities of mutant p53*. Proc Natl Acad Sci USA, 2014. 111(30): p. 11145-50.
86. Chen, J., T. Lan, W. Zhang, L. Dong, N. Kang, S. Zhang, M. Fu, B. Liu, K. Liu, and Q. Zhan, *Feed-Forward Reciprocal Activation of PAFR and STAT3 Regulates Epithelial-Mesenchymal Transition in Non-Small Cell Lung Cancer*. Cancer Res, 2015. 75(19): p. 4198-210.
87. Walpole, R., R. Myers, and S. Myers, *Probability and statistics for engineers and scientists.*, 1998, Prentice Hall.
88. Savage, R., *Probability Inequalities of the Tchebycheff Type*. JOURNAL OF RESEARCH of the National Bureau of Standards—B. Mathematics and Mathematical Physics 1961. 65B(3): p. 211-226.
89. Higuchi, T. and J. R. Jass, *My approach to serrated polyps of the colorectum*. J Clin Pathol, 2004. 57(7): p. 682-6.
90. Beggs, A. D., A. Jones, N. Shepherd, A. Arnaout, C. Finlayson, A. M. Abulafi, D. G. Morton, G. M. Matthews, S. V. Hodgson, and I. P. Tomlinson, *Loss of expression and promoter methylation of SLIT2 are associated with sessile serrated adenoma formation*. PLoS Genet, 2013. 9(5): p. e1003488.
91. Shon, W. J., Y. K. Lee, J. H. Shin, E. Y. Choi, and D. M. Shin, *Severity of DSS—induced colitis is reduced in Ido1-deficient mice with down-regulation of TLR-MyD88-NF-kB transcriptional networks*. Sci Rep, 2015. 5: p. 17305.
92. Prendergast, G. C., C. Smith, S. Thomas, L. Mandik-Nayak, L. Laury-Kleintop, R. Metz, and A. J. Muller,

*Indoleamine 2,3-dioxygenase pathways of pathogenic inflammation and immune escape in cancer.* Cancer Immunol Immunother, 2014. 63(7): p. 721-35.
93. Prendergast, G. C., R. Metz, and A. J. Muller, *Towards a genetic definition of cancer-associated inflammation: role of the IDO pathway.* Am J Pathol, 2010. 176(5): p. 2082-7.
94. Trapnell, C., A. Roberts, L. Goff, G. Pertea, D. Kim, D. R. Kelley, H. Pimentel, S. L. Salzberg, J. L. Rinn, and L. Pachter, *Differential gene and transcript expression analysis of RNA-seq experiments with TopHat and Cufflinks.* Nat Protoc, 2012. 7(3): p. 562-78.
95. Langmead, B., C. Trapnell, M. Pop, and S. L. Salzberg, *Ultrafast and memory-efficient alignment of short DNA sequences to the human genome.* Genome Biol, 2009. 10(3): p. R25.
96. Irizarry, R. A., B. Hobbs, F. Collin, Y. D. Beazer-Barclay, K. J. Antonellis, U. Scherf, and T. P. Speed, *Exploration, normalization, and summaries of high density oligonucleotide array probe level data.* Biostatistics, 2003. 4(2): p. 249-64.
97. Mestdagh, P., P. Van Vlierberghe, A. De Weer, D. Muth, F. Westermann, F. Speleman, and J. Vandesompele, *A novel and universal method for microRNA RT-qPCR data normalization.* Genome Biol, 2009. 10(6): p. R64.

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

TABLE 1

Up-regulated pathways (GO categories).

| Category | Pathway | FDR |
|---|---|---|
| Cell adhesion | CALCIUM_INDEPENDENT_CELL_CELL_ADHESION | 0.022 |
| | CELL_SUBSTRATE_ADHERENS_JUNCTION | 0.042 |
| Cell growth and death | CELL_STRUCTURE_DISASSEMBLY_DURING_APOPTOSIS | 0.033 |
| | POSITIVE_REGULATION_OF_CELL_PROLIFERATION | 0.033 |
| Immune system | INFLAMMATORY_RESPONSE | 0.033 |
| | IMMUNOLOGICAL_SYNAPSE | 0.045 |
| Signal transduction | POSITIVE_REGULATION_OF_SECRETION | 0.045 |
| | G_PROTEIN_COUPLED_RECEPTOR_PROTEIN_SIGNALING | 0.042 |
| | SECOND_MESSENGER_MEDIATED_SIGNALING | 0.045 |
| Metabolism | AROMATIC_COMPOUND_METABOLIC_PROCESS | 0.022 |
| | HETEROCYCLE_METABOLIC_PROCESS | 0.022 |
| Differentiation | CELLULAR_MORPHOGENESIS_DURING_DIFFERENTIATION | 0.045 |
| Cellular component organization | EXTRACELLULAR_STRUCTURE_ORGANIZATION_AND_BIOGENESIS | 0.042 |
| Neuron development | AXONOGENESIS | 0.042 |
| | NEURITE_DEVELOPMENT | 0.045 |

TABLE 2

Performance of the nearest shrunken centroid classifier in classifying independent SSA/P and HP samples acquired by microarray platforms using 3 signatures.

| Platforms | Concordant genes | Signature size | Signature | Ilium. errors | Affy. errors |
|---|---|---|---|---|---|
| Training: RNA-seq Testing: Illumina | C4BPA, CEMIP, CHGA, CLDN1, CPE, DPP10, FSIP2, GRAMD1B, GRIN2D, IL2RG, KIZ, KLK7, MEGF6, MYCN, NTRK2, PLA2G16, RAMP1, SBSPON, SEMG1, SLC7A9, SPIRE1, TM4SF4 | 18 | C4BPA, CHGA, CLDN1, CPE, DPP10, GRAMD1 B, GRIN2D, KIZ, KLK7, MEGF6, MYCN, NTRK2, PLA2G16, SBSPON, SEMG1, SLC7A9, SPIRE1, TM4SF4 | 0 | — |
| Training: RNA-seq Testing: Affymetrix | CLDN1, FOXD1, IDO1, IL2RG, KIZ, LMO4, MEGF6, NTRK2, PIK3R3, PLA2G16, PRUNE2, PTAFR, SBSPON, SEMG1, SLC7A9, SPIRE1, TACSTD2, TPD52L1, TRIB2, ZIC2 | 16 | CLDN1, FOXD1, KIZ, MEGF6, NTRK2, PIK3R3, PLA2G16, PRUNE2, PTAFR, SBSPON, SEMG1, SLC7A9, SPIRE1, TACSTD2, TPD52L1, TRIB2 | — | 3 |
| Training: RNA-seq Testing: Illumina and Affymetrix | CHFR, CHGA, CLDN1, IL2RG, KIZ, MEGF6, NTRK2, PLA2G16, PTAFR, SBSPON, SEMG1, SLC7A9, SPIRE1, TACSTD2, VSIG1, ZIC2 | 13 | CHFR, CHGA, CLDN1, KIZ, MEGF6, NTRK2, PLA2G16, PTAFR, SBSPON, SEMG1, SLC7A9, SPIRE1, TACSTD2 | 0 | 3 |

TABLE 3

Genes included in the smallest 13 genes signature.

| Gene | log$_2$FC | FC | Description |
|---|---|---|---|
| SLC7A9 | 3.22 | 9.34 | solute carrier family 7 member 9 |
| SEMG1 | 2.95 | 7.72 | semenogelin I |
| MEGF6 | 2.66 | 6.34 | multiple EGF like domains 6 |
| TACSTD2 | 1.93 | 3.82 | tumor-associated calcium signal transducer 2 |
| CLDN1 | 1.85 | 3.59 | claudin 1 |
| SBSPON | 1.23 | 2.35 | somatomedin B and thrombospondin type 1 domain containing |
| PLA2G16 | 1.18 | 2.27 | phospholipase A2 group XVI |
| PTAFR | 1.08 | 2.11 | platelet activating factor receptor |
| KIZ | 0.98 | 1.98 | kizuna centrosomal protein |
| SPIRE1 | 0.82 | 1.76 | spire type actin nucleation factor 1 |
| CHFR | −0.62 | 0.65 | checkpoint with forkhead and ring finger domains, E3 ubiquitin protein ligase |
| CHGA | −1.63 | 0.32 | chromogranin A |
| NTRK2 | −2.32 | 0.20 | neurotrophic tyrosine kinase, receptor, type 2 |

TABLE 4

List of 139 genes DE between HP and SSA/P and between CR and SSA/P but not between CR and CL.

| | gene | locus | mean_HP | mean SSA/P | log$_2$FC | test_stat | p_value | p$_{adj}$_value | Description |
|---|---|---|---|---|---|---|---|---|---|
| 1 | KLK7 | chr19: 51479734-51487320 | 0.17 | 6.77 | 5.33 | 2.90 | 2.50E−04 | 1.03E−02 | kallikrein-related peptidase 7 |
| 2 | MUC6 | chr11: 1012823-1036706 | 0.10 | 2.41 | 4.58 | 2.92 | 5.00E−05 | 2.53E−03 | mucin 6, oligomeric mucus/gel-forming |
| 3 | GRIN2D | chr19: 48898131-48948188 | 0.50 | 5.36 | 3.43 | 2.87 | 5.00E−05 | 2.53E−03 | glutamate receptor, ionotropic, N-methyl D-aspartate 2D |
| 4 | SLC7A9 | chr19: 33321418-33360683 | 0.28 | 2.63 | 3.22 | 1.96 | 5.00E−05 | 2.53E−03 | solute carrier family 7 (amino acid transporter light chain, bo, +system), member 9 |
| 5 | SEMG1 | chr20: 43835637-43838414 | 0.38 | 2.97 | 2.95 | 1.99 | 5.00E−05 | 2.53E−03 | semenogelin I |
| 6 | AMH | chr19: 2249112-2252072 | 0.33 | 2.50 | 2.91 | 1.84 | 5.00E−05 | 2.53E−03 | anti-Mullerian hormone |
| 7 | MEGF6 | chr1: 3404505-3528059 | 1.45 | 9.20 | 2.66 | 2.81 | 5.00E−05 | 2.53E−03 | multiple EGF-like-domains 6 |
| 8 | ZIC2 | chr13: 100634025-100639019 | 0.40 | 2.33 | 2.56 | 1.71 | 5.00E−05 | 2.53E−03 | Zic family member 2 |
| 9 | TM4SF4 | chr3: 149192367-149221181 | 14.79 | 82.89 | 2.49 | 2.58 | 5.00E−05 | 2.53E−03 | transmembrane 4 L six family member 4 |
| 10 | CA9 | chr9: 35673914-35681154 | 0.73 | 4.02 | 2.46 | 1.38 | 5.00E−05 | 2.53E−03 | carbonic anhydrase IX |
| 11 | CXCL9 | chr4: 76922622-76928641 | 1.79 | 9.09 | 2.35 | 1.94 | 5.00E−05 | 2.53E−03 | chemokine (C-X-C motif) ligand 9 |
| 12 | CXCL10 | chr4: 76932332-77033955 | 2.62 | 13.27 | 2.34 | 1.35 | 1.40E−03 | 3.88E−02 | chemokine (C-X-C motif) ligand 10 |
| 13 | CLDN2 | chrX: 106143292-106174091 | 1.37 | 6.53 | 2.25 | 2.16 | 5.00E−05 | 2.53E−03 | claudin 2 |
| 14 | CNTD2 | chr19: 40728114-40732597 | 0.37 | 1.71 | 2.22 | 1.28 | 1.50E−04 | 6.74E−03 | cyclin N-terminal domain containing 2 |
| 15 | DEFA5 | chr8: 6912828-6914259 | 4.34 | 19.74 | 2.19 | 1.34 | 1.50E−04 | 6.74E−03 | defensin, alpha 5, Paneth cell-specific |
| 16 | FOXD1 | chr5: 72742084-72744352 | 0.70 | 3.15 | 2.17 | 1.39 | 1.00E−04 | 4.83E−03 | forkhead box D1 |
| 17 | NR0B2 | chr1: 27237974-27240567 | 1.54 | 6.46 | 2.07 | 1.65 | 5.00E−05 | 2.53E−03 | nuclear receptor subfamily 0, group B, member 2 |
| 18 | C4BPA | chr1: 207277606-207318317 | 1.27 | 5.25 | 2.04 | 1.69 | 5.00E−05 | 2.53E−03 | complement component 4 binding protein, alpha |
| 19 | MYCN | chr2: 16076386-16087129 | 0.53 | 2.16 | 2.03 | 1.50 | 5.00E−05 | 2.53E−03 | v-myc avian myelocytomatosis viral oncogene neuroblastoma derived homolog |
| 20 | PLA2G3 | chr22: 31530792-31536593 | 0.39 | 1.53 | 1.98 | 1.45 | 5.00E−05 | 2.53E−03 | phospholipase A2, group III |
| 21 | MSX2 | chr5: 174151574-174157902 | 0.32 | 1.26 | 1.97 | 1.26 | 4.50E−04 | 1.62E−02 | msh homeobox 2 |
| 22 | URAD | chr13: 28552242-28562774 | 3.45 | 13.28 | 1.95 | 1.41 | 5.00E−05 | 2.53E−03 | ureidoimidazoline (2-oxo-4-hydroxy-4-carboxy-5-) decarboxylase |

TABLE 4-continued

List of 139 genes DE between HP and SSA/P and between CR and SSA/P but not between CR and CL.

| | gene | locus | mean_HP | mean SSA/P | log$_2$FC | test_stat | p_value | p$_{adj}$_value | Description |
|---|---|---|---|---|---|---|---|---|---|
| 23 | TACSTD2 | chr1: 59041094-59043166 | 3.03 | 11.57 | 1.93 | 1.87 | 5.00E-05 | 2.53E-03 | tumor-associated calcium signal transducer 2 |
| 24 | NOS2 | chr17: 26083791-26127555 | 6.56 | 24.21 | 1.88 | 1.66 | 5.00E-05 | 2.53E-03 | nitric oxide synthase 2, inducible |
| 25 | CLDN1 | chr3: 190023489-190040235 | 2.38 | 8.54 | 1.85 | 2.16 | 5.00E-05 | 2.53E-03 | claudin 1 |
| 26 | TFF2 | chr21: 43766466-43771208 | 42.79 | 152.57 | 1.83 | 2.01 | 5.00E-05 | 2.53E-03 | trefoil factor 2 |
| 27 | TLX1 | chr10: 102891060-102897546 | 0.44 | 1.52 | 1.77 | 1.25 | 1.75E-03 | 4.53E-02 | T-cell leukemia homeobox 1 |
| 28 | KLK11 | chr19: 51525486-51531290 | 10.61 | 34.70 | 1.71 | 2.12 | 5.00E-05 | 2.53E-03 | kallikrein-related peptidase 11 |
| 29 | LOC102723854 | chr2: 43254991-43266682 | 0.52 | 1.68 | 1.69 | 0.87 | 1.90E-03 | 4.85E-02 | uncharacterized LOC102723854 |
| 30 | CYP4X1 | chr1: 47489239-47516423 | 0.31 | 0.97 | 1.66 | 1.14 | 5.00E-05 | 2.53E-03 | cytochrome P450, family 4, subfamily X, polypeptide 1 |
| 31 | MMP1 | chr11: 102654406-102714342 | 5.37 | 16.68 | 1.64 | 1.80 | 5.00E-05 | 2.53E-03 | matrix metallopeptidase 1 |
| 32 | ATG9B | chr7: 150688143-150721586 | 1.11 | 3.44 | 1.63 | 1.36 | 5.50E-04 | 1.86E-02 | autophagy related 9B |
| 33 | GRAMD1B | chr11: 123396343-123498479 | 0.78 | 2.37 | 1.60 | 1.62 | 5.00E-05 | 2.53E-03 | GRAM domain containing 1B |
| 34 | WDR72 | chr15: 53805937-54055075 | 0.79 | 2.37 | 1.59 | 1.52 | 5.00E-05 | 2.53E-03 | WD repeat domain 72 |
| 35 | APOL1 | chr22: 36649116-36663577 | 15.22 | 44.08 | 1.53 | 2.10 | 5.00E-05 | 2.53E-03 | apolipoprotein L, 1 |
| 36 | RNF183 | chr9: 116059372-116061320 | 0.70 | 1.88 | 1.43 | 0.96 | 4.50E-04 | 1.62E-02 | ring finger protein 183 |
| 37 | CEMIP | chr15: 81071711-81243999 | 1.45 | 3.91 | 1.43 | 1.66 | 5.00E-05 | 2.53E-03 | cell migration inducing protein, hyaluronan binding |
| 38 | LYPD5 | chr19: 44300078-44324808 | 0.66 | 1.77 | 1.43 | 1.07 | 4.50E-04 | 1.62E-02 | LY6/PLAUR domain containing 5 |
| 39 | KLK10 | chr19: 51515999-51523431 | 15.31 | 41.05 | 1.42 | 1.69 | 5.00E-05 | 2.53E-03 | kallikrein-related peptidase 10 |
| 40 | HLA-DRB5 | chr6: 32485153-32498006 | 7.40 | 19.67 | 1.41 | 1.36 | 5.00E-05 | 2.53E-03 | major histocompatibility complex, class II, DR beta 5 |
| 41 | RAMP1 | chr2: 238768186-238820755 | 2.09 | 5.53 | 1.41 | 1.21 | 3.00E-04 | 1.18E-02 | receptor (G protein-coupled) activity modifying protein 1 |
| 42 | IDO1 | chr8: 39771327-39786309 | 2.18 | 5.76 | 1.40 | 1.32 | 5.00E-05 | 2.53E-03 | indoleamine 2,3-dioxygenase 1 |
| 43 | NBPF7 | chr1: 120377387-120387503 | 1.43 | 3.78 | 1.40 | 1.29 | 5.00E-05 | 2.53E-03 | neuroblastoma breakpoint family, member 7 |
| 44 | UBD | chr6_qbl_hap6: 826706-831021 | 6.92 | 17.76 | 1.36 | 1.25 | 5.00E-05 | 2.53E-03 | ubiquitin D |
| 45 | SLFN5 | chr17: 33570085-33594761 | 1.05 | 2.60 | 1.31 | 1.40 | 5.00E-05 | 2.53E-03 | schlafen family member 5 |
| 46 | APOD | chr3: 195295572-195311076 | 4.78 | 11.69 | 1.29 | 1.22 | 5.00E-05 | 2.53E-03 | apolipoprotein D |
| 47 | GBP4 | chr1: 89646830-89664633 | 2.19 | 5.23 | 1.26 | 1.51 | 5.00E-05 | 2.53E-03 | guanylate binding protein 4 |
| 48 | CARD6 | chr5: 40841409-40855456 | 1.51 | 3.58 | 1.24 | 1.41 | 5.00E-05 | 2.53E-03 | caspase recruitment domain family, member 6 |
| 49 | SBSPON | chr8: 73976777-74005507 | 0.70 | 1.63 | 1.23 | 1.17 | 5.00E-05 | 2.53E-03 | somatomedin B and thrombospondin, type 1 domain containing |
| 50 | LCN2 | chr9: 130911731-130915734 | 242.72 | 565.65 | 1.22 | 1.21 | 5.00E-05 | 2.53E-03 | lipocalin 2 |
| 51 | TRIB2 | chr2: 12856997-12882858 | 3.63 | 8.27 | 1.19 | 1.48 | 5.00E-05 | 2.53E-03 | tribbles pseudokinase 2 |
| 52 | PLA2G16 | chr11: 63341943-63381941 | 10.94 | 24.83 | 1.18 | 1.41 | 5.00E-05 | 2.53E-03 | phospholipase A2, group XVI |
| 53 | TPD52L1 | chr6: 125474878-125584644 | 6.24 | 14.12 | 1.18 | 1.45 | 5.00E-05 | 2.53E-03 | tumor protein D52-like 1 |
| 54 | CFB | chr6_ssto_hap7: 3246430-3252571 | 12.33 | 27.89 | 1.18 | 1.67 | 5.00E-05 | 2.53E-03 | complement factor B |
| 55 | TMEM92 | chr17: 48348766-48358846 | 4.61 | 10.25 | 1.15 | 1.43 | 5.00E-05 | 2.53E-03 | transmembrane protein 92 |
| 56 | CASP5 | chr11: 104864966-104893895 | 10.67 | 23.11 | 1.11 | 1.29 | 5.00E-05 | 2.53E-03 | caspase 5, apoptosis-related cysteine peptidase |
| 57 | GPD1 | chr12: 50497601-50505103 | 3.30 | 7.08 | 1.10 | 1.27 | 5.00E-05 | 2.53E-03 | glycerol-3-phosphate dehydrogenase 1 (soluble) |
| 58 | VSIG1 | chrX: 107288199-107322414 | 13.32 | 28.55 | 1.10 | 1.09 | 1.60E-03 | 4.26E-02 | V-set and immunoglobulin domain containing 1 |

TABLE 4-continued

List of 139 genes DE between HP and SSA/P and between CR and SSA/P but not between CR and CL.

| | gene | locus | mean_HP | mean SSA/P | log$_2$FC | test_stat | p_value | p$_{adj}$_value | Description |
|---|---|---|---|---|---|---|---|---|---|
| 59 | CCL22 | chr16: 57392694-57400102 | 0.89 | 1.90 | 1.09 | 0.91 | 7.00E−04 | 2.26E−02 | chemokine (C-C motif) ligand 22 |
| 60 | TRNP1 | chr1: 27320194-27327377 | 4.52 | 9.56 | 1.08 | 1.06 | 5.50E−04 | 1.86E−02 | TMF1-regulated nuclear protein 1 |
| 61 | LAMP3 | chr3: 182840002-182880667 | 0.97 | 2.04 | 1.08 | 0.99 | 9.50E−04 | 2.87E−02 | lysosomal-associated membrane protein 3 |
| 62 | PTAFR | chr1: 28473676-28520447 | 4.89 | 10.32 | 1.08 | 1.52 | 5.00E−05 | 2.53E−03 | platelet-activating factor receptor |
| 63 | CNGA1 | chr4: 47937993-48014961 | 1.36 | 2.84 | 1.06 | 1.06 | 8.00E−04 | 2.53E−02 | cyclic nucleotide gated channel alpha 1 |
| 64 | GZMA | chr5: 54398473-54406080 | 8.49 | 17.42 | 1.04 | 1.20 | 5.00E−05 | 2.53E−03 | granzyme A (granzyme 1, cytotoxic T-lymphocyte-associated serine esterase 3) |
| 65 | NXF3 | chrX: 102330749-102348022 | 3.67 | 7.47 | 1.03 | 1.11 | 2.00E−04 | 8.55E−03 | nuclear RNA export factor 3 |
| 66 | TMEM45A | chr3: 100211462-100296285 | 2.33 | 4.73 | 1.02 | 0.87 | 1.70E−03 | 4.44E−02 | transmembrane protein 45A |
| 67 | FKBP10 | chr17: 39968961-39979469 | 5.93 | 11.80 | 0.99 | 1.41 | 5.00E−05 | 2.53E−03 | FK506 binding protein 10, 65 kDa |
| 68 | KIZ | chr20: 21106623-21227258 | 2.73 | 5.40 | 0.98 | 1.17 | 2.00E−04 | 8.55E−03 | kizuna centrosomal protein |
| 69 | TESC | chr12: 117476727-117537251 | 4.93 | 9.66 | 0.97 | 0.93 | 1.25E−03 | 3.53E−02 | tescalcin |
| 70 | ZNF488 | chr10: 48355088-48373866 | 0.83 | 1.62 | 0.96 | 0.88 | 1.50E−03 | 4.05E−02 | zinc finger protein 488 |
| 71 | GOLGA7B | chr10: 99609994-99790585 | 0.79 | 1.53 | 0.96 | 0.97 | 8.50E−04 | 2.66E−02 | golgin A7 family, member B |
| 72 | CCL2 | chr17: 32582295-32584220 | 11.11 | 21.24 | 0.93 | 1.04 | 2.00E−04 | 8.55E−03 | chemokine (C-C motif) ligand 2 |
| 73 | HBB | chr11: 5246695-5248301 | 18.21 | 34.40 | 0.92 | 0.98 | 5.50E−04 | 1.86E−02 | hemoglobin, beta |
| 74 | GALNT6 | chr12: 51745832-51909547 | 6.65 | 12.55 | 0.92 | 1.32 | 5.00E−05 | 2.53E−03 | polypeptide N-acetyl-galactosaminyltransferase 6 |
| 75 | BIRC3 | chr11: 102188180-102210635 | 10.86 | 20.43 | 0.91 | 1.30 | 5.00E−05 | 2.53E−03 | baculoviral IAP repeat containing 3 |
| 76 | GBP2 | chr1: 89571815-89591842 | 13.55 | 25.31 | 0.90 | 1.51 | 5.00E−05 | 2.53E−03 | guanylate binding protein 2, interferon-inducible |
| 77 | SEC16B | chr1: 177898241-177939050 | 3.65 | 6.81 | 0.90 | 1.22 | 5.00E−05 | 2.53E−03 | SEC16 homolog B, endoplasmic reticulum export factor |
| 78 | EPSTI1 | chr13: 43460523-43566407 | 4.24 | 7.85 | 0.89 | 1.26 | 5.00E−05 | 2.53E−03 | epithelial stromal interaction 1 (breast) |
| 79 | XAF1 | chr17: 6659155-6678964 | 7.25 | 13.42 | 0.89 | 1.36 | 5.00E−05 | 2.53E−03 | XIAP associated factor 1 |
| 80 | GBP1 | chr1: 89517986-89531043 | 6.29 | 11.36 | 0.85 | 1.12 | 1.00E−04 | 4.83E−03 | guanylate binding protein 1, interferon-inducible |
| 81 | EVPL | chr17: 74002926-74023507 | 7.91 | 14.27 | 0.85 | 1.41 | 5.00E−05 | 2.53E−03 | envoplakin |
| 82 | IFIT3 | chr10: 91087575-91100725 | 3.66 | 6.60 | 0.85 | 1.06 | 2.00E−04 | 8.55E−03 | interferon-induced protein with tetratricopeptide repeats 3 |
| 83 | KIFC3 | chr16: 57792128-57836439 | 2.83 | 5.07 | 0.84 | 1.03 | 6.50E−04 | 2.11E−02 | kinesin family member C3 |
| 84 | RAB27B | chr18: 52495707-52562747 | 4.69 | 8.31 | 0.82 | 1.39 | 5.00E−05 | 2.53E−03 | RAB27B, member RAS oncogene family |
| 85 | SPIRE1 | chr18: 12446510-12657912 | 2.19 | 3.87 | 0.82 | 1.09 | 1.50E−04 | 6.74E−03 | spire-type actin nucleation factor 1 |
| 86 | TBX3 | chr12: 115108058-115121969 | 5.34 | 9.19 | 0.78 | 1.11 | 5.00E−05 | 2.53E−03 | T-box 3 |
| 87 | OAS2 | chr12: 113416273-113449528 | 5.11 | 8.70 | 0.77 | 1.02 | 5.50E−04 | 1.86E−02 | 2'-5'-oligoadenylate synthetase 2, 69/71 kDa |
| 88 | YBX2 | chr17: 7191570-7197876 | 9.82 | 16.73 | 0.77 | 0.91 | 9.00E−04 | 2.76E−02 | Y box binding protein 2 |
| 89 | DCDC2 | chr6: 24171982-24383520 | 2.88 | 4.90 | 0.77 | 0.97 | 1.50E−03 | 4.05E−02 | doublecortin domain containing 2 |
| 90 | MX1 | chr21: 42792484-42831141 | 10.08 | 16.99 | 0.75 | 1.09 | 5.00E−05 | 2.53E−03 | MX dynamin-like GTPase 1 |
| 91 | UNC5CL | chr6: 40994639-41006938 | 4.00 | 6.60 | 0.72 | 0.93 | 9.00E−04 | 2.76E−02 | unc-5 family C-terminal like |
| 92 | IFI6 | chr1: 27992571-27998724 | 29.98 | 49.49 | 0.72 | 0.95 | 1.15E−03 | 3.29E−02 | interferon, alpha-inducible protein 6 |
| 93 | CROT | chr7: 86974950-87029112 | 6.33 | 10.43 | 0.72 | 0.99 | 1.15E−03 | 3.29E−02 | carnitine O-octanoyltransferase |

TABLE 4-continued

List of 139 genes DE between HP and SSA/P and between CR and SSA/P but not between CR and CL.

| | gene | locus | mean_HP | mean SSA/P | log$_2$FC | test_stat | p_value | p$_{adj}$_value | Description |
|---|---|---|---|---|---|---|---|---|---|
| 94 | SAMD9L | chr7: 92759367-92777680 | 6.11 | 10.00 | 0.71 | 1.10 | 5.00E−05 | 2.53E−03 | sterile alpha motif domain containing 9-like |
| 95 | TNFSF15 | chr9: 117546914-117568408 | 6.06 | 9.90 | 0.71 | 1.03 | 3.50E−04 | 1.32E−02 | tumor necrosis factor (ligand) superfamily, member 15 |
| 96 | PRUNE2 | chr9: 79226291-79521003 | 1.24 | 2.02 | 0.71 | 1.00 | 2.50E−04 | 1.03E−02 | prune homolog 2 (*Drosophila*) |
| 97 | ADGRG6 | chr6: 142623055-142767403 | 9.79 | 15.85 | 0.70 | 1.07 | 6.50E−04 | 2.11E−02 | adhesion G protein-coupled receptor G6 |
| 98 | ANO1 | chr11: 69924407-70035652 | 5.25 | 8.45 | 0.69 | 0.99 | 4.50E−04 | 1.62E−02 | anoctamin 1, calcium activated chloride channel |
| 99 | ERO1A | chr14: 53108604-53162041 | 43.91 | 70.11 | 0.68 | 1.10 | 6.00E−04 | 1.99E−02 | endoplasmic reticulum oxidoreductase alpha |
| 100 | SLC7A7 | chr14: 23242431-23289020 | 7.94 | 12.66 | 0.67 | 0.92 | 1.75E−03 | 4.53E−02 | solute carrier family 7 (amino acid transporter light chain, y + L system), member 7 |
| 101 | PIK3R3 | chr1: 46505811-46598708 | 2.63 | 4.17 | 0.67 | 0.91 | 1.55E−03 | 4.17E−02 | phosphoinositide-3-kinase, regulatory subunit 3 (gamma) |
| 102 | CA13 | chr8: 86157715-86196302 | 4.69 | 7.42 | 0.66 | 0.94 | 1.10E−03 | 3.22E−02 | carbonic anhydrase XIII |
| 103 | RHOBTB1 | chr10: 62629197-62761198 | 6.43 | 10.16 | 0.66 | 0.95 | 8.00E−04 | 2.53E−02 | Rho-related BTB domain containing 1 |
| 104 | IRS2 | chr13: 110406183-110438914 | 9.42 | 14.73 | 0.65 | 1.04 | 1.50E−04 | 6.74E−03 | insulin receptor substrate 2 |
| 105 | MYRF | chr11: 61520120-61555989 | 13.30 | 20.75 | 0.64 | 0.99 | 5.00E−04 | 1.75E−02 | myelin regulatory factor |
| 106 | IFI27 | chr14: 94577078-94583036 | 715.46 | 1115.84 | 0.64 | 0.92 | 9.50E−04 | 2.87E−02 | interferon, alpha-inducible protein 27 |
| 107 | FSIP2 | chr2: 186584600-186698016 | 1.29 | 2.01 | 0.64 | 1.09 | 1.15E−03 | 3.29E−02 | fibrous sheath interacting protein 2 |
| 108 | LMO4 | chr1: 87794150-87814607 | 7.65 | 11.83 | 0.63 | 1.00 | 6.50E−04 | 2.11E−02 | LIM domain only 4 |
| 109 | IMPDH1 | chr7: 128032330-128050036 | 13.26 | 20.52 | 0.63 | 0.95 | 9.50E−04 | 2.87E−02 | IMP (inosine 5'-monophosphate) dehydrogenase 1 |
| 110 | APOL2 | chr22: 36622254-36636000 | 16.40 | 25.15 | 0.62 | 0.96 | 5.00E−04 | 1.75E−02 | apolipoprotein L, 2 |
| 111 | PARP14 | chr3: 122399671-122449687 | 10.79 | 16.24 | 0.59 | 0.93 | 9.00E−04 | 2.76E−02 | poly (ADP-ribose) polymerase family, member 14 |
| 112 | SLC5A1 | chr22: 32439018-32509011 | 12.26 | 18.42 | 0.59 | 0.91 | 1.30E−03 | 3.64E−02 | solute carrier family 5 (sodium/glucose cotransporter), member 1 |
| 113 | VSIG2 | chr11: 124617369-124622109 | 282.20 | 196.63 | −0.52 | −0.84 | 1.60E−03 | 4.26E−02 | V-set and immunoglobulin domain containing 2 |
| 114 | C11orf86 | chr11: 66742753-66744479 | 101.24 | 68.68 | −0.56 | −0.91 | 1.05E−03 | 3.10E−02 | chromosome 11 open reading frame 86 |
| 115 | AK1 | chr9: 130628758-130640022 | 66.42 | 44.84 | −0.57 | −0.95 | 3.00E−04 | 1.18E−02 | adenylate kinase 1 |
| 116 | AIM1L | chr1: 26648349-26680621 | 13.43 | 8.94 | −0.59 | −0.97 | 4.50E−04 | 1.62E−02 | absent in melanoma 1 -like |
| 117 | CHFR | chr12: 133416937-133464204 | 13.81 | 8.96 | −0.62 | −0.93 | 9.50E−04 | 2.87E−02 | checkpoint with forkhead and ring finger domains, E3 ubiquitin protein ligase |
| 118 | IL2RG | chrX: 70327253-70331481 | 184.79 | 116.15 | −0.67 | −1.00 | 1.00E−04 | 4.83E−03 | interleukin 2 receptor, gamma |
| 119 | CSRNP1 | chr3: 39183341-39195102 | 13.00 | 7.76 | −0.75 | −1.08 | 5.00E−05 | 2.53E−03 | cysteine-serine-rich nuclear protein 1 |
| 120 | RASL11A | chr13: 27844463-27847827 | 28.05 | 16.35 | −0.78 | −1.14 | 5.00E−05 | 2.53E−03 | RAS-like, family 11, member A |
| 121 | TRIM40 | chr6_ssto_hap7: 1434344-1446965 | 8.23 | 4.75 | −0.79 | −0.95 | 1.15E−03 | 3.29E−02 | tripartite motif containing 40 |
| 122 | CCND1 | chr11: 69455872-69469242 | 35.15 | 20.10 | −0.81 | −1.29 | 5.00E−05 | 2.53E−03 | cyclin D1 |
| 123 | NEU4 | chr2: 242750159-242758739 | 22.57 | 11.83 | −0.93 | −1.38 | 2.00E−04 | 8.55E−03 | sialidase 4 |
| 124 | JUNB | chr19: 12902309-12904125 | 155.87 | 81.48 | −0.94 | −1.35 | 5.00E−05 | 2.53E−03 | jun B proto-oncogene |
| 125 | SFRP1 | chr8: 41119475-41166990 | 1.99 | 1.03 | −0.95 | −0.91 | 1.30E−03 | 3.64E−02 | secreted frizzled-related protein 1 |
| 126 | WSCD1 | chr17: 5973933-6027747 | 8.34 | 4.32 | −0.95 | −1.34 | 5.00E−05 | 2.53E−03 | WSC domain containing 1 |
| 127 | SHROOM2 | chrX: 9754495-9917481 | 1.28 | 0.65 | −0.98 | −0.98 | 1.05E−03 | 3.10E−02 | shroom family member 2 |

TABLE 4-continued

List of 139 genes DE between HP and SSA/P and between CR and SSA/P but not between CR and CL.

| | gene | locus | mean_HP | mean SSA/P | log$_2$FC | test_stat | p_value | p$_{adj}$_value | Description |
|---|---|---|---|---|---|---|---|---|---|
| 128 | RNASE1 | chr14: 21269514-21271036 | 389.26 | 195.05 | −1.00 | −1.30 | 5.00E−05 | 2.53E−03 | ribonuclease, RNase A family, 1 (pancreatic) |
| 129 | C2orf54 | chr2: 241825464-241835573 | 3.81 | 1.89 | −1.01 | −1.00 | 1.20E−03 | 3.40E−02 | chromosome 2 open reading frame 54 |
| 130 | CPE | chr4: 166300096-166419482 | 17.08 | 8.21 | −1.06 | −1.48 | 5.00E−05 | 2.53E−03 | carboxypeptidase E |
| 131 | SLC6A14 | chrX: 115567746-115592625 | 24.17 | 10.92 | −1.15 | −1.67 | 5.00E−05 | 2.53E−03 | solute carrier family 6 (amino acid transporter), member 14 |
| 132 | HBEGF | chr5: 139712427-139726188 | 26.40 | 11.52 | −1.20 | −1.50 | 5.00E−05 | 2.53E−03 | heparin-binding EGF-like growth factor |
| 133 | BAMBI | chr10: 28966423-28971868 | 20.28 | 8.51 | −1.25 | −1.68 | 5.00E−05 | 2.53E−03 | BMP and activin membrane-bound inhibitor |
| 134 | DPP10 | chr2: 115199898-116602326 | 1.39 | 0.58 | −1.27 | −0.98 | 1.80E−03 | 4.63E−02 | dipeptidyl-peptidase 10 (non-functional) |
| 135 | CHGA | chr14: 93389444-93401638 | 219.86 | 71.16 | −1.63 | −1.87 | 5.00E−05 | 2.53E−03 | chromogranin A |
| 136 | NEUROD1 | chr2: 182540832-182545392 | 1.56 | 0.45 | −1.79 | −1.32 | 5.00E−05 | 2.53E−03 | neuronal differentiation 1 |
| 137 | VLDLR | chr9: 2535654-2654485 | 7.39 | 2.12 | −1.80 | −1.94 | 5.00E−05 | 2.53E−03 | very low density lipoprotein receptor |
| 138 | RPPH1 | chr14: 20811229-20811570 | 123.42 | 30.35 | −2.02 | −1.32 | 2.00E−04 | 8.55E−03 | ribonuclease P RNA component H1 |
| 139 | NTRK2 | chr9: 87283372-87641985 | 3.92 | 0.78 | −2.32 | −2.35 | 5.00E−05 | 2.53E−03 | neurotrophic tyrosine kinase, receptor, type 2 |

TABLE 5

The list of 134 genes exclusively DE between HP and SSA/P.

| | gene | locus | mean_HP | mean SSA/P | log$_2$FC | test_stat | p_value | p$_{adj}$_value | Description |
|---|---|---|---|---|---|---|---|---|---|
| 1 | MIR4800 | chr4: 2249159-2263739 | 0.00 | 37.38 | Inf | NA | 1.45E−03 | 3.98E−02 | microRNA 4800 |
| 2 | KLK8 | chr19: 51499263-51504958 | 0.17 | 4.74 | 4.83 | 1.36 | 1.65E−03 | 4.36E−02 | kallikrein-related peptidase 8 |
| 3 | DUSP27 | chr1: 167064086-167098402 | 0.36 | 6.91 | 4.25 | 2.54 | 5.00E−05 | 2.53E−03 | dual specificity phosphatase 27 (putative) |
| 4 | ANXA10 | chr4: 169013687-169108893 | 6.18 | 51.85 | 3.07 | 3.11 | 5.00E−05 | 2.53E−03 | annexin A10 |
| 5 | CLDN18 | chr3: 137717657-137752494 | 0.21 | 1.37 | 2.73 | 1.73 | 8.50E−04 | 2.66E−02 | claudin 18 |
| 6 | NMUR2 | chr5: 151771101-151784840 | 0.26 | 1.59 | 2.64 | 1.34 | 5.00E−05 | 2.53E−03 | neuromedin U receptor 2 |
| 7 | HLA-DQB1 | chr6_qbl_hap6: 3858964-3866565 | 4.59 | 23.80 | 2.37 | 2.45 | 5.00E−05 | 2.53E−03 | major histocompatibility complex, class II, DQ beta 1 |
| 8 | FEZF1-AS1 | chr7: 121941447-121950131 | 0.67 | 3.11 | 2.21 | 1.67 | 5.00E−05 | 2.53E−03 | FEZF1 antisense RNA 1 |
| 9 | SULT1C2P1 | chr1: 108938693-108970254 | 0.25 | 1.17 | 2.20 | 1.25 | 4.50E−04 | 1.62E−02 | sulfotransferase family, cytosolic, 1C, member 2 pseudogene 1 |
| 10 | SLCO1B3 | chr12: 20963637-21069843 | 0.43 | 1.92 | 2.16 | 1.77 | 1.00E−04 | 4.83E−03 | solute carrier organic anion transporter family, member 1B3 |
| 11 | TDO2 | chr4: 156824844-156841558 | 0.51 | 1.64 | 1.69 | 1.29 | 5.00E−05 | 2.53E−03 | tryptophan 2,3-dioxygenase |
| 12 | TCN1 | chr11: 59620280-59634041 | 2.32 | 7.25 | 1.64 | 1.58 | 5.00E−05 | 2.53E−03 | transcobalamin I (vitamin B12 binding protein, R binder family) |
| 13 | CCL8 | chr17: 32646065-32648421 | 1.47 | 4.41 | 1.59 | 1.38 | 5.00E−05 | 2.53E−03 | chemokine (C-C motif) ligand 8 |
| 14 | NAT8B | chr2: 73927635-73928467 | 1.88 | 5.33 | 1.51 | 1.11 | 5.00E−05 | 2.53E−03 | N-acetyltransferase 8B (GCN5-related, putative, gene/pseudogene) |
| 15 | PSCA | chr8: 143751725-143764145 | 11.23 | 31.23 | 1.48 | 1.58 | 5.00E−05 | 2.53E−03 | prostate stem cell antigen |
| 16 | LRRIQ4 | chr3: 169539709-169555560 | 0.46 | 1.26 | 1.45 | 1.07 | 1.50E−04 | 6.74E−03 | leucine-rich repeats and IQ motif containing 4 |
| 17 | CTHRC1 | chr8: 104383742-104395232 | 0.85 | 2.31 | 1.44 | 1.09 | 2.50E−04 | 1.03E−02 | collagen triple helix repeat containing 1 |
| 18 | SRMS | chr20: 62171276-62178857 | 0.95 | 2.42 | 1.36 | 1.27 | 5.00E−05 | 2.53E−03 | src-related kinase lacking C-terminal regulatory tyrosine and N-terminal myristylation sites |

TABLE 5-continued

The list of 134 genes exclusively DE between HP and SSA/P.

| | gene | locus | mean_HP | mean SSA/P | log$_2$FC | test_stat | p_value | p$_{adj}$_value | Description |
|---|---|---|---|---|---|---|---|---|---|
| 19 | MMP10 | chr11: 102641232-102651359 | 0.56 | 1.41 | 1.33 | 0.94 | 7.50E-04 | 2.40E-02 | matrix metallopeptidase 10 |
| 20 | DMBT1 | chr10: 124320180-124403252 | 4.66 | 11.35 | 1.29 | 1.48 | 5.00E-05 | 2.53E-03 | deleted in malignant brain tumors 1 |
| 21 | TRHDE | chr12: 72647286-73059422 | 1.17 | 2.85 | 1.28 | 1.46 | 5.00E-05 | 2.53E-03 | thyrotropin-releasing hormone degrading enzyme |
| 22 | SLC52A1 | chr17: 4935896-4938727 | 0.51 | 1.23 | 1.27 | 0.93 | 5.50E-04 | 1.86E-02 | solute carrier family 52 (riboflavin transporter), member 1 |
| 23 | PRAP1 | chr10: 135160843-135166187 | 81.41 | 188.04 | 1.21 | 1.88 | 5.00E-05 | 2.53E-03 | proline-rich acidic protein 1 |
| 24 | C4orf48 | chr4: 2043719-2045697 | 21.05 | 48.12 | 1.19 | 1.18 | 1.50E-04 | 6.74E-03 | chromosome 4 open reading frame 48 |
| 25 | CD244 | chr1: 160799949-160832692 | 0.59 | 1.24 | 1.07 | 0.89 | 1.50E-03 | 4.05E-02 | CD244 molecule, natural killer cell receptor 2B4 |
| 26 | S100A9 | chr1: 153330329-153333503 | 8.46 | 17.45 | 1.04 | 1.00 | 2.50E-04 | 1.03E-02 | S100 calcium binding protein A9 |
| 27 | RBBP8NL | chr20: 60985292-61002629 | 1.77 | 3.63 | 1.03 | 1.22 | 5.00E-05 | 2.53E-03 | RBBP8 N-terminal like |
| 28 | MNDA | chr1: 158801167-158819270 | 1.72 | 3.32 | 0.95 | 0.95 | 5.50E-04 | 1.86E-02 | myeloid cell nuclear differentiation antigen |
| 29 | PRKXP1 | chr15: 101087956-101099488 | 0.71 | 1.36 | 0.94 | 1.02 | 5.00E-04 | 1.75E-02 | protein kinase, X-linked, pseudogene 1 |
| 30 | NXPE2 | chr11: 114549199-114577652 | 2.50 | 4.66 | 0.90 | 0.95 | 1.05E-03 | 3.10E-02 | neurexophilin and PC-esterase domain family, member 2 |
| 31 | KLRB1 | chr12: 9747869-9760497 | 11.08 | 20.55 | 0.89 | 1.07 | 2.00E-04 | 8.55E-03 | killer cell lectin-like receptor subfamily B, member 1 |
| 32 | TRIP6 | chr7: 100464949-100471076 | 12.10 | 22.25 | 0.88 | 1.21 | 5.00E-05 | 2.53E-03 | thyroid hormone receptor interactor 6 |
| 33 | C3 | chr19: 6677845-6720662 | 6.29 | 11.51 | 0.87 | 1.21 | 5.00E-05 | 2.53E-03 | complement component 3 |
| 34 | PEAR1 | chr1: 156863522-156886226 | 1.25 | 2.28 | 0.87 | 0.92 | 9.00E-04 | 2.76E-02 | platelet endothelial aggregation receptor 1 |
| 35 | ANK3 | chr10: 61786055-62493284 | 4.83 | 8.57 | 0.83 | 1.30 | 5.00E-05 | 2.53E-03 | ankyrin 3, node of Ranvier (ankyrin G) |
| 36 | PRKCDBP | chr11: 6340175-6341740 | 6.23 | 11.03 | 0.82 | 0.96 | 1.80E-03 | 4.63E-02 | protein kinase C, delta binding protein |
| 37 | CSF3R | chr1: 36931643-36948915 | 1.10 | 1.94 | 0.82 | 0.89 | 1.70E-03 | 4.44E-02 | colony stimulating factor 3 receptor (granulocyte) |
| 38 | DDX60 | chr4: 169137441-169239958 | 10.72 | 18.82 | 0.81 | 1.25 | 5.00E-05 | 2.53E-03 | DEAD (Asp-Glu-Ala-Asp) box polypeptide 60 |
| 39 | GPT2 | chr16: 46918307-46965201 | 7.21 | 12.44 | 0.79 | 1.16 | 1.00E-04 | 4.83E-03 | glutamic pyruvate transaminase (alanine aminotransferase) 2 |
| 40 | SMOC2 | chr6: 168841830-169068674 | 4.50 | 7.76 | 0.78 | 1.00 | 1.50E-04 | 6.74E-03 | SPARC related modular calcium binding 2 |
| 41 | MX2 | chr21: 42733949-42780869 | 2.27 | 3.87 | 0.77 | 0.89 | 1.15E-03 | 3.29E-02 | MX dynamin-like GTPase 2 |
| 42 | FUOM | chr10: 135168657-135171529 | 20.79 | 35.24 | 0.76 | 0.90 | 1.65E-03 | 4.36E-02 | fucose mutarotase |
| 43 | PLEKHH2 | chr2: 43864438-43995126 | 1.35 | 2.24 | 0.73 | 0.94 | 9.00E-04 | 2.76E-02 | pleckstrin homology domain containing, family H (with MyTH4 domain) member 2 |
| 44 | PRRT2 | chr16: 29823408-29827202 | 8.71 | 14.40 | 0.72 | 1.02 | 1.50E-04 | 6.74E-03 | proline-rich transmembrane protein 2 |
| 45 | CCDC88A | chr2: 55514977-55647057 | 0.98 | 1.59 | 0.70 | 0.95 | 1.20E-03 | 3.40E-02 | coiled-coil domain containing 88A |
| 46 | ENPP1 | chr6: 132129155-132216295 | 2.38 | 3.87 | 0.70 | 1.04 | 2.00E-04 | 8.55E-03 | ectonucleotide pyrophosphatase/phosphodiesterase 1 |
| 47 | LCP1 | chr13: 46700057-46756459 | 17.79 | 28.70 | 0.69 | 1.09 | 5.00E-05 | 2.53E-03 | lymphocyte cytosolic protein 1 (L-plastin) |
| 48 | DISP2 | chr15: 40650433-40663256 | 6.09 | 9.75 | 0.68 | 1.00 | 4.50E-04 | 1.62E-02 | dispatched homolog 2 (Drosophila) |
| 49 | ATHL1 | chr11: 289137-295688 | 10.02 | 15.98 | 0.67 | 1.05 | 2.00E-04 | 8.55E-03 | ATH1, acid trehalase-like 1 (yeast) |
| 50 | LOC730102 | chr1: 177975274-178007142 | 12.59 | 19.86 | 0.66 | 1.06 | 2.00E-04 | 8.55E-03 | quinone oxidoreductase-like protein 2 pseudogene |
| 51 | ACE2 | chrX: 15579155-15620192 | 8.39 | 13.02 | 0.63 | 0.98 | 7.00E-04 | 2.26E-02 | angiotensin I converting enzyme 2 |
| 52 | ABCA7 | chr19: 1040101-1065570 | 4.22 | 6.52 | 0.63 | 1.02 | 3.00E-04 | 1.18E-02 | ATP-binding cassette, sub-family A (ABC1), member 7 |
| 53 | PTPRC | chr1: 198608097-198726605 | 9.24 | 14.12 | 0.61 | 0.97 | 8.00E-04 | 2.53E-02 | protein tyrosine phosphatase, receptor type, C |

TABLE 5-continued

The list of 134 genes exclusively DE between HP and SSA/P.

| | gene | locus | mean_HP | mean SSA/P | log$_2$FC | test_stat | p_value | p$_{adj}$_value | Description |
|---|---|---|---|---|---|---|---|---|---|
| 54 | LAMB2 | chr3: 49158546-49170599 | 9.70 | 14.52 | 0.58 | 0.92 | 6.50E−04 | 2.11E−02 | laminin, beta 2 (laminin S) |
| 55 | ITGAV | chr2: 187454789-187545629 | 13.14 | 19.55 | 0.57 | 0.92 | 1.60E−03 | 4.26E−02 | integrin, alpha V |
| 56 | CNNM4 | chr2: 97426638-97477628 | 62.68 | 43.69 | −0.52 | −0.85 | 1.55E−03 | 4.17E−02 | cyclin and CBS domain divalent metal cation transport mediator 4 |
| 57 | CYP2J2 | chr1: 60358979-60392423 | 29.69 | 20.41 | −0.54 | −0.88 | 1.50E−03 | 4.05E−02 | cytochrome P450, family 2, subfamily J, polypeptide 2 |
| 58 | VDR | chr12: 48235319-48298814 | 47.70 | 32.51 | −0.55 | −0.91 | 1.75E−03 | 4.53E−02 | vitamin D (1,25-dihydroxyvitamin D3) receptor |
| 59 | KCTD10 | chr12: 109886459-109915155 | 30.87 | 20.82 | −0.57 | −0.95 | 3.00E−04 | 1.18E−02 | potassium channel tetramerization domain containing 10 |
| 60 | NEDD9 | chr6: 11183530-11382581 | 30.10 | 20.30 | −0.57 | −0.82 | 1.15E−03 | 3.29E−02 | neural precursor cell expressed, developmentally down-regulated 9 |
| 61 | PIM1 | chr6: 37137921-37143204 | 45.23 | 30.41 | −0.57 | −0.91 | 1.15E−03 | 3.29E−02 | Pim-1 proto-oncogene, serine/threonine kinase |
| 62 | SIRT6 | chr19: 4174105-4182596 | 67.88 | 45.43 | −0.58 | −1.01 | 5.00E−04 | 1.75E−02 | sirtuin 6 |
| 63 | MUC20 | chr3: 195447752-195460424 | 63.08 | 42.21 | −0.58 | −0.92 | 1.60E−03 | 4.26E−02 | mucin 20, cell surface associated |
| 64 | TMEM98 | chr17: 31254927-31268667 | 87.80 | 58.68 | −0.58 | −0.97 | 3.00E−04 | 1.18E−02 | transmembrane protein 98 |
| 65 | CLCN2 | chr3: 184053716-184079439 | 37.60 | 25.13 | −0.58 | −0.93 | 1.65E−03 | 4.36E−02 | chloride channel, voltage-sensitive 2 |
| 66 | LEFTY1 | chr1: 226073981-226076846 | 62.02 | 40.94 | −0.60 | −0.99 | 5.50E−04 | 1.86E−02 | left-right determination factor 1 |
| 67 | TBC1D22B | chr6: 37179953-37300746 | 9.73 | 6.42 | −0.60 | −0.86 | 1.75E−03 | 4.53E−02 | TBC1 domain family, member 22B |
| 68 | ID1 | chr20: 30193085-30194317 | 236.63 | 154.07 | −0.62 | −1.05 | 6.00E−04 | 1.99E−02 | inhibitor of DNA binding 1, dominant negative helix-loop-helix protein |
| 69 | MIDN | chr19: 1248551-1259142 | 61.35 | 39.86 | −0.62 | −1.04 | 1.00E−04 | 4.83E−03 | midnolin |
| 70 | JUND | chr19: 18390503-18392466 | 142.42 | 92.25 | −0.63 | −1.09 | 4.00E−04 | 1.49E−02 | jun D proto-oncogene |
| 71 | PDGFA | chr7: 536896-559481 | 25.93 | 16.68 | −0.64 | −1.01 | 3.50E−04 | 1.32E−02 | platelet-derived growth factor alpha polypeptide |
| 72 | DNTTIP1 | chr20: 44420575-44440066 | 29.99 | 19.22 | −0.64 | −0.99 | 3.00E−04 | 1.18E−02 | deoxynucleotidyltransferase, terminal, interacting protein 1 |
| 73 | SH2B3 | chr12: 111843751-111889427 | 11.65 | 7.41 | −0.65 | −0.98 | 3.50E−04 | 1.32E−02 | SH2B adaptor protein 3 |
| 74 | HSPA1A | chr6_qbl_hap6: 3076937-3079366 | 18.87 | 11.74 | −0.68 | −1.12 | 1.50E−04 | 6.74E−03 | heat shock 70 kDa protein 1A |
| 75 | ZFP36 | chr19: 39897486-39900052 | 149.93 | 93.12 | −0.69 | −0.96 | 7.50E−04 | 2.40E−02 | ZFP36 ring finger protein |
| 76 | AQP3 | chr9: 33441151-33447631 | 11.73 | 7.24 | −0.70 | −0.88 | 1.35E−03 | 3.76E−02 | aquaporin 3 (Gill blood group) |
| 77 | DDAH2 | chr6_ssto_hap7: 3025633-3028856 | 87.31 | 53.77 | −0.70 | −1.03 | 2.50E−04 | 1.03E−02 | dimethylarginine dimethylaminohydrolase 2 |
| 78 | SERTAD1 | chr19: 40928408-40931932 | 33.04 | 20.20 | −0.71 | −1.07 | 1.50E−04 | 6.74E−03 | SERTA domain containing 1 |
| 79 | CD14 | chr5: 140011312-140013286 | 62.69 | 38.02 | −0.72 | −1.11 | 2.00E−04 | 8.55E−03 | CD14 molecule |
| 80 | LINC00675 | chr17: 10616638-10718481 | 54.21 | 32.59 | −0.73 | −1.01 | 1.50E−04 | 6.74E−03 | long intergenic non-protein coding RNA 675 |
| 81 | CLDN4 | chr7: 73245192-73247023 | 720.19 | 432.86 | −0.73 | −0.94 | 1.70E−03 | 4.44E−02 | claudin 4 |
| 82 | DENND2A | chr7: 140218219-140302342 | 4.92 | 2.96 | −0.74 | −0.91 | 1.45E−03 | 3.98E−02 | DENN/MADD domain containing 2A |
| 83 | PDE9A | chr21: 44073861-44195618 | 53.48 | 31.85 | −0.75 | −0.99 | 5.50E−04 | 1.86E−02 | phosphodiesterase 9A |
| 84 | PC | chr11: 66615996-66725847 | 18.59 | 11.05 | −0.75 | −0.94 | 1.15E−03 | 3.29E−02 | pyruvate carboxylase |
| 85 | DES | chr2: 220283098-220291461 | 20.13 | 11.91 | −0.76 | −0.93 | 6.00E−04 | 1.99E−02 | desmin |
| 86 | BTG2 | chr1: 203274663-203278729 | 77.53 | 45.56 | −0.77 | −1.00 | 1.05E−03 | 3.10E−02 | BTG family, member 2 |
| 87 | AVPI1 | chr10: 99437180-99447015 | 36.62 | 21.08 | −0.80 | −1.22 | 5.00E−05 | 2.53E−03 | arginine vasopressin-induced 1 |
| 88 | EMB | chr5: 49692030-49737234 | 8.04 | 4.61 | −0.80 | −1.24 | 5.00E−05 | 2.53E−03 | em bigin |
| 89 | KLF4 | chr9: 110247132-110252047 | 197.26 | 111.42 | −0.82 | −1.25 | 5.00E−05 | 2.53E−03 | Kruppel-like factor 4 (gut) |

TABLE 5-continued

The list of 134 genes exclusively DE between HP and SSA/P.

| | gene | locus | mean_HP | mean SSA/P | log$_2$FC | test_stat | p_value | p$_{adj}$_value | Description |
|---|---|---|---|---|---|---|---|---|---|
| 90 | IER2 | chr19: 13261281-13265718 | 109.13 | 61.47 | −0.83 | −1.30 | 5.00E−05 | 2.53E−03 | immediate early response 2 |
| 91 | TPPP3 | chr16: 67423709-67427438 | 9.48 | 5.32 | −0.83 | −0.93 | 1.90E−03 | 4.85E−02 | tubulin polymerization-promoting protein family member 3 |
| 92 | ILDR1 | chr3: 121706169-121741127 | 10.99 | 6.12 | −0.84 | −1.22 | 5.00E−05 | 2.53E−03 | immunoglobulin-like domain containing receptor 1 |
| 93 | TPPP | chr5: 659976-693510 | 3.08 | 1.69 | −0.87 | −1.12 | 5.00E−05 | 2.53E−03 | tubulin polymerization promoting protein |
| 94 | WNT5B | chr12: 1726221-1756378 | 5.41 | 2.90 | −0.90 | −0.97 | 9.00E−04 | 2.76E−02 | wingless-type MMTV integration site family, member 5B |
| 95 | N4BP3 | chr5: 177540555-177553107 | 1.68 | 0.90 | −0.90 | −1.00 | 6.50E−04 | 2.11E−02 | NEDD4 binding protein 3 |
| 96 | GREM1 | chr15: 33010204-33026870 | 5.55 | 2.96 | −0.91 | −1.13 | 1.50E−04 | 6.74E−02 | gremlin 1, DAN family BMP antagonist |
| 97 | NUPR1 | chr16: 28548661-28550495 | 68.19 | 35.67 | −0.93 | −1.19 | 5.00E−05 | 2.53E−03 | nuclear protein, transcriptional regulator, 1 |
| 98 | ADAMTS1 | chr21: 28208605-28217728 | 3.84 | 2.01 | −0.94 | −1.13 | 5.00E−05 | 2.53E−03 | ADAM metallopeptidase with thrombospondin type 1 motif, 1 |
| 99 | FRAS1 | chr4: 78978723-79465423 | 0.97 | 0.49 | −0.98 | −1.17 | 5.00E−05 | 2.53E−03 | Fraser extracellular matrix complex subunit 1 |
| 100 | IER3 | chr6_ssto_hap7: 2043292-2044644 | 104.82 | 52.52 | −1.00 | −1.40 | 5.00E−05 | 2.53E−03 | immediate early response 3 |
| 101 | RHOB | chr2: 20646834-20649201 | 57.49 | 28.46 | −1.01 | −1.42 | 5.00E−05 | 2.53E−03 | ras homolog family member B |
| 102 | CAP2 | chr6: 17393735-17558023 | 1.18 | 0.58 | −1.02 | −0.89 | 1.20E−03 | 3.40E−02 | CAP, adenylate cyclase-associated protein, 2 (yeast) |
| 103 | P3H2 | chr3: 189674516-189840226 | 18.52 | 9.08 | −1.03 | −1.49 | 5.00E−05 | 2.53E−03 | prolyl 3-hydroxylase 2 |
| 104 | MTRNR2L1 | chr17: 22022436-22023991 | 157.37 | 76.54 | −1.04 | −1.44 | 5.00E−05 | 2.53E−03 | MT-RNR2-like 1 |
| 105 | MST1P2 | chr1: 16972068-16976915 | 3.54 | 1.68 | −1.08 | −1.03 | 6.00E−04 | 1.99E−02 | macrophage stimulating 1 (hepatocyte growth factor-like) pseudogene 2 |
| 106 | CELSR1 | chr22: 46756730-46933067 | 2.16 | 0.98 | −1.13 | −1.49 | 5.00E−05 | 2.53E−03 | cadherin, EGF LAG seven-pass G-type receptor 1 |
| 107 | LYPD6B | chr2: 149894980-150071772 | 3.69 | 1.67 | −1.14 | −1.02 | 5.00E−05 | 2.53E−03 | LY6/PLAUR domain containing 6B |
| 108 | ZNF334 | chr20: 45128268-45142198 | 1.02 | 0.44 | −1.22 | −0.94 | 9.50E−04 | 2.87E−02 | zinc finger protein 334 |
| 109 | FAR2P2 | chr2: 131174325-131186119 | 0.94 | 0.39 | −1.28 | −0.98 | 8.50E−04 | 2.66E−02 | fatty acyl CoA reductase 2 pseudogene 2 |
| 110 | SOX8 | chr16: 1031807-1036979 | 1.64 | 0.67 | −1.29 | −1.07 | 1.50E−03 | 4.05E−02 | SRY (sex determining region Y)-box 8 |
| 111 | ITLN1 | chr1: 160846329-160854960 | 592.60 | 242.61 | −1.29 | −1.36 | 5.00E−05 | 2.53E−03 | intelectin 1 (galactofuranose binding) |
| 112 | RRAD | chr16: 66955581-66959439 | 2.59 | 1.06 | −1.29 | −0.96 | 1.40E−03 | 3.88E−02 | Ras-related associated with diabetes |
| 113 | VSTM2L | chr20: 36531498-36573747 | 1.24 | 0.48 | −1.36 | −0.97 | 1.10E−03 | 3.22E−02 | V-set and transmembrane domain containing 2 like |
| 114 | GP2 | chr16: 20321810-20338835 | 3.44 | 1.22 | −1.50 | −1.37 | 5.00E−05 | 2.53E−03 | glycoprotein 2 (zymogen granule membrane) |
| 115 | PPP1R3G | chr6: 5085719-5087455 | 3.67 | 1.28 | −1.52 | −1.27 | 1.50E−04 | 6.74E−03 | protein phosphatase 1, regulatory subunit 3G |
| 116 | PEG10 | chr7: 94285636-94299006 | 1.38 | 0.47 | −1.57 | −1.39 | 5.00E−05 | 2.53E−03 | paternally expressed 10 |
| 117 | BEX1 | chrX: 102317580-102319168 | 2.45 | 0.81 | −1.60 | −0.95 | 1.60E−03 | 4.26E−02 | brain expressed, X-linked 1 |
| 118 | SLC18A1 | chr8: 20002365-20040717 | 2.63 | 0.86 | −1.61 | −1.43 | 5.00E−05 | 2.53E−03 | solute carrier family 18 (vesicular monoamine transporter), member 1 |
| 119 | KLK15 | chr19: 51328544-51334779 | 7.78 | 2.54 | −1.62 | −1.52 | 5.00E−05 | 2.53E−03 | kallikrein-related peptidase 15 |
| 120 | RFX6 | chr6: 117198375-117253326 | 0.93 | 0.26 | −1.84 | −1.38 | 5.00E−05 | 2.53E−03 | regulatory factor X, 6 |
| 121 | SCG3 | chr15: 51973549-52013223 | 1.07 | 0.29 | −1.90 | −1.26 | 5.00E−04 | 1.75E−02 | secretogranin III |
| 122 | TTR | chr18: 29171729-29178986 | 5.66 | 1.50 | −1.92 | −1.26 | 5.00E−05 | 2.53E−03 | transthyretin |
| 123 | PYY2 | chr17: 26553588-26555085 | 1.76 | 0.46 | −1.95 | −1.05 | 1.85E−03 | 4.74E−02 | peptide YY, 2 (pseudogene) |
| 124 | RUNDC3A | chr17: 42385926-42396038 | 1.13 | 0.29 | −1.97 | −1.22 | 4.50E−04 | 1.62E−02 | RUN domain containing 3A |
| 125 | HOXD9 | chr2: 176987412-176989645 | 10.70 | 2.60 | −2.04 | −2.05 | 5.00E−05 | 2.53E−03 | homeobox D9 |

TABLE 5-continued

The list of 134 genes exclusively DE between HP and SSA/P.

| | gene | locus | mean_HP | mean SSA/P | log$_2$FC | test_stat | p_value | p$_{adj}$_value | Description |
|---|---|---|---|---|---|---|---|---|---|
| 126 | TMPRSS6 | chr22: 37461475-37505603 | 1.40 | 0.34 | −2.05 | −1.68 | 5.00E−05 | 2.53E−03 | transmembrane protease, serine 6 |
| 127 | NCCRP1 | chr19: 39687603-39692522 | 1.35 | 0.32 | −2.10 | −1.20 | 3.00E−04 | 1.18E−02 | non-specific cytotoxic cell receptor protein 1 homolog (zebrafish) |
| 128 | CRYBA2 | chr2: 219854911-219858127 | 7.02 | 1.54 | −2.19 | −1.32 | 3.00E−04 | 1.18E−02 | crystallin, beta A2 |
| 129 | NKX2-2 | chr20: 21491659-21494664 | 0.96 | 0.21 | −2.22 | −1.30 | 3.50E−04 | 1.32E−02 | NK2 homeobox 2 |
| 130 | LOC441454 | chr9: 99671356-99672737 | 1.71 | 0.36 | −2.24 | −1.27 | 1.00E−04 | 4.83E−03 | prothymosin, alpha pseudogene |
| 131 | HOXD10 | chr2: 176981491-176984670 | 10.02 | 1.72 | −2.55 | −2.52 | 5.00E−05 | 2.53E−03 | homeobox D10 |
| 132 | OR51E2 | chr11: 4701400-4719076 | 6.33 | 0.66 | −3.26 | −2.30 | 5.00E−05 | 2.53E−03 | olfactory receptor, family 51, subfamily E, member 2 |
| 133 | COL2A1 | chr12: 48366747-48398285 | 1.36 | 0.14 | −3.32 | −2.62 | 5.00E−05 | 2.53E−03 | collagen, type II, alpha 1 |
| 134 | ALDH1A2 | chr15: 58245621-58358121 | 1.13 | 0.10 | −3.49 | −1.81 | 1.00E−03 | 3.00E−02 | aldehyde dehydrogenase 1 family, member A2 |

TABLE 6

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 1 | KLK6 | chr19: 51461886-51472929 | 0.00 | 2.31 | Inf | NA | 5.00E−05 | 7.97E−04 | kallikrein-related peptidase 6 |
| 2 | CASC19 | chr8: 128200030-128209872 | 0.00 | 4.02 | Inf | NA | 5.00E−05 | 7.97E−04 | cancer susceptibility candidate 19 (non-protein coding) |
| 3 | MIR4687 | chr11: 3876932-4114440 | 0.00 | 12.04 | Inf | NA | 2.50E−04 | 3.38E−03 | microRNA 4687 |
| 4 | MIR6727 | chr1: 1243993-1260067 | 0.00 | 378.27 | Inf | NA | 3.50E−04 | 4.55E−03 | microRNA 6727 |
| 5 | FAM25A | chr10: 88780045-88784487 | 0.06 | 6.54 | 6.69 | 1.06 | 1.00E−04 | 1.51E−03 | family with sequence similarity 25, member A |
| 6 | HTR1D | chr1: 23518387-23521222 | 0.13 | 10.29 | 6.28 | 4.15 | 5.00E−05 | 7.97E−04 | 5-hydroxytryptamine (serotonin) receptor 1D, G protein-coupled |
| 7 | CDH3 | chr16: 68678150-68732957 | 0.14 | 9.02 | 5.97 | 3.87 | 5.00E−05 | 7.97E−04 | cadherin 3, type 1, P-cadherin (placental) |
| 8 | PIWIL1 | chr12: 130822432-130856877 | 0.05 | 2.21 | 5.50 | 2.91 | 5.00E−05 | 7.97E−04 | piwi-like RNA-mediated gene silencing 1 |
| 9 | AFAP1-AS1 | chr4: 7755816-7941653 | 0.03 | 1.31 | 5.29 | 0.86 | 1.50E−04 | 2.18E−03 | AFAP1 antisense RNA 1 |
| 10 | PRSS22 | chr16: 2902727-2908171 | 0.68 | 25.53 | 5.24 | 4.31 | 5.00E−05 | 7.97E−04 | protease, serine, 22 |
| 11 | EPHX4 | chr1: 92495532-92529093 | 0.19 | 6.74 | 5.13 | 3.11 | 5.00E−05 | 7.97E−04 | epoxide hydrolase 4 |
| 12 | KRT7 | chr12: 52626953-52642709 | 0.22 | 7.17 | 5.05 | 2.93 | 5.00E−05 | 7.97E−04 | keratin 7, type II |
| 13 | KLHL30 | chr2: 239047362-239061547 | 0.05 | 1.60 | 4.97 | 2.58 | 5.00E−05 | 7.97E−04 | kelch-like family member 30 |
| 14 | MYBPC1 | chr12: 101988708-102079658 | 0.11 | 3.16 | 4.90 | 3.30 | 5.00E−05 | 7.97E−04 | myosin binding protein C, slow type |
| 15 | SAA1 | chr11: 18287807-18291523 | 0.28 | 8.21 | 4.85 | 1.84 | 6.00E−04 | 7.22E−03 | serum amyloid A1 |
| 16 | CXCL11 | chr4: 76932332-77033955 | 0.17 | 4.70 | 4.79 | 1.59 | 5.75E−03 | 4.55E−02 | chemokine (C-X-C motif) ligand 11 |
| 17 | SH3PXD2A-AS1 | chr10: 105353783-105615164 | 0.29 | 8.08 | 4.78 | 0.81 | 5.00E−05 | 7.97E−04 | SH3PXD2A antisense RNA 1 |
| 18 | SFTA2 | chr_6qbl_hap6: 2192097-2192923 | 0.07 | 1.79 | 4.75 | 0.95 | 5.00E−05 | 7.97E−04 | surfactant associated 2 |
| 19 | DUSP4 | chr8: 29190578-29208267 | 0.40 | 9.96 | 4.62 | 4.75 | 5.00E−05 | 7.97E−04 | dual specificity phosphatase 4 |
| 20 | DUOXA1 | chr15: 45406522-45422075 | 0.69 | 15.69 | 4.51 | 1.68 | 5.00E−05 | 7.97E−04 | dual oxidase maturation factor 1 |
| 21 | CRNDE | chr16: 54952776-54963101 | 0.19 | 3.75 | 4.32 | 1.74 | 3.00E−04 | 3.97E−03 | colorectal neoplasia differentially expressed (non-protein coding) |
| 22 | SAA2 | chr11: 18252901-18270221 | 0.22 | 4.23 | 4.28 | 1.90 | 9.00E−04 | 1.01E−02 | serum amyloid A2 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 23 | CCAT1 | chr8: 128219626-128231513 | 0.14 | 2.62 | 4.26 | 2.62 | 5.00E−05 | 7.97E−04 | colon cancer associated transcript 1 (non-protein coding) |
| 24 | PDX1 | chr13: 28403895-28500451 | 0.24 | 4.61 | 4.24 | 3.12 | 5.00E−05 | 7.97E−04 | pancreatic and duodenal homeobox 1 |
| 25 | SSTR5 | chr16: 1114081-1131454 | 0.09 | 1.64 | 4.13 | 1.45 | 6.00E−04 | 7.22E−03 | somatostatin receptor 5 |
| 26 | LINC00520 | chr14: 56247852-56263392 | 0.56 | 8.76 | 3.97 | 3.32 | 5.00E−05 | 7.97E−04 | long intergenic non-protein coding RNA520 |
| 27 | KRT80 | chr12: 52562779-52585784 | 0.08 | 1.28 | 3.92 | 2.51 | 5.00E−05 | 7.97E−04 | keratin 80, type II |
| 28 | UGT1A3 | chr2: 234526290-234681951 | 0.21 | 2.90 | 3.75 | 0.34 | 7.50E−04 | 8.64E−03 | UDP glucuronosyltransferase 1 family, polypeptide A3 |
| 29 | F0SL1 | chr11: 65659691-65667997 | 0.18 | 2.46 | 3.74 | 2.34 | 5.00E−05 | 7.97E−04 | FOS-like antigen 1 |
| 30 | C11orf91 | chr11: 33719653-33722286 | 0.21 | 2.65 | 3.64 | 1.81 | 3.50E−04 | 4.55E−03 | chromosome 11 open reading frame 91 |
| 31 | MDFI | chr6: 41606194-41621982 | 0.59 | 7.08 | 3.59 | 3.13 | 5.00E−05 | 7.97E−04 | MyoD family inhibitor |
| 32 | LMO7DN | chr13: 76445173-76457948 | 0.15 | 1.72 | 3.54 | 1.84 | 1.00E−04 | 1.51E−03 | LMO7 downstream neighbor |
| 33 | KCTD14 | chr11: 77726760-77850699 | 0.30 | 3.52 | 3.53 | 0.59 | 5.90E−03 | 4.65E−02 | potassium channel tetramerization domain containing 14 |
| 34 | SSTR5-AS1 | chr16: 1114081-1131454 | 0.49 | 5.47 | 3.47 | 2.61 | 5.00E−05 | 7.97E−04 | SSTR5 antisense RNA 1 |
| 35 | KCP | chr7: 128516918-128550773 | 0.32 | 3.31 | 3.37 | 3.11 | 5.00E−05 | 7.97E−04 | kielin/chordin-like protein |
| 36 | CLDN14 | chr21: 37832919-37948867 | 0.16 | 1.64 | 3.37 | 1.29 | 5.00E−05 | 7.97E−04 | claudin 14 |
| 37 | DUOX2 | chr15: 45384851-45406359 | 11.84 | 118.72 | 3.33 | 1.76 | 5.00E−05 | 7.97E−04 | dual oxidase 2 |
| 38 | GJC2 | chr1: 228337414-228347527 | 0.16 | 1.59 | 3.30 | 1.96 | 1.50E−04 | 2.18E−03 | gap junction protein, gamma 2, 47 kDa |
| 39 | SLC6A20 | chr3: 45796940-45838035 | 1.53 | 15.01 | 3.30 | 4.52 | 5.00E−05 | 7.97E−04 | solute carrier family 6 (proline IMINO transporter), member 20 |
| 40 | C2CD4A | chr15: 62359175-62363116 | 0.24 | 2.24 | 3.24 | 2.41 | 5.00E−05 | 7.97E−04 | C2 calcium-dependent domain containing 4A |
| 41 | MYEOV | chr11: 69061621-69064754 | 2.61 | 24.67 | 3.24 | 3.75 | 5.00E−05 | 7.97E−04 | myeloma overexpressed |
| 42 | TFAP2A | chr6: 10396915-10419797 | 0.20 | 1.80 | 3.20 | 2.14 | 5.00E−05 | 7.97E−04 | transcription factor AP-2 alpha (activating enhancer binding protein 2 alpha) |
| 43 | TNFSF9 | chr19: 6531009-6535939 | 0.21 | 1.75 | 3.08 | 1.67 | 5.00E−05 | 7.97E−04 | tumor necrosis factor (ligand) superfamily, member 9 |
| 44 | SEC14L2 | chr22: 30792929-30821291 | 0.44 | 3.72 | 3.07 | 2.89 | 5.00E−05 | 7.97E−04 | SEC14-like lipid binding 2 |
| 45 | PLA2G2F | chr1: 20465822-20476879 | 0.16 | 1.24 | 2.98 | 1.45 | 5.00E−05 | 7.97E−04 | phospholipase A2, group IIF |
| 46 | C6orf223 | chr6: 43968336-43973694 | 0.97 | 7.57 | 2.97 | 2.90 | 5.00E−05 | 7.97E−04 | chromosome 6 open reading frame 223 |
| 47 | IRX2 | chr5: 2746278-2751769 | 0.19 | 1.50 | 2.94 | 1.90 | 5.00E−05 | 7.97E−04 | iroquois homeobox 2 |
| 48 | SIM2 | chr21: 38071990-38122510 | 0.27 | 2.06 | 2.92 | 2.28 | 5.00E−05 | 7.97E−04 | single-minded family bHLH transcription factor 2 |
| 49 | SLC4A11 | chr20: 3208062-3219887 | 0.31 | 2.32 | 2.91 | 2.39 | 5.00E−05 | 7.97E−04 | solute carrier family 4, sodium borate transporter, member 11 |
| 50 | TTC9 | chr14: 71108503-71142077 | 0.62 | 4.64 | 2.91 | 3.31 | 5.00E−05 | 7.97E−04 | tetratricopeptide repeat domain 9 |
| 51 | TMPRSS3 | chr21: 43791995-43816955 | 0.53 | 3.86 | 2.87 | 2.27 | 5.00E−05 | 7.97E−04 | transmembrane protease, serine 3 |
| 52 | SLC16A4 | chr1: 110905472-110933704 | 1.08 | 7.54 | 2.81 | 2.86 | 5.00E−05 | 7.97E−04 | solute carrier family 16, member 4 |
| 53 | XKR9 | chr8: 71581599-71648177 | 0.64 | 4.40 | 2.79 | 2.88 | 5.00E−05 | 7.97E−04 | XK, Kell blood group complex subunit-related family, member 9 |
| 54 | IL1RN | chr2: 113875469-113891593 | 3.40 | 23.19 | 2.77 | 3.42 | 5.00E−05 | 7.97E−04 | interleukin 1 receptor antagonist |
| 55 | C2CD4B | chr15: 62455736-62457482 | 0.53 | 3.62 | 2.76 | 2.03 | 5.00E−05 | 7.97E−04 | C2 calcium-dependent domain containing 4B |
| 56 | IL1B | chr2: 113587336-113594356 | 1.41 | 9.47 | 2.74 | 2.67 | 5.00E−05 | 7.97E−04 | interleukin 1, beta |
| 57 | DSG3 | chr18: 29027731-29058665 | 0.21 | 1.37 | 2.72 | 2.37 | 5.00E−05 | 7.97E−04 | desmoglein 3 |
| 58 | ANXA1 | chr9: 75766780-75785307 | 25.34 | 161.24 | 2.67 | 4.39 | 5.00E−05 | 7.97E−04 | annexin A1 |
| 59 | MTCL1 | chr18: 8717368-8832775 | 0.48 | 2.95 | 2.63 | 2.94 | 5.00E−05 | 7.97E−04 | microtubule crosslinking factor 1 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 60 | CXCL1 | chr4: 74735108-74737019 | 3.81 | 23.37 | 2.62 | 3.02 | 5.00E-05 | 7.97E-04 | chemokine (C-X-C motif) ligand 1 (melanoma growth stimulating activity, alpha) |
| 61 | CHAC1 | chr15: 41245635-41248717 | 1.72 | 10.35 | 2.59 | 2.51 | 5.00E-05 | 7.97E-04 | ChaC glutathione-specific gamma-glutamylcyclotransferase 1 |
| 62 | CXCL3 | chr4: 74902311-74904490 | 2.22 | 13.30 | 2.58 | 2.52 | 5.00E-05 | 7.97E-04 | chemokine (C-X-C motif) ligand 3 |
| 63 | AHNAK2 | chr14: 105403590-105444694 | 0.28 | 1.70 | 2.58 | 3.20 | 5.00E-05 | 7.97E-04 | AHNAK nucleoprotein 2 |
| 64 | IL33 | chr9: 6215785-6257983 | 1.69 | 10.04 | 2.57 | 3.21 | 5.00E-05 | 7.97E-04 | interleukin 33 |
| 65 | SYT12 | chr11: 66790189-66818334 | 0.27 | 1.57 | 2.53 | 1.60 | 5.00E-05 | 7.97E-04 | synaptotagmin XII |
| 66 | IRAK2 | chr3: 10206562-10285427 | 1.07 | 6.19 | 2.53 | 2.86 | 5.00E-05 | 7.97E-04 | interleukin-1 receptor-associated kinase 2 |
| 67 | TM4SF1 | chr3: 149086804-149104370 | 24.36 | 139.66 | 2.52 | 4.27 | 5.00E-05 | 7.97E-04 | transmembrane 4 L six family member 1 |
| 68 | CDSN | chr6_qbl_hap6: 2378425-2403713 | 0.68 | 3.84 | 2.50 | 1.41 | 4.00E-04 | 5.06E-03 | corneodesmosin |
| 69 | GRHL1 | chr2: 10091791-10142412 | 0.24 | 1.34 | 2.45 | 1.92 | 5.00E-05 | 7.97E-04 | grainyhead-like transcription factor 1 |
| 70 | PHLDA1 | chr12: 76419226-76425556 | 2.67 | 14.50 | 2.44 | 3.70 | 5.00E-05 | 7.97E-04 | pleckstrin homology-like domain, family A, member 1 |
| 71 | SERPINE2 | chr2: 224839764-224904036 | 8.44 | 43.34 | 2.36 | 3.56 | 5.00E-05 | 7.97E-04 | serpin peptidase inhibitor, clade E (nexin, plasminogen activator inhibitor type 1), member 2 |
| 72 | SRD5A3 | chr4: 56212387-56251747 | 2.95 | 14.76 | 2.32 | 3.49 | 5.00E-05 | 7.97E-04 | steroid 5 alpha-reductase 3 |
| 73 | PLEKHN1 | chr1: 901876-910484 | 0.47 | 2.37 | 2.32 | 1.94 | 5.00E-05 | 7.97E-04 | pleckstrin homology domain containing, family N member 1 |
| 74 | DUOX1 | chr15: 45422191-45457776 | 0.43 | 2.11 | 2.28 | 2.25 | 5.00E-05 | 7.97E-04 | dual oxidase 1 |
| 75 | FADS2 | chr11: 61567096-61634826 | 2.55 | 12.27 | 2.26 | 2.13 | 5.00E-05 | 7.97E-04 | fatty acid desaturase 2 |
| 76 | PHLDA2 | chr11: 2949502-2950650 | 15.13 | 72.46 | 2.26 | 2.94 | 5.00E-05 | 7.97E-04 | pleckstrin homology-like domain, family A, member 2 |
| 77 | RTN4R | chr22: 20228937-20255816 | 1.47 | 6.95 | 2.24 | 2.32 | 5.00E-05 | 7.97E-04 | reticulon 4 receptor |
| 78 | WFDC21P | chr17: 58160926-58165828 | 1.09 | 5.00 | 2.20 | 1.49 | 5.00E-05 | 7.97E-04 | WAP four-disulfide core domain 21, pseudogene |
| 79 | TNFRSF11B | chr8: 119935795-119964383 | 1.96 | 8.83 | 2.17 | 2.72 | 5.00E-05 | 7.97E-04 | tumor necrosis factor receptor superfamily, member 11b |
| 80 | CLIC3 | chr9: 139889059-139891024 | 2.05 | 9.10 | 2.15 | 1.72 | 5.00E-05 | 7.97E-04 | chloride intracellular channel 3 |
| 81 | S100A2 | chr1: 153533584-153538306 | 0.55 | 2.43 | 2.14 | 1.27 | 4.00E-04 | 5.06E-03 | S100 calcium binding protein A2 |
| 82 | NAT8 | chr2: 73867849-73869537 | 1.26 | 5.56 | 2.14 | 1.61 | 5.00E-05 | 7.97E-04 | N-acetyltransferase 8 (GCN5-related, putative) |
| 83 | TRIM7 | chr5: 180620923-180632293 | 3.12 | 13.61 | 2.13 | 2.07 | 5.00E-05 | 7.97E-04 | tripartite motif containing 7 |
| 84 | RGS2 | chr1: 192778168-192781407 | 10.92 | 47.56 | 2.12 | 3.33 | 5.00E-05 | 7.97E-04 | regulator of G-protein signaling 2 |
| 85 | ZSCAN12P1 | chr6: 28058584-28063493 | 0.55 | 2.36 | 2.09 | 2.02 | 5.00E-05 | 7.97E-04 | zinc finger and SCAN domain containing 12 pseudogene 1 |
| 86 | ELFN1-AS1 | chr7: 1748797-1787896 | 0.39 | 1.64 | 2.08 | 0.92 | 5.15E-03 | 4.16E-02 | ELFN1 antisense RNA 1 |
| 87 | TNFRSF12A | chr16: 3070312-3072383 | 7.12 | 29.77 | 2.06 | 2.52 | 5.00E-05 | 7.97E-04 | tumor necrosis factor receptor superfamily, member 12A |
| 88 | MYPN | chr10: 69865873-69971773 | 0.38 | 1.60 | 2.06 | 1.99 | 5.00E-05 | 7.97E-04 | myopalladin |
| 89 | KIAA0895 | chr7: 36363758-36493401 | 0.66 | 2.70 | 2.04 | 1.28 | 6.00E-04 | 7.22E-03 | KIAA0895 |
| 90 | ENTPD3 | chr3: 40428646-40494799 | 0.60 | 2.44 | 2.03 | 1.68 | 5.00E-05 | 7.97E-04 | ectonucleoside triphosphate diphosphohydrolase 3 |
| 91 | ADAMTSL5 | chr19: 1505016-1513188 | 1.06 | 4.31 | 2.02 | 2.03 | 5.00E-05 | 7.97E-04 | ADAMTS-like 5 |
| 92 | STX1A | chr7: 73113534-73134017 | 1.24 | 4.95 | 2.00 | 1.94 | 5.00E-05 | 7.97E-04 | syntaxin 1A (brain) |
| 93 | ME1 | chr6: 83920109-84140938 | 7.99 | 31.89 | 2.00 | 3.33 | 5.00E-05 | 7.97E-04 | malic enzyme 1, NADP(+)-dependent, cytosolic |
| 94 | ANXA3 | chr4: 79472741-79531605 | 18.26 | 72.68 | 1.99 | 3.37 | 5.00E-05 | 7.97E-04 | annexin A3 |
| 95 | TM4SF1-AS1 | chr3: 149086804-149104370 | 0.27 | 1.07 | 1.99 | 0.22 | 4.75E-03 | 3.89E-02 | TM4SF1 antisense RNA 1 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 96 | C10orf10 | chr10: 45455218-45490172 | 3.11 | 12.27 | 1.98 | 1.32 | 1.05E−03 | 1.15E−02 | chromosome 10 open reading frame 10 |
| 97 | LRRC8E | chr19: 7953389-7966908 | 0.60 | 2.37 | 1.97 | 1.94 | 5.00E−05 | 7.97E−04 | leucine rich repeat containing 8 family, member E |
| 98 | CATSPERB | chr14: 92047117-92198413 | 0.86 | 3.37 | 1.97 | 2.20 | 5.00E−05 | 7.97E−04 | catsper channel auxiliary subunit beta |
| 99 | CCNO | chr5: 54526980-54529508 | 1.46 | 5.71 | 1.96 | 1.57 | 5.00E−05 | 7.97E−04 | cyclin O |
| 100 | MIR614 | chr12: 13068762-13068852 | 673.60 | 2602.29 | 1.95 | 1.42 | 5.00E−05 | 7.97E−04 | microRNA 614 |
| 101 | C17orf67 | chr17: 54869273-54911256 | 0.98 | 3.74 | 1.94 | 1.79 | 5.00E−05 | 7.97E−04 | chromosome 17 open reading frame 67 |
| 102 | ETV4 | chr17: 41605210-41623800 | 2.02 | 7.73 | 1.93 | 2.11 | 5.00E−05 | 7.97E−04 | ets variant 4 |
| 103 | CAPN11 | chr6: 44126547-44152139 | 0.65 | 2.47 | 1.92 | 1.54 | 5.00E−05 | 7.97E−04 | calpain 11 |
| 104 | SMOX | chr20: 4129425-4168394 | 2.21 | 8.16 | 1.89 | 2.12 | 5.00E−05 | 7.97E−04 | spermine oxidase |
| 105 | ARX | chrX: 25021812-25034065 | 0.34 | 1.26 | 1.87 | 1.40 | 1.50E−04 | 2.18E−03 | aristaless related homeobox |
| 106 | TSPAN5 | chr4: 99391517-99579812 | 1.40 | 5.06 | 1.85 | 2.24 | 5.00E−05 | 7.97E−04 | tetraspanin 5 |
| 107 | TIMP1 | chrX: 47420498-47479256 | 61.09 | 216.38 | 1.82 | 1.94 | 5.00E−05 | 7.97E−04 | TIMP metallopeptidase inhibitor 1 |
| 108 | ARNTL2 | chr12: 27485786-27599567 | 0.85 | 3.00 | 1.82 | 2.44 | 5.00E−05 | 7.97E−04 | aryl hydrocarbon receptor nuclear translocator-like 2 |
| 109 | PARP8 | chr5: 49961732-50142356 | 1.43 | 5.02 | 1.81 | 2.66 | 5.00E−05 | 7.97E−04 | poly (ADP-ribose) polymerase family, member 8 |
| 110 | OTUB2 | chr14: 94492723-94515276 | 0.65 | 2.27 | 1.81 | 1.87 | 5.00E−05 | 7.97E−04 | OTU deubiquitinase, ubiquitin aldehyde binding 2 |
| 111 | MPP3 | chr17: 41878166-41910547 | 0.53 | 1.86 | 1.81 | 1.72 | 5.00E−05 | 7.97E−04 | membrane protein, palmitoylated 3 (MAGUK p55 subfamily member 3) |
| 112 | EIF5A2 | chr3: 170606203-170626426 | 0.33 | 1.14 | 1.78 | 1.82 | 5.00E−05 | 7.97E−04 | eukaryotic translation initiation factor 5A2 |
| 113 | RHOD | chr11: 66824288-66839488 | 8.98 | 30.71 | 1.77 | 2.30 | 5.00E−05 | 7.97E−04 | ras homolog family member D |
| 114 | ASPHD2 | chr22: 26825279-26840978 | 1.82 | 6.19 | 1.77 | 2.16 | 5.00E−05 | 7.97E−04 | aspartate beta-hydroxylase domain containing 2 |
| 115 | STRIP2 | chr7: 129074273-129128239 | 0.80 | 2.73 | 1.77 | 1.87 | 5.00E−05 | 7.97E−04 | striatin interacting protein 2 |
| 116 | INSC | chr11: 15133969-15268756 | 1.32 | 4.50 | 1.77 | 1.90 | 5.00E−05 | 7.97E−04 | inscuteable homolog (*Drosophila*) |
| 117 | SPTBN2 | chr11: 66452719-66488870 | 0.65 | 2.21 | 1.76 | 2.04 | 5.00E−05 | 7.97E−04 | spectrin, beta, non-erythrocytic 2 |
| 118 | PF4 | chr4: 74846541-74847841 | 0.42 | 1.40 | 1.75 | 1.00 | 3.05E−03 | 2.72E−02 | platelet factor 4 |
| 119 | ALPPL2 | chr2: 233271551-233275424 | 0.40 | 1.32 | 1.74 | 1.26 | 5.00E−05 | 7.97E−04 | alkaline phosphatase, placental-like 2 |
| 120 | CD82 | chr11: 44587140-44641315 | 18.88 | 62.74 | 1.73 | 2.81 | 5.00E−05 | 7.97E−04 | CD82 molecule |
| 121 | HAPLN4 | chr19: 19366451-19373596 | 0.53 | 1.75 | 1.72 | 1.53 | 5.00E−05 | 7.97E−04 | hyaluronan and proteoglycan link protein 4 |
| 122 | LOC100130705 | chr7: 128506463-128512101 | 0.78 | 2.56 | 1.72 | 1.65 | 5.00E−05 | 7.97E−04 | uncharacterized LOC100130705 |
| 123 | ARFGAP3 | chr22: 43192531-43253408 | 13.97 | 45.68 | 1.71 | 2.97 | 5.00E−05 | 7.97E−04 | ADP-ribosylation factor GTPase activating protein 3 |
| 124 | LDLR | chr19: 11200037-11244505 | 11.17 | 36.20 | 1.70 | 2.74 | 5.00E−05 | 7.97E−04 | low density lipoprotein receptor |
| 125 | UNC13D | chr17: 73823307-73840798 | 9.64 | 30.97 | 1.68 | 2.84 | 5.00E−05 | 7.97E−04 | unc-13 homolog D (*C. elegans*) |
| 126 | GPRIN1 | chr5: 176022802-176037131 | 2.98 | 9.37 | 1.66 | 2.31 | 5.00E−05 | 7.97E−04 | G protein regulated inducer of neurite outgrowth 1 |
| 127 | LAMC2 | chr1: 183155173-183214262 | 15.08 | 47.41 | 1.65 | 2.58 | 5.00E−05 | 7.97E−04 | laminin, gamma 2 |
| 128 | TRIB3 | chr20: 361307-378203 | 2.05 | 6.39 | 1.64 | 1.83 | 5.00E−05 | 7.97E−04 | tribbles pseudokinase 3 |
| 129 | SLC5A9 | chr1: 48688356-48714316 | 0.97 | 3.02 | 1.64 | 1.78 | 5.00E−05 | 7.97E−04 | solute carrier family 5 (sodium/sugar cotransporter), member 9 |
| 130 | ITGA2 | chr5: 52285155-52390609 | 4.93 | 15.24 | 1.63 | 2.75 | 5.00E−05 | 7.97E−04 | integrin, alpha 2 (CD49B, alpha 2 subunit of VLA-2 receptor) |
| 131 | SESTD1 | chr2: 179966418-180129350 | 1.58 | 4.88 | 1.62 | 2.74 | 5.00E−05 | 7.97E−04 | SEC14 and spectrin domains 1 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 132 | SIGLEC12 | chr19: 51994480-52005043 | 0.80 | 2.42 | 1.60 | 1.38 | 5.00E-05 | 7.97E-04 | sialic acid binding Ig-like lectin 12 (gene/pseudogene) |
| 133 | HSPA4L | chr4: 128703452-128754526 | 0.67 | 2.02 | 1.60 | 1.64 | 5.00E-05 | 7.97E-04 | heat shock 70 kDa protein 4-like |
| 134 | BTNL9 | chr5: 180467224-180488523 | 1.12 | 3.36 | 1.59 | 1.69 | 5.00E-05 | 7.97E-04 | butyrophilin-like 9 |
| 135 | BACE2 | chr21: 42539727-42654461 | 8.52 | 25.38 | 1.58 | 2.73 | 5.00E-05 | 7.97E-04 | beta-site APP-cleaving enzyme 2 |
| 136 | PRDM8 | chr4: 81106423-81125482 | 0.71 | 2.09 | 1.56 | 1.40 | 5.00E-05 | 7.97E-04 | PR domain containing 8 |
| 137 | TUBB2A | chr6: 3153901-3157783 | 6.96 | 20.52 | 1.56 | 2.16 | 5.00E-05 | 7.97E-04 | tubulin, beta 2A class IIa |
| 138 | ZG16B | chr16: 2880172-2882285 | 25.29 | 73.85 | 1.55 | 2.33 | 5.00E-05 | 7.97E-04 | zymogen granule protein 16B |
| 139 | CELSR3 | chr3: 48673895-48700348 | 0.49 | 1.42 | 1.53 | 1.83 | 5.00E-05 | 7.97E-04 | cadherin, EGF LAG seven-pass G-type receptor 3 |
| 140 | MET | chr7: 116312458-116438440 | 6.21 | 17.84 | 1.52 | 2.69 | 5.00E-05 | 7.97E-04 | MET proto-oncogene, receptor tyrosine kinase |
| 141 | TMEM163 | chr2: 135213329-135476571 | 0.48 | 1.37 | 1.51 | 1.03 | 4.00E-04 | 5.06E-03 | transmembrane protein 163 |
| 142 | SLC28A3 | chr9: 86890764-86983413 | 0.38 | 1.08 | 1.49 | 1.38 | 5.00E-05 | 7.97E-04 | solute carrier family 28 (concentrative nucleoside transporter), member 3 |
| 143 | LPL | chr8: 19796581-19824770 | 0.38 | 1.05 | 1.48 | 1.30 | 5.00E-05 | 7.97E-04 | lipoprotein lipase |
| 144 | TRIM16 | chr17: 15531279-15586193 | 4.49 | 12.55 | 1.48 | 2.22 | 5.00E-05 | 7.97E-04 | tripartite motif containing 16 |
| 145 | TPK1 | chr7: 144149033-144533146 | 4.47 | 12.38 | 1.47 | 2.13 | 5.00E-05 | 7.97E-04 | thiamin pyrophosphokinase 1 |
| 146 | ADM2 | chr22: 50919984-50924866 | 1.61 | 4.46 | 1.47 | 1.77 | 5.00E-05 | 7.97E-04 | adrenomedullin 2 |
| 147 | C8G | chr9: 139839697-139841426 | 3.94 | 10.79 | 1.45 | 1.35 | 5.00E-05 | 7.97E-04 | complement component 8, gamma polypeptide |
| 148 | S100A11 | chr1: 152004981-152009511 | 295.16 | 806.03 | 1.45 | 2.44 | 5.00E-05 | 7.97E-04 | S100 calcium binding protein A11 |
| 149 | RAPGEF3 | chr12: 48128452-48152889 | 1.60 | 4.34 | 1.44 | 1.96 | 5.00E-05 | 7.97E-04 | Rap guanine nucleotide exchange factor (GEF) 3 |
| 150 | TM4SF5 | chr17: 4675186-4686506 | 21.66 | 58.69 | 1.44 | 1.91 | 5.00E-05 | 7.97E-04 | transmembrane 4 L six family member 5 |
| 151 | BMP7 | chr20: 55743808-55841707 | 0.87 | 2.36 | 1.44 | 1.53 | 5.00E-05 | 7.97E-04 | bone morphogenetic protein 7 |
| 152 | SYT8 | chr11: 1855539-1858751 | 0.80 | 2.15 | 1.43 | 1.08 | 5.50E-04 | 6.69E-03 | synaptotagmin VIII |
| 153 | SSUH2 | chr3: 8661085-8693764 | 3.55 | 9.57 | 1.43 | 1.70 | 5.00E-05 | 7.97E-04 | ssu-2 homolog (C. elegans) |
| 154 | DPP4 | chr2: 162848754-162931052 | 12.22 | 32.97 | 1.43 | 2.43 | 5.00E-05 | 7.97E-04 | dipeptidyl-peptidase 4 |
| 155 | FAM83H-AS1 | chr8: 144816309-144828507 | 2.07 | 5.56 | 1.43 | 1.71 | 5.00E-05 | 7.97E-04 | FAM83H antisense RNA 1 (head to head) |
| 156 | LMO7 | chr13: 76123615-76434006 | 24.92 | 66.89 | 1.42 | 2.19 | 5.00E-05 | 7.97E-04 | LIM domain 7 |
| 157 | SLC7A4 | chr22: 21383006-21386847 | 1.46 | 3.88 | 1.41 | 1.29 | 5.00E-05 | 7.97E-04 | solute carrier family 7, member 4 |
| 158 | MLPH | chr2: 238395052-238463961 | 20.32 | 53.64 | 1.40 | 2.42 | 5.00E-05 | 7.97E-04 | melanophilin |
| 159 | ERRFI1 | chr1: 8071778-8086393 | 12.88 | 34.00 | 1.40 | 2.39 | 5.00E-05 | 7.97E-04 | ERBB receptor feedback inhibitor 1 |
| 160 | ARHGAP29 | chr1: 94634462-94703307 | 0.55 | 1.44 | 1.40 | 1.76 | 5.00E-05 | 7.97E-04 | Rho GTPase activating protein 29 |
| 161 | MUC3A | chr7: 100547051-100611619 | 25.38 | 66.35 | 1.39 | 2.26 | 5.00E-05 | 7.97E-04 | mucin 3A, cell surface associated |
| 162 | ISG15 | chr1: 948846-949919 | 20.73 | 53.92 | 1.38 | 1.84 | 5.00E-05 | 7.97E-04 | ISG15 ubiquitin-like modifier |
| 163 | PMAIP1 | chr18: 57567191-57571538 | 1.70 | 4.39 | 1.37 | 1.50 | 5.00E-05 | 7.97E-04 | phorbol-12-myristate-13-acetate-induced protein 1 |
| 164 | ZMYND15 | chr17: 4643309-4649414 | 1.08 | 2.80 | 1.37 | 1.29 | 5.00E-05 | 7.97E-04 | zinc finger, MYND-type containing 15 |
| 165 | PPL | chr16: 4932507-4987136 | 1.85 | 4.77 | 1.37 | 1.98 | 5.00E-05 | 7.97E-04 | periplakin |
| 166 | LPGAT1 | chr1: 211916798-212004114 | 8.03 | 20.49 | 1.35 | 2.52 | 5.00E-05 | 7.97E-04 | lysophosphatidylglycerol acyltransferase 1 |
| 167 | AGR2 | chr7: 16832263-16844738 | 1120.97 | 2856.30 | 1.35 | 1.43 | 5.00E-05 | 7.97E-04 | anterior gradient 2, protein disulphide isomerase family member |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 168 | GATSL2 | chr7: 74601103-74988276 | 0.61 | 1.54 | 1.34 | 1.53 | 5.00E-05 | 7.97E-04 | GATS protein-like 2 |
| 169 | CDKN2A | chr9: 21967137-21994490 | 0.56 | 1.43 | 1.34 | 0.76 | 3.45E-03 | 3.01E-02 | cyclin-dependent kinase inhibitor 2A |
| 170 | ZC3H12A | chr1: 37940118-37949978 | 8.19 | 20.58 | 1.33 | 2.08 | 5.00E-05 | 7.97E-04 | zinc finger CCCH-type containing 12A |
| 171 | ALDH3B1 | chr11: 67776016-67796749 | 9.36 | 23.45 | 1.33 | 2.17 | 5.00E-05 | 7.97E-04 | aldehyde dehydrogenase 3 family, member B1 |
| 172 | NDUFC2-KCTD14 | chr11: 77726760-77850699 | 9.47 | 23.70 | 1.32 | 1.11 | 2.50E-04 | 3.38E-03 | NDUFC2-KCTD14 readthrough |
| 173 | GIPR | chr19: 46171501-46185717 | 5.98 | 14.87 | 1.31 | 1.75 | 5.00E-05 | 7.97E-04 | gastric inhibitory polypeptide receptor |
| 174 | ZNF165 | chr6: 28048481-28057340 | 1.69 | 4.20 | 1.31 | 1.51 | 5.00E-05 | 7.97E-04 | zinc finger protein 165 |
| 175 | GMPR | chr6: 16238810-16295780 | 2.15 | 5.32 | 1.31 | 1.37 | 5.00E-05 | 7.97E-04 | guanosine monophosphate reductase |
| 176 | RTN2 | chr19: 45988545-46000313 | 3.17 | 7.83 | 1.30 | 1.18 | 5.00E-05 | 7.97E-04 | reticulon 2 |
| 177 | TYRO3 | chr15: 41851219-41871536 | 0.55 | 1.36 | 1.30 | 1.23 | 2.00E-04 | 2.80E-03 | TYRO3 protein tyrosine kinase |
| 178 | VSTM5 | chr11: 93553734-93583668 | 1.51 | 3.72 | 1.30 | 0.93 | 1.90E-03 | 1.87E-02 | V-set and transmembrane domain containing 5 |
| 179 | KYNU | chr2: 143635194-143799885 | 1.31 | 3.20 | 1.29 | 1.26 | 5.00E-05 | 7.97E-04 | kynureninase |
| 180 | SERPINB8 | chr18: 61637262-2-61656608 | 4.71 | 11.46 | 1.28 | 1.87 | 5.00E-05 | 7.97E-04 | serpin peptidase inhibitor, clade B (ovalbumin), member 8 |
| 181 | RSAD2 | chr2: 7017795-7038363 | 6.48 | 15.78 | 1.28 | 1.82 | 5.00E-05 | 7.97E-04 | radical S-adenosyl methionine domain containing 2 |
| 182 | PLAUR | chr19: 44150246-44174498 | 22.04 | 53.41 | 1.28 | 2.05 | 5.00E-05 | 7.97E-04 | plasminogen activator, urokinase receptor |
| 183 | TM6SF2 | chr19: 19375173-19384074 | 10.03 | 24.31 | 1.28 | 1.73 | 5.00E-05 | 7.97E-04 | transmembrane 6 superfamily member 2 |
| 184 | MMP12 | chr11: 102733463-102745764 | 15.23 | 36.65 | 1.27 | 1.87 | 5.00E-05 | 7.97E-04 | matrix metallopeptidase 12 |
| 185 | VSIG10L | chr19: 51834794-51845378 | 1.04 | 2.49 | 1.26 | 1.29 | 5.00E-05 | 7.97E-04 | V-set and immunoglobulin domain containing 10 like |
| 186 | CXCL16 | chr17: 4634722-4643223 | 17.88 | 42.76 | 1.26 | 1.88 | 5.00E-05 | 7.97E-04 | chemokine (C-X-C motif) ligand 16 |
| 187 | ABHD2 | chr15: 89631380-89745591 | 24.14 | 57.42 | 1.25 | 1.94 | 5.00E-05 | 7.97E-04 | abhydrolase domain containing 2 |
| 188 | MAPK15 | chr8: 144798506-144804633 | 0.60 | 1.42 | 1.25 | 0.99 | 1.95E-03 | 1.91E-02 | mitogen-activated protein kinase 15 |
| 189 | FGF2 | chr4: 123747862-123844159 | 0.49 | 1.17 | 1.24 | 0.97 | 2.40E-03 | 2.25E-02 | fibroblast growth factor 2 (basic) |
| 190 | ADAM9 | chr8: 38854504-38962779 | 29.81 | 70.07 | 1.23 | 2.16 | 5.00E-05 | 7.97E-04 | ADAM metallopeptidase domain 9 |
| 191 | CYP2S1 | chr19: 41699114-41713444 | 26.65 | 62.36 | 1.23 | 1.98 | 5.00E-05 | 7.97E-04 | cytochrome P450, family 2, subfamily S, polypeptide 1 |
| 192 | UST | chr6: 149068270-149398126 | 0.69 | 1.60 | 1.22 | 1.24 | 5.00E-05 | 7.97E-04 | uronyl-2-sulfotransferase |
| 193 | AP1S3 | chr2: 224620046-224702319 | 2.04 | 4.74 | 1.22 | 1.62 | 5.00E-05 | 7.97E-04 | adaptor-related protein complex 1, sigma 3 subunit |
| 194 | PITPNC1 | chr17: 65373396-65693379 | 1.64 | 3.81 | 1.22 | 1.74 | 5.00E-05 | 7.97E-04 | phosphatidylinositol transfer protein, cytoplasmic 1 |
| 195 | ST3GAL1 | chr8: 134467090-134584183 | 2.45 | 5.62 | 1.20 | 1.44 | 5.00E-05 | 7.97E-04 | ST3 beta-galactoside alpha-2,3-sialyltransferase 1 |
| 196 | GNA15 | chr19: 3136029-3163767 | 1.96 | 4.48 | 1.19 | 1.32 | 5.00E-05 | 7.97E-04 | guanine nucleotide binding protein (G protein), alpha 15 (Gq class) |
| 197 | PVRL4 | chr1: 161040780-161059385 | 1.50 | 3.42 | 1.19 | 1.29 | 5.00E-05 | 7.97E-04 | poliovirus receptor-related 4 |
| 198 | TSTA3 | chr8: 144694787-144699732 | 49.13 | 111.80 | 1.19 | 2.14 | 5.00E-05 | 7.97E-04 | tissue specific transplantation antigen P35B |
| 199 | SCD | chr10: 102106771-102124588 | 23.98 | 54.51 | 1.18 | 1.65 | 5.00E-05 | 7.97E-04 | stearoyl-CoA desaturase (delta-9-desaturase) |
| 200 | HTATSF1P2 | chr6: 3020389-3025005 | 0.63 | 1.43 | 1.18 | 1.22 | 5.00E-05 | 7.97E-04 | HIV-1 Tat specific factor 1 pseudogene 2 |
| 201 | AJUBA | chr14: 23440382-234518516- | 0.81 | 1.83 | 1.18 | 1.15 | 5.00E-05 | 7.97E-04 | ajuba LIM protein |
| 202 | PHLDA3 | chr1: 201434606-201438299 | 4.80 | 10.83 | 1.17 | 1.48 | 5.00E-05 | 7.97E-04 | pleckstrin homology-like domain, family A, member 3 |
| 203 | C1orf116 | chr1: 207191865-207206101 | 10.04 | 22.65 | 1.17 | 2.07 | 5.00E-05 | 7.97E-04 | chromosome 1 open reading frame 116 |
| 204 | C6orf141 | chr6: 49518112-49519808 | 3.21 | 7.24 | 1.17 | 1.26 | 5.00E-05 | 7.97E-04 | chromosome 6 open reading frame 141 |

TABLE 6-continued

The list of 1058 genes exclusively DE between CR and SSA/P samples.

| | gene | locus | mean_CR | mean SSA/P | log₂FC | test_stat | p_value | p_adj_value | Description |
|---|---|---|---|---|---|---|---|---|---|
| 205 | TMC7 | chr16: 18995255-19091417 | 3.65 | 8.19 | 1.16 | 1.33 | 5.00E-05 | 7.97E-04 | transmembrane channel-like 7 |
| 206 | KIAA1549 | chr7: 138516126-138666064 | 0.42 | 0.95 | 1.16 | 1.39 | 5.00E-05 | 7.97E-04 | KIAA1549 |
| 207 | DAPP1 | chr4: 100737980-100791346 | 2.00 | 4.48 | 1.16 | 1.49 | 5.00E-05 | 7.97E-04 | dual adaptor of phosphotyrosine and 3-phosphoinositides |
| 208 | ZNF432 | chr19: 52536676-52552073 | 2.29 | 5.12 | 1.16 | 1.49 | 5.00E-05 | 7.97E-04 | zinc finger protein 432 |
| 209 | DUSP5 | chr10: 112257624-112271302 | 14.15 | 31.63 | 1.16 | 1.87 | 5.00E-05 | 7.97E-04 | dual specificity phosphatase 5 |
| 210 | ISG20 | chr15: 89182038-89198879 | 32.62 | 72.51 | 1.15 | 1.94 | 5.00E-05 | 7.97E-04 | interferon stimulated exonuclease gene 20 kDa |
| 211 | TPM4 | chr19: 16178316-16213813 | 129.57 | 287.54 | 1.15 | 1.72 | 5.00E-05 | 7.97E-04 | tropomyosin 4 |
| 212 | PTPN13 | chr4: 87515467-87736328 | 0.60 | 1.32 | 1.15 | 1.35 | 5.00E-05 | 7.97E-04 | protein tyrosine phosphatase, non-receptor type 13 (APO-1/CD95 (Fas)-associated phosphatase) |
| 213 | AMOTL2 | chr3: 134074186-134094259 | 1.90 | 4.20 | 1.15 | 1.52 | 5.00E-05 | 7.97E-04 | angiomotin like 2 |
| 214 | PLK3 | chr1: 45266035-45272957 | 3.02 | 6.68 | 1.14 | 1.38 | 5.00E-05 | 7.97E-04 | polo-like kinase 3 |
| 215 | ADCY4 | chr14: 24787554-24804277 | 2.88 | 6.34 | 1.14 | 1.48 | 5.00E-05 | 7.97E-04 | adenylate cyclase 4 |
| 216 | TNS4 | chr17: 38632079-38657854 | 3.51 | 7.71 | 1.14 | 1.67 | 5.00E-05 | 7.97E-04 | tensin 4 |
| 217 | CITED4 | chr1: 41326727-41328018 | 1.39 | 3.06 | 1.14 | 0.91 | 4.10E-03 | 3.46E-02 | Cbp/p300-interacting transactivator, with Glu/Asp-rich carboxy-terminal domain, 4 |
| 218 | GLRA4 | chrX: 102962271-102983552 | 0.60 | 1.31 | 1.13 | 0.82 | 4.10E-03 | 3.46E-02 | glycine receptor, alpha 4 |
| 219 | ASPH | chr8: 62200524-62627199 | 31.72 | 69.58 | 1.13 | 1.92 | 5.00E-05 | 7.97E-04 | aspartate beta-hydroxylase |
| 220 | MSMO1 | chr4: 166248817-166264314 | 39.79 | 87.24 | 1.13 | 1.81 | 5.00E-05 | 7.97E-04 | methylsterol monooxygenase 1 |
| 221 | DDIT4 | chr10: 74033676-74035797 | 23.50 | 51.22 | 1.12 | 1.88 | 5.00E-05 | 7.97E-04 | DNA-damage-inducible transcript 4 |
| 222 | PAM | chr5: 102201526-102366808 | 8.73 | 18.99 | 1.12 | 2.01 | 5.00E-05 | 7.97E-04 | peptidylglycine alpha-amidating monooxygenase |
| 223 | SHF | chr15: 45459411-45493373 | 1.29 | 2.80 | 1.12 | 1.14 | 5.00E-05 | 7.97E-04 | Src homology 2 domain containing F |
| 224 | ARHGEF3 | chr3: 567614451-57113336 | 2.38 | 5.17 | 1.12 | 1.51 | 5.00E-05 | 7.97E-04 | Rho guanine nucleotide exchange factor (GEF) 3 |
| 225 | LPCAT1 | chr5: 1461541-1524056 | 7.26 | 15.73 | 1.11 | 1.77 | 5.00E-05 | 7.97E-04 | lysophosphatidylcholine acyltransferase 1 |
| 226 | ACY3 | chr11: 67410025-67418130 | 8.03 | 17.34 | 1.11 | 1.45 | 5.00E-05 | 7.97E-04 | aminoacylase 3 |
| 227 | PLXNA3 | chrX: 153686620-153701989 | 8.18 | 17.63 | 1.11 | 1.92 | 5.00E-05 | 7.97E-04 | plexin A3 |
| 228 | SEC24D | chr4: 119643977-119757326 | 14.58 | 31.42 | 1.11 | 1.95 | 5.00E-05 | 7.97E-04 | SEC24 homolog D, COPII coat complex component |
| 229 | AKR1B15 | chr7: 134233848-134264592 | 2.91 | 6.27 | 1.10 | 1.18 | 5.00E-05 | 7.97E-04 | aldo-keto reductase family 1, member B15 |
| 230 | SLC22A15 | chr1: 116519118-116612675 | 0.64 | 1.38 | 1.10 | 1.13 | 5.00E-05 | 7.97E-04 | solute carrier family 22, member 15 |
| 231 | MACC1 | chr7: 19958603-20257013 | 2.20 | 4.72 | 1.10 | 1.80 | 5.00E-05 | 7.97E-04 | metastasis associated in colon cancer 1 |
| 232 | FAM86DP | chr3: 75470702-75484266 | 1.68 | 3.60 | 1.10 | 1.23 | 5.00E-05 | 7.97E-04 | family with sequence similarity 86, member D, pseudogene |
| 233 | DAPK1 | chr9: 90112142-90323549 | 5.72 | 12.28 | 1.10 | 1.86 | 5.00E-05 | 7.97E-04 | death-associated protein kinase 1 |
| 234 | TSPAN8 | chr12: 71518876-71551779 | 1477.14 | 3166.40 | 1.10 | 1.17 | 7.00E-04 | 8.19E-03 | tetraspanin 8 |
| 235 | EPS8L1 | chr19: 55587220-55599291 | 18.44 | 39.39 | 1.09 | 1.89 | 5.00E-05 | 7.97E-04 | EPS8-like 1 |
| 236 | IL1R2 | chr2: 102608305-102644884 | 38.23 | 81.56 | 1.09 | 1.83 | 5.00E-05 | 7.97E-04 | interleukin 1 receptor, type II |
| 237 | AGRN | chr1: 955502-991499 | 14.45 | 30.82 | 1.09 | 1.96 | 5.00E-05 | 7.97E-04 | agrin |
| 238 | ACY1 | chr3: 52009041-52023218 | 54.72 | 116.70 | 1.09 | 1.89 | 5.00E-05 | 7.97E-04 | aminoacylase 1 |
| 239 | ATP13A2 | chr1: 17312452-17338467 | 17.04 | 36.30 | 1.09 | 1.94 | 5.00E-05 | 7.97E-04 | ATPase type 13A2 |
| 240 | SFXN3 | chr10: 102790995-102800998 | 7.52 | 16.00 | 1.09 | 1.75 | 5.00E-05 | 7.97E-04 | sideroflexin 3 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 241 | SGMS2 | chr4: 108745720-108836204 | 8.11 | 17.18 | 1.08 | 2.01 | 5.00E−05 | 7.97E−04 | sphingomyelin synthase 2 |
| 242 | KLK13 | chr19: 51559462-51568367 | 0.77 | 1.64 | 1.08 | 0.79 | 4.00E−03 | 3.39E−02 | kallikrein-related peptidase 13 |
| 243 | KPNA7 | chr7: 98771196-98805089 | 0.58 | 1.23 | 1.08 | 0.79 | 5.45E−03 | 4.37E−02 | karyopherin alpha 7 (importin alpha 8) |
| 244 | CHPF | chr2: 220403668-220408487 | 15.25 | 32.27 | 1.08 | 1.95 | 5.00E−05 | 7.97E−04 | chondroitin polymerizing factor |
| 245 | CCR6 | chr6: 167525294-167552629 | 1.61 | 3.41 | 1.08 | 1.26 | 5.00E−05 | 7.97E−04 | chemokine (C-C motif) receptor 6 |
| 246 | VWA1 | chr1: 1370902-1378262 | 5.71 | 12.01 | 1.07 | 1.78 | 5.00E−05 | 7.97E−04 | von Willebrand factor A domain containing 1 |
| 247 | MEIS2 | chr15: 37183221-37393500 | 0.75 | 1.57 | 1.06 | 0.98 | 4.00E−04 | 5.06E−03 | Meis homeobox 2 |
| 248 | USP18 | chr22: 18632757-18660162 | 3.62 | 7.53 | 1.06 | 1.35 | 5.00E−05 | 7.97E−04 | ubiquitin specific peptidase 18 |
| 249 | LIMCH1 | chr4: 41361623-41702061 | 1.51 | 3.13 | 1.05 | 1.42 | 5.00E−05 | 7.97E−04 | LIM and calponin homology domains 1 |
| 250 | PERP | chr6: 138409641-138428660 | 47.52 | 97.23 | 1.03 | 1.83 | 5.00E−05 | 7.97E−04 | PERP, TP53 apoptosis effector |
| 251 | GPX2 | chr14: 65381078-65569413 | 168.48 | 344.46 | 1.03 | 1.18 | 5.00E−05 | 7.97E−04 | glutathione peroxidase 2 |
| 252 | TIMP4 | chr3: 12045833-12233532 | 1.27 | 2.60 | 1.03 | 0.89 | 1.95E−03 | 1.91E−02 | TIMP metallopeptidase inhibitor 4 |
| 253 | DUSP14 | chr17: 35849950-35873588 | 1.53 | 3.13 | 1.03 | 0.93 | 1.65E−03 | 1.66E−02 | dual specificity phosphatase 14 |
| 254 | TMEM150B | chr19: 55824168-55836708 | 25.21 | 51.40 | 1.03 | 1.52 | 5.00E−05 | 7.97E−04 | transmembrane protein 150B |
| 255 | C8orf4 | chr8: 40010986-40012827 | 15.29 | 31.16 | 1.03 | 1.74 | 5.00E−05 | 7.97E−04 | chromosome 8 open reading frame 4 |
| 256 | DHRS9 | chr2: 169923544-169952677 | 148.32 | 302.30 | 1.03 | 1.67 | 5.00E−05 | 7.97E−04 | dehydrogenase/reductase (SDR family) member 9 |
| 257 | LAMA3 | chr18: 21269561-21535029 | 16.87 | 34.36 | 1.03 | 1.75 | 5.00E−05 | 7.97E−04 | laminin, alpha 3 |
| 258 | TRIM47 | chr17: 73870244-73874656 | 12.77 | 25.99 | 1.03 | 1.70 | 5.00E−05 | 7.97E−04 | tripartite motif containing 47 |
| 259 | IFIT1 | chr10: 91152302-91166244 | 1.69 | 3.42 | 1.02 | 1.32 | 5.00E−05 | 7.97E−04 | interferon-induced protein with tetratricopeptide repeats 1 |
| 260 | PGM3 | chr6: 83777384-83906256 | 10.48 | 21.26 | 1.02 | 1.33 | 5.00E−05 | 7.97E−04 | phosphoglucomutase 3 |
| 261 | NABP1 | chr2: 192542797-192553248 | 7.63 | 15.43 | 1.02 | 1.75 | 5.00E−05 | 7.97E−04 | nucleic acid binding protein 1 |
| 262 | FCHO1 | chr19: 17858526-17899377 | 2.21 | 4.46 | 1.01 | 1.26 | 5.00E−05 | 7.97E−04 | FCH domain only 1 |
| 263 | PNMA1 | chr14: 74178485-74181128 | 10.79 | 21.73 | 1.01 | 1.63 | 5.00E−05 | 7.97E−04 | paraneoplastic Ma antigen 1 |
| 264 | PPP1R13L | chr19: 45882891-45927177 | 6.68 | 13.43 | 1.01 | 0.96 | 2.05E−03 | 1.98E−02 | protein phosphatase 1, regulatory subunit 13 like |
| 265 | INPP1 | chr2: 191208195-191236391 | 15.81 | 31.68 | 1.00 | 1.71 | 5.00E−05 | 7.97E−04 | inositol polyphosphate-1-phosphatase |
| 266 | IL1RL2 | chr2: 102803432-102855811 | 0.50 | 1.00 | 1.00 | 0.80 | 2.25E−03 | 2.14E−02 | interleukin 1 receptor-like 2 |
| 267 | GBP3 | chr1: 89472359-89488549 | 32.08 | 64.03 | 1.00 | 1.71 | 5.00E−05 | 7.97E−04 | guanylate binding protein 3 |
| 268 | BAG3 | chr10: 121410881-121437329 | 8.77 | 17.47 | 0.99 | 1.61 | 5.00E−05 | 7.97E−04 | BCL2-associated athanogene 3 |
| 269 | SLC2A1 | chr1: 43391045-43449029 | 20.36 | 40.51 | 0.99 | 1.71 | 5.00E−05 | 7.97E−04 | solute carrier family 2 (facilitated glucose transporter), member 1 |
| 270 | WWC1 | chr5: 167719064-167899308 | 4.39 | 8.69 | 0.98 | 1.65 | 5.00E−05 | 7.97E−04 | WW and C2 domain containing 1 |
| 271 | MAPK8IP1 | chr11: 45907046-45928016 | 0.72 | 1.43 | 0.98 | 0.92 | 2.30E−03 | 2.18E−02 | mitogen-activated protein kinase 8 interacting protein 1 |
| 272 | NOCT | chr4: 139936912-139967093 | 1.80 | 3.56 | 0.98 | 1.01 | 2.50E−04 | 3.38E−03 | nocturnin |
| 273 | BHLHE40 | chr3: 5021096-5026865 | 14.64 | 28.84 | 0.98 | 1.62 | 5.00E−05 | 7.97E−04 | basic helix-loop-helix family, member e40 |
| 274 | LINC01138 | chr1: 143717587-143744519 | 1.98 | 3.90 | 0.98 | 0.95 | 9.00E−04 | 1.01E−02 | long intergenic non-protein coding RNA 1138 |
| 275 | RHOF | chr12: 122150657-122231594 | 38.24 | 75.22 | 0.98 | 1.57 | 5.00E−05 | 7.97E−04 | ras homolog family member F (in filopodia) |
| 276 | FAM214B | chr9: 35104117-35115893 | 14.72 | 28.95 | 0.98 | 1.69 | 5.00E−05 | 7.97E−04 | family with sequence similarity 214, member B |
| 277 | SPRED1 | chr15: 38545051-38649450 | 7.77 | 15.29 | 0.98 | 1.77 | 5.00E−05 | 7.97E−04 | sprouty-related, EVH1 domain containing 1 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 278 | NUCB2 | chr11: 17298285-17353070 | 21.28 | 41.76 | 0.97 | 1.80 | 5.00E−05 | 7.97E−04 | nucleobindin 2 |
| 279 | MST1 | chr3: 49721379-49726196 | 1.97 | 3.86 | 0.97 | 1.06 | 2.00E−04 | 2.80E−03 | macrophage stimulating 1 |
| 280 | ANTXR2 | chr4: 80822770-80994626 | 16.05 | 31.45 | 0.97 | 1.35 | 5.00E−05 | 7.97E−04 | anthrax toxin receptor 2 |
| 281 | CD59 | chr11: 33724555-33758025 | 38.45 | 75.33 | 0.97 | 1.58 | 5.00E−05 | 7.97E−04 | CD59 molecule, complement regulatory protein |
| 282 | ITGB4 | chr17: 73717515-73753899 | 45.05 | 88.26 | 0.97 | 1.64 | 5.00E−05 | 7.97E−04 | integrin, beta 4 |
| 283 | CYP4F11 | chr19: 16023179-16045676 | 2.99 | 5.86 | 0.97 | 1.19 | 1.50E−04 | 2.18E−03 | cytochrome P450, family 4, subfamily F, polypeptide 11 |
| 284 | LINC01207 | chr4: 165675282-165724947 | 9.06 | 17.62 | 0.96 | 1.63 | 5.00E−05 | 7.97E−04 | long intergenic non-protein coding RNA 1207 |
| 285 | CCNG2 | chr4: 78078356-78091213 | 16.17 | 31.43 | 0.96 | 1.78 | 5.00E−05 | 7.97E−04 | cyclin G2 |
| 286 | PODN | chr1: 53527723-53551174 | 1.61 | 3.08 | 0.94 | 1.06 | 5.50E−04 | 6.69E−03 | podocan |
| 287 | BAIAP2L1 | chr7: 97910978-98030427 | 34.22 | 65.52 | 0.94 | 1.32 | 5.00E−05 | 7.97E−04 | BAH-associated protein 2-like 1 |
| 288 | ITGA6 | chr2: 173292313-173371181 | 49.72 | 95.14 | 0.94 | 1.51 | 5.00E−05 | 7.97E−04 | integrin, alpha 6 |
| 289 | FLJ32255 | chr5: 42985500-42993435 | 1.55 | 2.95 | 0.94 | 0.99 | 6.50E−04 | 7.69E−03 | uncharacterized LOC643977 |
| 290 | ETV7 | chr6: 36321997-36355577 | 2.55 | 4.88 | 0.93 | 0.99 | 1.20E−03 | 1.28E−02 | ets variant 7 |
| 291 | LYZ | chr12: 69742133-69748013 | 249.84 | 477.20 | 0.93 | 1.42 | 5.00E−05 | 7.97E−04 | lysozyme |
| 292 | RIPK3 | chr14: 24805226-24809242 | 24.96 | 47.65 | 0.93 | 1.63 | 5.00E−05 | 7.97E−04 | receptor-interacting serine-threonine kinase 3 |
| 293 | RHBDF1 | chr16: 108057-122629 | 13.85 | 26.42 | 0.93 | 1.60 | 5.00E−05 | 7.97E−04 | rhomboid 5 homolog 1 (*Drosophila*) |
| 294 | OPTN | chr10: 13142081-13180276 | 28.46 | 54.27 | 0.93 | 1.71 | 5.00E−05 | 7.97E−04 | optineurin |
| 295 | ZNF200 | chr16: 3272324-3285457 | 2.58 | 4.91 | 0.93 | 1.20 | 5.00E−05 | 7.97E−04 | zinc finger protein 200 |
| 296 | LRRC8A | chr9: 131644390-131680317 | 11.56 | 21.99 | 0.93 | 1.62 | 5.00E−05 | 7.97E−04 | leucine rich repeat containing 8 family, member A |
| 297 | CNN2 | chr19: 1026297-1039064 | 22.16 | 42.14 | 0.93 | 1.62 | 5.00E−05 | 7.97E−04 | calponin 2 |
| 298 | NOS3 | chr7: 150688143-150721586 | 0.90 | 1.71 | 0.93 | 0.73 | 5.75E−03 | 4.55E−02 | nitric oxide synthase 3 (endothelial cell) |
| 299 | TNFRSF21 | chr6: 47199262-47277683 | 35.07 | 66.68 | 0.93 | 1.62 | 5.00E−05 | 7.97E−04 | tumor necrosis factor receptor superfamily, member 21 |
| 300 | PODXL | chr7: 131185020-131241376 | 3.84 | 7.30 | 0.93 | 1.49 | 5.00E−05 | 7.97E−04 | podocalyxin-like |
| 301 | TIFAB | chr5: 134784557-134788089 | 1.16 | 2.20 | 0.92 | 0.75 | 4.40E−03 | 3.65E−02 | TRAF-interacting protein with forkhead-associated domain, family member B |
| 302 | TNFRSF10B | chr8: 22844929-22941132 | 13.00 | 24.63 | 0.92 | 1.43 | 5.00E−05 | 7.97E−04 | tumor necrosis factor receptor superfamily, member 10b |
| 303 | SLC25A29 | chr14: 100757447-100772884 | 7.64 | 14.47 | 0.92 | 1.38 | 5.00E−05 | 7.97E−04 | solute carrier family 25 (mitochondrial carnitine/acylcarnitine carrier), member 29 |
| 304 | PHKA1 | chrX: 71798663-71934029 | 1.33 | 2.51 | 0.92 | 1.18 | 5.00E−05 | 7.97E−04 | phosphorylase kinase, alpha 1 (muscle) |
| 305 | ARHGAP10 | chr4: 148653452-148993927 | 1.18 | 2.22 | 0.92 | 1.02 | 2.50E−04 | 3.38E−03 | Rho GTPase activating protein 10 |
| 306 | PMEPA1 | chr20: 56223447-56286592 | 5.99 | 11.32 | 0.92 | 1.48 | 5.00E−05 | 7.97E−04 | prostate transmembrane protein, androgen induced 1 |
| 307 | HAPLN3 | chr15: 89420518-89438770 | 1.79 | 3.37 | 0.92 | 0.83 | 3.30E−03 | 2.90E−02 | hyaluronan and proteoglycan link protein 3 |
| 308 | KRT19 | chr17: 39679868-39684641 | 875.64 | 1652.07 | 0.92 | 1.06 | 1.50E−04 | 2.18E−03 | keratin 19, type I |
| 309 | PPP4R1L | chr20: 56807832-56884495 | 0.90 | 1.69 | 0.92 | 0.82 | 4.45E−03 | 3.68E−02 | protein phosphatase 4, regulatory subunit 1-like (pseudogene) |
| 310 | FHL2 | chr2: 105977282-106055230 | 59.88 | 112.80 | 0.91 | 1.64 | 5.00E−05 | 7.97E−04 | four and a half LIM domains 2 |
| 311 | GALE | chr1: 24122088-24127294 | 72.79 | 136.72 | 0.91 | 1.64 | 5.00E−05 | 7.97E−04 | UDP-galactose-4-epimerase |
| 312 | BCL2L1 | chr20: 30252260-30310656 | 33.07 | 62.07 | 0.91 | 1.64 | 5.00E−05 | 7.97E−04 | BCL2-like 1 |
| 313 | CASP4 | chr11: 104813593-104839325 | 16.46 | 30.81 | 0.90 | 1.52 | 5.00E−05 | 7.97E−04 | caspase 4, apoptosis-related cysteine peptidase |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 314 | MXRA8 | chr1: 1288068-1298921 | 13.33 | 24.92 | 0.90 | 1.52 | 5.00E−05 | 7.97E−04 | matrix-remodelling associated 8 |
| 315 | NFKBIZ | chr3: 101498028-101579869 | 16.54 | 30.88 | 0.90 | 1.45 | 5.00E−05 | 7.97E−04 | nuclear factor of kappa light polypeptide gene enhancer in B-cells inhibitor, zeta |
| 316 | LPIN1 | chr2: 11817704-11967533 | 6.17 | 11.50 | 0.90 | 1.44 | 5.00E−05 | 7.97E−04 | lipin 1 |
| 317 | NBPF15 | chr1: 147574322-149109725 | 1.62 | 3.02 | 0.90 | 1.08 | 1.50E−04 | 2.18E−03 | neuroblastoma breakpoint family, member 15 |
| 318 | UACA | chr15: 70946892-71055850 | 6.58 | 12.26 | 0.90 | 1.71 | 5.00E−05 | 7.97E−04 | uveal autoantigen with coiled-coil domains and ankyrin repeats |
| 319 | CPD | chr17: 28705941-28796675 | 12.89 | 24.02 | 0.90 | 1.67 | 5.00E−05 | 7.97E−04 | carboxypeptidase D |
| 320 | S100A6 | chr1: 153507075-153508717 | 3434.60 | 6398.04 | 0.90 | 0.96 | 2.85E−03 | 2.59E−02 | S100 calcium binding protein A6 |
| 321 | TLR4 | chr9: 120466452-120479769 | 3.64 | 6.76 | 0.89 | 1.46 | 5.00E−05 | 7.97E−04 | toll-like receptor 4 |
| 322 | SYTL1 | chr1: 27668482-27680423 | 10.19 | 18.91 | 0.89 | 1.39 | 5.00E−05 | 7.97E−04 | synaptotagmin-like 1 |
| 323 | TIMP2 | chr17: 76849058-76921472 | 36.71 | 68.02 | 0.89 | 1.55 | 5.00E−05 | 7.97E−04 | TIMP metallopeptidase inhibitor 2 |
| 324 | RAB37 | chr17: 72667255-72743474 | 6.30 | 11.65 | 0.89 | 1.16 | 5.00E−05 | 7.97E−04 | RAB37, member RAS oncogene family |
| 325 | SORD | chr15: 45315301-45367287 | 12.55 | 23.21 | 0.89 | 1.50 | 5.00E−05 | 7.97E−04 | sorbitol dehydrogenase |
| 326 | ARL5B | chr10: 18948312-18966940 | 3.96 | 7.31 | 0.88 | 1.31 | 5.00E−05 | 7.97E−04 | ADP-ribosylation factor-like 5B |
| 327 | MAP3K6 | chr1: 27681669-27693337 | 4.43 | 8.16 | 0.88 | 1.37 | 5.00E−05 | 7.97E−04 | mitogen-activated protein kinase kinase kinase 6 |
| 328 | FAM57A | chr17: 635846-646075 | 7.74 | 14.27 | 0.88 | 1.28 | 5.00E−05 | 7.97E−04 | family with sequence similarity 57, member A |
| 329 | PLA2G4C | chr19: 48551099-48614109 | 1.73 | 3.19 | 0.88 | 0.94 | 1.35E−03 | 1.41E−02 | phospholipase A2, group IVC (cytosolic, calcium-independent) |
| 330 | TTC7A | chr2: 47129008-47303275 | 8.10 | 14.93 | 0.88 | 0.99 | 5.00E−04 | 6.13E−03 | tetratricopeptide repeat domain 7A |
| 331 | SGMS1 | chr10: 520653444-52383737 | 3.77 | 6.95 | 0.88 | 1.32 | 5.00E−05 | 7.97E−04 | sphingomyelin synthase 1 |
| 332 | SETD7 | chr4: 140427191-140477577 | 5.58 | 10.24 | 0.88 | 1.53 | 5.00E−05 | 7.97E−04 | SET domain containing (lysine methyltransferase) 7 |
| 333 | RPL22L1 | chr3: 170582664-170588045 | 9.10 | 16.68 | 0.87 | 1.32 | 5.00E−05 | 7.97E−04 | ribosomal protein L22-like 1 |
| 334 | ANXA2 | chr15: 60639349-60690185 | 576.09 | 1055.30 | 0.87 | 1.11 | 2.50E−04 | 3.38E−03 | annexin A2 |
| 335 | IBTK | chr6: 82879955-82957448 | 14.47 | 26.46 | 0.87 | 1.61 | 5.00E−05 | 7.97E−04 | inhibitor of Bruton agammaglobulinemia tyrosine kinase |
| 336 | COL9A2 | chr1: 40766162-40782939 | 3.72 | 6.78 | 0.87 | 1.21 | 1.50E−04 | 2.18E−03 | collagen, type IX, alpha 2 |
| 337 | TMEM165 | chr4: 56262079-56292342 | 34.83 | 63.43 | 0.86 | 1.56 | 5.00E−05 | 7.97E−04 | transmembrane protein 165 |
| 338 | KCNK6 | chr19: 38810483-38819649 | 14.23 | 25.91 | 0.86 | 1.47 | 5.00E−05 | 7.97E−04 | potassium channel, two pore domain subfamily K, member 6 |
| 339 | SP110 | chr2: 231033644-231090444 | 4.45 | 8.11 | 0.86 | 1.22 | 5.00E−05 | 7.97E−04 | SP110 nuclear body protein |
| 340 | ORAI3 | chr16: 30960404-30966259 | 7.04 | 12.80 | 0.86 | 1.22 | 5.00E−05 | 7.97E−04 | ORAI calcium release-activated calcium modulator 3 |
| 341 | KCNQ4 | chr1: 41249683-41336124 | 1.04 | 1.89 | 0.86 | 0.92 | 1.50E−03 | 1.53E−02 | potassium channel, voltage gated KQT-like subfamily Q, member 4 |
| 342 | SNX9 | chr6: 158244202-158366109 | 29.39 | 53.33 | 0.86 | 1.54 | 5.00E−05 | 7.97E−04 | sorting nexin 9 |
| 343 | CABLES1 | chr18: 20714527-20840434 | 3.44 | 6.25 | 0.86 | 1.27 | 5.00E−05 | 7.97E−04 | Cdk5 and Abl enzyme substrate 1 |
| 344 | GGT1 | chr22: 24979717-25024972 | 8.14 | 14.77 | 0.86 | 1.04 | 9.00E−04 | 1.01E−02 | gamma-glutamyltransferase 1 |
| 345 | DDX60L | chr4: 169277885-169401665 | 7.16 | 12.99 | 0.86 | 1.58 | 5.00E−05 | 7.97E−04 | DEAD (Asp-Glu-Ala-Asp) box polypeptide 60-like |
| 346 | SLC16A3 | chr17: 80186281-80197375 | 57.19 | 103.38 | 0.85 | 1.49 | 5.00E−05 | 7.97E−04 | solute carrier family 16 (monocarboxylate transporter), member 3 |
| 347 | WWC2 | chr4: 184020462-184241929 | 0.61 | 1.10 | 0.85 | 0.97 | 7.00E−04 | 8.19E−03 | WW and C2 domain containing 2 |
| 348 | MAP2K3 | chr17: 21187967-21218551 | 30.45 | 54.88 | 0.85 | 1.50 | 5.00E−05 | 7.97E−04 | mitogen-activated protein kinase kinase 3 |
| 349 | IFIT2 | chr10: 91061705-91069033 | 2.39 | 4.30 | 0.85 | 1.18 | 5.00E−05 | 7.97E−04 | interferon-induced protein with tetratricopeptide repeats 2 |

TABLE 6-continued

The list of 1058 genes exclusively DE between CR and SSA/P samples.

| | gene | locus | mean_CR | mean SSA/P | log₂FC | test_stat | p_value | p_adj_value | Description |
|---|---|---|---|---|---|---|---|---|---|
| 350 | ERAP2 | chr5: 96211643-96255406 | 8.96 | 16.14 | 0.85 | 1.26 | 5.00E-05 | 7.97E-04 | endoplasmic reticulum aminopeptidase 2 |
| 351 | CALU | chr7: 128379345-128415844 | 12.79 | 23.01 | 0.85 | 1.56 | 5.00E-05 | 7.97E-04 | calumenin |
| 352 | PFKFB3 | chr10: 6186842-6277507 | 5.30 | 9.53 | 0.85 | 1.33 | 5.00E-05 | 7.97E-04 | 6-phosphofructo-2-kinase/fructose-2,6-biphosphatase 3 |
| 353 | SNHG5 | chr6: 86386724-86388451 | 96.63 | 173.62 | 0.85 | 1.32 | 5.00E-05 | 7.97E-04 | small nucleolar RNA host gene 5 |
| 354 | GCNT3 | chr15: 59903981-59912210 | 204.61 | 367.58 | 0.85 | 1.22 | 5.00E-05 | 7.97E-04 | glucosaminyl (N-acetyl) transferase 3, mucin type |
| 355 | NUP62CL | chrX: 106366656-106449670 | 1.59 | 2.85 | 0.84 | 0.83 | 6.30E-03 | 4.91E-02 | nucleoporin 62 kDa C-terminal like |
| 356 | CD276 | chr15: 73976621-74006859 | 10.23 | 18.36 | 0.84 | 1.40 | 5.00E-05 | 7.97E-04 | CD276 molecule |
| 357 | SLCO4A1 | chr20: 61273796-61303647 | 3.44 | 6.15 | 0.84 | 0.97 | 8.00E-04 | 9.10E-03 | solute carrier organic anion transporter family, member 4A1 |
| 358 | COL17A1 | chr10: 105791045-105845638 | 57.93 | 103.64 | 0.84 | 1.31 | 5.00E-05 | 7.97E-04 | collagen, type XVII, alpha 1 |
| 359 | ABTB1 | chr3: 127391780-127399769 | 12.64 | 22.53 | 0.83 | 1.33 | 5.00E-05 | 7.97E-04 | ankyrin repeat and BTB (POZ) domain containing 1 |
| 360 | TNFRSF1B | chr1: 12226999-12269277 | 11.28 | 20.07 | 0.83 | 1.43 | 5.00E-05 | 7.97E-04 | tumor necrosis factor receptor superfamily, member 1B |
| 361 | GNPNAT1 | chr14: 53241910-53258386 | 18.14 | 32.26 | 0.83 | 1.57 | 5.00E-05 | 7.97E-04 | glucosamine-phosphate N-acetyltransferase 1 |
| 362 | ICA1 | chr7: 8152814-8302242 | 13.90 | 24.68 | 0.83 | 1.41 | 5.00E-05 | 7.97E-04 | islet cell autoantigen 1, 69 kDa |
| 363 | RRAS | chr19: 50138551-50143400 | 41.18 | 73.08 | 0.83 | 1.41 | 5.00E-05 | 7.97E-04 | related RAS viral (r-ras) oncogene homolog |
| 364 | TRANK1 | chr3: 36868307-36986548 | 13.30 | 23.57 | 0.83 | 1.43 | 5.00E-05 | 7.97E-04 | tetratricopeptide repeat and ankyrin repeat containing 1 |
| 365 | NFE2L3 | chr7: 26191846-26226756 | 6.13 | 10.86 | 0.82 | 1.35 | 5.00E-05 | 7.97E-04 | nuclear factor, erythroid 2-like 3 |
| 366 | STXBP6 | chr14: 25281305-25519095 | 6.42 | 11.35 | 0.82 | 1.14 | 1.00E-04 | 1.51E-03 | syntaxin binding protein 6 (amisyn) |
| 367 | ACPP | chr3: 132036210-132087146 | 2.96 | 5.21 | 0.82 | 0.92 | 1.75E-03 | 1.74E-02 | acid phosphatase, prostate |
| 368 | LOC100288778 | chr12: 87983-91263 | 3.19 | 5.63 | 0.82 | 0.82 | 1.65E-03 | 1.66E-02 | WAS protein family homolog 1 pseudogene |
| 369 | SC5D | chr11: 121163387-121184119 | 6.78 | 11.94 | 0.82 | 1.43 | 5.00E-05 | 7.97E-04 | sterol-C5-desaturase |
| 370 | CYP51A1 | chr7: 91741462-91764059 | 48.27 | 84.95 | 0.82 | 1.38 | 5.00E-05 | 7.97E-04 | cytochrome P450, family 51, subfamily A, polypeptide 1 |
| 371 | GLMP | chr1: 156262477-156265480 | 21.65 | 38.09 | 0.81 | 1.30 | 5.00E-05 | 7.97E-04 | glycosylated lysosomal membrane protein |
| 372 | SOCS3 | chr17: 76352857-76356160 | 3.69 | 6.48 | 0.81 | 1.02 | 8.50E-04 | 9.59E-03 | suppressor of cytokine signaling 3 |
| 373 | EHD1 | chr11: 64620198-64647185 | 18.85 | 33.13 | 0.81 | 1.47 | 5.00E-05 | 7.97E-04 | EH-domain containing 1 |
| 374 | KLF2 | chr19: 16435650-16438339 | 9.99 | 17.55 | 0.81 | 1.14 | 3.50E-04 | 4.55E-03 | Kruppel-like factor 2 |
| 375 | LIF | chr22: 30636435-30642840 | 4.62 | 8.11 | 0.81 | 1.23 | 5.00E-05 | 7.97E-04 | leukemia inhibitory factor |
| 376 | PLS3 | chrX: 114752496-114885179 | 9.47 | 16.60 | 0.81 | 1.45 | 5.00E-05 | 7.97E-04 | plastin 3 |
| 377 | HS3ST1 | chr4: 11399987-11430537 | 3.42 | 6.00 | 0.81 | 0.93 | 1.00E-03 | 1.10E-02 | heparan sulfate (glucosamine) 3-O-sulfotransferase 1 |
| 378 | SLC17A9 | chr20: 61583998-61599949 | 10.48 | 18.37 | 0.81 | 1.27 | 5.00E-05 | 7.97E-04 | solute carrier family 17 (vesicular nucleotide transporter), member 9 |
| 379 | SCG5 | chr15: 32933869-32989298 | 4.74 | 8.30 | 0.81 | 0.92 | 9.50E-04 | 1.05E-02 | secretogranin V |
| 380 | C1GALT1 | chr7: 7222245-7288280 | 6.53 | 11.43 | 0.81 | 1.48 | 5.00E-05 | 7.97E-04 | core 1 synthase, glycoprotein-N-acetylgalactosamine 3-beta-galactosyltransferase 1 |
| 381 | BOK | chr2: 242483800-242513553 | 5.68 | 9.94 | 0.81 | 1.18 | 1.50E-04 | 2.18E-03 | BCL2-related ovarian killer |
| 382 | SHB | chr9: 37915894-38069210 | 3.58 | 6.27 | 0.81 | 1.27 | 5.00E-05 | 7.97E-04 | Src homology 2 domain containing adaptor protein B |
| 383 | PDLIM7 | chr5: 176910394-176924606 | 11.66 | 20.39 | 0.81 | 1.12 | 2.00E-04 | 2.80E-03 | PDZ and LIM domain 7 (enigma) |
| 384 | P4HB | chr17: 79801033-79818544 | 318.06 | 556.16 | 0.81 | 1.09 | 5.00E-05 | 7.97E-04 | prolyl 4-hydroxylase, beta polypeptide |
| 385 | ANKRD22 | chr10: 90562486-90611732 | 5.76 | 10.06 | 0.81 | 1.41 | 5.00E-05 | 7.97E-04 | ankyrin repeat domain 22 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 386 | INSIG2 | chr2: 118846049-118867597 | 8.45 | 14.76 | 0.80 | 1.37 | 5.00E−05 | 7.97E−04 | insulin induced gene 2 |
| 387 | GABRE | chrX: 151121595-151143151 | 7.51 | 13.07 | 0.80 | 1.25 | 5.00E−05 | 7.97E−04 | gamma-aminobutyric acid (GABA) A receptor, epsilon |
| 388 | TXNDC17 | chr17: 6481644-6554954 | 23.91 | 41.54 | 0.80 | 1.19 | 5.00E−05 | 7.97E−04 | thioredoxin domain containing 17 |
| 389 | GAN | chr16: 81348570-81413803 | 1.00 | 1.73 | 0.80 | 0.92 | 1.15E−03 | 1.24E−02 | gigaxonin |
| 390 | MST1R | chr3: 49924435-49941306 | 31.40 | 54.48 | 0.79 | 1.41 | 5.00E−05 | 7.97E−04 | macrophage stimulating 1 receptor |
| 391 | ITGB6 | chr2: 160956176-161056824 | 11.17 | 19.32 | 0.79 | 1.40 | 5.00E−05 | 7.97E−04 | integrin, beta 6 |
| 392 | MFSD2A | chr1: 40420783-40435640 | 10.01 | 17.30 | 0.79 | 1.17 | 5.00E−05 | 7.97E−04 | major facilitator superfamily domain containing 2A |
| 393 | FUT8 | chr14: 65877309-66210839 | 6.81 | 11.75 | 0.79 | 1.34 | 5.00E−05 | 7.97E−04 | fucosyltransferase 8 (alpha (1,6) fucosyltransferase) |
| 394 | RIMS3 | chr1: 41086351-41131324 | 3.48 | 6.01 | 0.79 | 1.27 | 5.00E−05 | 7.97E−04 | regulating synaptic membrane exocytosis 3 |
| 395 | SERPINA1 | chr14: 94843083-94857029 | 48.63 | 83.86 | 0.79 | 1.28 | 5.00E−05 | 7.97E−04 | serpin peptidase inhibitor, clade A (alpha-1 antiproteinase, antitrypsin), member 1 |
| 396 | SMURF2 | chr17: 62540734-62658386 | 4.42 | 7.63 | 0.79 | 1.22 | 5.00E−05 | 7.97E−04 | SMAD specific E3 ubiquitin protein ligase 2 |
| 397 | TMEM61 | chr1: 55446464-55457966 | 6.34 | 10.89 | 0.78 | 0.86 | 3.15E−03 | 2.79E−02 | transmembrane protein 61 |
| 398 | SH3D21 | chr1: 36771993-36786948 | 10.24 | 17.59 | 0.78 | 1.27 | 5.00E−05 | 7.97E−04 | SH3 domain containing 21 |
| 399 | OAS3 | chr12: 113376248-113411054 | 8.44 | 14.50 | 0.78 | 1.28 | 5.00E−05 | 7.97E−04 | 2'-5'-oligoadenylate synthetase 3, 100 kDa |
| 400 | CBLB | chr3: 105377108-105587887 | 6.14 | 10.53 | 0.78 | 1.31 | 5.00E−05 | 7.97E−04 | Cbl proto-oncogene B, E3 ubiquitin protein ligase |
| 401 | LOC101927391 | chr7: 7589734-7605696 | 0.95 | 1.62 | 0.78 | 0.82 | 5.75E−03 | 4.55E−02 | uncharacterized LOC101927391 |
| 402 | PFKFB4 | chr3: 48555116-48594227 | 3.33 | 5.70 | 0.78 | 1.07 | 2.50E−04 | 3.38E−03 | 6-phosphofructo-2-kinase/fructose-2,6-biphosphatase 4 |
| 403 | KIAA1551 | chr12: 32112352-32146043 | 5.70 | 9.75 | 0.77 | 1.40 | 5.00E−05 | 7.97E−04 | KIAA1551 |
| 404 | STXBP1 | chr9: 130374485-130454995 | 2.15 | 3.68 | 0.77 | 1.00 | 5.00E−04 | 6.13E−03 | syntaxin binding protein 1 |
| 405 | DFNB31 | chr9: 117164359-117267736 | 2.57 | 4.40 | 0.77 | 0.97 | 1.60E−03 | 1.62E−02 | deafness, autosomal recessive 31 |
| 406 | VWA7 | chr6_ssto_hap7: 3064183-3075920 | 2.21 | 3.78 | 0.77 | 0.92 | 1.45E−03 | 1.49E−02 | von Willebrand factor A domain containing 7 |
| 407 | IL18 | chr11: 112013973-112034840 | 39.19 | 66.93 | 0.77 | 1.41 | 5.00E−05 | 7.97E−04 | interleukin 18 |
| 408 | RNF149 | chr2: 101892062-101925178 | 18.58 | 31.64 | 0.77 | 1.42 | 5.00E−05 | 7.97E−04 | ring finger protein 149 |
| 409 | LACTB2 | chr8: 71520811-71581447 | 13.48 | 22.91 | 0.77 | 1.27 | 5.00E−05 | 7.97E−04 | lactamase, beta 2 |
| 410 | DPY19L1 | chr7: 34968492-35077653 | 7.14 | 12.13 | 0.76 | 1.35 | 5.00E−05 | 7.97E−04 | dpy-19-like 1 (*C. elegans*) |
| 411 | PLIN3 | chr19: 4838345-4867780 | 49.01 | 83.23 | 0.76 | 1.35 | 5.00E−05 | 7.97E−04 | perilipin 3 |
| 412 | STX18 | chr4: 4387982-4543775 | 14.44 | 24.52 | 0.76 | 1.25 | 5.00E−05 | 7.97E−04 | syntaxin 18 |
| 413 | ALS2CL | chr3: 46710484-46735194 | 20.13 | 34.15 | 0.76 | 1.27 | 5.00E−05 | 7.97E−04 | ALS2 C-terminal like |
| 414 | REEP6 | chr19: 1491164-1497924 | 3.65 | 6.18 | 0.76 | 0.83 | 3.55E−03 | 3.07E−02 | receptor accessory protein 6 |
| 415 | SERPINB1 | chr6: 2832565-2842283 | 95.42 | 161.49 | 0.76 | 1.33 | 5.00E−05 | 7.97E−04 | serpin peptidase inhibitor, clade B (ovalbumin), member 1 |
| 416 | AFAP1L2 | chr10: 116054582-116164537 | 5.04 | 8.52 | 0.76 | 1.21 | 5.00E−05 | 7.97E−04 | actin filament associated protein 1-like 2 |
| 417 | BIK | chr22: 43506753-43525718 | 10.12 | 17.11 | 0.76 | 0.88 | 1.60E−03 | 1.62E−02 | BCL2-interacting killer (apoptosis-inducing) |
| 418 | CCDC68 | chr18: 52568739-52626739 | 17.33 | 29.29 | 0.76 | 1.44 | 5.00E−05 | 7.97E−04 | coiled-coil domain containing 68 |
| 419 | GEM | chr8: 95261484-95274547 | 2.04 | 3.45 | 0.75 | 0.82 | 3.30E−03 | 2.90E−02 | GTP binding protein overexpressed in skeletal muscle |
| 420 | MCFD2 | chr2: 47129008-47303275 | 12.30 | 20.72 | 0.75 | 1.01 | 6.50E−04 | 7.69E−03 | multiple coagulation factor deficiency 2 |
| 421 | TCP11L2 | chr12: 106696568-106740792 | 4.71 | 7.93 | 0.75 | 1.02 | 5.00E−05 | 7.97E−04 | t-complex 11, testis-specific-like 2 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 422 | NOSTRIN | chr2: 169643048-169721849 | 12.71 | 21.39 | 0.75 | 1.33 | 1.00E-04 | 1.51E-03 | nitric oxide synthase trafficking |
| 423 | RARG | chr12: 53604349-53626040 | 4.98 | 8.36 | 0.75 | 1.05 | 1.00E-04 | 1.51E-03 | retinoic acid receptor, gamma |
| 424 | ST6GALNAC4 | chr9: 130670164-130679305 | 15.43 | 25.90 | 0.75 | 1.17 | 5.00E-05 | 7.97E-04 | ST6 (alpha-N-acetyl-neuraminyl-2,3-beta-galactosyl-1,3)-N-acetylgalactosaminide alpha-2,6-sialyltransferase 4 |
| 425 | HIST1H1C | chr6: 26055967-26056699 | 67.62 | 113.43 | 0.75 | 1.24 | 5.00E-05 | 7.97E-04 | histone cluster 1, H1c |
| 426 | FRY | chr13: 32598195-5-32870776 | 0.85 | 1.42 | 0.75 | 0.97 | 5.00E-04 | 6.13E-03 | furry homolog (*Drosophila*) |
| 427 | FAM109B | chr22: 42470254-42475442 | 7.37 | 12.35 | 0.75 | 1.11 | 5.00E-05 | 7.97E-04 | family with sequence similarity 109, member B |
| 428 | TMEM140 | chr7: 134832765-134855578 | 9.03 | 15.13 | 0.74 | 0.85 | 2.60E-03 | 2.41E-02 | transmembrane protein 140 |
| 429 | GK | chrX: 30671475-30749577 | 12.29 | 20.57 | 0.74 | 1.39 | 5.00E-05 | 7.97E-04 | glycerol kinase |
| 430 | CREB3L2 | chr7: 137559724-137686847 | 12.24 | 20.48 | 0.74 | 1.21 | 5.00E-05 | 7.97E-04 | cAMP responsive element binding protein 3-like 2 |
| 431 | ACOT9 | chrX: 23721776-23761407 | 14.34 | 23.98 | 0.74 | 1.22 | 5.00E-05 | 7.97E-04 | acyl-CoA thioesterase 9 |
| 432 | RBPMS | chr8: 30239634-30429778 | 11.58 | 19.36 | 0.74 | 0.99 | 8.00E-04 | 9.10E-03 | RNA binding protein with multiple splicing |
| 433 | GDAP1 | chr8: 75262617-75279335 | 1.13 | 1.89 | 0.74 | 0.86 | 3.05E-03 | 2.72E-02 | ganglioside induced differentiation associated protein 1 |
| 434 | BCO1 | chr16: 81272295-81324747 | 1.66 | 2.78 | 0.74 | 0.78 | 3.00E-03 | 2.69E-02 | beta-carotene oxygenase 1 |
| 435 | GALK2 | chr15: 49447955-49913118 | 7.84 | 13.10 | 0.74 | 1.18 | 5.00E-05 | 7.97E-04 | galactokinase 2 |
| 436 | GSTO2 | chr10: 106028630-106059176 | 10.13 | 16.90 | 0.74 | 0.92 | 1.05E-03 | 1.15E-02 | glutathione S-transferase omega 2 |
| 437 | CEP85 | chr1: 26560643-26605529 | 5.56 | 9.27 | 0.74 | 1.01 | 7.50E-04 | 8.64E-03 | centrosomal protein 85 kDa |
| 438 | ETV5 | chr3: 185764105-185826901 | 1.92 | 3.19 | 0.74 | 0.92 | 1.05E-03 | 1.15E-02 | ets variant 5 |
| 439 | SLC45A4 | chr8: 142217264-142264728 | 6.10 | 10.17 | 0.74 | 1.15 | 5.00E-05 | 7.97E-04 | solute carrier family 45, member 4 |
| 440 | FDPS | chr1: 155278538-155300909 | 104.25 | 173.68 | 0.74 | 1.00 | 7.50E-04 | 8.64E-03 | farnesyl diphosphate synthase |
| 441 | BACH1 | chr21: 30671219-30734217 | 6.63 | 11.04 | 0.73 | 1.28 | 5.00E-05 | 7.97E-04 | BTB and CNC homology 1, basic leucine zipper transcription factor 1 |
| 442 | KIAA1217 | chr10: 23983674-24836777 | 11.97 | 19.92 | 0.73 | 1.12 | 5.00E-05 | 7.97E-04 | KIAA1217 |
| 443 | MAOB | chrX: 43625856-43741721 | 5.58 | 9.27 | 0.73 | 1.08 | 5.00E-05 | 7.97E-04 | monoamine oxidase B |
| 444 | SPRY4 | chr5: 141689991-141704620 | 5.11 | 8.47 | 0.73 | 1.15 | 1.00E-04 | 1.51E-03 | sprouty RTK signaling antagonist 4 |
| 445 | IL7R | chr5: 35856976-35879705 | 5.04 | 8.34 | 0.73 | 1.15 | 1.00E-04 | 1.51E-03 | interleukin 7 receptor |
| 446 | YIPF5 | chr5: 143537722-143550278 | 16.40 | 27.15 | 0.73 | 1.39 | 5.00E-05 | 7.97E-04 | Yip1 domain family, member 5 |
| 447 | MMP14 | chr14: 23305741-23316808 | 27.80 | 45.99 | 0.73 | 1.28 | 5.00E-05 | 7.97E-04 | matrix metallopeptidase 14 (membrane-inserted) |
| 448 | RASEF | chr9: 85594499-85678043 | 15.99 | 26.46 | 0.73 | 1.28 | 5.00E-05 | 7.97E-04 | RAS and EF-hand domain containing |
| 449 | GLRX | chr5: 95149552-95158577 | 51.86 | 85.78 | 0.73 | 1.29 | 5.00E-05 | 7.97E-04 | glutaredoxin (thioltransferase) |
| 450 | FAXDC2 | chr5: 154198051-154230213 | 5.97 | 9.86 | 0.73 | 1.11 | 1.50E-04 | 2.18E-03 | fatty acid hydroxylase domain containing 2 |
| 451 | SMIM3 | chr5: 150157507-150176298 | 7.36 | 12.17 | 0.73 | 1.06 | 1.00E-04 | 1.51E-03 | small integral membrane protein 3 |
| 452 | YPEL3 | chr16: 30103634-30107537 | 35.25 | 58.05 | 0.72 | 1.15 | 5.00E-05 | 7.97E-04 | yippee-like 3 |
| 453 | TINAGL1 | chr1: 32042085-32053287 | 59.52 | 98.00 | 0.72 | 1.28 | 5.00E-05 | 7.97E-04 | tubulointerstitial nephritis antigen-like 1 |
| 454 | CRYZ | chr1: 75171171-75232360 | 8.39 | 13.77 | 0.72 | 0.83 | 4.60E-03 | 3.78E-02 | crystallin, zeta (quinone reductase) |
| 455 | SRXN1 | chr20: 627267-634014 | 11.46 | 18.81 | 0.71 | 1.18 | 5.00E-05 | 7.97E-04 | sulfiredoxin 1 |
| 456 | RASA4 | chr7: 102220092-102257205 | 4.62 | 7.58 | 0.71 | 1.17 | 5.00E-05 | 7.97E-04 | RAS p21 protein activator 4 |
| 457 | RSPH1 | chr21: 43892596-43916464 | 3.87 | 6.33 | 0.71 | 0.80 | 3.50E-03 | 3.04E-02 | radial spoke head 1 homolog (*Chlamydomonas*) |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 458 | ZNF292 | chr6: 87865268-87973406 | 3.26 | 5.33 | 0.71 | 1.26 | 5.00E−05 | 7.97E−04 | zinc finger protein 292 |
| 459 | LRP10 | chr14: 23340959-23347291 | 124.41 | 202.86 | 0.71 | 1.14 | 1.00E−04 | 1.51E−03 | low density lipoprotein receptor-related protein 10 |
| 460 | CAPN8 | chr1: 223714971-223853436 | 53.82 | 87.75 | 0.71 | 1.22 | 5.00E−05 | 7.97E−04 | calpain 8 |
| 461 | LOC146880 | chr17: 62745779-62778117 | 21.87 | 35.64 | 0.70 | 1.25 | 5.00E−05 | 7.97E−04 | Rho GTPase activating protein 27 pseudogene |
| 462 | TMEM263 | chr12: 107349543-107367813 | 10.60 | 17.27 | 0.70 | 1.28 | 5.00E−05 | 7.97E−04 | transmembrane protein 263 |
| 463 | BBS12 | chr4: 123653856-123666098 | 1.70 | 2.77 | 0.70 | 0.81 | 4.25E−03 | 3.56E−02 | Bardet-Biedl syndrome 12 |
| 464 | RAPH1 | chr2: 204298404-204400058 | 5.04 | 8.20 | 0.70 | 1.16 | 5.00E−05 | 7.97E−04 | Ras association (RalGDS/AF-6) and pleckstrin homology domains 1 |
| 465 | TANK | chr2: 161993465-162111154 | 19.25 | 31.30 | 0.70 | 1.15 | 1.00E−04 | 1.51E−03 | TRAF family member-associated NFKB activator |
| 466 | SLC30A7 | chr1: 101361631-101447311 | 5.81 | 9.44 | 0.70 | 1.29 | 5.00E−05 | 7.97E−04 | solute carrier family 30 (zinc transporter), member 7 |
| 467 | NID2 | chr14: 52471519-52535946 | 2.46 | 4.00 | 0.70 | 0.96 | 3.50E−04 | 4.55E−03 | nidogen 2 (osteonidogen) |
| 468 | PTPN12 | chr7: 77166772-77269388 | 12.85 | 20.86 | 0.70 | 1.29 | 5.00E−05 | 7.97E−04 | protein tyrosine phosphatase, non-receptor type 12 |
| 469 | ABHD11-AS1 | chr7: 73149398-73150330 | 32.52 | 52.76 | 0.70 | 0.91 | 1.25E−03 | 1.33E−02 | ABHD11 antisense RNA 1 (tail to tail) |
| 470 | SEMA4B | chr15: 90728151-90772892 | 36.01 | 58.43 | 0.70 | 1.28 | 5.00E−05 | 7.97E−04 | sema domain, immunoglobulin domain (Ig), transmembrane domain (TM) and short cytoplasmic domain, (semaphorin) 4B |
| 471 | GTF2E2 | chr8: 30436030-30515738 | 14.84 | 24.09 | 0.70 | 1.17 | 5.00E−05 | 7.97E−04 | general transcription factor IIE, polypeptide 2, beta 34 kDa |
| 472 | CYTH2 | chr19: 48972464-48985571 | 17.54 | 28.41 | 0.70 | 1.27 | 5.00E−05 | 7.97E−04 | cytohesin 2 |
| 473 | TSPAN1 | chr1: 46640748-46651634 | 1044.92 | 1691.96 | 0.70 | 0.77 | 4.55E−03 | 3.75E−02 | tetraspanin 1 |
| 474 | SEC13 | chr3: 10342612-10362872 | 68.75 | 111.28 | 0.69 | 1.28 | 5.00E−05 | 7.97E−04 | SEC13 homolog, nuclear pore and COPII coat complex component |
| 475 | DYNLT3 | chrX: 37698088-37706889 | 16.59 | 26.79 | 0.69 | 1.30 | 5.00E−05 | 7.97E−04 | dynein, light chain, Tctex-type 3 |
| 476 | INSIG1 | chr7: 155089485-155101945 | 26.44 | 42.70 | 0.69 | 1.11 | 5.00E−05 | 7.97E−04 | insulin induced gene 1 |
| 477 | DVL1 | chr1: 1270657-1284492 | 21.31 | 34.39 | 0.69 | 1.29 | 5.00E−05 | 7.97E−04 | dishevelled segment polarity protein 1 |
| 478 | CNKSR3 | chr6: 154726432-154831753 | 8.64 | 13.93 | 0.69 | 1.15 | 5.00E−05 | 7.97E−04 | CNKSR family member 3 |
| 479 | DCUN1D5 | chr11: 102921412-102962944 | 0.92 | 1.49 | 0.69 | 1.08 | 4.00E−04 | 5.06E−03 | DCN1, defective in cullin neddylation 1, domain containing 5 |
| 480 | PRKY | chrY: 7142012-7249588 | 1.33 | 2.15 | 0.69 | 0.78 | 6.20E−03 | 4.85E−02 | protein kinase, Y-linked, pseudogene |
| 481 | OSBPL8 | chr12: 76745577-76953589 | 4.59 | 7.38 | 0.68 | 1.18 | 5.00E−05 | 7.97E−04 | oxysterol binding protein-like 8 |
| 482 | CAPG | chr2: 85621870-85641197 | 77.07 | 123.87 | 0.68 | 1.25 | 5.00E−05 | 7.97E−04 | capping protein (actin filament), gelsolin-like |
| 483 | ETV3 | chr1: 157094458-157108383 | 4.17 | 6.69 | 0.68 | 0.86 | 2.40E−03 | 2.25E−02 | ets variant 3 |
| 484 | FBXO6 | chr1: 11724149-11734409 | 5.04 | 8.09 | 0.68 | 0.80 | 4.85E−03 | 3.96E−02 | F-box protein 6 |
| 485 | TNFRSF10A | chr8: 23048969-23082680 | 4.04 | 6.47 | 0.68 | 0.84 | 9.50E−04 | 1.05E−02 | tumor necrosis factor receptor superfamily, member 10a |
| 486 | MYDGF | chr19: 4657556-4670415 | 90.58 | 144.76 | 0.68 | 1.22 | 5.00E−05 | 7.97E−04 | myeloid-derived growth factor |
| 487 | TGM2 | chr20: 36756863-36793700 | 10.34 | 16.51 | 0.68 | 1.08 | 5.00E−05 | 7.97E−04 | transglutaminase 2 |
| 488 | ZFYVE1 | chr14: 73436152-73493920 | 5.78 | 9.24 | 0.68 | 0.96 | 7.50E−04 | 8.64E−03 | zinc finger, FYVE domain containing 1 |
| 489 | HERC4 | chr10: 69681655-69835103 | 15.20 | 24.25 | 0.67 | 1.25 | 5.00E−05 | 7.97E−04 | HECT and RLD domain containing E3 ubiquitin protein ligase 4 |
| 490 | IL15RA | chr10: 5994333-6020150 | 6.27 | 10.00 | 0.67 | 0.88 | 2.65E−03 | 2.44E−02 | interleukin 15 receptor, alpha |
| 491 | CKLF | chr16: 66586465-66613038 | 27.10 | 43.23 | 0.67 | 0.96 | 8.50E−04 | 9.59E−03 | chemokine-like factor |
| 492 | PCBP4 | chr3: 51989329-52001482 | 8.08 | 12.89 | 0.67 | 0.97 | 9.00E−04 | 1.01E−02 | poly(rC) binding protein 4 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 493 | ARHGEF28 | chr5: 72921982-73237818 | 2.05 | 3.26 | 0.67 | 0.96 | 5.00E-04 | 6.13E-03 | Rho guanine nucleotide exchange factor (GEF) 28 |
| 494 | CD2 | chr1: 117297085-117311851 | 6.39 | 10.18 | 0.67 | 0.92 | 1.25E-03 | 1.33E-02 | CD2 molecule |
| 495 | STX19 | chr3: 93698982-93774522 | 11.60 | 18.49 | 0.67 | 1.01 | 9.50E-04 | 1.05E-02 | syntaxin 19 |
| 496 | LYST | chr1: 235824330-236047008 | 2.89 | 4.60 | 0.67 | 0.93 | 2.40E-03 | 2.25E-02 | lysosomal trafficking regulator |
| 497 | RPL37 | chr5: 40831429-40835387 | 230.43 | 366.73 | 0.67 | 1.13 | 3.00E-04 | 3.97E-03 | ribosomal protein L37 |
| 498 | BZW1 | chr2: 201560445-201688569 | 99.09 | 157.57 | 0.67 | 1.15 | 5.00E-05 | 7.97E-04 | basic leucine zipper and W2 domains 1 |
| 499 | EEPD1 | chr7: 36192835-36341152 | 2.96 | 4.71 | 0.67 | 0.93 | 6.50E-04 | 7.69E-03 | endonuclease/exonuclease/phosphatase family domain containing 1 |
| 500 | PPA1 | chr10: 71962585-71993190 | 104.60 | 166.05 | 0.67 | 1.26 | 5.00E-05 | 7.97E-04 | pyrophosphatase (inorganic) 1 |
| 501 | S100A16 | chr1: 153579366-153585514 | 274.09 | 434.63 | 0.67 | 1.14 | 5.00E-05 | 7.97E-04 | S100 calcium binding protein A16 |
| 502 | RIN1 | chr11: 66099541-66104000 | 4.90 | 7.76 | 0.66 | 0.90 | 2.15E-03 | 2.06E-02 | Ras and Rab interactor 1 |
| 503 | IFI44 | chr1: 79115476-79129763 | 3.07 | 4.85 | 0.66 | 0.77 | 6.40E-03 | 4.97E-02 | interferon-induced protein 44 |
| 504 | ECT2 | chr3: 172468474-172539264 | 8.05 | 12.74 | 0.66 | 1.18 | 5.00E-05 | 7.97E-04 | epithelial cell transforming 2 |
| 505 | RNASE4 | chr14: 21152335-21168761 | 59.94 | 94.78 | 0.66 | 1.04 | 5.00E-05 | 7.97E-04 | ribonuclease, RNase A family, 4 |
| 506 | CD247 | chr1: 167399876-167487847 | 3.79 | 5.99 | 0.66 | 0.75 | 5.20E-03 | 4.20E-02 | CD247 molecule |
| 507 | AGR3 | chr7: 16899029-16921613 | 132.11 | 208.74 | 0.66 | 1.24 | 5.00E-05 | 7.97E-04 | anterior gradient 3, protein disulphide isomerase family member |
| 508 | KDSR | chr18: 60994970-61034506 | 6.40 | 10.11 | 0.66 | 1.19 | 5.00E-05 | 7.97E-04 | 3-ketodihydrosphingosine reductase |
| 509 | AP3S1 | chr5: 115177618-115249778 | 49.87 | 78.68 | 0.66 | 1.25 | 5.00E-05 | 7.97E-04 | adaptor-related protein complex 3, sigma 1 subunit |
| 510 | TMED9 | chr5: 177019212-177023099 | 115.33 | 181.81 | 0.66 | 1.18 | 5.00E-05 | 7.97E-04 | transmembrane p24 trafficking protein 9 |
| 511 | SLC37A1 | chr21: 43919741-44001550 | 27.45 | 43.28 | 0.66 | 1.17 | 5.00E-05 | 7.97E-04 | solute carrier family 37 (glucose-6-phosphate transporter), member 1 |
| 512 | NTHL1 | chr16: 2089815-2097867 | 11.06 | 17.41 | 0.66 | 0.84 | 2.90E-03 | 2.62E-02 | nth-like DNA glycosylase 1 |
| 513 | IFNLR1 | chr1: 24480646-24513765 | 4.41 | 6.94 | 0.65 | 1.02 | 2.50E-04 | 3.38E-03 | interferon, lambda receptor 1 |
| 514 | B4GALT6 | chr18: 29202208-29264686 | 1.46 | 2.30 | 0.65 | 0.85 | 3.85E-03 | 3.28E-02 | UDP-Gal: betaGlcNAc beta 1,4-galactosyltransferase, polypeptide 6 |
| 515 | TFF3 | chr21: 43731776-43735706 | 685.72 | 1079.30 | 0.65 | 0.81 | 3.45E-03 | 3.01E-02 | trefoil factor 3 (intestinal) |
| 516 | TC2N | chr14: 92246095-92333880 | 17.32 | 27.25 | 0.65 | 1.27 | 5.00E-05 | 7.97E-04 | tandem C2 domains, nuclear |
| 517 | CTNNAL1 | chr9: 111704848-111775874 | 5.08 | 7.99 | 0.65 | 1.01 | 3.50E-04 | 4.55E-03 | catenin (cadherin-associated protein), alpha-like 1 |
| 518 | DNAJC10 | chr2: 183580767-183644750 | 17.97 | 28.23 | 0.65 | 1.19 | 5.00E-05 | 7.97E-04 | DnaJ (Hsp40) homolog, subfamily C, member 10 |
| 519 | DEDD2 | chr19: 42702744-42724304 | 24.45 | 38.37 | 0.65 | 1.12 | 3.50E-04 | 4.55E-03 | death effector domain containing 2 |
| 520 | SH2D3A | chr19: 6752172-6767523 | 18.47 | 28.99 | 0.65 | 1.16 | 1.00E-04 | 1.51E-03 | SH2 domain containing 3A |
| 521 | SERAC1 | chr6: 158530535-158589312 | 2.77 | 4.34 | 0.65 | 0.87 | 1.40E-03 | 1.45E-02 | serine active site containing 1 |
| 522 | TMED3 | chr15: 79603490-79615189 | 51.61 | 80.91 | 0.65 | 1.16 | 5.00E-05 | 7.97E-04 | transmembrane p24 trafficking protein 3 |
| 523 | THY1 | chr11: 119252487-119369944 | 6.57 | 10.30 | 0.65 | 0.90 | 2.30E-03 | 2.18E-02 | Thy-1 cell surface antigen |
| 524 | TOR4A | chr9: 140172279-140177093 | 22.28 | 34.93 | 0.65 | 1.22 | 1.00E-04 | 1.51E-03 | torsin family 4, member A |
| 525 | GDA | chr9: 74729510-74867140 | 18.87 | 29.56 | 0.65 | 1.19 | 5.00E-05 | 7.97E-04 | guanine deaminase |
| 526 | HELZ2 | chr20: 62189438-62205592 | 4.77 | 7.47 | 0.65 | 1.09 | 2.50E-04 | 3.38E-03 | helicase with zinc finger 2, transcriptional coactivator |
| 527 | AHR | chr7: 17338275-17385775 | 9.54 | 14.95 | 0.65 | 1.14 | 5.00E-05 | 7.97E-04 | aryl hydrocarbon receptor |
| 528 | OCIAD2 | chr4: 48887396-48908845 | 131.44 | 205.76 | 0.65 | 1.17 | 5.00E-05 | 7.97E-04 | OCIA domain containing 2 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 529 | CCL5 | chr17: 34198495-34207377 | 15.82 | 24.76 | 0.65 | 0.98 | 1.50E−04 | 2.18E−03 | chemokine (C-C motif) ligand 5 |
| 530 | SEC14L1 | chr17: 7508472-75213181 | 12.89 | 20.18 | 0.65 | 1.03 | 3.00E−04 | 3.97E−03 | SEC14-like lipid binding 1 |
| 531 | S100A14 | chr1: 153586731-153588808 | 370.73 | 579.89 | 0.65 | 1.02 | 1.00E−04 | 1.51E−03 | S100 calcium binding protein A14 |
| 532 | EMP1 | chr12: 13349601-13369708 | 171.36 | 267.93 | 0.64 | 0.94 | 7.50E−04 | 8.64E−03 | epithelial membrane protein 1 |
| 533 | SQLE | chr8: 126010719-126034525 | 24.28 | 37.93 | 0.64 | 1.01 | 2.50E−04 | 3.38E−03 | squalene epoxidase |
| 534 | ATG4A | chrX: 107334898-107397901 | 12.72 | 19.85 | 0.64 | 1.14 | 1.00E−04 | 1.51E−03 | autophagy related 4A, cysteine peptidase |
| 535 | TNK2 | chr3: 195590235-195635880 | 10.38 | 16.18 | 0.64 | 1.16 | 5.00E−05 | 7.97E−04 | tyrosine kinase, non-receptor, 2 |
| 536 | KIAA0040 | chr1: 175126122-175162229 | 6.97 | 10.86 | 0.64 | 1.09 | 2.00E−04 | 2.80E−03 | KIAA0040 |
| 537 | FOXP4 | chr6: 41514163-41570122 | 8.28 | 12.91 | 0.64 | 1.13 | 2.00E−04 | 2.80E−03 | forkhead box P4 |
| 538 | HM13 | chr20: 30102212-30161066 | 69.16 | 107.78 | 0.64 | 1.15 | 1.00E−04 | 1.51E−03 | histocompatibility (minor) 13 |
| 539 | PMP22 | chr17: 15133093-15168674 | 27.45 | 42.76 | 0.64 | 1.11 | 1.00E−04 | 1.51E−03 | peripheral myelin protein 22 |
| 540 | KCNE3 | chr11: 74165885-74178600 | 9.33 | 14.53 | 0.64 | 1.09 | 5.00E−05 | 7.97E−04 | potassium channel, voltage gated subfamily E regulatory beta subunit 3 |
| 541 | TMEM2 | chr9: 74298281-74383800 | 19.87 | 30.91 | 0.64 | 1.14 | 5.00E−05 | 7.97E−04 | transmembrane protein 2 |
| 542 | SUCO | chr1: 172501488-172580975 | 6.49 | 10.09 | 0.64 | 1.08 | 2.00E−04 | 2.80E−03 | SUN domain containing ossification factor |
| 543 | GPCPD1 | chr20: 5525079-5591672 | 9.60 | 14.93 | 0.64 | 1.20 | 5.00E−05 | 7.97E−04 | glycerophosphocholine phosphodiesterase 1 |
| 544 | CDHR2 | chr5: 175969511-176022769 | 61.21 | 95.10 | 0.64 | 1.06 | 3.50E−04 | 4.55E−03 | cadherin-related family member 2 |
| 545 | LRCH1 | chr13: 47127295-47327175 | 3.75 | 5.82 | 0.63 | 0.99 | 4.00E−04 | 5.06E−03 | leucine-rich repeats and calponin homology (CH) domain containing 1 |
| 546 | IFNGR1 | chr6: 137518620-137540567 | 59.23 | 91.94 | 0.63 | 1.20 | 5.00E−05 | 7.97E−04 | interferon gamma receptor 1 |
| 547 | ARRDC2 | chr19: 18111940-18124911 | 15.23 | 23.65 | 0.63 | 1.09 | 1.00E−04 | 1.51E−03 | arrestin domain containing 2 |
| 548 | MID1IP1 | chrX: 38660500-38665783 | 18.29 | 28.38 | 0.63 | 1.00 | 4.00E−04 | 5.06E−03 | MID1 interacting protein 1 |
| 549 | FA2H | chr16: 74746855-74808729 | 28.66 | 44.45 | 0.63 | 1.14 | 5.00E−05 | 7.97E−04 | fatty acid 2-hydroxylase |
| 550 | RIPK4 | chr21: 43159528-43187249 | 5.38 | 8.34 | 0.63 | 0.97 | 4.00E−04 | 5.06E−03 | receptor-interacting serine-threonine kinase 4 |
| 551 | RHPN1 | chr8: 144451024-144466390 | 2.06 | 3.19 | 0.63 | 0.78 | 5.60E−03 | 4.46E−02 | rhophilin, Rho GTPase binding protein 1 |
| 552 | RAB3D | chr19: 11406814-11450344 | 5.49 | 8.50 | 0.63 | 1.00 | 4.00E−04 | 5.06E−03 | RAB3D, member RAS oncogene family |
| 553 | ALDH1A3 | chr15: 101420008-101456830 | 2.98 | 4.62 | 0.63 | 0.85 | 2.05E−03 | 1.98E−02 | aldehyde dehydrogenase 1 family, member A3 |
| 554 | HLA-F | chr6_ssto_hap7: 1028896-1054576 | 64.83 | 100.33 | 0.63 | 1.10 | 5.00E−05 | 7.97E−04 | major histocompatibility complex, class I, F |
| 555 | TCF12 | chr15: 57210832-57580714 | 12.44 | 19.24 | 0.63 | 1.10 | 1.50E−04 | 2.18E−03 | transcription factor 12 |
| 556 | B4GALT2 | chr1: 44444873-44456843 | 14.91 | 23.06 | 0.63 | 1.00 | 2.50E−04 | 3.38E−03 | UDP-Gal: betaGlcNAc beta 1,4-galactosyltransferase, polypeptide 2 |
| 557 | STIM2 | chr4: 26862312-27027003 | 5.64 | 8.72 | 0.63 | 1.08 | 1.50E−04 | 2.18E−03 | stromal interaction molecule 2 |
| 558 | ALCAM | chr3: 105085556-105295757 | 5.05 | 7.80 | 0.63 | 1.06 | 5.00E−05 | 7.97E−04 | activated leukocyte cell adhesion molecule |
| 559 | C6orf132 | chr6: 42068856-42110715 | 5.22 | 8.04 | 0.62 | 1.07 | 5.00E−05 | 7.97E−04 | chromosome 6 open reading frame 132 |
| 560 | BTNL3 | chr5: 180415844-180433727 | 45.84 | 70.52 | 0.62 | 1.06 | 1.50E−04 | 2.18E−03 | butyrophilin-like 3 |
| 561 | ANXA5 | chr4: 122589151-122618147 | 78.32 | 120.46 | 0.62 | 1.13 | 5.00E−05 | 7.97E−04 | annexin A5 |
| 562 | HYAL2 | chr3: 50355220-50360281 | 12.04 | 18.51 | 0.62 | 0.99 | 6.50E−04 | 7.69E−03 | hyaluronoglucosaminidase 2 |
| 563 | TRERF1 | chr6: 42192668-42419783 | 2.06 | 3.17 | 0.62 | 0.91 | 5.00E−04 | 6.13E−03 | transcriptional regulating factor 1 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 564 | P4HA1 | chr10: 74766979-74856732 | 12.34 | 18.96 | 0.62 | 1.09 | 1.00E−04 | 1.51E−03 | prolyl 4-hydroxylase, alpha polypeptide I |
| 565 | LATS2 | chr13: 21547175-21635722 | 2.10 | 3.22 | 0.62 | 0.84 | 2.05E−03 | 1.98E−02 | large tumor suppressor kinase 2 |
| 566 | UBE2L6 | chr11: 57319127-57335803 | 23.06 | 35.43 | 0.62 | 0.98 | 6.00E−04 | 7.22E−03 | ubiquitin-conjugating enzyme E2L 6 |
| 567 | SOWAHC | chr2: 110371910-110376564 | 12.09 | 18.58 | 0.62 | 1.12 | 5.00E−05 | 7.97E−04 | sosondowah ankyrin repeat domain family member C |
| 568 | PALD1 | chr10: 72238563-72328206 | 1.98 | 3.03 | 0.62 | 0.82 | 3.80E−03 | 3.25E−02 | phosphatase domain containing, paladin 1 |
| 569 | C4orf32 | chr4: 113066552-113110237 | 3.49 | 5.35 | 0.62 | 0.82 | 5.40E−03 | 4.34E−02 | chromosome 4 open reading frame 32 |
| 570 | UBA6 | chr4: 68481478-68566889 | 6.70 | 10.29 | 0.62 | 1.17 | 5.00E−05 | 7.97E−04 | ubiquitin-like modifier activating enzyme 6 |
| 571 | PFKP | chr10: 3109711-3178997 | 35.94 | 55.13 | 0.62 | 1.12 | 5.00E−05 | 7.97E−04 | phosphofructokinase, platelet |
| 572 | OSGIN1 | chr16: 83986826-83999937 | 6.30 | 9.66 | 0.62 | 0.82 | 3.95E−03 | 3.35E−02 | oxidative stress induced growth inhibitor 1 |
| 573 | TJP1 | chr15: 29992356-30114706 | 11.11 | 17.04 | 0.62 | 1.11 | 1.00E−04 | 1.51E−03 | tight junction protein 1 |
| 574 | TUBA4A | chr2: 220110191-220136910 | 32.10 | 49.18 | 0.62 | 0.93 | 7.50E−04 | 8.64E−03 | tubulin, alpha 4a |
| 575 | ZNFX1 | chr20: 47862438-47905795 | 9.19 | 14.08 | 0.61 | 0.88 | 1.60E−03 | 1.62E−02 | zinc finger, NFX1-type containing 1 |
| 576 | ITGA1 | chr5: 52083773-52249485 | 5.29 | 8.09 | 0.61 | 0.88 | 2.65E−03 | 2.44E−02 | integrin, alpha 1 |
| 577 | IL20RA | chr6: 137321107-137366317 | 5.72 | 8.75 | 0.61 | 0.98 | 9.00E−04 | 1.01E−02 | interleukin 20 receptor, alpha |
| 578 | MARCKSL1 | chr1: 32799429-32801840 | 122.79 | 187.82 | 0.61 | 1.12 | 5.00E−05 | 7.97E−04 | MARCKS-like 1 |
| 579 | GALNT3 | chr2: 166604312-166650803 | 39.67 | 60.67 | 0.61 | 1.13 | 1.00E−04 | 1.51E−03 | polypeptide N-acetylgalactosaminyltransferase 3 |
| 580 | F3 | chr1: 94994731-95007413 | 28.22 | 43.16 | 0.61 | 1.09 | 1.50E−04 | 2.18E−03 | coagulation factor III (thromboplastin, tissue factor) |
| 581 | PARD6B | chr20: 49348080-49370278 | 3.14 | 4.80 | 0.61 | 0.90 | 1.55E−03 | 1.57E−02 | par-6 family cell polarity regulator beta |
| 582 | PPP2R2A | chr8: 26149006-26230195 | 13.21 | 20.17 | 0.61 | 1.19 | 5.00E−05 | 7.97E−04 | protein phosphatase 2, regulatory subunit B, alpha |
| 583 | CASP10 | chr2: 202047620-202094129 | 10.18 | 15.54 | 0.61 | 1.08 | 1.50E−04 | 2.18E−03 | caspase 10, apoptosis-related cysteine peptidase |
| 584 | PIM3 | chr22: 50354142-50357720 | 26.30 | 40.16 | 0.61 | 1.10 | 5.00E−05 | 7.97E−04 | Pim-3 proto-oncogene, serine/threonine kinase |
| 585 | LAMB3 | chr1: 209788217-209825820 | 41.79 | 63.79 | 0.61 | 1.09 | 5.00E−05 | 7.97E−04 | laminin, beta 3 |
| 586 | SLC35C1 | chr11: 45825622-45834567 | 32.10 | 48.98 | 0.61 | 1.12 | 5.00E−05 | 7.97E−04 | solute carrier family 35 (GDP-fucose transporter), member C1 |
| 587 | CCDC120 | chrX: 48910960-48927510 | 5.26 | 8.03 | 0.61 | 0.92 | 2.15E−03 | 2.06E−02 | coiled-coil domain containing 120 |
| 588 | DHRS7 | chr14: 60611499-60632211 | 59.83 | 91.23 | 0.61 | 1.10 | 2.00E−04 | 2.80E−03 | dehydrogenase/reductase (SDR family) member 7 |
| 589 | HPSE | chr4: 84213613-84256306 | 4.04 | 6.16 | 0.61 | 0.94 | 9.50E−04 | 1.05E−02 | heparanase |
| 590 | ENPP4 | chr6: 46097700-46114436 | 9.04 | 13.78 | 0.61 | 1.15 | 5.00E−05 | 7.97E−04 | ectonucleotide pyrophosphatase/phosphodiesterase 4 (putative) |
| 591 | MAL2 | chr8: 120220609-120257914 | 153.69 | 234.21 | 0.61 | 1.01 | 3.50E−04 | 4.55E−03 | mal, T-cell differentiation protein 2 (gene/pseudogene) |
| 592 | MAP4K3 | chr2: 39476406-39664453 | 7.34 | 11.19 | 0.61 | 1.06 | 3.50E−04 | 4.55E−03 | mitogen-activated protein kinase kinase kinase kinase 3 |
| 593 | IFI27L2 | chr14: 94594117-94595957 | 46.92 | 71.47 | 0.61 | 0.81 | 2.45E−03 | 2.29E−02 | interferon, alpha-inducible protein 27-like 2 |
| 594 | MPG | chr16: 127017-188697 | 28.23 | 42.96 | 0.61 | 0.83 | 4.35E−03 | 3.63E−02 | N-methylpurine DNA glycosylase |
| 595 | SMAD3 | chr15: 67358194-67487533 | 14.15 | 21.52 | 0.61 | 1.07 | 5.00E−05 | 7.97E−04 | SMAD family member 3 |
| 596 | CCDC127 | chr5: 204874-218297 | 6.07 | 9.22 | 0.60 | 0.75 | 6.15E−03 | 4.82E−02 | coiled-coil domain containing 127 |
| 597 | ZNF37BP | chr10: 43008960-43048318 | 1.52 | 2.30 | 0.60 | 0.93 | 4.00E−04 | 5.06E−03 | zinc finger protein 37B, pseudogene |
| 598 | THEM4 | chr1: 151843342-151882361 | 2.01 | 3.05 | 0.60 | 0.82 | 2.90E−03 | 2.62E−02 | thioesterase superfamily member 4 |
| 599 | TM9SF3 | chr10: 98277866-98346809 | 83.43 | 126.41 | 0.60 | 1.02 | 6.00E−04 | 7.22E−03 | transmembrane 9 superfamily member 3 |
| 600 | ARHGAP12 | chr10: 32094325-32217804 | 12.11 | 18.34 | 0.60 | 1.12 | 5.00E−05 | 7.97E−04 | Rho GTPase activating protein 12 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 601 | ZNF706 | chr8: 102209265-102218292 | 29.25 | 44.30 | 0.60 | 1.21 | 1.50E−04 | 2.18E−03 | zinc finger protein 706 |
| 602 | PVRL2 | chr19: 45349392-45392485 | 35.79 | 54.20 | 0.60 | 1.08 | 5.00E−05 | 7.97E−04 | poliovirus receptor-related 2 (herpesvirus entry mediator B) |
| 603 | RASSF6 | chr4: 74437266-74486348 | 10.28 | 15.55 | 0.60 | 1.10 | 2.00E−04 | 2.80E−03 | Ras association (RalGDS/AF-6) domain family member 6 |
| 604 | YAE1D1 | chr7: 39605974-39651688 | 14.13 | 21.37 | 0.60 | 0.88 | 2.05E−03 | 1.98E−02 | Yae1 domain containing 1 |
| 605 | ARL14 | chr3: 160394947-160396235 | 37.06 | 56.02 | 0.60 | 1.08 | 2.00E−04 | 2.80E−03 | ADP-ribosylation factor-like 14 |
| 606 | JMJD1C | chr10: 64926980-65226322 | 5.09 | 7.70 | 0.60 | 1.09 | 2.50E−04 | 3.38E−03 | jumonji domain containing 1C |
| 607 | ZNF841 | chr19: 52567718-52599018 | 4.11 | 6.21 | 0.59 | 0.91 | 9.00E−04 | 1.01E−02 | zinc finger protein 841 |
| 608 | CAPRIN2 | chr12: 30862485-30907448 | 3.07 | 4.63 | 0.59 | 0.89 | 2.10E−03 | 2.02E−02 | caprin family member 2 |
| 609 | NMRK1 | chr9: 77676115-77703133 | 17.59 | 26.54 | 0.59 | 0.95 | 5.00E−04 | 6.13E−03 | nicotinamide riboside kinase 1 |
| 610 | TMC6 | chr17: 76108998-76139049 | 23.85 | 35.96 | 0.59 | 0.88 | 3.25E−03 | 2.86E−02 | transmembrane channel-like 6 |
| 611 | DNAJC3 | chr13: 96329392-96447243 | 20.29 | 30.58 | 0.59 | 1.08 | 1.50E−04 | 2.18E−03 | DnaJ (Hsp40) homolog, subfamily C, member 3 |
| 612 | PRRG1 | chrX: 37208527-37316548 | 3.11 | 4.69 | 0.59 | 0.85 | 2.25E−03 | 2.14E−02 | proline rich Gla (G-carboxyglutamic acid) 1 |
| 613 | SERPINB6 | chr6: 2948392-2972399 | 147.22 | 221.74 | 0.59 | 1.02 | 2.50E−04 | 3.38E−03 | serpin peptidase inhibitor, clade B (ovalbumin), member 6 |
| 614 | DST | chr6: 56137688-56819426 | 9.54 | 14.37 | 0.59 | 1.03 | 5.00E−04 | 6.13E−03 | dystonin |
| 615 | PYCR1 | chr17: 79890261-79895204 | 32.64 | 49.11 | 0.59 | 1.06 | 2.50E−04 | 3.38E−03 | pyrroline-5-carboxylate reductase 1 |
| 616 | OSBPL3 | chr7: 24836155-25019831 | 4.32 | 6.49 | 0.59 | 0.99 | 9.50E−04 | 1.05E−02 | oxysterol binding protein-like 3 |
| 617 | CHMP4C | chr8: 82644687-82671748 | 14.92 | 22.42 | 0.59 | 1.00 | 6.00E−04 | 7.22E−03 | charged multivesicular body protein 4C |
| 618 | CERS2 | chr1: 150937648-150947479 | 53.63 | 80.50 | 0.59 | 1.06 | 1.00E−04 | 1.51E−03 | ceramide synthase 2 |
| 619 | TSPAN3 | chr15: 77336359-77363570 | 164.57 | 246.93 | 0.59 | 0.87 | 9.50E−04 | 1.05E−02 | tetraspanin 3 |
| 620 | KCTD21 | chr11: 77850838-77899664 | 3.64 | 5.46 | 0.58 | 0.82 | 3.20E−03 | 2.82E−02 | potassium channel tetramerization domain containing 21 |
| 621 | GUK1 | chr1: 228327784-228336655 | 130.54 | 195.74 | 0.58 | 1.06 | 1.50E−04 | 2.18E−03 | guanylate kinase 1 |
| 622 | MRPL17 | chr11: 6701615-6704632 | 9.26 | 13.88 | 0.58 | 0.95 | 3.00E−04 | 3.97E−03 | mitochondrial ribosomal protein L17 |
| 623 | PLEKHM1 | chr17_ctg5_hap1: 128327-183214 | 8.99 | 13.47 | 0.58 | 1.06 | 2.50E−04 | 3.38E−03 | pleckstrin homology domain containing, family M (with RUN domain) member 1 |
| 624 | CD58 | chr1: 117057155-117113715 | 20.54 | 30.79 | 0.58 | 0.97 | 7.50E−04 | 8.64E−03 | CD58 molecule |
| 625 | NDEL1 | chr17: 8339169-8371495 | 15.87 | 23.79 | 0.58 | 1.01 | 3.00E−04 | 3.97E−03 | nudE neurodevelopment protein 1-like 1 |
| 626 | GSTP1 | chr11: 67351065-67354124 | 304.06 | 455.64 | 0.58 | 1.03 | 3.00E−04 | 3.97E−03 | glutathione S-transferase pi 1 |
| 627 | FEM1C | chr5: 114856607-114880591 | 11.81 | 17.70 | 0.58 | 1.10 | 5.00E−05 | 7.97E−04 | fem-1 homolog c (C. elegans) |
| 628 | MAP1LC3B | chr16: 87425800-87438380 | 29.29 | 43.86 | 0.58 | 1.08 | 1.00E−04 | 1.51E−03 | microtubule-associated protein 1 light chain 3 beta |
| 629 | PSENEN | chr19: 36236477-36238056 | 50.58 | 75.70 | 0.58 | 0.95 | 6.50E−04 | 7.69E−03 | presenilin enhancer gamma secretase subunit |
| 630 | PTPRR | chr12: 71031852-71314584 | 16.69 | 24.96 | 0.58 | 1.05 | 3.00E−04 | 3.97E−03 | protein tyrosine phosphatase, receptor type, R |
| 631 | BFAR | chr16: 14726667-14763093 | 16.41 | 24.54 | 0.58 | 1.04 | 2.50E−04 | 3.38E−03 | bifunctional apoptosis regulator |
| 632 | GRB7 | chr17: 37894161-37903538 | 13.24 | 19.77 | 0.58 | 0.91 | 1.35E−03 | 1.41E−02 | growth factor receptor-bound protein 7 |
| 633 | BTNL8 | chr5: 180326076-180377906 | 34.27 | 51.17 | 0.58 | 0.99 | 1.50E−04 | 2.18E−03 | butyrophilin-like 8 |
| 634 | TWF2 | chr3: 52262625-52273183 | 32.82 | 48.99 | 0.58 | 1.03 | 2.00E−04 | 2.80E−03 | twinfilin actin binding protein 2 |
| 635 | CD63 | chr12: 56119226-56123457 | 804.12 | 1200.00 | 0.58 | 0.85 | 1.85E−03 | 1.82E−02 | CD63 molecule |
| 636 | RAP1B | chr12: 69004618-69054385 | 95.48 | 142.33 | 0.58 | 1.06 | 5.00E−05 | 7.97E−04 | RAP1B, member of RAS oncogene family |
| 637 | TMEM62 | chr15: 43425721-43477341 | 12.84 | 19.14 | 0.58 | 1.00 | 5.00E−05 | 7.97E−04 | transmembrane protein 62 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 638 | FURIN | chr15: 91411821-91426688 | 26.45 | 39.41 | 0.58 | 1.06 | 4.00E-04 | 5.06E-03 | furin (paired basic amino acid cleaving enzyme) |
| 639 | DIAPH1 | chr5: 140894587-140998622 | 22.87 | 34.07 | 0.58 | 1.02 | 3.00E-04 | 3.97E-03 | diaphanous-related formin 1 |
| 640 | HID1 | chr17: 72946838-72971823 | 19.28 | 28.71 | 0.57 | 1.02 | 2.50E-04 | 3.38E-03 | HID1 domain containing |
| 641 | ZDHHC9 | chrX: 128937263-128977910 | 11.29 | 16.81 | 0.57 | 1.03 | 2.50E-04 | 3.38E-03 | zinc finger, DHHC-type containing 9 |
| 642 | PRKAG2 | chr7: 151253200-151576308 | 14.00 | 20.82 | 0.57 | 0.98 | 9.50E-04 | 1.05E-02 | protein kinase, AMP-activated, gamma 2 non-catalytic subunit |
| 643 | PLD2 | chr17: 4710395-4726727 | 7.56 | 11.24 | 0.57 | 0.94 | 5.50E-04 | 6.69E-03 | phospholipase D2 |
| 644 | NOP10 | chr15: 34633916-34635362 | 133.64 | 198.50 | 0.57 | 1.00 | 2.00E-04 | 2.80E-03 | NOP 10 ribonucleoprotein |
| 645 | LCOR | chr10: 98592016-98724198 | 8.56 | 12.72 | 0.57 | 1.04 | 4.00E-04 | 5.06E-03 | ligand dependent nuclear receptor corepressor |
| 646 | JAK2 | chr9: 4985244-5128183 | 3.57 | 5.30 | 0.57 | 0.92 | 8.00E-04 | 9.10E-03 | Janus kinase 2 |
| 647 | ZNF468 | chr19: 53341784-53360902 | 4.75 | 7.04 | 0.57 | 0.91 | 1.75E-03 | 1.74E-02 | zinc finger protein 468 |
| 648 | DLL4 | chr15: 41221530-41231258 | 4.73 | 7.02 | 0.57 | 0.82 | 2.40E-03 | 2.25E-02 | delta-like 4 (*Drosophila*) |
| 649 | TTC39A | chr1: 51752929-51810785 | 24.82 | 36.76 | 0.57 | 1.02 | 3.00E-04 | 3.97E-03 | tetratricopeptide repeat domain 39A |
| 650 | MIA3 | chr1: 222791443-222841351 | 9.37 | 13.86 | 0.56 | 1.07 | 2.00E-04 | 2.80E-03 | melanoma inhibitory activity family, member 3 |
| 651 | PSMA5 | chr1: 109941652-109969108 | 25.78 | 38.12 | 0.56 | 1.15 | 5.00E-05 | 7.97E-04 | proteasome subunit alpha 5 |
| 652 | GRINA | chr8: 145064225-145067583 | 35.27 | 52.15 | 0.56 | 1.00 | 3.00E-04 | 3.97E-03 | glutamate receptor, ionotropic, N-methyl D-aspartate-associated protein 1 (glutamate binding) |
| 653 | MVD | chr16: 88718347-88729495 | 39.02 | 57.69 | 0.56 | 1.00 | 5.00E-04 | 6.13E-03 | mevalonate (diphospho) decarboxylase |
| 654 | PIK3IP1 | chr22: 31677578-31688520 | 13.51 | 19.96 | 0.56 | 0.95 | 9.50E-04 | 1.05E-02 | phosphoinositide-3-kinase interacting protein 1 |
| 655 | MTHFD2 | chr2: 74425689-74442424 | 15.35 | 22.68 | 0.56 | 0.98 | 6.50E-04 | 7.69E-03 | methylenetetrahydrofolate dehydrogenase (NADP + dependent) 2, methenyltetrahydrofolate cyclohydrolase |
| 656 | RAP2B | chr3: 152880000-152888413 | 3.97 | 5.87 | 0.56 | 1.01 | 2.50E-04 | 3.38E-03 | RAP2B, member of RAS oncogene family |
| 657 | MORF4L2 | chrX: 102930425-102947484 | 68.30 | 100.82 | 0.56 | 1.03 | 8.50E-04 | 9.59E-03 | mortality factor 4 like 2 |
| 658 | CCDC64 | chr12: 120427647-120532299 | 5.33 | 7.86 | 0.56 | 0.85 | 2.35E-03 | 2.22E-02 | coiled-coil domain containing 64 |
| 659 | HDAC9 | chr7: 18126571-19036992 | 2.54 | 3.74 | 0.56 | 0.77 | 6.45E-03 | 5.00E-02 | histone deacetylase 9 |
| 660 | HERC6 | chr4: 89299890-89364249 | 3.60 | 5.30 | 0.56 | 0.85 | 2.50E-03 | 2.33E-02 | HECT and RLD domain containing E3 ubiquitin protein ligase family member 6 |
| 661 | FAM83H | chr8: 144806102-144815914 | 21.29 | 31.33 | 0.56 | 1.08 | 1.00E-04 | 1.51E-03 | family with sequence similarity 83, member H |
| 662 | H2AFJ | chr12: 14927269-14930936 | 14.87 | 21.86 | 0.56 | 0.98 | 4.50E-04 | 5.61E-03 | H2A histone family, member J |
| 663 | CLOCK | chr4: 56294067-56413076 | 3.23 | 4.75 | 0.56 | 1.00 | 5.00E-04 | 6.13E-03 | clock circadian regulator |
| 664 | YIPF3 | chr6: 43479564-43484728 | 69.02 | 101.42 | 0.56 | 1.01 | 3.00E-04 | 3.97E-03 | Yip1 domain family, member 3 |
| 665 | SDCBP | chr8: 59465727-59495419 | 93.98 | 138.10 | 0.56 | 1.04 | 4.00E-04 | 5.06E-03 | syndecan binding protein (syntenin) |
| 666 | RABAC1 | chr19: 42460832-42463528 | 107.53 | 157.92 | 0.55 | 0.98 | 2.50E-04 | 3.38E-03 | Rab acceptor 1 (prenylated) |
| 667 | MAGED2 | chrX: 54834031-54842448 | 25.06 | 36.80 | 0.55 | 0.99 | 1.00E-04 | 1.51E-03 | melanoma antigen family D2 |
| 668 | PTTG1IP | chr21: 46269499-46293818 | 133.45 | 195.94 | 0.55 | 0.91 | 6.50E-04 | 7.69E-03 | pituitary tumor-transforming 1 interacting protein |
| 669 | CIR1 | chr2: 175212877-175260443 | 12.13 | 17.81 | 0.55 | 0.99 | 4.50E-04 | 5.61E-03 | corepressor interacting with RBPJ, 1 |
| 670 | TBC1D1 | chr4: 37892704-38170796 | 10.37 | 15.22 | 0.55 | 0.88 | 9.50E-04 | 1.05E-02 | TBC1 (tre-2/USP6, BUB2, cdc16) domain family, member 1 |
| 671 | YIPF4 | chr2: 32502957-32531658 | 26.02 | 38.18 | 0.55 | 1.03 | 2.50E-04 | 3.38E-03 | Yip1 domain family, member 4 |
| 672 | RDH11 | chr14: 68143518-68162510 | 22.47 | 32.95 | 0.55 | 1.00 | 2.00E-04 | 2.80E-03 | retinol dehydrogenase 11 (all-trans/9-cis/11-cis) |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 673 | SEC24A | chr5: 133984474-134063601 | 10.28 | 15.07 | 0.55 | 0.97 | 4.50E-04 | 5.61E-03 | SEC24 homolog A, COPII coat complex component |
| 674 | VIMP | chr15: 101811113-101817725 | 92.90 | 136.12 | 0.55 | 1.02 | 4.00E-04 | 5.06E-03 | VCP-interacting membrane selenoprotein |
| 675 | CCNYL1 | chr2: 208576263-208620896 | 19.95 | 29.22 | 0.55 | 1.01 | 4.00E-04 | 5.06E-03 | cyclin Y-like 1 |
| 676 | SAT1 | chrX: 23801274-23804327 | 361.01 | 528.26 | 0.55 | 0.93 | 1.20E-03 | 1.28E-02 | spermidine/spermine N1-acetyltransferase 1 |
| 677 | SLC29A1 | chr6: 44187241-44201888 | 8.91 | 13.04 | 0.55 | 0.82 | 3.90E-03 | 3.32E-02 | solute carrier family 29 (equilibrative nucleoside transporter), member 1 |
| 678 | C19orf33 | chr19: 38794199-38806606 | 356.92 | 522.09 | 0.55 | 0.83 | 2.80E-03 | 2.55E-02 | chromosome 19 open reading frame 33 |
| 679 | VILL | chr3: 38035077-38048676 | 79.87 | 116.82 | 0.55 | 0.96 | 4.50E-04 | 5.61E-03 | villin-like |
| 680 | RB1CC1 | chr8: 53535017-53627026 | 5.94 | 8.68 | 0.55 | 1.03 | 7.50E-04 | 8.64E-03 | RB1-inducible coiled-coil 1 |
| 681 | SLC1A1 | chr9: 4490426-4587469 | 20.15 | 29.47 | 0.55 | 1.00 | 1.50E-04 | 2.18E-03 | solute carrier family 1 (neuronal/epithelial high affinity glutamate transporter, system Xag), member 1 |
| 682 | PLEKHA1 | chr10: 124134093-124191871 | 16.40 | 23.97 | 0.55 | 1.02 | 5.00E-04 | 6.13E-03 | pleckstrin homology domain containing, family A (phosphoinositide binding specific) member 1 |
| 683 | GCC2 | chr2: 1090655761 109125854 | 8.24 | 12.04 | 0.55 | 1.03 | 3.50E-04 | 4.55E-03 | GRIP and coiled-coil domain containing 2 |
| 684 | PTMS | chr12: 6875540-6880118 | 58.23 | 85.01 | 0.55 | 0.99 | 3.50E-04 | 4.55E-03 | parathymosin |
| 685 | NSDHL | chrX: 151999510-152037907 | 16.25 | 23.71 | 0.55 | 0.87 | 1.45E-03 | 1.49E-02 | NAD(P) dependent steroid dehydrogenase-like |
| 686 | DAP | chr5: 10679341-10761387 | 50.35 | 73.47 | 0.55 | 0.98 | 2.50E-04 | 3.38E-03 | death-associated protein |
| 687 | STX7 | chr6: 132778662-132834337 | 15.81 | 23.07 | 0.55 | 1.04 | 2.00E-04 | 2.80E-03 | syntaxin 7 |
| 688 | AGAP3 | chr7: 150782917-150841523 | 13.79 | 20.11 | 0.55 | 0.93 | 1.75E-03 | 1.74E-02 | ArfGAP with GTPase domain, ankyrin repeat and PH domain 3 |
| 689 | LRRC42 | chr1: 54411998-54433841 | 9.72 | 14.18 | 0.54 | 0.83 | 2.10E-03 | 2.02E-02 | leucine rich repeat containing 42 |
| 690 | NMD3 | chr3: 160939098-160969795 | 9.79 | 14.28 | 0.54 | 0.96 | 2.50E-04 | 3.38E-03 | NMD3 ribosome export adaptor |
| 691 | ARL8A | chr1: 202102531-202113871 | 12.72 | 18.55 | 0.54 | 0.84 | 2.80E-03 | 2.55E-02 | ADP-ribosylation factor-like 8A |
| 692 | UBE2H | chr7: 129470572-129592800 | 17.51 | 25.53 | 0.54 | 1.00 | 3.00E-04 | 3.97E-03 | ubiquitin-conjugating enzyme E2H |
| 693 | AGFG1 | chr2: 228336847-228425938 | 8.08 | 11.78 | 0.54 | 1.06 | 4.50E-04 | 5.61E-03 | ArfGAP with FG repeats 1 |
| 694 | SWAP70 | chr11: 9685627-9774507 | 8.38 | 12.20 | 0.54 | 0.95 | 8.50E-04 | 9.59E-03 | SWAP switching B-cell complex 70 kDa subunit |
| 695 | AGA | chr4: 178351928-178363657 | 7.75 | 11.28 | 0.54 | 0.85 | 3.20E-03 | 2.82E-02 | aspartylglucosaminidase |
| 696 | SLK | chr10: 105727469-105787342 | 13.07 | 19.01 | 0.54 | 1.01 | 3.00E-04 | 3.97E-03 | STE20-like kinase |
| 697 | USO1 | chr4: 76649705-76735442 | 24.81 | 36.06 | 0.54 | 1.02 | 1.50E-04 | 2.18E-03 | USO1 vesicle transport factor |
| 698 | SLC6A6 | chr3: 14444075-14581850 | 3.28 | 4.77 | 0.54 | 0.76 | 3.40E-03 | 2.97E-02 | solute carrier family 6 (neurotransmitter transporter), member 6 |
| 699 | PDIA4 | chr7: 148700153-148725782 | 91.30 | 132.58 | 0.54 | 0.91 | 4.00E-04 | 5.06E-03 | protein disulfide isomerase family A, member 4 |
| 700 | TIPARP | chr3: 156390959-156424557 | 7.14 | 10.36 | 0.54 | 0.87 | 1.80E-03 | 1.78E-02 | TCDD-inducible poly(ADP-ribose) polymerase |
| 701 | ODC1 | chr2: 10580496-10588680 | 49.06 | 71.17 | 0.54 | 0.97 | 5.50E-04 | 6.69E-03 | ornithine decarboxylase 1 |
| 702 | CLSTN3 | chr12: 7282966-7311530 | 5.67 | 8.22 | 0.54 | 0.85 | 2.15E-03 | 2.06E-02 | calsyntenin 3 |
| 703 | OSBPL5 | chr11: 3108345-3186582 | 11.35 | 16.44 | 0.54 | 0.98 | 8.00E-04 | 9.10E-03 | oxysterol binding protein-like 5 |
| 704 | GSKIP | chr14: 96829788-96853627 | 73.03 | 105.83 | 0.54 | 1.01 | 7.50E-04 | 8.64E-03 | GSK3B interacting protein |
| 705 | TMBIM1 | chr2: 219135114-219211516 | 164.53 | 238.40 | 0.54 | 0.76 | 5.65E-03 | 4.49E-02 | transmembrane BAX inhibitor motif containing 1 |
| 706 | RAB22A | chr20: 56884770-56942563 | 7.20 | 10.43 | 0.53 | 1.01 | 2.50E-04 | 3.38E-03 | RAB22A, member RAS oncogene family |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 707 | PLOD1 | chr1: 11994723-12035599 | 18.69 | 27.05 | 0.53 | 0.95 | 2.00E-04 | 2.80E-03 | procollagen-lysine, 2-oxoglutarate 5-dioxygenase 1 |
| 708 | CLTB | chr5: 175819455-175843570 | 177.54 | 256.76 | 0.53 | 0.94 | 1.15E-03 | 1.24E-02 | clathrin, light chain B |
| 709 | VEZT | chr12: 95611521-95696566 | 9.90 | 14.30 | 0.53 | 0.99 | 7.50E-04 | 8.64E-03 | vezatin, adherens junctions transmembrane protein |
| 710 | STAT1 | chr2: 191833761-191878976 | 26.71 | 38.59 | 0.53 | 0.92 | 1.40E-03 | 1.45E-02 | signal transducer and activator of transcription 1, 91 kDa |
| 711 | TSSC1 | chr2: 3192740-3381653 | 11.64 | 16.81 | 0.53 | 0.83 | 2.80E-03 | 2.55E-02 | tumor suppressing subtransferable candidate 1 |
| 712 | SH3BP2 | chr4: 2794749-2842823 | 12.60 | 18.19 | 0.53 | 0.94 | 8.00E-04 | 9.10E-03 | SH3-domain binding protein 2 |
| 713 | IDI1 | chr10: 1064846-1095061 | 60.42 | 87.18 | 0.53 | 0.90 | 1.75E-03 | 1.74E-02 | isopentenyl-diphosphate delta isomerase 1 |
| 714 | RNF8 | chr6: 37321747-37362514 | 2.24 | 3.23 | 0.53 | 0.77 | 5.55E-03 | 4.44E-02 | ring finger protein 8, E3 ubiquitin protein ligase |
| 715 | FAM114A1 | chr4: 38869353-38947365 | 17.15 | 24.71 | 0.53 | 0.96 | 7.50E-04 | 8.64E-03 | family with sequence similarity 114, member A1 |
| 716 | RHOC | chr1: 113243748-113250025 | 337.22 | 485.78 | 0.53 | 0.86 | 2.35E-03 | 2.22E-02 | ras homolog family member C |
| 717 | SREK1IP1 | chr5: 63986134-64064496 | 3.42 | 4.92 | 0.53 | 0.93 | 1.75E-03 | 1.74E-02 | SREK1-interacting protein 1 |
| 718 | CTTN | chr11: 70244611-70282690 | 85.89 | 123.71 | 0.53 | 0.91 | 1.40E-03 | 1.45E-02 | cortactin |
| 719 | TXN | chr9: 113006091-113018920 | 402.08 | 578.79 | 0.53 | 0.89 | 1.65E-03 | 1.66E-02 | thioredoxin |
| 720 | ITGB1 | chr10: 33189245-33247293 | 107.84 | 155.19 | 0.53 | 0.86 | 2.55E-03 | 2.37E-02 | integrin, beta 1 (fibronectin receptor, beta polypeptide, antigen CD29 includes MDF2, MSK12) |
| 721 | SLC35F5 | chr2: 114470368-114514400 | 20.78 | 29.89 | 0.52 | 0.99 | 9.00E-04 | 1.01E-02 | solute carrier family 35, member F5 |
| 722 | CD68 | chr17: 7482804-7485429 | 92.32 | 132.65 | 0.52 | 0.92 | 6.50E-04 | 7.69E-03 | CD68 molecule |
| 723 | SLC38A5 | chrX: 48316919-48328644 | 12.07 | 17.33 | 0.52 | 0.81 | 3.50E-03 | 3.04E-02 | solute carrier family 38, member 5 |
| 724 | GPR180 | chr13: 95254103-95286899 | 1.76 | 2.53 | 0.52 | 0.79 | 3.05E-03 | 2.72E-02 | G protein-coupled receptor 180 |
| 725 | PRKAB2 | chr1: 146626684-146644168 | 9.96 | 14.29 | 0.52 | 0.95 | 6.50E-04 | 7.69E-03 | protein kinase, AMP-activated, beta 2 non-catalytic subunit |
| 726 | ATP6V1G1 | chr9: 117349993-117361152 | 47.11 | 67.58 | 0.52 | 0.97 | 5.00E-04 | 6.13E-03 | ATPase, H+ transporting, lysosomal 13 kDa, V1 subunit G1 |
| 727 | FGL2 | chr7: 76751933-76924521 | 22.62 | 32.43 | 0.52 | 0.94 | 1.80E-03 | 1.78E-02 | fibrinogen-like 2 |
| 728 | POLD4 | chr11: 67085309-67159158 | 103.01 | 147.68 | 0.52 | 0.89 | 1.95E-03 | 1.91E-02 | polymerase (DNA-directed), delta 4, accessory subunit |
| 729 | MLKL | chr16: 74705752-74734789 | 9.50 | 13.62 | 0.52 | 0.86 | 2.10E-03 | 2.02E-02 | mixed lineage kinase domain-like |
| 730 | TRAM1 | chr8: 71485452-71520694 | 60.50 | 86.70 | 0.52 | 0.97 | 9.00E-04 | 1.01E-02 | translocation associated membrane protein 1 |
| 731 | ERI1 | chr8: 8860313-8890849 | 3.47 | 4.97 | 0.52 | 0.80 | 4.55E-03 | 3.75E-02 | exoribonuclease 1 |
| 732 | PLAC8 | chr4: 84011210-84035911 | 321.83 | 460.37 | 0.52 | 0.87 | 2.45E-03 | 2.29E-02 | placenta-specific 8 |
| 733 | C14orf1 | chr14: 76117232-76127538 | 32.02 | 45.78 | 0.52 | 0.88 | 8.00E-04 | 9.10E-03 | chromosome 14 open reading frame 1 |
| 734 | LPIN2 | chr18: 2916991-3011945 | 14.18 | 20.27 | 0.52 | 0.93 | 5.00E-05 | 7.97E-04 | lipin 2 |
| 735 | POMP | chr13: 29233140-29253093 | 68.08 | 97.26 | 0.51 | 1.02 | 5.00E-04 | 6.13E-03 | proteasome maturation protein |
| 736 | PLA2G4F | chr15: 42433331-42448839 | 12.51 | 17.87 | 0.51 | 0.92 | 6.50E-04 | 7.69E-03 | phospholipase A2, group IVF |
| 737 | SDC4 | chr20: 43953928-43977064 | 51.59 | 73.67 | 0.51 | 0.95 | 2.00E-04 | 2.80E-03 | syndecan 4 |
| 738 | BTF3 | chr5: 72794249-72801448 | 310.90 | 443.90 | 0.51 | 0.90 | 1.35E-03 | 1.41E-02 | basic transcription factor 3 |
| 739 | GBA | chr1: 155204238-155214653 | 25.44 | 36.33 | 0.51 | 0.90 | 1.00E-03 | 1.10E-02 | glucosidase, beta, acid |
| 740 | OSTC | chr4: 109571740-109588978 | 88.50 | 126.30 | 0.51 | 0.98 | 5.50E-04 | 6.69E-03 | oligosaccharyltransferase complex subunit (non-catalytic) |
| 741 | TAX1BP1 | chr7: 27778991-27869386 | 37.91 | 54.10 | 0.51 | 0.99 | 7.00E-04 | 8.19E-03 | Tax1 (human T-cell leukemia virus type 1) binding protein 1 |
| 742 | ARHGAP5 | chr14: 32546494-32628934 | 9.74 | 13.90 | 0.51 | 0.98 | 1.15E-03 | 1.24E-02 | Rho GTPase activating protein 5 |
| 743 | TMEM173 | chr5: 138855112-138862343 | 19.23 | 27.43 | 0.51 | 0.88 | 1.00E-03 | 1.10E-02 | transmembrane protein 173 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 744 | NFKB2 | chr10: 104153866-104162286 | 11.74 | 16.74 | 0.51 | 0.88 | 1.95E-03 | 1.91E-02 | nuclear factor of kappa light polypeptide gene enhancer in B-cells 2 (p49/p100) |
| 745 | FRMD8 | chr11: 65154040-65180995 | 15.26 | 21.75 | 0.51 | 0.90 | 1.15E-03 | 1.24E-02 | FERM domain containing 8 |
| 746 | JAGN1 | chr3: 9932270-9936031 | 25.51 | 36.33 | 0.51 | 0.88 | 1.20E-03 | 1.28E-02 | jagunal homolog 1 |
| 747 | PLEK2 | chr14: 67853699-67878828 | 37.15 | 52.88 | 0.51 | 0.91 | 6.00E-04 | 7.22E-03 | pleckstrin 2 |
| 748 | ERLEC1 | chr2: 53897116-54087170 | 29.35 | 41.74 | 0.51 | 0.86 | 2.05E-03 | 1.98E-02 | endoplasmic reticulum lectin 1 |
| 749 | COPB1 | chr11: 14479048-14521441 | 44.05 | 62.65 | 0.51 | 0.95 | 1.05E-03 | 1.15E-02 | coatomer protein complex, subunit beta 1 |
| 750 | SBNO2 | chr19: 1107632-1174282 | 17.39 | 24.72 | 0.51 | 0.97 | 8.00E-04 | 9.10E-03 | strawberry notch homolog 2 (Drosophila) |
| 751 | PSMB9 | chr6_ssto_hap7: 4252710-4258398 | 30.29 | 43.06 | 0.51 | 0.79 | 2.45E-03 | 2.29E-02 | proteasome subunit beta 9 |
| 752 | RALGPS2 | chr1: 178694281-178890760 | 8.34 | 11.85 | 0.51 | 0.95 | 1.15E-03 | 1.24E-02 | Ral GEF with PH domain and SH3 binding motif 2 |
| 753 | NAPG | chr18: 10525872-10552766 | 13.16 | 18.69 | 0.51 | 0.93 | 1.10E-03 | 1.20E-02 | N-ethylmaleimide-sensitive factor attachment protein, gamma |
| 754 | WHAMM | chr15: 83478379-83503613 | 5.58 | 7.92 | 0.51 | 0.81 | 2.60E-03 | 2.41E-02 | WAS protein homolog associated with actin, golgi membranes and microtubules |
| 755 | FAM109A | chr12: 111798454-111806925 | 12.97 | 18.42 | 0.51 | 0.89 | 2.05E-03 | 1.98E-02 | family with sequence similarity 109, member A |
| 756 | IL17RE | chr3: 9944295-9958084 | 31.04 | 44.08 | 0.51 | 0.90 | 1.00E-03 | 1.10E-02 | interleukin 17 receptor E |
| 757 | MYO7B | chr2: 128293377-128395303 | 44.94 | 63.78 | 0.51 | 0.87 | 1.45E-03 | 1.49E-02 | myosin VIIB |
| 758 | 10-Sep | chr2: 110300373-110371783 | 19.30 | 27.38 | 0.50 | 0.94 | 7.00E-04 | 8.19E-03 | septin 10 |
| 759 | TMEM106B | chr7: 12250847-12276890 | 11.77 | 16.71 | 0.50 | 1.00 | 1.50E-03 | 1.53E-02 | transmembrane protein 106B |
| 760 | EFNA2 | chr19: 1286152-1301429 | 18.89 | 26.79 | 0.50 | 0.82 | 3.00E-03 | 2.69E-02 | ephrin-A2 |
| 761 | CHIC1 | chrX: 72782983-72906937 | 2.18 | 3.08 | 0.50 | 0.79 | 5.60E-03 | 4.46E-02 | cysteine-rich hydrophobic domain 1 |
| 762 | EHBP1L1 | chr11: 65343508-65360116 | 27.59 | 39.07 | 0.50 | 0.95 | 7.00E-04 | 8.19E-03 | EH domain binding protein 1-like 1 |
| 763 | SERPING1 | chr11: 57365026-57382326 | 19.79 | 28.01 | 0.50 | 0.84 | 2.35E-03 | 2.22E-02 | serpin peptidase inhibitor, clade G (C1 inhibitor), member 1 |
| 764 | LMAN1 | chr18: 56995055-57026508 | 23.57 | 33.34 | 0.50 | 0.95 | 7.00E-04 | 8.19E-03 | lectin, mannose-binding, 1 |
| 765 | CXCL12 | chr10: 44865600-44880545 | 25.41 | 17.95 | -0.50 | -0.74 | 3.50E-03 | 3.04E-02 | chemokine (C-X-C motif) ligand 12 |
| 766 | SLC9A2 | chr2: 103236165-103327809 | 22.28 | 15.73 | -0.50 | -0.89 | 1.35E-03 | 1.41E-02 | solute carrier family 9, subfamily A (NHE2, cation proton antiporter 2), member 2 |
| 767 | SFXN1 | chr5: 174905513-174955621 | 38.66 | 27.29 | -0.50 | -0.92 | 7.50E-04 | 8.64E-03 | sideroflexin 1 |
| 768 | GRAMD3 | chr5: 125695787-125829853 | 30.37 | 21.41 | -0.50 | -0.93 | 7.00E-04 | 8.19E-03 | GRAM domain containing 3 |
| 769 | HMOX1 | chr22: 35777059-35790207 | 62.11 | 43.78 | -0.50 | -0.86 | 1.35E-03 | 1.41E-02 | heme oxygenase 1 |
| 770 | HNF1B | chr17: 36046433-36105096 | 16.35 | 11.52 | -0.51 | -0.84 | 2.55E-03 | 2.37E-02 | HNF1 homeobox B |
| 771 | UQCRFS1 | chr19: 29698166-29704136 | 243.33 | 171.33 | -0.51 | -0.88 | 6.00E-04 | 7.22E-03 | ubiquinol-cytochrome c reductase, Rieske iron-sulfur polypeptide 1 |
| 772 | G0LGA2P5 | chr12: 100550174-100567121 | 12.14 | 8.55 | -0.51 | -0.79 | 3.60E-03 | 3.10E-02 | golgin A2 pseudogene 5 |
| 773 | ABCA1 | chr9: 107543283-107690527 | 4.46 | 3.14 | -0.51 | -0.83 | 2.65E-03 | 2.44E-02 | ATP-binding cassette, sub-family A (ABC1), member 1 |
| 774 | PPTC7 | chr12: 110972236-111021064 | 13.84 | 9.73 | -0.51 | -0.84 | 2.15E-03 | 2.06E-02 | PTC7 protein phosphatase homolog |
| 775 | NDUFV1 | chr11: 67374322-67380012 | 164.54 | 115.65 | -0.51 | -0.83 | 3.40E-03 | 2.97E-02 | NADH dehydrogenase (ubiquinone) flavoprotein 1, 51 kDa |
| 776 | PWWP2A | chr5: 159502891-159546452 | 14.18 | 9.96 | -0.51 | -0.88 | 1.75E-03 | 1.74E-02 | PWWP domain containing 2A |
| 777 | PAPD5 | chr16: 50186828-50269219 | 3.62 | 2.53 | -0.51 | -0.83 | 3.90E-03 | 3.32E-02 | PAP associated domain containing 5 |
| 778 | CECR1 | chr22: 17659679-17702744 | 15.97 | 11.18 | -0.51 | -0.86 | 1.75E-03 | 1.74E-02 | cat eye syndrome chromosome region, candidate 1 |

TABLE 6-continued

The list of 1058 genes exclusively DE between CR and SSA/P samples.

| | gene | locus | mean_CR | mean SSA/P | log₂FC | test_stat | p_value | p_adj_value | Description |
|---|---|---|---|---|---|---|---|---|---|
| 779 | FLVCR2 | chr14: 76041246-76114512 | 12.44 | 8.68 | −0.52 | −0.82 | 2.95E−03 | 2.66E−02 | feline leukemia virus subgroup C cellular receptor family, member 2 |
| 780 | CC2D1A | chr19: 14016955-14041693 | 39.58 | 27.56 | −0.52 | −0.97 | 5.50E−04 | 6.69E−03 | coiled-coil and C2 domain containing 1A |
| 781 | DDC | chr7: 50526133-50633154 | 48.89 | 34.04 | −0.52 | −0.92 | 6.50E−04 | 7.69E−03 | dopa decarboxylase (aromatic L-amino acid decarboxylase) |
| 782 | CPOX | chr3: 98298289-98312455 | 12.79 | 8.90 | −0.52 | −0.85 | 1.55E−03 | 1.57E−02 | coproporphyrinogen oxidase |
| 783 | ABAT | chr16: 8768443-8878432 | 10.03 | 6.97 | −0.52 | −0.89 | 1.40E−03 | 1.45E−02 | 4-aminobutyrate aminotransferase |
| 784 | MYBL2 | chr20: 42295658-42345136 | 9.16 | 6.36 | −0.53 | −0.77 | 4.95E−03 | 4.02E−02 | v-myb avian myeloblastosis viral oncogene homolog-like 2 |
| 785 | TRPM4 | chr19: 49661015-49715098 | 109.31 | 75.95 | −0.53 | −0.93 | 1.40E−03 | 1.45E−02 | transient receptor potential cation channel, subfamily M, member 4 |
| 786 | GAB2 | chr11: 77926335-78128868 | 7.49 | 5.20 | −0.53 | −0.93 | 9.50E−04 | 1.05E−02 | GRB2-associated binding protein 2 |
| 787 | RRM2B | chr8: 103216728-103251346 | 8.75 | 6.07 | −0.53 | −0.91 | 2.50E−03 | 2.33E−02 | ribonucleotide reductase M2 B (TP53 inducible) |
| 788 | LYRM7 | chr5: 130506640-130541119 | 5.03 | 3.49 | −0.53 | −0.88 | 2.10E−03 | 2.02E−02 | LYR motif containing 7 |
| 789 | ABO | chr9: 136130562-136150630 | 37.30 | 25.84 | −0.53 | −0.94 | 8.00E−04 | 9.10E−03 | ABO blood group (transferase A, alpha 1-3-N-acetylgalactosaminyltransferase; transferase B, alpha 1-3-galactosyltransferase) |
| 790 | ACOX1 | chr17: 73937588-74002080 | 47.96 | 33.17 | −0.53 | −0.83 | 2.60E−03 | 2.41E−02 | acyl-CoA oxidase 1, palmitoyl |
| 791 | CAAP1 | chr9: 26840682-26892826 | 19.24 | 13.28 | −0.53 | −0.96 | 1.20E−03 | 1.28E−02 | caspase activity and apoptosis inhibitor 1 |
| 792 | MAMDC4 | chr9: 139746818-139755251 | 12.27 | 8.45 | −0.54 | −0.90 | 8.50E−04 | 9.59E−03 | MAM domain containing 4 |
| 793 | FGFR3 | chr4: 1795038-1810599 | 24.26 | 16.72 | −0.54 | −1.00 | 3.00E−03 | 3.97E−03 | fibroblast growth factor receptor 3 |
| 794 | ALDH1B1 | chr9: 38392660-38398662 | 25.85 | 17.81 | −0.54 | −0.93 | 9.00E−04 | 1.01E−02 | aldehyde dehydrogenase 1 family, member B1 |
| 795 | DPYD | chr1: 97543299-98386615 | 4.34 | 2.99 | −0.54 | −0.75 | 5.20E−03 | 4.20E−02 | dihydropyrimidine dehydrogenase |
| 796 | SNX30 | chr9: 115513133-115637267 | 10.39 | 7.15 | −0.54 | −0.95 | 3.50E−04 | 4.55E−03 | sorting nexin family member 30 |
| 797 | ACSF3 | chr16: 89160216-89222254 | 10.15 | 6.98 | −0.54 | −0.85 | 2.55E−03 | 2.37E−02 | acyl-CoA synthetase family member 3 |
| 798 | SGK2 | chr20: 42187634-42214273 | 66.68 | 45.87 | −0.54 | −0.97 | 4.00E−04 | 5.06E−03 | serum/glucocorticoid regulated kinase 2 |
| 799 | KDM4A | chr1: 44115796-44173012 | 20.94 | 14.39 | −0.54 | −0.97 | 5.00E−04 | 6.13E−03 | lysine (K)-specific demethylase 4A |
| 800 | SLC17A4 | chr6: 25754926-25781403 | 41.09 | 28.22 | −0.54 | −0.98 | 3.50E−04 | 4.55E−03 | solute carrier family 17, member 4 |
| 801 | SEC31B | chr10: 102246402-102279595 | 7.55 | 5.18 | −0.54 | −0.89 | 1.10E−03 | 1.20E−02 | SEC31 homolog B, COPII coat complex component |
| 802 | SEPHS2 | chr16: 30454945-30457296 | 113.79 | 78.03 | −0.54 | −0.98 | 1.50E−04 | 2.18E−03 | selenophosphate synthetase 2 |
| 803 | LPCAT3 | chr12: 7085346-7125842 | 71.15 | 48.77 | −0.54 | −0.99 | 3.00E−04 | 3.97E−03 | lysophosphatidylcholine acyltransferase 3 |
| 804 | DEPDC5 | chr22: 32149936-32303020 | 6.48 | 4.43 | −0.55 | −0.88 | 1.55E−03 | 1.57E−02 | DEP domain containing 5 |
| 805 | PDK4 | chr7: 95212808-95225925 | 23.85 | 16.30 | −0.55 | −0.97 | 4.00E−04 | 5.06E−03 | pyruvate dehydrogenase kinase, isozyme 4 |
| 806 | MEST | chr7: 130126015-130371406 | 23.02 | 15.73 | −0.55 | −0.82 | 4.15E−03 | 3.50E−02 | mesoderm specific transcript |
| 807 | ZNF704 | chr8: 81540685-81787016 | 3.21 | 2.19 | −0.55 | −0.95 | 4.00E−04 | 5.06E−03 | zinc finger protein 704 |
| 808 | ZNF462 | chr9: 109625377-109848716 | 2.19 | 1.49 | −0.55 | −0.80 | 3.00E−04 | 2.69E−02 | zinc finger protein 462 |
| 809 | SGPP1 | chr14: 64150934-64194756 | 15.01 | 10.22 | −0.55 | −0.95 | 4.50E−04 | 5.61E−03 | sphingosine-1-phosphate phosphatase 1 |
| 810 | COL14A1 | chr8: 121137346-121384273 | 6.24 | 4.24 | −0.56 | −0.94 | 6.00E−04 | 7.22E−03 | collagen, type XIV, alpha 1 |
| 811 | IGSF9 | chr1: 159896828-159915386 | 34.14 | 23.21 | −0.56 | −1.03 | 4.00E−04 | 5.06E−03 | immunoglobulin superfamily, member 9 |
| 812 | NIPSNAP3A | chr9: 107509968-107522403 | 41.39 | 28.12 | −0.56 | −0.99 | 4.50E−04 | 5.61E−03 | nipsnap homolog 3A (C. elegans) |
| 813 | FN3K | chr17: 80693451-80709073 | 20.04 | 13.61 | −0.56 | −0.79 | 4.85E−03 | 3.96E−02 | fructosamine 3 kinase |

TABLE 6-continued

The list of 1058 genes exclusively DE between CR and SSA/P samples.

| | gene | locus | mean_CR | mean SSA/P | log₂FC | test_stat | p_value | p_adj_value | Description |
|---|---|---|---|---|---|---|---|---|---|
| 814 | TRIM24 | chr7: 138145078-138270332 | 8.23 | 5.59 | −0.56 | −0.92 | 9.50E-04 | 1.05E-02 | tripartite motif containing 24 |
| 815 | SNHG18 | chr5: 9546311-9550409 | 19.52 | 13.23 | −0.56 | −0.83 | 2.30E-03 | 2.18E-02 | small nucleolar RNA host gene 18 |
| 816 | HOXA3 | chr7: 27145808-27166639 | 8.58 | 5.81 | −0.56 | −0.83 | 3.05E-03 | 2.72E-02 | homeobox A3 |
| 817 | TLE3 | chr15: 70340129-70390256 | 14.77 | 9.99 | −0.56 | −0.97 | 8.50E-04 | 9.59E-03 | transducin-like enhancer of split 3 |
| 818 | ADH6 | chr4: 100010007-100222513 | 13.20 | 8.93 | −0.56 | −0.83 | 5.10E-03 | 4.13E-02 | alcohol dehydrogenase 6 (class V) |
| 819 | PLCD1 | chr3: 38048986-38071154 | 33.01 | 22.31 | −0.57 | −0.94 | 1.45E-03 | 1.49E-02 | phospholipase C, delta 1 |
| 820 | PAPSS2 | chr10: 89419475-89507462 | 132.95 | 89.82 | −0.57 | −0.93 | 4.00E-04 | 5.06E-03 | 3'-phosphoadenosine 5'-phosphosulfate synthase 2 |
| 821 | LRRC19 | chr9: 26903367-27062931 | 57.59 | 38.91 | −0.57 | −0.91 | 2.35E-03 | 2.22E-02 | leucine rich repeat containing 19 |
| 822 | MAGI1 | chr3: 65339905-66024509 | 7.17 | 4.84 | −0.57 | −0.98 | 7.50E-04 | 8.64E-03 | membrane associated guanylate kinase, WW and PDZ domain containing 1 |
| 823 | DNAH1 | chr3: 52350334-52434513 | 3.18 | 2.14 | −0.57 | −0.99 | 3.00E-04 | 3.97E-03 | dynein, axonemal, heavy chain 1 |
| 824 | ARHGAP33 | chr19: 36266416-36279724 | 5.23 | 3.51 | −0.57 | −0.82 | 5.10E-03 | 4.13E-02 | Rho GTPase activating protein 33 |
| 825 | PRR5L | chr11: 36317724-36486754 | 30.51 | 20.49 | −0.57 | −1.02 | 4.00E-04 | 5.06E-03 | proline rich 5 like |
| 826 | P2RY1 | chr3: 152552735-152555843 | 7.86 | 5.28 | −0.57 | −0.82 | 1.80E-03 | 1.78E-02 | purinergic receptor P2Y, G-protein coupled, 1 |
| 827 | MAVS | chr20: 3827445-3856770 | 34.18 | 22.95 | −0.57 | −1.00 | 4.50E-04 | 5.61E-03 | mitochondrial antiviral signaling protein |
| 828 | MIR600HG | chr9: 125871772-125877756 | 4.72 | 3.17 | −0.57 | −0.89 | 1.30E-03 | 1.37E-02 | MIR600 host gene |
| 829 | TPRN | chr9: 140086068-140095163 | 68.40 | 45.91 | −0.58 | −1.00 | 1.10E-03 | 1.20E-02 | taperin |
| 830 | NXPE4 | chr11: 114441312-114466484 | 84.23 | 56.49 | −0.58 | −1.02 | 6.50E-04 | 7.69E-03 | neurexophilin and PC-esterase domain family, member 4 |
| 831 | LETM1 | chr4: 1813205-1857974 | 39.16 | 26.20 | −0.58 | −1.06 | 1.50E-03 | 2.18E-03 | leucine zipper-EF-hand containing transmembrane protein 1 |
| 832 | CBFA2T3 | chr16: 88941262-89043504 | 4.20 | 2.81 | −0.58 | −0.77 | 6.45E-03 | 5.00E-02 | core-binding factor, runt domain, alpha subunit 2; translocated to, 3 |
| 833 | GPR160 | chr3: 169755734-169803183 | 74.24 | 49.55 | −0.58 | −1.08 | 5.00E-05 | 7.97E-04 | G protein-coupled receptor 160 |
| 834 | SCO1 | chr17: 10583648-10600885 | 36.47 | 24.32 | −0.58 | −1.04 | 1.00E-04 | 1.51E-03 | SCO1 cytochrome c oxidase assembly protein |
| 835 | ENGASE | chr17: 77071018-77084685 | 34.01 | 22.67 | −0.59 | −1.07 | 5.00E-05 | 7.97E-04 | endo-beta-N-acetylglucosaminidase |
| 836 | PDXP | chr22: 38054736-38062939 | 26.96 | 17.93 | −0.59 | −0.97 | 4.50E-04 | 5.61E-03 | pyridoxal (pyridoxine, vitamin B6) phosphatase |
| 837 | BDH1 | chr3: 197236653-197300194 | 59.31 | 39.30 | −0.59 | −1.03 | 2.00E-04 | 2.80E-03 | 3-hydroxybutyrate dehydrogenase, type 1 |
| 838 | TFRC | chr3: 195776154-195809032 | 79.84 | 52.86 | −0.60 | −0.89 | 1.75E-03 | 1.74E-02 | transferrin receptor |
| 839 | PDK2 | chr17: 48172100-48207246 | 35.38 | 23.41 | −0.60 | −0.95 | 1.05E-03 | 1.15E-02 | pyruvate dehydrogenase kinase, isozyme 2 |
| 840 | GNA11 | chr19: 3094407-3124000 | 116.16 | 76.65 | −0.60 | −1.07 | 1.50E-04 | 2.18E-03 | guanine nucleotide binding protein (G protein), alpha 11 (Gq class) |
| 841 | GOLGA8A | chr15: 34671269-34729667 | 6.89 | 4.54 | −0.60 | −0.93 | 7.00E-04 | 8.19E-03 | golgin A8 family, member A |
| 842 | KIFC2 | chr8: 145691737-145701718 | 30.52 | 20.11 | −0.60 | −0.97 | 1.05E-03 | 1.15E-02 | kinesin family member C2 |
| 843 | C15orf52 | chr15: 40623652-40633168 | 14.06 | 9.23 | −0.61 | −1.09 | 3.00E-04 | 3.97E-03 | chromosome 15 open reading frame 52 |
| 844 | CDH24 | chr14: 23516269-23526747 | 4.16 | 2.72 | −0.61 | −0.80 | 6.00E-04 | 4.72E-02 | cadherin 24, type 2 |
| 845 | CPA3 | chr3: 148583042-148614872 | 25.76 | 16.81 | −0.62 | −0.79 | 3.65E-03 | 3.14E-02 | carboxypeptidase A3 (mast cell) |
| 846 | LOX | chr5: 121398889-121414055 | 2.94 | 1.92 | −0.62 | −0.83 | 4.50E-03 | 3.72E-02 | lysyl oxidase |
| 847 | ZDHHC2 | chr8: 17013835-17080241 | 10.15 | 6.62 | −0.62 | −1.03 | 1.50E-04 | 2.18E-03 | zinc finger, DHHC-type containing 2 |
| 848 | FOXD2-AS1 | chr1: 47897806-47900313 | 10.58 | 6.90 | −0.62 | −0.86 | 1.95E-03 | 1.91E-02 | FOXD2 antisense RNA 1 (head to head) |
| 849 | MYO1D | chr17: 30819627-31203902 | 163.85 | 106.54 | −0.62 | −0.93 | 3.50E-04 | 4.55E-03 | myosin ID |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 850 | CLUH | chr17: 2592679-2614927 | 45.24 | 29.39 | −0.62 | −1.17 | 5.00E−05 | 7.97E−04 | clustered mitochondria (cluA/CLU1) homolog |
| 851 | ACADS | chr12: 121163570-121177811 | 132.93 | 86.33 | −0.62 | −1.02 | 1.00E−04 | 1.51E−03 | acyl-CoA dehydrogenase, C-2 to C-3 short chain |
| 852 | BCL2 | chr18: 60790578-60986613 | 4.52 | 2.93 | −0.63 | −0.83 | 4.50E−04 | 5.61E−03 | B-cell CLL/lymphoma 2 |
| 853 | B3GNT6 | chr11: 76745384-767530054- | 35.42 | 22.93 | −0.63 | −1.16 | 1.00E−04 | 1.51E−03 | UDP-GlcNAc: betaGal beta-1,3-N-acetylglucosaminyltransferase 6 |
| 854 | ZNF764 | chr16: 30565084-30569642 | 6.17 | 3.99 | −0.63 | −0.86 | 2.25E−03 | 2.14E−02 | zinc finger protein 764 |
| 855 | ACAT1 | chr11: 107992257-108018891 | 65.08 | 42.01 | −0.63 | −1.14 | 5.00E−05 | 7.97E−04 | acetyl-CoA acetyltransferase 1 |
| 856 | TMEM8B | chr9: 35829221-35854844 | 8.77 | 5.66 | −0.63 | −0.91 | 2.45E−03 | 2.29E−02 | transmembrane protein 8B |
| 857 | GADD45B | chr19: 2476122-2478257 | 14.41 | 9.29 | −0.63 | −0.84 | 3.75E−03 | 3.22E−02 | growth arrest and DNA-damage-inducible, beta |
| 858 | NRARP | chr9: 140194082-140196703 | 88.57 | 57.08 | −0.63 | −1.15 | 5.00E−05 | 7.97E−04 | NOTCH-regulated ankyrin repeat protein |
| 859 | RCN3 | chr19: 50030874-50046690 | 34.55 | 22.26 | −0.63 | −0.94 | 1.10E−03 | 1.20E−02 | reticulocalbin 3, EF-hand calcium binding domain |
| 860 | NHSL1 | chr6: 138743180-138893668 | 21.09 | 13.58 | −0.64 | −1.14 | 1.00E−04 | 1.51E−03 | NHS-like 1 |
| 861 | LAPTM4B | chr8: 98787808-98864830 | 31.25 | 20.09 | −0.64 | −1.11 | 5.00E−05 | 7.97E−04 | lysosomal protein transmembrane 4 beta |
| 862 | KCNK10 | chr14: 88646451-88793256 | 1.20 | 0.77 | −0.64 | −0.75 | 5.90E−03 | 4.65E−02 | potassium channel, two pore domain subfamily K, member 10 |
| 863 | NR6A1 | chr9: 127279553-127533589 | 2.46 | 1.58 | −0.64 | −0.87 | 1.45E−03 | 1.49E−02 | nuclear receptor subfamily 6, group A, member 1 |
| 864 | AHCYL2 | chr7: 128864854-129070052 | 141.01 | 90.52 | −0.64 | −0.96 | 6.50E−04 | 7.69E−03 | adenosylhomocysteinase-like 2 |
| 865 | GLIPR2 | chr9: 36136532-36163910 | 19.21 | 12.33 | −0.64 | −0.95 | 7.00E−04 | 8.19E−03 | GLI pathogenesis-related 2 |
| 866 | DMD | chrX: 31137344-33357726 | 2.86 | 1.83 | −0.64 | −0.81 | 5.30E−03 | 4.27E−02 | dystrophin |
| 867 | PKIG | chr20: 43160421-43247678 | 40.24 | 25.79 | −0.64 | −1.04 | 2.50E−04 | 3.38E−03 | protein kinase (cAMP-dependent, catalytic) inhibitor gamma |
| 868 | GCSHP3 | chr2: 206980296-206981296 | 16.68 | 10.69 | −0.64 | −0.85 | 2.70E−03 | 2.48E−02 | glycine cleavage system protein H (aminomethyl carrier) pseudogene 3 |
| 869 | E2F8 | chr11: 19245609-19263202 | 4.10 | 2.63 | −0.64 | −0.87 | 1.60E−03 | 1.62E−02 | E2F transcription factor 8 |
| 870 | SCARA5 | chr8: 27727398-27850369 | 14.59 | 9.33 | −0.64 | −1.11 | 1.00E−04 | 1.51E−03 | scavenger receptor class A, member 5 |
| 871 | MAP2K6 | chr17: 67410837-67538470 | 16.77 | 10.72 | −0.65 | −1.02 | 2.50E−04 | 3.38E−03 | mitogen-activated protein kinase kinase 6 |
| 872 | ARHGEF9 | chrX: 62854847-63005426 | 8.54 | 5.45 | −0.65 | −1.08 | 2.00E−04 | 2.80E−03 | Cdc42 guanine nucleotide exchange factor (GEF) 9 |
| 873 | SSTR1 | chr14: 38677203-38682268 | 4.43 | 2.82 | −0.65 | −0.84 | 3.00E−03 | 2.69E−02 | somatostatin receptor 1 |
| 874 | FAM43A | chr3: 194406621-194409766 | 8.47 | 5.39 | −0.65 | −0.93 | 1.55E−03 | 1.57E−02 | family with sequence similarity 43, member A |
| 875 | BRINP3 | chr1: 190066796-190446759 | 3.28 | 2.08 | −0.65 | −0.75 | 3.70E−03 | 3.18E−02 | bone morphogenetic protein/retinoic acid inducible neural-specific 3 |
| 876 | PLCG2 | chr16: 81812862-81996298 | 5.66 | 3.59 | −0.66 | −1.05 | 5.00E−05 | 7.97E−04 | phospholipase C, gamma 2 (phosphatidylinositol-specific) |
| 877 | FABP5 | chr8: 82192717-82197102 | 255.22 | 161.88 | −0.66 | −1.14 | 5.00E−05 | 7.97E−04 | fatty acid binding protein 5 (psoriasis-associated) |
| 878 | TTC30A | chr2: 178479025-178483694 | 2.18 | 1.38 | −0.66 | −0.81 | 5.30E−03 | 4.27E−02 | tetratricopeptide repeat domain 30A |
| 879 | 1-Mar | chr1: 220960038-220987741 | 18.60 | 11.74 | −0.66 | −1.06 | 2.00E−04 | 2.80E−03 | mitochondrial amidoxime reducing component 1 |
| 880 | ME2 | chr18: 48405431-48476162 | 31.18 | 19.68 | −0.66 | −1.22 | 5.00E−05 | 7.97E−04 | malic enzyme 2, NAD(+)-dependent, mitochondrial |
| 881 | MEGF8 | chr19: 42829760-42882921 | 5.71 | 3.60 | −0.66 | −1.21 | 1.00E−04 | 1.51E−03 | multiple EGF-like-domains 8 |
| 882 | FRRS1 | chr1: 100111430-100231349 | 5.79 | 3.65 | −0.66 | −0.81 | 5.70E−03 | 4.52E−02 | ferric-chelate reductase 1 |
| 883 | SFXN5 | chr2: 73169164-73298965 | 11.09 | 6.99 | −0.67 | −1.10 | 5.00E−05 | 7.97E−04 | sideroflexin 5 |
| 884 | LINC01004 | chr7: 104622193-104631612 | 6.51 | 4.10 | −0.67 | −1.20 | 5.00E−05 | 7.97E−04 | long intergenic non-protein coding RNA 1004 |
| 885 | GIPC2 | chr1: 78511588-78603112 | 19.87 | 12.52 | −0.67 | −1.19 | 5.00E−05 | 7.97E−04 | GIPC PDZ domain containing family, member 2 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 886 | ALDH5A1 | chr6: 24495196-24537435 | 8.33 | 5.24 | −0.67 | −1.09 | 1.50E-04 | 2.18E-03 | aldehyde dehydrogenase 5 family, member A1 |
| 887 | PTGDR | chr14: 52734430-52743442 | 7.62 | 4.79 | −0.67 | −0.95 | 1.40E-03 | 1.45E-02 | prostaglandin D2 receptor (DP) |
| 888 | PDE8A | chr15: 85523743-85682376 | 39.74 | 24.98 | −0.67 | −1.21 | 5.00E-05 | 7.97E-04 | phosphodiesterase 8A |
| 889 | PIGZ | chr3: 196673214-196695742 | 54.26 | 34.10 | −0.67 | −1.12 | 1.00E-04 | 1.51E-03 | phosphatidylinositol glycan anchor biosynthesis, class Z |
| 890 | ENTPD5 | chr14: 74433180-74486026 | 73.01 | 45.71 | −0.68 | −1.17 | 5.00E-05 | 7.97E-04 | ectonucleoside triphosphate diphosphohydrolase 5 |
| 891 | KREMEN1 | chr22: 29469065-29564321 | 13.91 | 8.70 | −0.68 | −1.19 | 5.00E-05 | 7.97E-04 | kringle containing transmembrane protein 1 |
| 892 | PGAP3 | chr17: 37827374-37844323 | 38.45 | 23.97 | −0.68 | −1.16 | 1.00E-04 | 1.51E-03 | post-GPI attachment to proteins 3 |
| 893 | NRG1 | chr8: 31497267-32622558 | 3.11 | 1.94 | −0.68 | −0.73 | 6.25E-03 | 4.88E-02 | neuregulin 1 |
| 894 | HADH | chr4: 108910869-108956331 | 116.76 | 72.02 | −0.70 | −1.22 | 5.00E-05 | 7.97E-04 | hydroxyacyl-CoA dehydrogenase |
| 895 | ARHGEF37 | chr5: 148961134-149014521 | 10.02 | 6.18 | −0.70 | −1.20 | 5.00E-05 | 7.97E-04 | Rho guanine nucleotide exchange factor (GEF) 37 |
| 896 | PBX1 | chr1: 164528596-164821060 | 9.57 | 5.90 | −0.70 | −1.13 | 5.00E-05 | 7.97E-04 | pre-B-cell leukemia homeobox 1 |
| 897 | MAOA | chrX: 43514154-43606071 | 103.83 | 63.98 | −0.70 | −1.11 | 5.00E-05 | 7.97E-04 | monoamine oxidase A |
| 898 | CAMK1D | chr10: 12875132-12877545 | 11.95 | 7.34 | −0.70 | −1.01 | 5.00E-04 | 6.13E-03 | |
| 899 | BAHCC1 | chr17: 79373520-79433358 | 2.84 | 1.75 | −0.70 | −1.11 | 2.00E-04 | 2.80E-03 | BAH domain and coiled-coil containing 1 |
| 900 | MAN1A1 | chr6: 119498365-119670931 | 36.51 | 22.41 | −0.70 | −1.24 | 5.00E-05 | 7.97E-04 | mannosidase, alpha, class 1A, member 1 |
| 901 | KIT | chr4: 55524094-55606881 | 6.51 | 3.99 | −0.70 | −1.05 | 2.00E-04 | 2.80E-03 | v-kit Hardy-Zuckerman 4 feline sarcoma viral oncogene homolog |
| 902 | MEIS3P1 | chr17: 15690163-15693019 | 4.60 | 2.82 | −0.71 | −0.91 | 1.05E-03 | 1.15E-02 | Meis homeobox 3 pseudogene 1 |
| 903 | HAPLN1 | chr5: 82934016-83016896 | 4.46 | 2.72 | −0.71 | −1.06 | 4.50E-04 | 5.61E-03 | hyaluronan and proteoglycan link protein 1 |
| 904 | SDR42E1 | chr16: 82031250-82045093 | 5.65 | 3.45 | −0.71 | −0.92 | 1.20E-03 | 1.28E-02 | short chain dehydrogenase/reductase family 42E, member 1 |
| 905 | WNK2 | chr9: 95947211-96108696 | 13.74 | 8.38 | −0.71 | −1.26 | 5.00E-05 | 7.97E-04 | WNK lysine deficient protein kinase 2 |
| 906 | PLOD2 | chr3: 145787227-145879282 | 41.40 | 25.25 | −0.71 | −1.33 | 1.00E-04 | 1.51E-03 | procollagen-lysine, 2-oxoglutarate 5-dioxygenase 2 |
| 907 | IL6R | chr1: 154377668-154441926 | 20.00 | 12.20 | −0.71 | −1.27 | 5.00E-05 | 7.97E-04 | interleukin 6 receptor |
| 908 | PCSK5 | chr9: 78505559-78977255 | 10.92 | 6.66 | −0.71 | −1.25 | 5.00E-05 | 7.97E-04 | proprotein convertase subtilisin/kexin type 5 |
| 909 | TMEM209 | chr7: 129804554-129845338 | 9.41 | 5.73 | −0.71 | −1.16 | 5.00E-05 | 7.97E-04 | transmembrane protein 209 |
| 910 | MOGAT2 | chr11: 75428933-75442331 | 48.08 | 29.26 | −0.72 | −1.17 | 5.00E-05 | 7.97E-04 | monoacylglycerol O-acyltransferase 2 |
| 911 | SLC4A7 | chr3: 27414211-27525911 | 4.69 | 2.85 | −0.72 | −1.16 | 5.00E-05 | 7.97E-04 | solute carrier family 4, sodium bicarbonate cotransporter, member 7 |
| 912 | ZNF132 | chr19: 58944180-58951589 | 1.44 | 0.87 | −0.72 | −0.71 | 6.40E-03 | 4.97E-02 | zinc finger protein 132 |
| 913 | C7orf31 | chr7: 25174315-25219817 | 4.99 | 3.03 | −0.72 | −1.03 | 1.50E-04 | 2.18E-03 | chromosome 7 open reading frame 31 |
| 914 | ZBTB10 | chr8: 81397853-81438500 | 3.27 | 1.98 | −0.72 | −1.13 | 4.00E-04 | 5.06E-03 | zinc finger and BTB domain containing 10 |
| 915 | FLJ22763 | chr3: 108855560-108868951 | 8.70 | 5.26 | −0.73 | −0.95 | 2.55E-03 | 2.37E-02 | uncharacterized LOC401081 |
| 916 | SCAP | chr3: 47455183-47517445 | 43.81 | 26.48 | −0.73 | −1.35 | 5.00E-05 | 7.97E-04 | SREBF chaperone |
| 917 | MTSS1 | chr8: 125563010-125740748 | 8.18 | 4.95 | −0.73 | −1.19 | 5.00E-05 | 7.97E-04 | metastasis suppressor 1 |
| 918 | CES3 | chr16: 66995131-67009052 | 53.33 | 31.98 | −0.74 | −1.27 | 5.00E-05 | 7.97E-04 | carboxylesterase 3 |
| 919 | ACACB | chr12: 109577201-109706030 | 7.25 | 4.33 | −0.74 | −1.30 | 5.00E-05 | 7.97E-04 | acetyl-CoA carboxylase beta |
| 920 | ZNF813 | chr19: 53970988-53997546 | 1.20 | 0.72 | −0.75 | −0.75 | 5.15E-03 | 4.16E-02 | zinc finger protein 813 |
| 921 | CLDN15 | chr7: 100875372-100882101 | 26.77 | 15.95 | −0.75 | −1.13 | 5.00E-05 | 7.97E-04 | claudin 15 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 922 | DLL1 | chr6: 170591293-170599697 | 9.55 | 5.67 | −0.75 | −1.15 | 5.00E−05 | 7.97E−04 | delta-like 1 (*Drosophila*) |
| 923 | NCAM1 | chr11: 112830002-113149158 | 1.83 | 1.08 | −0.75 | −0.91 | 1.25E−03 | 1.33E−02 | neural cell adhesion molecule 1 |
| 924 | LRP12 | chr8: 105501458-105601252 | 3.70 | 2.19 | −0.76 | −1.00 | 6.00E−04 | 7.22E−03 | low density lipoprotein receptor-related protein 12 |
| 925 | ATOH1 | chr4: 94750077-94751142 | 21.83 | 12.89 | −0.76 | −1.07 | 4.00E−04 | 5.06E−03 | atonal bHLH transcription factor 1 |
| 926 | FOXD2 | chr1: 47901688-47906363 | 10.10 | 5.95 | −0.76 | −1.25 | 5.00E−05 | 7.97E−04 | forkhead box D2 |
| 927 | ID3 | chr1: 23884420-23886285 | 105.85 | 62.35 | −0.76 | −1.27 | 5.00E−05 | 7.97E−04 | inhibitor of DNA binding 3, dominant negative helix-loop-helix protein |
| 928 | SLC35G1 | chr10: 95653729-95662491 | 10.01 | 5.90 | −0.76 | −1.04 | 2.00E−04 | 2.80E−03 | solute carrier family 35, member G1 |
| 929 | HPGDS | chr4: 95219706-95264027 | 5.71 | 3.35 | −0.77 | −0.89 | 3.65E−03 | 3.14E−02 | hematopoietic prostaglandin D synthase |
| 930 | NOTCH1 | chr9: 139388895-139440238 | 13.34 | 7.78 | −0.78 | −1.49 | 5.00E−05 | 7.97E−04 | notch 1 |
| 931 | CPT1A | chr11: 68522087-68609399 | 93.66 | 54.51 | −0.78 | −1.31 | 5.00E−05 | 7.97E−04 | carnitine palmitoyltransferase 1A (liver) |
| 932 | HR | chr8: 21971931-21988565 | 19.15 | 11.13 | −0.78 | −1.46 | 5.00E−05 | 7.97E−04 | hair growth associated |
| 933 | KRT12 | chr17: 39017429-39023462 | 4.53 | 2.63 | −0.78 | −0.88 | 6.50E−04 | 7.69E−03 | keratin 12, type I |
| 934 | KITLG | chr12: 88886569-88974250 | 13.52 | 7.86 | −0.78 | −1.38 | 5.00E−05 | 7.97E−04 | KIT ligand |
| 935 | SLC39A5 | chr12: 56623819-56652143 | 107.72 | 62.56 | −0.78 | −0.93 | 4.00E−03 | 3.39E−02 | solute carrier family 39 (zinc transporter), member 5 |
| 936 | E2F2 | chr1: 23832919-23857712 | 7.97 | 4.62 | −0.79 | −1.26 | 5.00E−05 | 7.97E−04 | E2F transcription factor 2 |
| 937 | TBC1D9 | chr4: 141541935-141677471 | 6.23 | 3.60 | −0.79 | −1.24 | 5.00E−05 | 7.97E−04 | TBC1 domain family, member 9 (with GRAM domain) |
| 938 | CDX2 | chr13: 28536204-28543505 | 154.63 | 89.40 | −0.79 | −1.31 | 5.00E−05 | 7.97E−04 | caudal type homeobox 2 |
| 939 | ACSF2 | chr17: 48503518-48552206 | 51.16 | 29.40 | −0.80 | −0.91 | 4.25E−03 | 3.56E−02 | acyl-CoA synthetase family member 2 |
| 940 | ZFP3 | chr17: 4981753-4999669 | 5.11 | 2.94 | −0.80 | −1.20 | 5.00E−05 | 7.97E−04 | ZFP3 zinc finger protein |
| 941 | TSPAN7 | chrX: 38420730-38548172 | 64.64 | 37.09 | −0.80 | −1.37 | 5.00E−05 | 7.97E−04 | tetraspanin 7 |
| 942 | KCNJ2 | chr17: 68165675-68176183 | 3.48 | 2.00 | −0.80 | −1.09 | 1.00E−04 | 1.51E−03 | potassium channel, inwardly rectifying subfamily J, member 2 |
| 943 | PPP1R14C | chr6: 150464187-150571528 | 19.38 | 11.10 | −0.80 | −1.28 | 5.00E−05 | 7.97E−04 | protein phosphatase 1, regulatory (inhibitor) subunit 14C |
| 944 | WDR78 | chr1: 67278571-67390570 | 5.47 | 3.13 | −0.80 | −1.17 | 2.50E−04 | 3.38E−03 | WD repeat domain 78 |
| 945 | SATB2 | chr2: 200134222-200337481 | 40.25 | 23.04 | −0.81 | −1.14 | 5.00E−05 | 7.97E−04 | SATB homeobox 2 |
| 946 | AIFM3 | chr22: 21319417-21335649 | 41.52 | 23.75 | −0.81 | −1.17 | 5.00E−05 | 7.97E−04 | apoptosis-inducing factor, mitochondrion-associated, 3 |
| 947 | SCAMP5 | chr15: 75287875-75313836 | 7.90 | 4.51 | −0.81 | −1.07 | 2.50E−04 | 3.38E−03 | secretory carrier membrane protein 5 |
| 948 | ZNF606 | chr19: 58488440-58518574 | 2.16 | 1.23 | −0.81 | −0.88 | 3.00E−03 | 2.69E−02 | zinc finger protein 606 |
| 949 | C10orf99 | chr10: 85933553-85945050 | 314.00 | 178.88 | −0.81 | −1.13 | 5.00E−05 | 7.97E−04 | chromosome 10 open reading frame 99 |
| 950 | RNLS | chr10: 90033620-90343082 | 4.75 | 2.71 | −0.81 | −1.01 | 1.40E−03 | 1.45E−02 | renalase, FAD-dependent amine oxidase |
| 951 | HRCT1 | chr9: 35906188-35907138 | 58.04 | 32.98 | −0.82 | −1.25 | 5.00E−05 | 7.97E−04 | histidine rich carboxyl terminus 1 |
| 952 | SYNM | chr15: 99645285-99675800 | 1.62 | 0.91 | −0.83 | −0.98 | 3.00E−04 | 3.97E−03 | synemin, intermediate filament protein |
| 953 | USP32P2 | chr17: 18414575-18424566 | 0.97 | 0.55 | −0.83 | −0.77 | 3.80E−03 | 3.25E−02 | ubiquitin specific peptidase 32 pseudogene 2 |
| 954 | SYNPO | chr5: 149980641-150038792 | 30.81 | 17.30 | −0.83 | −1.54 | 5.00E−05 | 7.97E−04 | synaptopodin |
| 955 | CYCS | chr7: 25158269-25164980 | 114.56 | 64.22 | −0.84 | −1.30 | 5.00E−05 | 7.97E−04 | cytochrome c, somatic |
| 956 | HOXD4 | chr2: 177016112-177017949 | 5.77 | 3.23 | −0.84 | −0.86 | 1.50E−03 | 1.53E−02 | homeobox D4 |
| 957 | PAQR5 | chr15: 69591293-69699976 | 18.45 | 10.33 | −0.84 | −1.48 | 5.00E−05 | 7.97E−04 | progestin and adipoQ receptor family member V |

TABLE 6-continued

The list of 1058 genes exclusively DE between CR and SSA/P samples.

| | gene | locus | mean_CR | mean SSA/P | log₂FC | test_stat | p_value | p_adj_value | Description |
|---|---|---|---|---|---|---|---|---|---|
| 958 | SLC4A4 | chr4: 72053002-72437804 | 43.20 | 24.14 | −0.84 | −1.33 | 5.00E−05 | 7.97E−04 | solute carrier family 4 (sodium bicarbonate cotransporter), member 4 |
| 959 | LRRC26 | chr9: 140033608-140064491 | 50.87 | 28.28 | −0.85 | −1.12 | 8.00E−04 | 9.10E−03 | leucine rich repeat containing 26 |
| 960 | GDPD1 | chr17: 57297827-57353330 | 2.58 | 1.43 | −0.85 | −0.82 | 5.75E−03 | 4.55E−02 | glycerophosphodiester phosphodiesterase domain containing 1 |
| 961 | DHRS11 | chr17: 34948225-349572339 | 158.57 | 87.93 | −0.85 | −1.39 | 5.00E−05 | 7.97E−04 | dehydrogenase/reductase (SDR family) member 11 |
| 962 | LGI4 | chr19: 35615416-35626178 | 6.00 | 3.32 | −0.85 | −0.94 | 6.50E−04 | 7.69E−03 | leucine-rich repeat LGI family, member 4 |
| 963 | INPP5J | chr22: 31518908-31530683 | 18.03 | 9.99 | −0.85 | −1.37 | 5.00E−05 | 7.97E−04 | inositol polyphosphate-5-phosphatase J |
| 964 | AMOT | chrX: 112018104-112084043 | 4.18 | 2.32 | −0.85 | −1.25 | 5.00E−05 | 7.97E−04 | angiomotin |
| 965 | BCL2L15 | chr1: 114356432-114447741 | 40.09 | 22.19 | −0.85 | −1.29 | 5.00E−05 | 7.97E−04 | BCL2-like 15 |
| 966 | PDE4C | chr19: 18318770-18359010 | 2.98 | 1.65 | −0.86 | −1.06 | 2.00E−04 | 2.80E−03 | phosphodiesterase 4C, cAMP-specific |
| 967 | CYP27A1 | chr2: 219646471-219680016 | 27.19 | 14.98 | −0.86 | −1.39 | 5.00E−05 | 7.97E−04 | cytochrome P450, family 27, subfamily A, polypeptide 1 |
| 968 | SLC19A3 | chr2: 228549925-228582745 | 4.07 | 2.23 | −0.87 | −1.05 | 2.50E−04 | 3.38E−03 | solute carrier family 19 (thiamine transporter), member 3 |
| 969 | SEMA5A | chr5: 9035137-9546233 | 6.75 | 3.70 | −0.87 | −1.45 | 5.00E−05 | 7.97E−04 | sema domain, seven thrombospondin repeats (type 1 and type 1-like), transmembrane domain (TM) and short cytoplasmic domain, (semaphorin) 5A |
| 970 | SH3BP1 | chr22: 38035683-38054384 | 36.87 | 20.12 | −0.87 | −1.41 | 5.00E−05 | 7.97E−04 | SH3-domain binding protein 1 |
| 971 | TTPA | chr8: 63972047-63998612 | 3.44 | 1.88 | −0.87 | −0.98 | 1.00E−03 | 1.10E−02 | tocopherol (alpha) transfer protein |
| 972 | GLIS3 | chr9: 3824127-4300035 | 1.43 | 0.78 | −0.88 | −0.95 | 5.00E−04 | 6.13E−03 | GLIS family zinc finger 3 |
| 973 | RPS6KA6 | chrX: 83313353-83442943 | 3.55 | 1.93 | −0.88 | −1.43 | 5.00E−05 | 7.97E−04 | ribosomal protein S6 kinase, 90 kDa, polypeptide 6 |
| 974 | ZNF518B | chr4: 10441503-10459032 | 2.13 | 1.15 | −0.88 | −1.18 | 5.00E−05 | 7.97E−04 | zinc finger protein 518B |
| 975 | EFNA5 | chr5: 106712589-107006596 | 2.23 | 1.21 | −0.88 | −1.06 | 5.00E−05 | 7.97E−04 | ephrin-A5 |
| 976 | MIPOL1 | chr14: 37667117-38020464 | 3.04 | 1.64 | −0.89 | −1.30 | 5.00E−05 | 7.97E−04 | mirror-image polydactyly 1 |
| 977 | CNN3 | chr1: 95362504-95392779 | 68.19 | 36.78 | −0.89 | −1.62 | 5.00E−05 | 7.97E−04 | calponin 3, acidic |
| 978 | PHLPP2 | chr16: 71678828-71758604 | 21.57 | 11.62 | −0.89 | −1.58 | 5.00E−05 | 7.97E−04 | PH domain and leucine rich repeat protein phosphatase 2 |
| 979 | PPP2R3A | chr3: 135684514-135866752 | 5.34 | 2.88 | −0.89 | −1.27 | 1.00E−04 | 1.51E−03 | protein phosphatase 2, regulatory subunit B'', alpha |
| 980 | NCKAP5 | chr2: 133429371-134326031 | 1.00 | 0.54 | −0.90 | −0.85 | 3.40E−03 | 2.97E−02 | NCK-associated protein 5 |
| 981 | SH2D7 | chr15: 78384926-78396393 | 3.31 | 1.78 | −0.90 | −0.89 | 3.20E−03 | 2.82E−02 | SH2 domain containing 7 |
| 982 | RNF157 | chr17: 74132414-74236390 | 7.83 | 4.19 | −0.90 | −1.30 | 5.00E−05 | 7.97E−04 | ring finger protein 157 |
| 983 | CAMK1D | chr10: 12391582-12871733 | 7.03 | 3.76 | −0.90 | −1.09 | 4.00E−04 | 5.06E−03 | calcium/calmodulin-dependent protein kinase ID |
| 984 | TMEM171 | chr5: 72416387-72427644 | 87.05 | 46.45 | −0.91 | −1.58 | 5.00E−05 | 7.97E−04 | transmembrane protein 171 |
| 985 | GPM6B | chrX: 13789061-13956831 | 2.91 | 1.55 | −0.91 | −0.78 | 6.20E−03 | 4.85E−02 | glycoprotein M6B |
| 986 | SLC51B | chr15: 65337707-65360388 | 108.87 | 57.67 | −0.92 | −1.45 | 5.00E−05 | 7.97E−04 | solute carrier family 51, beta subunit |
| 987 | PLAGL1 | chr6: 144261436-144385736 | 19.36 | 10.24 | −0.92 | −1.52 | 5.00E−05 | 7.97E−04 | pleiomorphic adenoma gene-like 1 |
| 988 | ACVR1C | chr2: 158383278-158485399 | 2.12 | 1.12 | −0.92 | −1.29 | 5.00E−05 | 7.97E−04 | activin A receptor, type IC |
| 989 | SEMA6D | chr15: 47476402-48066420 | 12.04 | 6.34 | −0.93 | −1.52 | 5.00E−05 | 7.97E−04 | sema domain, transmembrane domain (TM), and cytoplasmic domain, (semaphorin) 6D |
| 990 | ANO7 | chr2: 242127923-242164791 | 24.00 | 12.62 | −0.93 | −1.39 | 5.00E−05 | 7.97E−04 | anoctamin 7 |
| 991 | GAREML | chr2: 26395959-26412532 | 2.92 | 1.53 | −0.93 | −1.02 | 8.00E−04 | 9.10E−03 | GRB2 associated, regulator of MAPK1-like |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 992 | PROM2 | chr2: 95940200-95957055 | 19.61 | 10.29 | −0.93 | −1.63 | 5.00E−05 | 7.97E−04 | prominin 2 |
| 993 | TMEM38B | chr9: 108456805-108538892 | 9.34 | 4.90 | −0.93 | −1.45 | 5.00E−05 | 7.97E−04 | transmembrane protein 38B |
| 994 | RMDN2 | chr2: 38152461-38294285 | 13.93 | 7.29 | −0.93 | −1.44 | 5.00E−05 | 7.97E−04 | regulator of microtubule dynamics 2 |
| 995 | SLC22A5 | chr5: 131630144-131731306 | 35.37 | 18.48 | −0.94 | −1.53 | 5.00E−05 | 7.97E−04 | solute carrier family 22 (organic cation/carnitine transporter), member 5 |
| 996 | HDC | chr15: 50534145-50558162 | 3.33 | 1.73 | −0.95 | −0.97 | 2.00E−04 | 2.80E−03 | histidine decarboxylase |
| 997 | SOWAHA | chr5: 132149015-132152489 | 17.81 | 9.13 | −0.96 | −1.63 | 5.00E−05 | 7.97E−04 | sosondowah ankyrin repeat domain family member A |
| 998 | PPFIA3 | chr19: 49622645-49654287 | 6.16 | 3.16 | −0.97 | −1.40 | 5.00E−05 | 7.97E−04 | protein tyrosine phosphatase, receptor type, f polypeptide (PTPRF), interacting protein (liprin), alpha 3 |
| 999 | CA2 | chr8: 86376130-86393721 | 1265.25 | 647.13 | −0.97 | −1.11 | 5.00E−05 | 7.97E−04 | carbonic anhydrase II |
| 1000 | BEST2 | chr19: 12863406-12869271 | 40.64 | 20.75 | −0.97 | −1.20 | 2.50E−04 | 3.38E−03 | bestrophin 2 |
| 1001 | ADTRP | chr6: 11713887-11779280 | 94.06 | 48.00 | −0.97 | −1.65 | 5.00E−05 | 7.97E−04 | androgen-dependent TFPI-regulating protein |
| 1002 | HSD11B2 | chr16: 67465035-67471454 | 445.70 | 226.79 | −0.97 | −1.03 | 9.00E−04 | 1.01E−02 | hydroxysteroid (11-beta) dehydrogenase 2 |
| 1003 | MPP7 | chr10: 28339922-28571067 | 12.28 | 6.22 | −0.98 | −1.72 | 5.00E−05 | 7.97E−04 | membrane protein, palmitoylated 7 (MAGUK p55 subfamily member 7) |
| 1004 | ADAMTSL1 | chr9: 18474078-18910947 | 1.83 | 0.93 | −0.98 | −1.19 | 5.00E−05 | 7.97E−04 | ADAMTS-like 1 |
| 1005 | ZNF575 | chr19: 44037339-44040284 | 12.36 | 6.25 | −0.98 | −1.24 | 5.00E−05 | 7.97E−04 | zinc finger protein 575 |
| 1006 | MPV17L | chr16: 15489610-15503543 | 4.08 | 2.05 | −0.99 | −1.06 | 3.00E−04 | 3.97E−03 | MPV17 mitochondrial membrane protein-like |
| 1007 | CEACAM7 | chr19: 42177234-42192206 | 1097.39 | 550.57 | −1.00 | −1.01 | 8.50E−04 | 9.59E−03 | carcinoembryonic antigen-related cell adhesion molecule 7 |
| 1008 | METTL7A | chr12: 51318533-51326300 | 67.39 | 33.59 | −1.00 | −1.79 | 5.00E−05 | 7.97E−04 | methyltransferase like 7A |
| 1009 | MPZ | chr1: 161274524-161279762 | 2.83 | 1.41 | −1.01 | −0.90 | 1.70E−03 | 1.71E−02 | myelin protein zero |
| 1010 | CNTN4 | chr3: 2140549-3099645 | 3.10 | 1.53 | −1.02 | −1.26 | 5.00E−05 | 7.97E−04 | contactin 4 |
| 1011 | CHRNA1 | chr2: 175612322-175629200 | 1.70 | 0.84 | −1.02 | −0.84 | 4.55E−03 | 3.75E−02 | cholinergic receptor, nicotinic, alpha 1 (muscle) |
| 1012 | PKIB | chr6: 122793061-123047518 | 120.04 | 59.26 | −1.02 | −1.80 | 5.00E−05 | 7.97E−04 | protein kinase (cAMP-dependent, catalytic) inhibitor beta |
| 1013 | NLRP2 | chr19: 55476651-55512510 | 5.55 | 2.74 | −1.02 | −1.26 | 5.00E−05 | 7.97E−04 | NLR family, pyrin domain containing 2 |
| 1014 | AZIN2 | chr1: 33546713-33585995 | 5.22 | 2.57 | −1.02 | −1.09 | 2.50E−04 | 3.38E−03 | antizyme inhibitor 2 |
| 1015 | PBLD | chr10: 70042416-70167051 | 46.52 | 22.90 | −1.02 | −0.94 | 1.65E−03 | 1.66E−02 | phenazine biosynthesis-like protein domain containing |
| 1016 | SCN7A | chr2: 167260082-167343481 | 1.12 | 0.55 | −1.03 | −1.13 | 2.00E−04 | 2.80E−03 | sodium channel, voltage gated, type VII alpha subunit |
| 1017 | ARHGAP44 | chr17: 12569206-12921381 | 21.26 | 10.42 | −1.03 | −1.11 | 1.15E−03 | 1.24E−02 | Rho GTPase activating protein 44 |
| 1018 | NPY1R | chr4: 164245116-164253947 | 6.45 | 3.15 | −1.03 | −1.36 | 5.00E−05 | 7.97E−04 | neuropeptide Y receptor Y1 |
| 1019 | SLC2A5 | chr1: 9097004-9129887 | 5.15 | 2.51 | −1.04 | −1.14 | 1.00E−04 | 1.51E−03 | solute carrier family 2 (facilitated glucose/fructose transporter), member 5 |
| 1020 | APOBEC3B | chr22: 39353526-39394225 | 15.42 | 7.46 | −1.05 | −1.18 | 1.00E−04 | 1.51E−03 | apolipoprotein B mRNA editing enzyme, catalytic polypeptide-like 3B |
| 1021 | TINCR | chr19: 5558177-5568005 | 2.98 | 1.44 | −1.05 | −1.14 | 2.00E−04 | 2.80E−03 | tissue differentiation-inducing non-protein coding RNA |
| 1022 | PCDH20 | chr13: 61983818-61989655 | 3.32 | 1.58 | −1.07 | −1.24 | 5.00E−05 | 7.97E−04 | protocadherin 20 |
| 1023 | KLK3 | chr19: 51358170-51364020 | 2.92 | 1.39 | −1.07 | −0.96 | 2.20E−03 | 2.11E−02 | kallikrein-related peptidase 3 |
| 1024 | PPARGC1B | chr5: 149109814-149234585 | 7.44 | 3.53 | −1.08 | −1.85 | 5.00E−05 | 7.97E−04 | peroxisome proliferator-activated receptor gamma, coactivator 1 beta |
| 1025 | TMEM56 | chr1: 95558072-95712781 | 20.12 | 9.49 | −1.08 | −1.68 | 5.00E−05 | 7.97E−04 | transmembrane protein 56 |

TABLE 6-continued

The list of 1058 genes exclusively DE between CR and SSA/P samples.

| | gene | locus | mean_CR | mean SSA/P | log$_2$FC | test_stat | p_value | p$_{adj}$_value | Description |
|---|---|---|---|---|---|---|---|---|---|
| 1026 | LOC102723344 | chr15: 63682428-63729735 | 4.67 | 2.20 | −1.08 | −1.02 | 5.00E−04 | 6.13E−03 | uncharacterized LOC102723344 |
| 1027 | FAM189A1 | chr15: 29412454-29862927 | 3.64 | 1.70 | −1.10 | −1.10 | 1.30E−03 | 1.37E−02 | family with sequence similarity 189, member A1 |
| 1028 | CWH43 | chr4: 48988264-49064095 | 20.77 | 9.72 | −1.10 | −1.63 | 5.00E−05 | 7.97E−04 | cell wall biogenesis 43 C-terminal homolog |
| 1029 | PDE6A | chr5: 149237518-149324356 | 2.51 | 1.17 | −1.10 | −1.34 | 5.00E−05 | 7.97E−04 | phosphodiesterase 6A, cGMP-specific, rod, alpha |
| 1030 | PTGDR2 | chr11: 60609428-60623444 | 8.13 | 3.77 | −1.11 | −1.15 | 3.50E−04 | 4.55E−03 | prostaglandin D2 receptor 2 |
| 1031 | MESP2 | chr15: 90319588-90321982 | 1.76 | 0.80 | −1.14 | −0.88 | 2.50E−03 | 2.33E−02 | mesoderm posterior bHLH transcription factor 2 |
| 1032 | CNTN3 | chr3: 74311721-74570343 | 2.70 | 1.22 | −1.15 | −1.43 | 5.00E−05 | 7.97E−04 | contactin 3 (plasmacytoma associated) |
| 1033 | CHP2 | chr16: 23765947-23770272 | 211.39 | 94.76 | −1.16 | −1.71 | 5.00E−05 | 7.97E−04 | calcineurin-like EF-hand protein 2 |
| 1034 | AQP8 | chr16: 25228284-25240253 | 1108.72 | 496.18 | −1.16 | −0.70 | 2.05E−03 | 1.98E−02 | aquaporin 8 |
| 1035 | NEURL1B | chr5: 172068275-172118533 | 32.47 | 14.49 | −1.16 | −2.03 | 5.00E−05 | 7.97E−04 | neuralized E3 ubiquitin protein ligase 1B |
| 1036 | HOXD3 | chr2: 177028804-177037826 | 1.23 | 0.55 | −1.16 | −0.89 | 3.20E−03 | 2.82E−02 | homeobox D3 |
| 1037 | DRAIC | chr15: 69854058-69863779 | 2.07 | 0.92 | −1.17 | −1.04 | 2.50E−04 | 3.38E−03 | downregulated RNA in cancer, inhibitor of cell invasion and migration |
| 1038 | ASPG | chr14: 104552022-104579046 | 7.31 | 3.23 | −1.18 | −1.00 | 1.95E−03 | 1.91E−02 | asparaginase |
| 1039 | VSTM1 | chr19: 54544079-54567207 | 1.61 | 0.71 | −1.18 | −0.74 | 2.75E−03 | 2.52E−02 | V-set and transmembrane domain containing 1 |
| 1040 | SYP | chrX: 49044264-49058913 | 4.51 | 1.99 | −1.18 | −1.24 | 5.00E−05 | 7.97E−04 | synaptophysin |
| 1041 | CLCA1 | chr1: 86934525-86965974 | 905.45 | 397.19 | −1.19 | −0.94 | 4.00E−04 | 5.06E−03 | chloride channel accessory 1 |
| 1042 | KCNG1 | chr20: 49620192-49639675 | 3.48 | 1.48 | −1.23 | −1.06 | 1.30E−03 | 1.37E−02 | potassium channel, voltage gated modifier subfamily G, member 1 |
| 1043 | SLC26A2 | chr5: 149340299-149396963 | 264.43 | 111.38 | −1.25 | −1.23 | 5.00E−05 | 7.97E−04 | solute carrier family 26 (anion exchanger), member 2 |
| 1044 | EPB41L3 | chr18: 5392379-5628990 | 22.76 | 9.32 | −1.29 | −2.15 | 5.00E−05 | 7.97E−04 | erythrocyte membrane protein band 4.1-like 3 |
| 1045 | MSI1 | chr12: 120779132-120806983 | 1.27 | 0.52 | −1.29 | −1.04 | 1.15E−03 | 1.24E−02 | musashi RNA-binding protein 1 |
| 1046 | SOX10 | chr22: 38368318-38380539 | 1.56 | 0.63 | −1.30 | −1.13 | 1.25E−03 | 1.33E−02 | SRY (sex determining region Y)-box 10 |
| 1047 | SUGCT | chr7: 40174574-40900366 | 7.67 | 3.05 | −1.33 | −1.47 | 5.00E−05 | 7.97E−04 | succinyl-CoA: glutarate-CoA transferase |
| 1048 | GFRA3 | chr5: 137588068-137610253 | 1.51 | 0.59 | −1.37 | −1.06 | 4.00E−04 | 5.06E−03 | GDNF family receptor alpha 3 |
| 1049 | TMEM236 | chr10: 17851341-18200091 | 0.95 | 0.36 | −1.41 | −1.18 | 1.00E−03 | 1.51E−02 | transmembrane protein 236 |
| 1050 | UGT2A3 | chr4_ctg9_hap1: 506427-529760 | 46.59 | 17.22 | −1.44 | −2.28 | 5.00E−05 | 7.97E−04 | UDP glucuronosyltransferase 2 family, polypeptide A3 |
| 1051 | OTUD7A | chr15: 31775328-31947542 | 1.37 | 0.47 | −1.54 | −1.30 | 5.00E−05 | 7.97E−04 | OTU deubiquitinase 7A |
| 1052 | IL13RA2 | chrX: 114238537-114252207 | 1.20 | 0.40 | −1.59 | −1.00 | 3.00E−03 | 2.69E−02 | interleukin 13 receptor, alpha 2 |
| 1053 | HAVCR1 | chr5: 156456530-156485970 | 2.55 | 0.84 | −1.59 | −1.11 | 6.10E−03 | 4.79E−02 | hepatitis A virus cellular receptor 1 |
| 1054 | HTR4 | chr5: 147830594-148034090 | 4.13 | 1.29 | −1.68 | −1.43 | 1.00E−03 | 1.10E−02 | 5-hydroxytryptamine (serotonin) receptor 4, G protein-coupled |
| 1055 | GPR143 | chrX: 9693452-9734005 | 1.59 | 0.43 | −1.87 | −1.34 | 5.00E−05 | 7.97E−04 | G protein-coupled receptor 143 |
| 1056 | TRIM9 | chr14: 51441980-51562422 | 1.49 | 0.40 | −1.91 | −1.59 | 1.50E−04 | 2.18E−03 | tripartite motif containing 9 |
| 1057 | MIR6506 | chr16: 15688225-15737023 | 22.14 | 0.00 | −Inf | NA | 1.70E−03 | 1.71E−02 | microRNA 6506 |
| 1058 | MIR6739 | chr1: 201617449-201853422 | 107.57 | 0.00 | −Inf | NA | 3.50E−04 | 4.55E−03 | microRNA 6739 |

TABLE 7

Differentially expressed genes in three comparisons. In Cuffdiff2, samples are normalized for differences in library sizes relative to each other and therefore the normalized expression is affected by which samples are included in the comparison. For this reason mean expression of a gene under one phenotype can appear slightly different in different comparisons.

| | | | HP versus SSA/P | | | | |
|---|---|---|---|---|---|---|---|
| | gene | locus | mean_HP | mean_SSA/P | log$_2$FC | p_value | p$_{adj}$ |
| 1 | ABTB2 | chr11:34172533-34379555 | 8.75 | 5.20 | -0.75 | 5.00E-05 | 2.53E-03 |
| 2 | ADRA2A | chr10:112836789-112840662 | 6.22 | 15.15 | 1.28 | 5.00E-05 | 2.53E-03 |
| 3 | ALDH1A1 | chr9:75515577-75568233 | 25.81 | 52.32 | 1.02 | 5.00E-05 | 2.53E-03 |
| 4 | ALDH1L1 | chr3:125822403-125929011 | 11.68 | 44.11 | 1.92 | 5.00E-05 | 2.53E-03 |
| 5 | ALDOB | chr9:104182841-104198062 | 40.96 | 111.78 | 1.45 | 2.00E-04 | 8.55E-03 |
| 6 | ALDOC | chr17:26900132-26903951 | 28.45 | 17.11 | -0.73 | 1.50E-04 | 6.74E-03 |
| 7 | APOBEC1 | chr12:7801995-7818502 | 4.06 | 24.17 | 2.57 | 5.00E-05 | 2.53E-03 |
| 8 | ARSJ | chr4:114821439-114900878 | 3.88 | 1.74 | -1.15 | 5.00E-05 | 2.53E-03 |
| 9 | ATF3 | chr1:212738675-212794119 | 41.76 | 13.43 | -1.64 | 5.00E-05 | 2.53E-03 |
| 10 | B3GNT7 | chr2:232260334-232265875 | 114.58 | 15.38 | -2.90 | 5.00E-05 | 2.53E-03 |
| 11 | B4GALNT2 | chr17:47209821-47247351 | 8.12 | 22.20 | 1.45 | 5.00E-05 | 2.53E-03 |
| 12 | C12orf75 | chr12:105724413-105765296 | 87.70 | 56.94 | -0.62 | 1.00E-04 | 4.83E-03 |
| 13 | B3GALT5-AS1 | chr21:40969074-40984749 | 15.21 | 2.81 | -2.44 | 5.00E-05 | 2.53E-03 |
| 14 | C4BPB | chr1:207262211-207273337 | 7.74 | 24.18 | 1.64 | 5.00E-05 | 2.53E-03 |
| 15 | CCL13 | chr17:32683470-32685629 | 7.16 | 21.01 | 1.55 | 5.00E-05 | 2.53E-03 |
| 16 | CD55 | chr1:207494816-207534311 | 93.25 | 188.00 | 1.01 | 1.00E-04 | 4.83E-03 |
| 17 | CDA | chr1:20915443-20945400 | 87.05 | 55.46 | -0.65 | 1.00E-04 | 4.83E-03 |
| 18 | CHGB | chr20:5891973-5906005 | 9.53 | 2.88 | -1.73 | 5.00E-05 | 2.53E-03 |
| 19 | CHST5 | chr16:75562427-75569068 | 67.08 | 36.24 | -0.89 | 5.00E-05 | 2.53E-03 |
| 20 | CLC | chr19:40221892-40228669 | 3.48 | 11.71 | 1.75 | 5.00E-05 | 2.53E-03 |
| 21 | CLDN8 | chr21:31586323-31588469 | 35.70 | 3.80 | -3.23 | 5.00E-05 | 2.53E-03 |
| 22 | CNNM2 | chr10:104678074-104838344 | 7.99 | 4.63 | -0.79 | 6.00E-04 | 1.99E-02 |
| 23 | COL18A1 | chr21:46825096-46933634 | 7.26 | 14.11 | 0.96 | 5.00E-05 | 2.53E-03 |
| 24 | COL5A3 | chr19:10070236-10121147 | 1.50 | 2.51 | 0.74 | 6.50E-04 | 2.11E-02 |
| 25 | CPB1 | chr3:148545587-148577972 | 25.47 | 1.31 | -4.28 | 5.00E-05 | 2.53E-03 |
| 26 | CPNE8 | chr12:39046001-39299420 | 9.30 | 4.27 | -1.12 | 5.00E-05 | 2.53E-03 |
| 27 | CTGF | chr6:132269316-132272518 | 30.53 | 17.58 | -0.80 | 5.00E-05 | 2.53E-03 |
| 28 | CYP2C18 | chr10:96443250-96495947 | 5.42 | 9.35 | 0.79 | 4.00E-04 | 1.49E-02 |
| 29 | CYP2C9 | chr10:96698414-96749148 | 2.20 | 5.77 | 1.39 | 5.00E-05 | 2.53E-03 |
| 30 | CYP2W1 | chr7:1022834-1029276 | 3.99 | 1.22 | -1.71 | 5.00E-05 | 2.53E-03 |
| 31 | CYP3A5 | chr7:99245811-99277649 | 86.67 | 134.53 | 0.63 | 1.70E-03 | 4.44E-02 |
| 32 | EFNA3 | chr1:155051347-155060014 | 13.94 | 5.42 | -1.36 | 5.00E-05 | 2.53E-03 |
| 33 | EGR1 | chr5:137801180-137805004 | 38.90 | 12.69 | -1.62 | 5.00E-05 | 2.53E-03 |
| 34 | ETNK1 | chr12:22778075-22843608 | 21.99 | 48.21 | 1.13 | 5.00E-05 | 2.53E-03 |
| 35 | FAM213A | chr10:82167584-82192753 | 31.10 | 47.73 | 0.62 | 1.10E-03 | 3.22E-02 |
| 36 | FAM3D | chr3:58619669-58652561 | 559.43 | 349.35 | -0.68 | 6.50E-04 | 2.11E-02 |
| 37 | FER1L4 | chr20:34146506-34195484 | 3.98 | 7.26 | 0.87 | 5.00E-05 | 2.53E-03 |
| 38 | FFAR4 | chr10:95326421-95349829 | 34.44 | 14.86 | -1.21 | 5.00E-05 | 2.53E-03 |
| 39 | FOS | chr14:75745480-75748937 | 188.02 | 46.34 | -2.02 | 5.00E-05 | 2.53E-03 |
| 40 | FOSB | chr19:45971252-45978437 | 9.39 | 1.96 | -2.26 | 5.00E-05 | 2.53E-03 |
| 41 | FOXA2 | chr20:22561641-22566101 | 13.89 | 7.52 | -0.88 | 5.00E-05 | 2.53E-03 |
| 42 | FOXQ1 | chr6:1312674-1314993 | 2.47 | 12.74 | 2.37 | 5.00E-05 | 2.53E-03 |
| 43 | FREM1 | chr9:14734663-14910993 | 0.31 | 2.68 | 3.14 | 5.00E-05 | 2.53E-03 |
| 44 | FRMD3 | chr9:85857904-86153348 | 10.47 | 5.49 | -0.93 | 5.00E-05 | 2.53E-03 |
| 45 | FSCN1 | chr7:5632435-5646287 | 5.43 | 20.43 | 1.91 | 5.00E-05 | 2.53E-03 |
| 46 | GBA3 | chr4:22694536-22821195 | 3.97 | 7.33 | 0.88 | 1.25E-03 | 3.53E-02 |
| 47 | GBP5 | chr1:89724633-89738544 | 1.41 | 3.01 | 1.09 | 5.00E-05 | 2.53E-03 |
| 48 | GDF15 | chr19:18496967-18499986 | 28.32 | 14.08 | -1.01 | 5.00E-05 | 2.53E-03 |
| 49 | GPC3 | chrX:132669775-133119673 | 0.34 | 2.89 | 3.08 | 5.00E-05 | 2.53E-03 |
| 50 | ADGRF1 | chr6:46967812-47010082 | 2.99 | 7.66 | 1.35 | 5.00E-05 | 2.53E-03 |
| 51 | H19 | chr11:2016405-2019065 | 0.95 | 2.94 | 1.63 | 5.00E-05 | 2.53E-03 |
| 52 | HOXB13 | chr17:46802126-46806111 | 71.01 | 11.46 | -2.63 | 5.00E-05 | 2.53E-03 |
| 53 | HSD3B2 | chr1:119957553-119965662 | 0.82 | 4.19 | 2.36 | 5.00E-04 | 1.75E-02 |
| 54 | HSPA2 | chr14:65007185-65009954 | 11.23 | 5.77 | -0.96 | 5.00E-05 | 2.53E-03 |
| 55 | IGFBP2 | chr2:217498126-217529158 | 46.82 | 82.33 | 0.81 | 5.00E-05 | 2.53E-03 |
| 56 | IGFBP5 | chr2:217536827-217560272 | 5.58 | 8.61 | 0.62 | 4.00E-04 | 1.49E-02 |
| 57 | INSL5 | chr1:67263423-67266942 | 335.40 | 9.96 | -5.07 | 5.00E-05 | 2.53E-03 |
| 58 | JUN | chr1:59246462-59249785 | 62.51 | 38.23 | -0.71 | 5.00E-04 | 1.75E-02 |
| 59 | KLF8 | chrX:56258821-56314322 | 0.76 | 1.61 | 1.08 | 3.50E-04 | 1.32E-02 |
| 60 | L1TD1 | chr1:62660473-62678001 | 2.01 | 6.07 | 1.59 | 5.00E-05 | 2.53E-03 |
| 61 | LINC00261 | chr20:22541191-22559280 | 18.71 | 12.55 | -0.58 | 8.00E-04 | 2.53E-02 |
| 62 | LOC283177 | chr11:134306375-134375555 | 1.38 | 3.09 | 1.16 | 6.00E-04 | 1.99E-02 |
| 63 | LOC284454 | chr19:13945329-13947173 | 22.05 | 12.85 | -0.78 | 3.00E-04 | 1.18E-02 |
| 64 | LOC389602 | chr7:155755325-155759037 | 5.80 | 10.59 | 0.87 | 1.50E-04 | 6.74E-03 |
| 65 | MFAP5 | chr12:8798539-8815433 | 3.98 | 1.85 | -1.11 | 5.00E-05 | 2.53E-03 |
| 66 | MFSD4 | chr1:205538111-205572046 | 22.34 | 9.75 | -1.20 | 5.00E-05 | 2.53E-03 |
| 67 | MROH6 | chr8:144648362-144654928 | 7.36 | 11.87 | 0.69 | 3.50E-04 | 1.32E-02 |
| 68 | MS4A12 | chr11:60260250-60274901 | 328.68 | 160.33 | -1.04 | 5.00E-05 | 2.53E-03 |
| 69 | MUC12 | chr7:100612903-100662230 | 75.53 | 21.34 | -1.82 | 5.00E-05 | 2.53E-03 |
| 70 | MUC17 | chr7:100663363-100702140 | 22.05 | 71.19 | 1.69 | 5.00E-05 | 2.53E-03 |
| 71 | NOX1 | chrX:100098312-100129334 | 61.82 | 40.86 | -0.60 | 3.00E-04 | 1.18E-02 |

TABLE 7-continued

Differentially expressed genes in three comparisons. In Cuffdiff2, samples are normalized for differences in library sizes relative to each other and therefore the normalized expression is affected by which samples are included in the comparison. For this reason mean expression of a gene under one phenotype can appear slightly different in different comparisons.

| | gene | locus | | | | | |
|---|---|---|---|---|---|---|---|
| 72 | NPY6R | chr5:137136881-137146439 | 1.27 | 3.15 | 1.31 | 1.10E-03 | 3.22E-02 |
| 73 | NQO1 | chr16:69743303-69760571 | 76.50 | 144.60 | 0.92 | 5.00E-05 | 2.53E-03 |
| 74 | NR1H4 | chr12:100867550-100957645 | 2.59 | 6.41 | 1.31 | 2.50E-04 | 1.03E-02 |
| 75 | NR4A1 | chr12:52416615-52453291 | 56.79 | 8.93 | -2.67 | 5.00E-05 | 2.53E-03 |
| 76 | NR4A2 | chr2:157180943-157189287 | 10.30 | 2.09 | -2.30 | 5.00E-05 | 2.53E-03 |
| 77 | NT5DC3 | chr12:104166080-104234975 | 3.62 | 2.27 | -0.67 | 9.50E-04 | 2.87E-02 |
| 78 | PCSK1 | chr5:95726039-95768985 | 3.08 | 1.18 | -1.39 | 5.00E-05 | 2.53E-03 |
| 79 | PDE3A | chr12:20522178-20837041 | 7.57 | 3.95 | -0.94 | 5.00E-05 | 2.53E-03 |
| 80 | PDZK1IP1 | chr1:47649260-47655771 | 106.93 | 266.07 | 1.32 | 5.00E-05 | 2.53E-03 |
| 81 | PITX2 | chr4:111538579-111563279 | 1.46 | 12.53 | 3.10 | 5.00E-05 | 2.53E-03 |
| 82 | PLLP | chr16:57290008-57318584 | 57.05 | 33.66 | -0.76 | 5.00E-05 | 2.53E-03 |
| 83 | PP7080 | chr5:470624-473080 | 92.49 | 199.57 | 1.11 | 5.00E-05 | 2.53E-03 |
| 84 | PPP1R12B | chr1:202317829-202557697 | 15.60 | 10.54 | -0.57 | 1.05E-03 | 3.10E-02 |
| 85 | PPP1R15A | chr19:49375648-49379319 | 36.17 | 21.95 | -0.72 | 1.00E-04 | 4.83E-03 |
| 86 | PRAC1 | chr17:46799081-46799882 | 152.89 | 31.74 | -2.27 | 5.00E-05 | 2.53E-03 |
| 87 | PTGDS | chr9:139871955-139876194 | 8.40 | 16.79 | 1.00 | 2.00E-04 | 8.55E-03 |
| 88 | RBP4 | chr10:95351592-95360993 | 23.68 | 9.91 | -1.26 | 5.00E-05 | 2.53E-03 |
| 89 | RGS1 | chr1:192544856-192549159 | 14.62 | 7.62 | -0.94 | 5.00E-05 | 2.53E-03 |
| 90 | RHBDL2 | chr1:39351478-39407456 | 32.16 | 19.88 | -0.69 | 1.50E-04 | 6.74E-03 |
| 91 | SCG2 | chr2:224461657-224467217 | 10.83 | 2.68 | -2.01 | 5.00E-05 | 2.53E-03 |
| 92 | SDR16C5 | chr8:57212569-57233241 | 23.24 | 35.78 | 0.62 | 1.50E-03 | 4.05E-02 |
| 93 | SIDT1 | chr3:113251217-113348422 | 14.17 | 8.96 | -0.66 | 1.50E-04 | 6.74E-03 |
| 94 | SIK4 | chr21:44834397-44847002 | 16.20 | 3.98 | -2.03 | 5.00E-05 | 2.53E-03 |
| 95 | SLC14A2 | chr18:42792946-43263060 | 0.13 | 2.42 | 4.22 | 5.00E-05 | 2.53E-03 |
| 96 | SLC15A1 | chr13:99336054-99404929 | 16.00 | 7.95 | -1.01 | 5.00E-05 | 2.53E-03 |
| 97 | SLC37A2 | chr11:124933012-124960412 | 7.36 | 37.13 | 2.34 | 5.00E-05 | 2.53E-03 |
| 98 | SLC51A | chr3:195943382-195960301 | 13.44 | 28.16 | 1.07 | 1.35E-03 | 3.76E-02 |
| 99 | SLC9A3 | chr5:473333-524549 | 49.72 | 114.65 | 1.21 | 5.00E-05 | 2.53E-03 |
| 100 | SPINK5 | chr5:147443534-147516925 | 15.59 | 5.13 | -1.60 | 5.00E-05 | 2.53E-03 |
| 101 | SPON1 | chr11:13984183-14289679 | 43.37 | 20.70 | -1.07 | 5.00E-05 | 2.53E-03 |
| 102 | ST3GAL4 | chr11:126225539-126284536 | 162.38 | 66.72 | -1.28 | 5.00E-05 | 2.53E-03 |
| 103 | ST6GALNAC6 | chr9:130647599-130667627 | 276.43 | 116.79 | -1.24 | 5.00E-05 | 2.53E-03 |
| 104 | STOM | chr9:124101265-124132582 | 19.56 | 48.34 | 1.31 | 5.00E-05 | 2.53E-03 |
| 105 | SULT1C2 | chr2:108905094-108926371 | 11.22 | 30.35 | 1.44 | 5.00E-05 | 2.53E-03 |
| 106 | SULT2B1 | chr19:49055428-49102684 | 2.64 | 6.07 | 1.20 | 5.00E-05 | 2.53E-03 |
| 107 | TBX10 | chr11:67398773-67407031 | 18.20 | 8.82 | -1.05 | 5.00E-05 | 2.53E-03 |
| 108 | TFCP2L1 | chr2:121974163-122042778 | 28.31 | 15.57 | -0.86 | 5.00E-05 | 2.53E-03 |
| 109 | THRB | chr3:24158644-24541502 | 5.39 | 2.79 | -0.95 | 5.00E-05 | 2.53E-03 |
| 110 | TM4SF20 | chr2:228226873-228244022 | 5.69 | 33.22 | 2.54 | 5.00E-05 | 2.53E-03 |
| 111 | TMC5 | chr16:19422056-19510434 | 20.27 | 30.20 | 0.58 | 1.20E-03 | 3.40E-02 |
| 112 | TMEM200A | chr6:130687425-130764210 | 11.88 | 3.93 | -1.60 | 5.00E-05 | 2.53E-03 |
| 113 | TMEM231 | chr16:75572014-75590184 | 9.16 | 4.54 | -1.01 | 5.00E-05 | 2.53E-03 |
| 114 | TMIGD1 | chr17:28643365-28661065 | 71.95 | 38.40 | -0.91 | 5.00E-05 | 2.53E-03 |
| 115 | TNNC1 | chr3:52485106-52488057 | 10.03 | 1.09 | -3.20 | 5.00E-05 | 2.53E-03 |
| 116 | TPH1 | chr11:18042083-18062335 | 6.70 | 1.81 | -1.89 | 5.00E-05 | 2.53E-03 |
| 117 | TUSC3 | chr8:15397595-15624158 | 7.52 | 2.23 | -1.75 | 5.00E-05 | 2.53E-03 |
| 118 | UGT2B7 | chr4:69962192-69978705 | 2.31 | 5.90 | 1.35 | 5.00E-05 | 2.53E-03 |
| 119 | VNN1 | chr6:133001996-133035194 | 3.75 | 14.48 | 1.95 | 5.00E-05 | 2.53E-03 |
| 120 | VWA2 | chr10:115999012-116054259 | 1.17 | 2.78 | 1.25 | 5.00E-05 | 2.53E-03 |
| 121 | WFDC2 | chr20:44098393-44110172 | 249.52 | 62.76 | -1.99 | 5.00E-05 | 2.53E-03 |

| | | | CR versus SSA/P | | | | |
|---|---|---|---|---|---|---|---|
| | gene | locus | mean_CR | mean_SSA/P | $\log_2$FC | p_value | $p_{adj}$ |
| 1 | ABTB2 | chr11:34172533-34379555 | 2.83 | 5.36 | 0.92 | 5.00E-05 | 7.97E-04 |
| 2 | ADRA2A | chr10:112836789-112840662 | 28.80 | 15.54 | -0.89 | 5.00E-05 | 7.97E-04 |
| 3 | ALDH1A1 | chr9:75515577-75568233 | 78.28 | 54.36 | -0.53 | 2.50E-04 | 3.38E-03 |
| 4 | ALDH1L1 | chr3:125822403-125929011 | 17.54 | 45.47 | 1.37 | 5.00E-05 | 7.97E-04 |
| 5 | ALDOB | chr9:104182841-104198062 | 14.59 | 116.11 | 2.99 | 5.00E-05 | 7.97E-04 |
| 6 | ALDOC | chr17:26900132-26903951 | 7.60 | 17.67 | 1.22 | 5.00E-05 | 7.97E-04 |
| 7 | APOBEC1 | chr12:7801995-7818526 | 8.30 | 25.07 | 1.59 | 5.00E-05 | 7.97E-04 |
| 8 | ARSJ | chr4:114821439-114900878 | 0.66 | 1.81 | 1.45 | 5.00E-05 | 7.97E-04 |
| 9 | ATF3 | chr1:212738675-212794119 | 4.84 | 13.90 | 1.52 | 5.00E-05 | 7.97E-04 |
| 10 | B3GNT7 | chr2:232260334-232265875 | 7.50 | 15.87 | 1.08 | 5.00E-05 | 7.97E-04 |
| 11 | B4GALNT2 | chr17:47209821-47247351 | 88.58 | 22.95 | -1.95 | 5.00E-05 | 7.97E-04 |
| 12 | C12orf 75 | chr12:105724413-105765296 | 25.83 | 58.39 | 1.18 | 5.00E-05 | 7.97E-04 |
| 13 | B3GALT5-AS1 | chr21:40969074-40984749 | 0.54 | 2.90 | 2.42 | 5.00E-05 | 7.97E-04 |
| 14 | C4BPB | chr1:207262211-207273337 | 5.55 | 25.05 | 2.18 | 5.00E-05 | 7.97E-04 |
| 15 | CCL13 | chr17:32683470-32685629 | 42.01 | 21.58 | -0.96 | 5.00E-05 | 7.97E-04 |
| 16 | CD55 | chr1:207494816-207534311 | 25.68 | 194.65 | 2.92 | 5.00E-05 | 7.97E-04 |
| 17 | CDA | chr1:20915443-20945400 | 21.65 | 57.17 | 1.40 | 5.00E-05 | 7.97E-04 |
| 18 | CHGB | chr20:5891973-5906005 | 8.07 | 2.99 | -1.43 | 5.00E-05 | 7.97E-04 |
| 19 | CHST5 | chr16:75562427-75569068 | 12.57 | 37.20 | 1.56 | 5.00E-05 | 7.97E-04 |
| 20 | CLC | chr19:40221892-40228669 | 21.80 | 12.10 | -0.85 | 1.50E-04 | 2.18E-03 |

TABLE 7-continued

Differentially expressed genes in three comparisons. In Cuffdiff2, samples are normalized for differences in library sizes relative to each other and therefore the normalized expression is affected by which samples are included in the comparison. For this reason mean expression of a gene under one phenotype can appear slightly different in different comparisons.

| | | | | | | | |
|---|---|---|---|---|---|---|---|
| 21 | CLDN8 | chr21:31586323-31588469 | 1.70 | 3.93 | 1.21 | 5.50E-04 | 6.69E-03 |
| 22 | CNNM2 | chr10:104678074-104838344 | 7.37 | 4.80 | -0.62 | 4.40E-03 | 3.65E-02 |
| 23 | COL18A1 | chr21:46825096-46933634 | 23.26 | 14.53 | -0.68 | 1.00E-04 | 1.51E-03 |
| 24 | COL5A3 | chr19:10070236-10121147 | 4.06 | 2.57 | -0.66 | 7.50E-04 | 8.64E-03 |
| 25 | CPB1 | chr3:148545587-148577972 | 0.10 | 1.36 | 3.79 | 5.00E-05 | 7.97E-04 |
| 26 | CPNE8 | chr12:39046001-39299420 | 6.68 | 4.44 | -0.59 | 2.45E-03 | 2.29E-02 |
| 27 | CTGF | chr6:132269316-132272518 | 10.99 | 18.12 | 0.72 | 5.00E-05 | 7.97E-04 |
| 28 | CYP2C18 | chr10:96443250-96495947 | 17.00 | 9.69 | -0.81 | 5.00E-05 | 7.97E-04 |
| 29 | CYP2C9 | chr10:96698414-96749148 | 11.44 | 5.96 | -0.94 | 5.00E-05 | 7.97E-04 |
| 30 | CYP2W1 | chr7:1022834-1029276 | 0.44 | 1.25 | 1.50 | 5.00E-05 | 7.97E-04 |
| 31 | CYP3A5 | chr7:99245811-99277649 | 39.96 | 139.97 | 1.81 | 5.00E-05 | 7.97E-04 |
| 32 | EFNA3 | chr1:155051347-155060014 | 3.36 | 5.57 | 0.73 | 5.45E-03 | 4.37E-02 |
| 33 | EGR1 | chr5:137801180-137805004 | 4.44 | 13.08 | 1.56 | 5.00E-05 | 7.97E-04 |
| 34 | ETNK1 | chr12:22778075-22843608 | 134.13 | 49.89 | -1.43 | 5.00E-05 | 7.97E-04 |
| 35 | FAM213A | chr10:82167584-82192753 | 70.97 | 49.42 | -0.52 | 1.15E-03 | 1.24E-02 |
| 36 | FAM3D | chr3:58619669-58652561 | 251.01 | 361.22 | 0.53 | 1.65E-03 | 1.66E-02 |
| 37 | FER1L4 | chr20:34146506-34195484 | 4.42 | 7.45 | 0.75 | 5.00E-05 | 7.97E-04 |
| 38 | FFAR4 | chr10:95326421-95349829 | 6.41 | 15.32 | 1.26 | 5.00E-05 | 7.97E-04 |
| 39 | FOS | chr14:75745480-75748937 | 15.58 | 47.68 | 1.61 | 5.00E-05 | 7.97E-04 |
| 40 | FOSB | chr19:45971252-45978437 | 0.41 | 2.01 | 2.31 | 5.00E-05 | 7.97E-04 |
| 41 | FOXA2 | chr20:22561641-22566101 | 3.75 | 7.77 | 1.05 | 5.00E-05 | 7.97E-04 |
| 42 | FOXQ1 | chr6:1312674-1314993 | 1.83 | 13.06 | 2.84 | 5.00E-05 | 7.97E-04 |
| 43 | FREM1 | chr9:14734663-14910993 | 1.02 | 2.81 | 1.47 | 5.00E-05 | 7.97E-04 |
| 44 | FRMD3 | chr9:85857904-86153348 | 3.51 | 5.74 | 0.71 | 5.00E-05 | 7.97E-04 |
| 45 | FSCN1 | chr7:5632435-5646287 | 7.00 | 20.88 | 1.58 | 5.00E-05 | 7.97E-04 |
| 46 | GBA3 | chr4:22694536-22821195 | 21.87 | 7.54 | -1.54 | 5.00E-05 | 7.97E-04 |
| 47 | GBP5 | chr1:89724633-89738544 | 1.95 | 3.12 | 0.68 | 4.35E-03 | 3.63E-02 |
| 48 | GDF15 | chr19:18496967-18499986 | 6.15 | 14.54 | 1.24 | 5.00E-05 | 7.97E-04 |
| 49 | GPC3 | chrX:132669775-133119673 | 9.40 | 2.99 | -1.65 | 5.00E-05 | 7.97E-04 |
| 50 | ADGRF1 | chr6:46967812-47010082 | 1.19 | 8.02 | 2.75 | 5.00E-05 | 7.97E-04 |
| 51 | H19 | chr11:2016405-2019065 | 1.28 | 3.02 | 1.24 | 1.50E-03 | 1.53E-02 |
| 52 | HOXB13 | chr17:46802126-46806111 | 0.34 | 11.83 | 5.11 | 5.00E-05 | 7.97E-04 |
| 53 | HSD3B2 | chr1:119957553-119965662 | 18.40 | 4.32 | -2.09 | 5.00E-05 | 7.97E-04 |
| 54 | HSPA2 | chr14:65007185-65009954 | 10.07 | 5.99 | -0.75 | 5.00E-05 | 7.97E-04 |
| 55 | IGFBP2 | chr2:217498126-217529158 | 170.45 | 84.99 | -1.00 | 5.00E-05 | 7.97E-04 |
| 56 | IGFBP5 | chr2:217536827-217560272 | 17.50 | 8.84 | -0.99 | 5.00E-05 | 7.97E-04 |
| 57 | INSL5 | chr1:67263423-67266942 | 1.29 | 10.37 | 3.00 | 5.00E-05 | 7.97E-04 |
| 58 | JUN | chr1:59246462-59249785 | 25.77 | 39.35 | 0.61 | 5.00E-05 | 7.97E-04 |
| 59 | KLF8 | chrX:56258821-56314322 | 3.36 | 1.66 | -1.02 | 5.00E-05 | 7.97E-04 |
| 60 | L1TD1 | chr1:62660473-62678001 | 10.17 | 6.32 | -0.69 | 5.00E-04 | 6.13E-03 |
| 61 | LINC00261 | chr20:22541191-22559280 | 4.53 | 13.04 | 1.53 | 5.00E-05 | 7.97E-04 |
| 62 | LOC283177 | chr11:134306375-134375555 | 5.05 | 3.19 | -0.66 | 1.70E-03 | 1.71E-02 |
| 63 | LOC284454 | chr19:13945329-13947173 | 7.45 | 13.21 | 0.83 | 1.00E-04 | 1.51E-03 |
| 64 | LOC389602 | chr7:155755325-155759037 | 1.88 | 10.94 | 2.54 | 5.00E-05 | 7.97E-04 |
| 65 | MFAP5 | chr12:8798539-8815433 | 0.62 | 1.94 | 1.65 | 5.00E-05 | 7.97E-04 |
| 66 | MFSD4 | chr1:205538111-205572046 | 6.56 | 10.06 | 0.62 | 3.00E-04 | 3.97E-03 |
| 67 | MROH6 | chr8:144648362-144654928 | 6.94 | 12.23 | 0.82 | 5.00E-05 | 7.97E-04 |
| 68 | MS4A12 | chr11:60260250-60274901 | 267.62 | 164.87 | -0.70 | 4.00E-04 | 5.06E-03 |
| 69 | MUC12 | chr7:100612903-100662230 | 12.37 | 22.10 | 0.84 | 1.00E-04 | 1.51E-03 |
| 70 | MUC17 | chr7:100663363-100702140 | 2.42 | 74.14 | 4.94 | 5.00E-05 | 7.97E-04 |
| 71 | NOX1 | chrX:100098312-100129334 | 24.05 | 42.36 | 0.82 | 5.00E-05 | 7.97E-04 |
| 72 | NPY6R | chr5:137136881-137146439 | 4.98 | 3.25 | -0.61 | 3.55E-03 | 3.07E-02 |
| 73 | NQO1 | chr16:69743303-69760571 | 92.08 | 149.67 | 0.70 | 5.00E-05 | 7.97E-04 |
| 74 | NR1H4 | chr12:100867550-100957645 | 17.72 | 6.62 | -1.42 | 5.00E-05 | 7.97E-04 |
| 75 | NR4A1 | chr12:52416615-52453291 | 4.22 | 9.19 | 1.12 | 5.00E-05 | 7.97E-04 |
| 76 | NR4A2 | chr2:157180943-157189287 | 0.85 | 2.16 | 1.35 | 5.00E-05 | 7.97E-04 |
| 77 | NT5DC3 | chr12:104166080-104234975 | 1.04 | 2.35 | 1.17 | 5.00E-05 | 7.97E-04 |
| 78 | PCSK1 | chr5:95726039-95768985 | 0.58 | 1.22 | 1.08 | 1.00E-04 | 1.51E-03 |
| 79 | PDE3A | chr12:20522178-20837041 | 8.66 | 4.08 | -1.09 | 5.00E-05 | 7.97E-04 |
| 80 | PDZK1IP1 | chr1:47649260-47655771 | 21.40 | 273.29 | 3.67 | 5.00E-05 | 7.97E-04 |
| 81 | PITX2 | chr4:111538579-111563279 | 45.04 | 12.98 | -1.80 | 5.00E-05 | 7.97E-04 |
| 82 | PLLP | chr16:57290008-57318584 | 7.25 | 34.68 | 2.26 | 5.00E-05 | 7.97E-04 |
| 83 | PP7080 | chr5:470624-473080 | 564.44 | 206.58 | -1.45 | 5.00E-05 | 7.97E-04 |
| 84 | PPP1R12B | chr1:202317829-202557697 | 6.15 | 10.90 | 0.83 | 5.00E-05 | 7.97E-04 |
| 85 | PPP1R15A | chr19:49375648-49379319 | 12.71 | 22.53 | 0.83 | 5.00E-05 | 7.97E-04 |
| 86 | PRAC1 | chr17:46799081-46799882 | 1.53 | 32.82 | 4.43 | 5.00E-05 | 7.97E-04 |
| 87 | PTGDS | chr9:139871955-139876194 | 31.17 | 17.27 | -0.85 | 2.00E-04 | 2.80E-03 |
| 88 | RBP4 | chr10:95351592-95360993 | 4.66 | 10.05 | 1.11 | 5.00E-05 | 7.97E-04 |
| 89 | RGS1 | chr1:192544856-192549159 | 5.04 | 7.98 | 0.66 | 2.70E-03 | 2.48E-02 |
| 90 | RHBDL2 | chr1:39351478-39407456 | 11.06 | 20.55 | 0.89 | 5.00E-05 | 7.97E-04 |
| 91 | SCG2 | chr2:224461657-224467217 | 1.29 | 2.79 | 1.12 | 1.55E-03 | 1.57E-02 |
| 92 | SDR16C5 | chr8:57212569-57233241 | 2.46 | 37.01 | 3.91 | 5.00E-05 | 7.97E-04 |
| 93 | SIDT1 | chr3:113251217-113348422 | 5.95 | 9.23 | 0.63 | 5.00E-05 | 7.97E-04 |
| 94 | SIK1 | chr21:44834397-44847002 | 1.75 | 4.09 | 1.22 | 5.00E-05 | 7.97E-04 |
| 95 | SLC14A2 | chr18:42792946-43263060 | 10.40 | 2.51 | -2.05 | 5.00E-05 | 7.97E-04 |

TABLE 7-continued

Differentially expressed genes in three comparisons. In Cuffdiff2, samples are normalized for differences in library sizes relative to each other and therefore the normalized expression is affected by which samples are included in the comparison. For this reason mean expression of a gene under one phenotype can appear slightly different in different comparisons.

| | gene | locus | | | | | |
|---|---|---|---|---|---|---|---|
| 96 | SLC15A1 | chr13:99336054-99404929 | 1.88 | 8.23 | 2.13 | 5.00E−05 | 7.97E−04 |
| 97 | SLC37A2 | chr11:124933012-124960412 | 196.43 | 38.34 | −2.36 | 5.00E−05 | 7.97E−04 |
| 98 | SLC51A | chr3:195943382-195960301 | 96.90 | 28.78 | −1.75 | 5.00E−05 | 7.97E−04 |
| 99 | SLC9A3 | chr5:473333-524549 | 398.94 | 120.06 | −1.73 | 5.00E−05 | 7.97E−04 |
| 100 | SPINK5 | chr5:147443534-147516925 | 1.87 | 5.36 | 1.52 | 5.00E−05 | 7.97E−04 |
| 101 | SPON1 | chr11:13984183-14289679 | 14.15 | 21.35 | 0.59 | 1.50E−04 | 2.18E−03 |
| 102 | ST3GAL4 | chr11:126225539-126284536 | 5.42 | 68.82 | 3.67 | 5.00E−05 | 7.97E−04 |
| 103 | ST6GALNAC6 | chr9:130647599-130667627 | 32.74 | 120.19 | 1.88 | 5.00E−05 | 7.97E−04 |
| 104 | STOM | chr9:124101265-124132582 | 33.99 | 50.37 | 0.57 | 1.30E−03 | 1.37E−02 |
| 105 | SULT1C2 | chr2:108905094-108926371 | 0.58 | 31.49 | 5.77 | 5.00E−05 | 7.97E−04 |
| 106 | SULT2B1 | chr19:49055428-49102684 | 3.47 | 6.23 | 0.84 | 1.30E−03 | 1.37E−02 |
| 107 | TBX10 | chr11:67398773-67407031 | 3.73 | 9.04 | 1.28 | 5.00E−05 | 7.97E−04 |
| 108 | TFCP2L1 | chr2:121974163-122042778 | 23.00 | 16.01 | −0.52 | 6.50E−04 | 7.69E−03 |
| 109 | THRB | chr3:24158644-24541502 | 0.93 | 2.88 | 1.63 | 5.00E−05 | 7.97E−04 |
| 110 | TM4SF20 | chr2:228226873-228244022 | 3.33 | 34.74 | 3.38 | 5.00E−05 | 7.97E−04 |
| 111 | TMC5 | chr16:19422056-19510434 | 13.73 | 31.35 | 1.19 | 5.00E−05 | 7.97E−04 |
| 112 | TMEM200A | chr6:130687425-130764210 | 2.33 | 4.06 | 0.80 | 1.30E−03 | 1.37E−02 |
| 113 | TMEM231 | chr16:75572014-75590184 | 2.63 | 4.67 | 0.83 | 2.50E−04 | 3.38E−03 |
| 114 | TMIGD1 | chr17:28643365-28661065 | 80.33 | 39.78 | −1.01 | 5.00E−05 | 7.97E−04 |
| 115 | TNNC1 | chr3:52485106-52488057 | 0.24 | 1.13 | 2.23 | 1.55E−03 | 1.57E−02 |
| 116 | TPH1 | chr11:18042083-18062335 | 3.84 | 1.86 | −1.04 | 2.50E−04 | 3.38E−03 |
| 117 | TUSC3 | chr8:15397595-15624158 | 1.39 | 2.30 | 0.73 | 4.40E−03 | 3.65E−02 |
| 118 | UGT2B7 | chr4:69962192-69978705 | 1.61 | 6.19 | 1.94 | 5.00E−05 | 7.97E−04 |
| 119 | VNN1 | chr6:133001996-133035194 | 0.39 | 15.17 | 5.27 | 5.00E−05 | 7.97E−04 |
| 120 | VWA2 | chr10:115999012-116054259 | 1.18 | 2.85 | 1.27 | 5.00E−05 | 7.97E−04 |
| 121 | WFDC2 | chr20:44098393-44110172 | 29.07 | 64.83 | 1.16 | 5.00E−05 | 7.97E−04 |

| | | | CR versus CL | | | | |
|---|---|---|---|---|---|---|---|
| | gene | locus | mean_CR | mean_CL | log$_2$FC | p_value | p$_{adj}$ |
| 1 | ABTB2 | chr11:34172533-34379555 | 2.92 | 6.12 | 1.07 | 5.00E−05 | 1.05E−03 |
| 2 | ADRA2A | chr10:112836789-112840662 | 29.66 | 8.07 | −1.88 | 5.00E−05 | 1.05E−03 |
| 3 | ALDH1A1 | chr9:75515577-75568233 | 80.57 | 52.01 | −0.63 | 5.00E−05 | 1.05E−03 |
| 4 | ALDH1L1 | chr3:125822403-125929011 | 18.09 | 6.30 | −1.52 | 5.00E−05 | 1.05E−03 |
| 5 | ALDOB | chr9:104182841-104198062 | 15.05 | 2.93 | −2.36 | 5.00E−05 | 1.05E−03 |
| 6 | ALDOC | chr17:26900132-26903951 | 7.84 | 21.10 | 1.43 | 5.00E−05 | 1.05E−03 |
| 7 | APOBEC1 | chr12:7801995-7818502 | 8.55 | 3.02 | −1.50 | 5.00E−05 | 1.05E−03 |
| 8 | ARSJ | chr4:114821439-114900878 | 0.68 | 1.59 | 1.22 | 5.00E−05 | 1.05E−03 |
| 9 | ATF3 | chr1:212738675-212794119 | 5.00 | 20.46 | 2.03 | 5.00E−05 | 1.05E−03 |
| 10 | B3GNT7 | chr2:232260334-232265875 | 7.72 | 73.01 | 3.24 | 5.00E−05 | 1.05E−03 |
| 11 | B4GALNT2 | chr17:47209821-47247351 | 91.30 | 32.24 | −1.50 | 5.00E−05 | 1.05E−03 |
| 12 | C12orf75 | chr12:105724413-105765296 | 26.58 | 71.16 | 1.42 | 5.00E−05 | 1.05E−03 |
| 13 | B3GALT5-AS1 | chr21:40969074-40984749 | 0.56 | 12.47 | 4.48 | 5.00E−05 | 1.05E−03 |
| 14 | C4BPB | chr1:207262211-207273337 | 5.71 | 3.25 | −0.82 | 2.75E−03 | 3.13E−02 |
| 15 | CCL13 | chr17:32683470-32685629 | 43.28 | 22.80 | −0.92 | 5.00E−05 | 1.05E−03 |
| 16 | CD55 | chr1:207494816-207534311 | 26.49 | 15.08 | −0.81 | 5.00E−05 | 1.05E−03 |
| 17 | CDA | chr1:20915443-20945400 | 22.30 | 51.39 | 1.20 | 5.00E−05 | 1.05E−03 |
| 18 | CHGB | chr20:5891973-5906005 | 8.32 | 4.84 | −0.78 | 5.00E−05 | 1.05E−03 |
| 19 | CHST5 | chr16:75562427-75569068 | 12.95 | 44.11 | 1.77 | 5.00E−05 | 1.05E−03 |
| 20 | CLC | chr19:40221892-40228669 | 22.51 | 8.72 | −1.37 | 5.00E−05 | 1.05E−03 |
| 21 | CLDN8 | chr21:31586323-31588469 | 1.75 | 50.41 | 4.85 | 5.00E−05 | 1.05E−03 |
| 22 | CNNM2 | chr10:104678074-104838344 | 7.59 | 11.76 | 0.63 | 1.50E−04 | 2.76E−03 |
| 23 | COL18A1 | chr21:46825096-46933634 | 23.98 | 10.17 | −1.24 | 5.00E−05 | 1.05E−03 |
| 24 | COL5A3 | chr19:10070236-10121147 | 4.19 | 1.49 | −1.50 | 5.00E−05 | 1.05E−03 |
| 25 | CPB1 | chr3:148545587-148577972 | 0.10 | 1.54 | 3.93 | 5.00E−05 | 1.05E−03 |
| 26 | CPNE8 | chr12:39046001-39299420 | 6.87 | 10.99 | 0.68 | 5.00E−05 | 1.05E−03 |
| 27 | CTGF | chr6:132269316-132272518 | 11.32 | 18.80 | 0.73 | 5.00E−05 | 1.05E−03 |
| 28 | CYP2C18 | chr10:96443250-96495947 | 17.49 | 5.79 | −1.60 | 5.00E−05 | 1.05E−03 |
| 29 | CYP2C9 | chr10:96698414-96749148 | 11.77 | 2.07 | −2.50 | 5.00E−05 | 1.05E−03 |
| 30 | CYP2W1 | chr7:1022834-1029276 | 0.45 | 2.27 | 2.32 | 5.00E−05 | 1.05E−03 |
| 31 | CYP3A5 | chr7:99245811-99277649 | 41.12 | 67.62 | 0.72 | 5.00E−05 | 1.05E−03 |
| 32 | EFNA3 | chr1:155051347-155060014 | 3.46 | 7.52 | 1.12 | 5.00E−05 | 1.05E−03 |
| 33 | EGR1 | chr5:137801180-137805004 | 4.57 | 15.96 | 1.80 | 5.00E−05 | 1.05E−03 |
| 34 | ETNK1 | chr12:22778075-22843608 | 137.99 | 35.89 | −1.94 | 5.00E−05 | 1.05E−03 |
| 35 | FAM213A | chr10:82167584-82192753 | 73.04 | 50.96 | −0.52 | 5.00E−05 | 1.05E−03 |
| 36 | FAM3D | chr3:58619669-58652561 | 258.54 | 409.90 | 0.66 | 5.00E−05 | 1.05E−03 |
| 37 | FER1L4 | chr20:34146506-34195484 | 4.56 | 2.13 | −1.10 | 5.00E−05 | 1.05E−03 |
| 38 | FFAR4 | chr10:95326421-95349829 | 6.61 | 20.46 | 1.63 | 5.00E−05 | 1.05E−03 |
| 39 | FOS | chr14:75745480-75748937 | 16.05 | 75.85 | 2.24 | 5.00E−05 | 1.05E−03 |
| 40 | FOSB | chr19:45971252-45978437 | 0.42 | 5.31 | 3.67 | 5.00E−05 | 1.05E−03 |
| 41 | FOXA2 | chr20:22561641-22566101 | 3.87 | 10.61 | 1.46 | 5.00E−05 | 1.05E−03 |
| 42 | FOXQ1 | chr6:1312674-1314993 | 1.88 | 0.31 | −2.59 | 5.00E−05 | 1.05E−03 |
| 43 | FREM1 | chr9:14734663-14910993 | 1.05 | 0.22 | −2.27 | 5.00E−05 | 1.05E−03 |
| 44 | FRMD3 | chr9:85857904-86153348 | 3.61 | 7.20 | 0.99 | 5.00E−05 | 1.05E−03 |

TABLE 7-continued

Differentially expressed genes in three comparisons. In Cuffdiff2, samples are normalized for differences in library sizes relative to each other and therefore the normalized expression is affected by which samples are included in the comparison. For this reason mean expression of a gene under one phenotype can appear slightly different in different comparisons.

| | | | | | | | |
|---|---|---|---|---|---|---|---|
| 45 | FSCN1 | chr7:5632435-5646287 | 7.21 | 4.41 | −0.71 | 2.00E−04 | 3.55E−03 |
| 46 | GBA3 | chr4:22694536-22821195 | 22.49 | 8.51 | −1.40 | 5.00E−05 | 1.05E−03 |
| 47 | GBP5 | chr1:89724633-89738544 | 2.01 | 1.26 | −0.68 | 2.00E−03 | 2.43E−02 |
| 48 | GDF15 | chr19:18496967-18499986 | 6.34 | 11.32 | 0.84 | 2.50E−04 | 4.29E−03 |
| 49 | GPC3 | chrX:132669775-133119673 | 9.68 | 0.57 | −4.08 | 5.00E−05 | 1.05E−03 |
| 50 | ADGRF1 | chr6:46967812-47010082 | 1.23 | 0.65 | −0.92 | 1.60E−03 | 2.03E−02 |
| 51 | H19 | chr11:2016405-2019065 | 1.32 | 0.45 | −1.54 | 1.00E−04 | 1.95E−03 |
| 52 | HOXB13 | chr17:46802126-46806111 | 0.35 | 54.89 | 7.28 | 5.00E−05 | 1.05E−03 |
| 53 | HSD3B2 | chr1:119957553-119965662 | 19.01 | 1.65 | −3.53 | 5.00E−05 | 1.05E−03 |
| 54 | HSPA2 | chr14:65007185-65009954 | 10.38 | 15.10 | 0.54 | 2.00E−04 | 3.55E−03 |
| 55 | IGFBP2 | chr2:217498126-217529158 | 175.71 | 60.48 | −1.54 | 5.00E−05 | 1.05E−03 |
| 56 | IGFBP5 | chr2:217536827-217560272 | 18.02 | 9.16 | −0.98 | 5.00E−05 | 1.05E−03 |
| 57 | INSL5 | chr1:67263423-67266942 | 1.33 | 77.20 | 5.86 | 5.00E−05 | 1.05E−03 |
| 58 | JUN | chr1:59246462-59249785 | 26.56 | 45.42 | 0.77 | 5.00E−05 | 1.05E−03 |
| 59 | KLF8 | chrX:56258821-56314322 | 3.46 | 1.10 | −1.66 | 5.00E−05 | 1.05E−03 |
| 60 | L1TD1 | chr1:62660473-62678001 | 10.49 | 2.06 | −2.34 | 5.00E−05 | 1.05E−03 |
| 61 | LINC00261 | chr20:22541191-22559280 | 4.66 | 13.47 | 1.53 | 5.00E−05 | 1.05E−03 |
| 62 | LOC283177 | chr11:134306375-134375555 | 5.19 | 3.50 | −0.57 | 1.85E−03 | 2.29E−02 |
| 63 | LOC284454 | chr19:13945329-13947173 | 7.67 | 12.73 | 0.73 | 5.00E−05 | 1.05E−03 |
| 64 | LOC389602 | chr7:155755325-155759037 | 1.95 | 3.35 | 0.78 | 2.20E−03 | 2.63E−02 |
| 65 | MFAP5 | chr12:8798539-8815433 | 0.64 | 2.70 | 2.09 | 5.00E−05 | 1.05E−03 |
| 66 | MFSD4 | chr1:205538111-205572046 | 6.75 | 22.34 | 1.73 | 5.00E−05 | 1.05E−03 |
| 67 | MROH6 | chr8:144648362-144654928 | 7.15 | 5.05 | −0.50 | 4.75E−03 | 4.76E−02 |
| 68 | MS4A12 | chr11:60260250-60274901 | 275.22 | 460.74 | 0.74 | 5.00E−05 | 1.05E−03 |
| 69 | MUC12 | chr7:100612903-100662230 | 12.73 | 47.67 | 1.91 | 5.00E−05 | 1.05E−03 |
| 70 | MUC17 | chr7:100663363-100702140 | 2.49 | 6.86 | 1.46 | 5.00E−05 | 1.05E−03 |
| 71 | NOX1 | chrX:100098312-100129334 | 24.77 | 61.03 | 1.30 | 5.00E−05 | 1.05E−03 |
| 72 | NPY6R | chr5:137136881-137146439 | 5.12 | 2.61 | −0.97 | 5.00E−05 | 1.05E−03 |
| 73 | NQO1 | chr16:69743303-69760571 | 94.80 | 58.34 | −0.70 | 5.00E−05 | 1.05E−03 |
| 74 | NR1H4 | chr12:100867550-100957645 | 18.23 | 5.09 | −1.84 | 5.00E−05 | 1.05E−03 |
| 75 | NR4A1 | chr12:52416615-52453291 | 4.34 | 8.55 | 0.98 | 5.00E−05 | 1.05E−03 |
| 76 | NR4A2 | chr2:157180943-157189287 | 0.87 | 1.62 | 0.89 | 4.50E−04 | 6.98E−03 |
| 77 | NT5DC3 | chr12:104166080-104234975 | 1.08 | 2.19 | 1.02 | 5.00E−05 | 1.05E−03 |
| 78 | PCSK1 | chr5:95726039-95768985 | 0.59 | 1.29 | 1.12 | 5.00E−05 | 1.05E−03 |
| 79 | PDE3A | chr12:20522178-20837041 | 8.91 | 14.93 | 0.75 | 5.00E−05 | 1.05E−03 |
| 80 | PDZK1IP1 | chr1:47649260-47655771 | 22.03 | 35.74 | 0.70 | 5.00E−05 | 1.05E−03 |
| 81 | PITX2 | chr4:111538579-111563279 | 46.39 | 0.92 | −5.66 | 5.00E−05 | 1.05E−03 |
| 82 | PLLP | chr16:57290008-57318584 | 7.47 | 14.23 | 0.93 | 5.00E−05 | 1.05E−03 |
| 83 | PP7080 | chr5:470624-473080 | 581.11 | 130.86 | −2.15 | 5.00E−05 | 1.05E−03 |
| 84 | PPP1R12B | chr1:202317829-202557697 | 6.35 | 13.73 | 1.11 | 5.00E−05 | 1.05E−03 |
| 85 | PPP1R15A | chr19:49375648-49379319 | 13.12 | 20.35 | 0.63 | 5.00E−05 | 1.05E−03 |
| 86 | PRAC1 | chr17:46799081-46799882 | 1.57 | 198.20 | 6.98 | 5.00E−05 | 1.05E−03 |
| 87 | PTGDS | chr9:139871955-139876194 | 32.14 | 10.87 | −1.56 | 5.00E−05 | 1.05E−03 |
| 88 | RBP4 | chr10:95351592-95360993 | 4.80 | 16.22 | 1.76 | 5.00E−05 | 1.05E−03 |
| 89 | RGS1 | chr1:192544856-192549159 | 5.19 | 8.46 | 0.71 | 2.50E−04 | 4.29E−03 |
| 90 | RHBDL2 | chr1:39351478-39407456 | 11.40 | 21.90 | 0.94 | 5.00E−05 | 1.05E−03 |
| 91 | SCG2 | chr2:224461657-224467217 | 1.32 | 3.78 | 1.52 | 5.00E−05 | 1.05E−03 |
| 92 | SDR16C5 | chr8:57212569-57233241 | 2.53 | 5.28 | 1.06 | 5.00E−05 | 1.05E−03 |
| 93 | SIDT1 | chr3:113251217-113348422 | 6.13 | 11.75 | 0.94 | 5.00E−05 | 1.05E−03 |
| 94 | SIK1 | chr21:44834397-44847002 | 1.80 | 2.80 | 0.63 | 4.95E−03 | 4.91E−02 |
| 95 | SLC14A2 | chr18:42792946-43263060 | 10.71 | 0.12 | −6.51 | 5.00E−05 | 1.05E−03 |
| 96 | SLC15A1 | chr13:99336054-99404929 | 1.94 | 10.44 | 2.43 | 5.00E−05 | 1.05E−03 |
| 97 | SLC37A2 | chr11:124933012-124960412 | 202.30 | 5.51 | −5.20 | 5.00E−05 | 1.05E−03 |
| 98 | SLC51A | chr3:195943382-195960301 | 99.86 | 27.31 | −1.87 | 5.00E−05 | 1.05E−03 |
| 99 | SLC9A3 | chr5:473333-524549 | 411.65 | 94.88 | −2.12 | 5.00E−05 | 1.05E−03 |
| 100 | SPINK5 | chr5:147443534-147516925 | 1.93 | 5.69 | 1.56 | 5.00E−05 | 1.05E−03 |
| 101 | SPON1 | chr11:13984183-14289679 | 14.58 | 36.49 | 1.32 | 5.00E−05 | 1.05E−03 |
| 102 | ST3GAL4 | chr11:126225539-126284536 | 5.58 | 99.06 | 4.15 | 5.00E−05 | 1.05E−03 |
| 103 | ST6GALNAC6 | chr9:130647599-130667627 | 33.72 | 176.77 | 2.39 | 5.00E−05 | 1.05E−03 |
| 104 | STOM | chr9:124101265-124132582 | 34.99 | 22.70 | −0.62 | 5.00E−05 | 1.05E−03 |
| 105 | SULT1C2 | chr2:108905094-108926371 | 0.59 | 2.21 | 1.90 | 5.00E−05 | 1.05E−03 |
| 106 | SULT2B1 | chr19:49055428-49102684 | 3.57 | 1.44 | −1.31 | 5.00E−05 | 1.05E−03 |
| 107 | TBX10 | chr11:67398773-67407031 | 3.85 | 10.01 | 1.38 | 5.00E−05 | 1.05E−03 |
| 108 | TFCP2L1 | chr2:121974163-122042778 | 23.68 | 38.09 | 0.69 | 5.00E−05 | 1.05E−03 |
| 109 | THRB | chr3:24158644-24541502 | 0.96 | 6.97 | 2.86 | 5.00E−05 | 1.05E−03 |
| 110 | TM4SF20 | chr2:228226873-228244022 | 3.44 | 6.33 | 0.88 | 5.00E−05 | 1.05E−03 |
| 111 | TMC5 | chr16:19422056-19510434 | 14.13 | 20.66 | 0.55 | 5.00E−05 | 1.05E−03 |
| 112 | TMEM200A | chr6:130687425-130764210 | 2.41 | 13.64 | 2.50 | 5.00E−05 | 1.05E−03 |
| 113 | TMEM231 | chr16:75572014-75590184 | 2.71 | 5.24 | 0.95 | 5.00E−05 | 1.05E−03 |
| 114 | TMIGD1 | chr17:28643365-28661065 | 82.69 | 160.65 | 0.96 | 5.00E−05 | 1.05E−03 |
| 115 | TNNC1 | chr3:52485106-52488057 | 0.25 | 1.96 | 2.98 | 1.60E−03 | 2.03E−02 |
| 116 | TPH1 | chr11:18042083-18062335 | 3.95 | 7.71 | 0.96 | 5.00E−05 | 1.05E−03 |
| 117 | TUSC3 | chr8:15397595-15624158 | 1.43 | 4.25 | 1.57 | 5.00E−05 | 1.05E−03 |
| 118 | UGT2B7 | chr4:69962192-69978705 | 1.65 | 4.15 | 1.33 | 5.00E−05 | 1.05E−03 |
| 119 | VNN1 | chr6:133001996-133035194 | 0.40 | 1.19 | 1.56 | 5.00E−05 | 1.05E−03 |

TABLE 7-continued

Differentially expressed genes in three comparisons. In Cuffdiff2, samples are normalized for
differences in library sizes relative to each other and therefore the normalized expression is affected by
which samples are included in the comparison. For this reason mean expression of a gene under one
phenotype can appear slightly different in different comparisons.

| | | | | | | | |
|---|---|---|---|---|---|---|---|
| 120 | VWA2 | chr10:115999012-116054259 | 1.22 | 0.40 | −1.63 | 5.00E−05 | 1.05E−03 |
| 121 | WFDC2 | chr20:44098393-44110172 | 29.90 | 246.61 | 3.04 | 5.00E−05 | 1.05E−03 |

TABLE 8

Number of common genes between 3 different platforms (there
are 16849 genes common in all the 3 platforms).

| platform | RNA-seq | Illumina (IlluminaHumanWGDASLv4) | Affymetrix (hgu133plus2) |
|---|---|---|---|
| RNA-seq | 25268 | 19181 | 18989 |
| Illumina (IlluminaHumanWGDASLv4) | 19181 | 19463 | 17004 |
| Affymetrix (hgu133plus2) | 18989 | 17004 | 20388 |

TABLE 9

Class probabilties assigned using empirical approach, normal approximation, shrunken centroid
classifier (independent of the summary metric), and the Cantelli's inequality lower bound when the 18-
gene signature from Table 2 is used.

| Sample | True.class | SM.standardized | Empirical.HP | Empirical.SSA/P | Normal.HP | Normal.SSA/P |
|---|---|---|---|---|---|---|
| GSM1072010 | HP | −3.76 | 9.91E−01 | 9.50E−03 | 1.00E+00 | 8.40E−05 |
| GSM1072011 | HP | −4.79 | 9.97E−01 | 2.65E−03 | 1.00E+00 | 8.46E−07 |
| GSM1072012 | HP | −5.26 | 9.99E−01 | 1.22E−03 | 1.00E+00 | 7.02E−08 |
| GSM1072013 | HP | −5.75 | 9.99E−01 | 6.67E−04 | 1.00E+00 | 4.38E−09 |
| GSM1072014 | HP | −5.54 | 9.99E−01 | 9.00E−04 | 1.00E+00 | 1.54E−08 |
| GSM1072015 | HP | −6.97 | 1.00E+00 | 1.25E−04 | 1.00E+00 | 1.56E−12 |
| GSM1072016 | SSA/P | 3.50 | 8.42E−04 | 9.99E−01 | 2.32E−04 | 1.00E+00 |
| GSM1072017 | SSA/P | 7.39 | 0.00E+00 | 1.00E+00 | 7.39E−14 | 1.00E+00 |
| GSM1072018 | SSA/P | 5.97 | 1.67E−05 | 1.00E+00 | 1.19E−09 | 1.00E+00 |
| GSM1072019 | SSA/P | 7.70 | 0.00E+00 | 1.00E+00 | 6.77E−15 | 1.00E+00 |
| GSM1072020 | SSA/P | 7.29 | 0.00E+00 | 1.00E+00 | 1.54E−13 | 1.00E+00 |
| GSM1072021 | SSA/P | 2.48 | 5.48E−03 | 9.95E−01 | 6.56E−03 | 9.93E−01 |

| Sample | CLB.HP | CLB.SSA/P | CLB.decision | SCC.HP | SCC.SSA/P | SCC.decision |
|---|---|---|---|---|---|---|
| GSM1072010 | 9.34E−01 | 0.00E+00 | HP | 8.34E−01 | 1.66E−01 | HP |
| GSM1072011 | 9.58E−01 | 0.00E+00 | HP | 9.32E−01 | 6.78E−02 | HP |
| GSM1072012 | 9.65E−01 | 0.00E+00 | HP | 9.62E−01 | 3.75E−02 | HP |
| GSM1072013 | 9.71E−01 | 0.00E+00 | HP | 9.61E−01 | 3.86E−02 | HP |
| GSM1072014 | 9.68E−01 | 0.00E+00 | HP | 9.64E−01 | 3.62E−02 | HP |
| GSM1072015 | 9.80E−01 | 0.00E+00 | HP | 9.88E−01 | 1.16E−02 | HP |
| GSM1072016 | 0.00E+00 | 9.25E−01 | SSA/P | 1.10E−02 | 9.89E−01 | SSA/P |
| GSM1072017 | 0.00E+00 | 9.82E−01 | SSA/P | 6.09E−04 | 9.99E−01 | SSA/P |
| GSM1072018 | 0.00E+00 | 9.73E−01 | SSA/P | 2.00E−03 | 9.98E−01 | SSA/P |
| GSM1072019 | 0.00E+00 | 9.83E−01 | SSA/P | 4.53E−04 | 1.00E+00 | SSA/P |
| GSM1072020 | 0.00E+00 | 9.82E−01 | SSA/P | 6.30E−04 | 9.99E−01 | SSA/P |
| GSM1072021 | 0.00E+00 | 8.60E−01 | SSA/P | 2.60E−02 | 9.74E−01 | SSA/P |

TABLE 10

Class probabilties assigned using empirical approach, normal approximation, shrunken centroid
classifier (independent of the summary metric), and the Cantelli's inequality lower bound when the 16-
gene signature from Table 2 is used.

| Sample | True.class | SM.standardized | Empirical.HP | Empirical.SSA/P | Normal.HP | Normal.SSA/P |
|---|---|---|---|---|---|---|
| G5M270797.CEL | HP | 0.38 | 3.33E−01 | 6.67E−01 | 3.52E−01 | 6.48E−01 |
| G5M270798.CEL | HP | −4.70 | 9.97E−01 | 3.03E−03 | 1.00E+00 | 1.27E−06 |

TABLE 10-continued

Class probabilties assigned using empirical approach, normal approximation, shrunken centroid classifier (independent of the summary metric), and the Cantelli's inequality lower bound when the 16-gene signature from Table 2 is used.

| | | | | | | |
|---|---|---|---|---|---|---|
| G5M270799.CEL | HP | −5.12 | 9.98E−01 | 1.53E−03 | 1.00E+00 | 1.54E−07 |
| G5M270800.CEL | HP | −5.79 | 9.99E−01 | 6.50E−04 | 1.00E+00 | 3.50E−09 |
| G5M270801.CEL | HP | −5.44 | 9.99E−01 | 1.00E−03 | 1.00E+00 | 2.73E−08 |
| G5M270802.CEL | HP | −0.76 | 8.50E−01 | 1.50E−01 | 7.75E+00 | 2.25E−01 |
| G5M270803.CEL | HP | −5.40 | 9.99E−01 | 1.03E−03 | 1.00E+00 | 3.26E−08 |
| G5M270804.CEL | HP | −4.16 | 9.94E−01 | 6.05E−03 | 1.00E+00 | 1.62E−05 |
| G5M270805.CEL | HP | −3.26 | 9.85E−01 | 1.53E−02 | 9.99E−01 | 5.49E−04 |
| G5M270806.CEL | HP | −2.35 | 9.72E−01 | 2.77E−02 | 9.91E−01 | 9.44E−03 |
| G5M270807.CEL | HP | 4.35 | 2.00E−04 | 1.00E+00 | 6.89E−06 | 1.00E+00 |
| G5M1100490_EXT_417.CEL | SSA/P | 7.82 | 0.00E+00 | 1.00E+00 | 2.60E−15 | 1.00E+00 |
| G5M1100491_EXT_418.CEL | SSA/P | 9.36 | 0.00E+00 | 1.00E+00 | 3.85E−21 | 1.00E+00 |
| G5M1100492_EXT_419.CEL | SSA/P | 6.42 | 0.00E+00 | 1.00E+00 | 6.64E−11 | 1.00E+00 |
| GSM1100493_EXT_420.CEL | SSA/P | 5.44 | 1.67E−05 | 1.00E+00 | 2.62E−08 | 1.00E+00 |
| G5M1100494_EXT_421.CEL | SSA/P | 7.35 | 0.00E+00 | 1.00E+00 | 9.64E−14 | 1.00E+00 |
| G5M1100495_EXT_422.CEL | SSA/P | 7.75 | 0.00E+00 | 1.00E+00 | 4.55E−15 | 1.00E+00 |

| Sample | CLB.HP | CLBSSA/P | SCC.decision | SCC.HP | SCC.SSA/P | SCC.decision |
|---|---|---|---|---|---|---|
| G5M270797.CEL | 0.00E+00 | 1.26E−01 | uncertain | 5.35E−02 | 9.46E−01 | SSA/P |
| G5M270798.CEL | 9.57E−01 | 0.00E+00 | HP | 9.71E−01 | 2.93E−02 | HP |
| G5M270799.CEL | 9.63E−01 | 0.00E+00 | HP | 9.93E−01 | 6.80E−03 | HP |
| G5M270800.CEL | 9.71E−01 | 0.00E+00 | HP | 9.95E−01 | 5.45E−03 | HP |
| G5M270801.CEL | 9.67E−01 | 0.00E+00 | HP | 9.91E−01 | 8.82E−03 | HP |
| G5M270802.CEL | 3.63E−01 | 0.00E+00 | uncertain | 2.42E−01 | 7.58E−01 | SSA/P |
| G5M270803.CEL | 9.67E−01 | 0.00E+00 | HP | 9.88E−01 | 1.24E−02 | HP |
| G5M270804.CEL | 9.45E−01 | 0.00E+00 | HP | 9.75E−01 | 2.52E−02 | HP |
| G5M270805.CEL | 9.14E−01 | 0.00E+00 | HP | 8.30E−01 | 1.70E−01 | HP |
| G5M270806.CEL | 8.46E−01 | 0.00E+00 | HP | 7.97E−01 | 2.03E−01 | HP |
| G5M270807.CEL | 0.00E+00 | 9.50E−01 | SSA/P | 8.33E−04 | 9.99E−01 | SSA/P |
| GSM1100490_EXT_417.CEL | 0.00E+00 | 9.84E−01 | SSA/P | 1.56E−05 | 1.00E+00 | SSA/P |
| G5M1100491_EXT_418.CEL | 0.00E+00 | 9.89E−01 | SSA/P | 2.91E−06 | 1.00E+00 | SSA/P |
| G5M1100492_EXT_419.CEL | 0.00E+00 | 9.76E−01 | SSA/P | 1.21E−04 | 1.00E+00 | SSA/P |
| GSM1100493_EXT_420.CEL | 0.00E+00 | 9.67E−01 | SSA/P | 2.68E−04 | 1.00E+00 | SSA/P |
| GSM1100494_EXT_421.CEL | 0.00E+00 | 9.82E−01 | SSA/P | 2.97E−05 | 1.00E+00 | SSA/P |
| GSM1100495_EXT_422.CEL | 0.00E+00 | 9.84E−01 | SSA/P | 1.94E−05 | 1.00E+00 | SSA/P |

TABLE 11

Class probabilties assigned using empirical approach, normal approximation, shrunken centroid classifier (independent of the summary metric), and the Cantelli's inequality lower bound when the 13-gene signature from Table 2 is used.

Illumina samples

| Sample | True.class | SM.standardized | Empirical.HP | Empirical.SSA/P | Normal.HP | Normal.SSA/P |
|---|---|---|---|---|---|---|
| G5M1072010 | HP | −3.01 | 9.82E−01 | 1.84E−02 | 9.99E−01 | 1.30E−03 |
| G5M1072011 | HP | −4.54 | 9.96E−01 | 3.74E−03 | 1.00E+00 | 2.84E−06 |
| G5M1072012 | HP | −4.35 | 9.95E−01 | 4.77E−03 | 1.00E+00 | 6.72E−06 |
| G5M1072013 | HP | −5.28 | 9.99E−01 | 1.17E−03 | 1.00E+00 | 6.34E−08 |
| G5M1072014 | HP | −3.60 | 9.89E−01 | 1.13E−02 | 1.00E+00 | 1.59E−04 |
| G5M1072015 | HP | −5.02 | 9.98E−01 | 1.87E−03 | 1.00E+00 | 2.52E−07 |
| G5M1072016 | SSA/P | 3.79 | 5.50E−04 | 9.99E−01 | 7.69E−05 | 1.00E+00 |
| G5M1072017 | SSA/P | 7.28 | 0.00E+00 | 1.00E+00 | 1.70E−13 | 1.00E+00 |
| G5M1072018 | SSA/P | 5.73 | 1.67E−05 | 1.00E+00 | 5.04E−09 | 1.00E+00 |
| G5M1072019 | SSA/P | 6.92 | 0.00E+00 | 1.00E+00 | 2.21E−12 | 1.00E+00 |
| G5M1072020 | SSA/P | 6.94 | 0.00E+00 | 1.00E+00 | 1.93E−12 | 1.00E+00 |
| G5M1072021 | SSA/P | 2.12 | 1.11E−02 | 9.89E−01 | 1.70E−02 | 9.83E−01 |

Affymetrix samples

| Sample | True.class | SM.standardized | Empirical.HP | Empirical.SSA/P | Normal.HP | Normal.SSA/P |
|---|---|---|---|---|---|---|
| G5M270797.CEL | HP | 2.12 | 1.11E−02 | 9.89E−01 | 1.71E−02 | 9.83E−01 |
| G5M270798.CEL | HP | −4.31 | 9.95E−01 | 4.97E−03 | 1.00E+00 | 8.07E−06 |
| G5M270799.CEL | HP | −6.04 | 1.00E+00 | 4.50E−04 | 1.00E+00 | 7.69E−10 |
| G5M270800.CEL | HP | −5.42 | 9.99E−01 | 1.01E−03 | 1.00E+00 | 2.96E−08 |
| G5M270801.CEL | HP | −5.00 | 9.98E−01 | 1.92E−03 | 1.00E+00 | 2.82E−07 |
| G5M270802.CEL | HP | −0.50 | 7.74E−01 | 2.26E−01 | 6.91E−01 | 3.09E−01 |
| G5M270803.CEL | HP | −5.39 | 9.99E−01 | 1.06E−03 | 1.00E+00 | 3.61E−08 |
| G5M270804.CEL | HP | −5.12 | 9.98E−01 | 1.53E−03 | 1.00E+00 | 1.53E−07 |
| G5M270805.CEL | HP | −2.91 | 9.80E−01 | 1.98E−02 | 9.98E−01 | 1.82E−03 |
| G5M270806.CEL | HP | −2.95 | 9.81E−01 | 1.91E−02 | 9.98E−01 | 1.57E−03 |

TABLE 11-continued

Class probabilties assigned using empirical approach, normal approximation, shrunken centroid classifier (independent of the summary metric), and the Cantelli's inequality lower bound when the 13-gene signature from Table 2 is used.

| | | | | | | |
|---|---|---|---|---|---|---|
| G5M270807.CEL | HP | 4.33 | 2.00E−04 | 1.00E+00 | 7.36E−06 | 1.00E+00 |
| G5M1100490_EXT_417.CEL | SSA/P | 6.69 | 0.00E+00 | 1.00E+00 | 1.15E−11 | 1.00E+00 |
| G5M1100491_EXT_418.CEL | SSA/P | 9.11 | 0.00E+00 | 1.00E+00 | 4.02E−20 | 1.00E+00 |
| G5M1100492_EXT_419.CEL | SSA/P | 4.72 | 9.17E−05 | 1.00E+00 | 1.20E−06 | 1.00E+00 |
| G5M1100493_EXT_420.CEL | SSA/P | 5.20 | 2.50E−05 | 1.00E+00 | 1.01E−07 | 1.00E+00 |
| G5M1100494_EXT_421.CEL | SSA/P | 4.83 | 7.50E−05 | 1.00E+00 | 6.99E−07 | 1.00E+00 |
| G5M1100495_EXT_422.CEL | SSA/P | 6.04 | 8.33E−06 | 1.00E+00 | 7.64E−10 | 1.00E+00 |

Illumina samples

| Sample | CLB.HP | CLB.SSA/P | CLB.decision | SCC.HP | SCC.SSA/P | SCC.decision |
|---|---|---|---|---|---|---|
| G5M1072010 | 9.01E−01 | 0.00E+00 | HP | 5.54E−01 | 4.46E−01 | HP |
| G5M1072011 | 9.54E−01 | 0.00E+00 | HP | 8.74E−01 | 1.26E−01 | HP |
| G5M1072012 | 9.50E−01 | 0.00E+00 | HP | 8.15E−01 | 1.85E−01 | HP |
| G5M1072013 | 9.65E−01 | 0.00E+00 | HP | 8.77E−01 | 1.23E−01 | HP |
| G5M1072014 | 9.28E−01 | 0.00E+00 | HP | 8.03E−01 | 1.97E−01 | HP |
| G5M1072015 | 9.62E−01 | 0.00E+00 | HP | 8.79E−01 | 1.21E−01 | HP |
| G5M1072016 | 0.00E+00 | 9.35E−01 | SSA/P | 2.39E−02 | 9.76E−01 | SSA/P |
| G5M1072017 | 0.00E+00 | 9.81E−01 | SSA/P | 2.28E−03 | 9.98E−01 | SSA/P |
| G5M1072018 | 0.00E+00 | 9.70E−01 | SSA/P | 5.74E−03 | 9.94E−01 | SSA/P |
| G5M1072019 | 0.00E+00 | 9.80E−01 | SSA/P | 3.38E−03 | 9.97E−01 | SSA/P |
| G5M1072020 | 0.00E+00 | 9.80E−01 | SSA/P | 3.16E−03 | 9.97E−01 | SSA/P |
| G5M1072021 | 0.00E+00 | 8.18E−01 | SSA/P | 6.93E−02 | 9.31E−01 | SSA/P |

Affymetrix samples

| Sample | CLB.HP | CLB.SSA.P | CLB.decision | SCC.HP | SCC.SSA/P | SCC.decision |
|---|---|---|---|---|---|---|
| G5M270797.CEL | 0.00E+00 | 8.18E−01 | SSA/P | 5.26E−02 | 9.47E−01 | SSA/P |
| G5M270798.CEL | 9.49E−01 | 0.00E+00 | HP | 8.41E−01 | 1.59E−01 | HP |
| G5M270799.CEL | 9.73E−01 | 0.00E+00 | HP | 9.63E−01 | 3.74E−02 | HP |
| G5M270800.CEL | 9.67E−01 | 0.00E+00 | HP | 9.19E−01 | 8.13E−02 | HP |
| G5M270801.CEL | 9.62E−01 | 0.00E+00 | HP | 8.90E−01 | 1.10E−01 | HP |
| G5M270802.CEL | 2.00E−01 | 0.00E+00 | uncertain | 2.79E−01 | 7.21E−01 | SSA/P |
| G5M270803.CEL | 9.67E−01 | 0.00E+00 | HP | 8.85E−01 | 1.15E−01 | HP |
| G5M270804.CEL | 9.63E−01 | 0.00E+00 | HP | 9.32E−01 | 6.84E−02 | HP |
| G5M270805.CEL | 8.94E−01 | 0.00E+00 | HP | 6.52E−01 | 3.48E−01 | HP |
| G5M270806.CEL | 8.97E−01 | 0.00E+00 | HP | 7.36E−01 | 2.64E−01 | HP |
| G5M270807.CEL | 0.00E+00 | 9.49E−01 | SSA/P | 7.19E−03 | 9.93E−01 | SSA/P |
| G5M1100490_EXT_417.CEL | 0.00E+00 | 9.78E−01 | SSA/P | 1.42E−03 | 9.99E−01 | SSA/P |
| G5M1100491_EXT_418.CEL | 0.00E+00 | 9.88E−01 | SSA/P | 4.49E−04 | 1.00E+00 | SSA/P |
| G5M1100492_EXT_419.CEL | 0.00E+00 | 9.57E−01 | SSA/P | 1.63E−02 | 9.84E−01 | SSA/P |
| GSM1100493_EXT_420.CEL | 0.00E+00 | 9.64E−01 | SSA/P | 9.54E−03 | 9.90E−01 | SSA/P |
| G5M1100494_EXT_421.CEL | 0.00E+00 | 9.59E−01 | SSA/P | 5.76E−03 | 9.94E−01 | SSA/P |
| G5M1100495_EXT_422.CEL | 0.00E+00 | 9.73E−01 | SSA/P | 1.76E−03 | 9.98E−01 | SSA/P |

TABLE 12

Normalized expression levels (median and MAD) obtained by qPCR from 45 independent FFPE samples and the classification result obtained using the summary metric (SM) of the 13 genes molecular signature with different sample normalizations.

| sample name | class | SPIRE1 | KIZ | MEGF6 | SLC7A9 | PLA2G16 | NTRK2 | CHFR |
|---|---|---|---|---|---|---|---|---|
| HP1 | HP | −0.79 | 0.00 | 1.28 | 0.51 | −0.02 | 1.61 | 1.73 |
| HP2 | HP | −0.48 | −0.75 | −0.09 | −0.02 | 0.06 | −1.77 | −0.02 |
| HP3 | HP | −0.79 | −1.08 | 0.39 | 0.48 | 2.48 | 0.90 | 1.66 |
| HP4 | HP | 0.08 | 0.56 | −1.28 | −0.63 | −0.12 | 0.74 | 0.38 |
| HP5 | HP | 0.01 | 0.64 | −0.85 | 0.49 | −0.54 | 0.42 | 0.68 |
| HP6 | HP | 0.36 | 1.37 | −1.05 | −0.40 | −0.45 | 2.06 | 0.57 |
| HP7 | HP | −0.79 | 0.87 | −1.87 | −1.54 | 0.10 | 2.09 | 1.18 |
| HP8 | HP | 1.80 | −2.13 | 0.07 | −0.30 | −0.65 | 0.42 | 1.15 |
| HP9 | HP | −0.44 | −1.16 | −3.80 | −1.13 | −0.73 | 0.46 | −0.28 |
| HP10 | HP | −0.17 | 0.31 | −2.32 | −1.41 | −0.12 | 0.63 | 0.49 |
| HP11 | HP | 1.25 | 0.93 | −0.22 | 0.55 | −0.12 | 2.28 | 2.19 |
| HP12 | HP | 0.86 | 0.56 | −0.98 | −0.17 | −0.12 | 2.42 | 2.02 |
| HP13 | HP | 0.89 | 0.96 | −0.83 | −0.27 | −0.20 | 1.21 | 1.35 |
| HP14 | HP | 0.97 | 1.66 | 0.00 | 2.44 | −0.12 | 2.99 | 2.39 |
| HP15 | HP | 0.70 | 0.87 | −0.43 | 0.60 | −0.38 | 1.42 | 1.57 |
| HP16 | HP | 0.23 | −0.13 | −2.80 | −1.43 | −1.23 | 2.35 | 0.68 |
| HP17 | HP | 0.90 | 1.30 | 0.35 | 0.00 | −0.12 | 1.24 | 1.38 |
| HP18 | HP | −0.12 | 0.60 | −2.30 | −0.70 | −0.12 | 1.71 | −0.62 |

TABLE 12-continued

Normalized expression levels (median and MAD) obtained by qPCR from 45 independent FFPE samples and the classification result obtained using the summary metric (SM) of the 13 genes molecular signature with different sample normalizations.

| HP19 | HP | 0.17 | −0.31 | −2.58 | −1.03 | 0.24 | −1.89 | −0.28 |
|---|---|---|---|---|---|---|---|---|
| HP20 | HP | 0.64 | −0.40 | 0.40 | 0.11 | 0.00 | 0.16 | 2.04 |
| HP21 | HP | 1.00 | 1.29 | 0.58 | 2.12 | 0.24 | 0.00 | 1.80 |
| HP22 | HP | −0.70 | −1.79 | −3.23 | −4.21 | 0.06 | 0.00 | −0.28 |
| HP23 | HP | 1.41 | 1.49 | −0.41 | 0.86 | −0.37 | 2.00 | 1.87 |
| HP24 | HP | 0.92 | 1.33 | −0.06 | 0.59 | −0.12 | 0.06 | 1.89 |
| SSA/P1 | SSP | −0.79 | −1.10 | 0.70 | 1.74 | 0.77 | −2.48 | −0.97 |
| SSA/P2 | SSP | −0.68 | −0.26 | −0.36 | 1.05 | 0.03 | −2.28 | 0.00 |
| SSA/P3 | SSP | −1.14 | −0.49 | 0.07 | −0.09 | 0.50 | −2.92 | −0.23 |
| SSA/P4 | SSP | −0.79 | −0.62 | 0.72 | −0.11 | 0.14 | −0.72 | 0.29 |
| SSA/P5 | SSP | −0.42 | −0.75 | 0.19 | −1.49 | 0.58 | −1.49 | −0.01 |
| SSA/P6 | SSP | −1.51 | −1.17 | −1.40 | 1.57 | −0.12 | −1.58 | −1.69 |
| SSA/P7 | SSP | −1.12 | 0.51 | 1.62 | −0.37 | 1.43 | −4.25 | −2.40 |
| SSA/P8 | SSP | −1.17 | −0.64 | 1.56 | 0.75 | 1.39 | −3.74 | −1.27 |
| SSA/P9 | SSP | −0.14 | 0.14 | 0.27 | 0.01 | −0.77 | −0.60 | −0.12 |
| SSA/P10 | SSP | −0.77 | −0.14 | 0.41 | 0.00 | −1.33 | −1.26 | −0.67 |
| SSA/P11 | SSP | 0.00 | −0.09 | 1.73 | −0.55 | 0.70 | −4.78 | −1.93 |
| SSA/P12 | SSP | −0.58 | 0.99 | 0.24 | 2.42 | 1.93 | −3.01 | −0.92 |
| SSA/P13 | SSP | 0.42 | 0.41 | 0.60 | −0.10 | −0.26 | 0.82 | 0.15 |
| SSA/P14 | SSP | 0.03 | −0.38 | −0.01 | 1.83 | 0.63 | −1.48 | −1.21 |
| SSA/P15 | SSP | 0.07 | 0.55 | 5.39 | 2.40 | 1.51 | −3.51 | −1.00 |
| SSA/P16 | SSP | −0.79 | −1.18 | 2.29 | 1.32 | 0.22 | −3.46 | −2.31 |
| SSA/P17 | SSP | 1.24 | 3.15 | 4.63 | 1.31 | 2.04 | −1.40 | −0.94 |
| SSA/P18 | SSP | −0.34 | 1.73 | 1.99 | −0.96 | 1.03 | −1.26 | 0.16 |
| SSA/P19 | SSP | 0.74 | −1.42 | 1.13 | −0.54 | −0.12 | −2.60 | −0.28 |
| SSA/P20 | SSP | −0.21 | −0.58 | −1.93 | −0.81 | 0.15 | −2.30 | −0.65 |
| SSA/P21 | SSP | 0.13 | −0.40 | −0.80 | 1.14 | 0.06 | −2.26 | −0.74 |

| sample name | CHGA | PTAFR | CLDN1 | TACSTD2 | SEMG1 | SBSPON | SM with median and MAD normalization | SM with mean and MAD normalization | SM with geometric mean and MAD normalization |
|---|---|---|---|---|---|---|---|---|---|
| HP1 | 2.05 | −0.12 | −0.75 | −0.67 | −0.43 | 1.60 | −0.37 | −0.72 | −0.70 |
| HP2 | 0.00 | 0.22 | −2.20 | 0.25 | −1.04 | 1.08 | −0.09 | 0.00 | 0.04 |
| HP3 | 0.84 | −0.17 | −0.16 | −2.14 | −3.07 | 1.89 | −0.43 | −0.58 | −0.58 |
| HP4 | 1.22 | −0.02 | 0.01 | −2.00 | −0.91 | −1.04 | −0.59 | −0.57 | −0.61 |
| HP5 | 1.17 | 0.83 | −0.32 | −0.90 | 1.19 | −0.19 | −0.15 | −0.36 | −0.35 |
| HP6 | 2.90 | 0.71 | −0.32 | −0.14 | −0.96 | −1.11 | −0.58 | −0.83 | −0.93 |
| HP7 | 2.37 | 0.07 | −2.90 | −1.55 | 0.93 | −0.85 | −1.01 | −1.04 | −1.11 |
| HP8 | 2.28 | 0.20 | 0.23 | −1.28 | 2.07 | 1.95 | −0.15 | −0.49 | −0.49 |
| HP9 | 1.00 | 0.04 | 0.01 | −0.15 | −2.35 | −4.50 | −1.19 | −0.75 | −0.84 |
| HP10 | 0.68 | 0.19 | −0.59 | −1.60 | −1.58 | 0.05 | −0.70 | −0.57 | −0.59 |
| HP11 | 3.32 | 1.24 | −0.60 | −0.88 | −1.34 | 0.33 | −0.51 | −0.99 | −1.05 |
| HP12 | 1.55 | −0.15 | 0.41 | −0.78 | −0.30 | −3.26 | −0.76 | −0.95 | −1.01 |
| HP13 | 2.32 | 0.00 | −1.61 | 0.86 | −3.56 | −1.03 | −0.75 | −0.85 | −0.92 |
| HP14 | 2.55 | 1.18 | −1.43 | −0.77 | −1.46 | −0.99 | −0.50 | −0.99 | −1.05 |
| HP15 | 1.65 | 1.15 | −0.32 | −1.18 | 1.48 | 1.72 | −0.03 | −0.50 | −0.48 |
| HP16 | 0.77 | 0.00 | 0.72 | −1.82 | −0.36 | −2.12 | −0.98 | −0.87 | −0.92 |
| HP17 | 2.46 | 0.46 | −0.65 | −2.08 | −0.61 | 0.54 | −0.38 | −0.70 | −0.74 |
| HP18 | 0.68 | 0.24 | 0.47 | −2.25 | 0.56 | −0.06 | −0.42 | −0.45 | −0.46 |
| HP19 | 0.93 | 1.45 | 1.71 | −0.41 | 1.71 | −2.10 | 0.01 | 0.00 | −0.02 |
| HP20 | 1.91 | 0.00 | −3.56 | −0.36 | −1.23 | 0.39 | −0.62 | −0.73 | −0.74 |
| HP21 | 2.28 | 0.86 | −0.32 | −0.71 | −1.31 | 2.68 | 0.18 | −0.36 | −0.34 |
| HP22 | −0.84 | −0.11 | 0.40 | 0.13 | −1.57 | −3.05 | −1.00 | −0.47 | −0.50 |
| HP23 | 1.85 | 0.66 | −0.32 | −1.24 | 0.72 | 0.95 | −0.15 | −0.65 | −0.66 |
| HP24 | 3.77 | 1.09 | −2.15 | −0.35 | −0.65 | 1.67 | −0.27 | −0.70 | −0.75 |
| SSA/P1 | −4.26 | 0.52 | 0.24 | 0.47 | 1.61 | 1.91 | 1.06 | 1.02 | 1.10 |
| SSA/P2 | −2.20 | −0.07 | −0.32 | 1.48 | −0.28 | 0.00 | 0.39 | 0.45 | 0.49 |
| SSA/P3 | −1.77 | 0.00 | 0.00 | 2.28 | 1.50 | 0.81 | 0.64 | 0.60 | 0.64 |
| SSA/P4 | −2.20 | −0.68 | −0.07 | 0.25 | −0.92 | −2.56 | −0.15 | 0.04 | 0.07 |
| SSA/P5 | −0.80 | 0.00 | −0.13 | 0.00 | 0.00 | −1.75 | −0.11 | 0.03 | 0.05 |
| SSA/P6 | −3.21 | 0.18 | 0.05 | 0.38 | 2.77 | −1.88 | 0.41 | 0.62 | 0.67 |
| SSA/P7 | −3.25 | −0.42 | 1.56 | 2.43 | 3.42 | 0.69 | 1.51 | 1.41 | 1.43 |
| SSA/P8 | −2.19 | 0.00 | −0.15 | 1.33 | 0.77 | −0.53 | 0.81 | 0.87 | 0.91 |
| SSA/P9 | −1.05 | −0.35 | 0.86 | 0.79 | 2.09 | −0.56 | 0.32 | 0.19 | 0.23 |
| SSA/P10 | −1.11 | 0.00 | 0.16 | 2.06 | 2.11 | −1.38 | 0.32 | 0.30 | 0.33 |
| SSA/P11 | −4.12 | −0.02 | 0.34 | 2.32 | 2.09 | 0.30 | 1.36 | 1.42 | 1.44 |
| SSA/P12 | −4.28 | −0.14 | −0.32 | 1.19 | 2.84 | 5.32 | 1.70 | 1.36 | 1.41 |
| SSA/P13 | −0.65 | −0.71 | 1.16 | −0.10 | 1.43 | −0.19 | 0.18 | −0.05 | 0.00 |
| SSA/P14 | −2.76 | 0.00 | 1.06 | 2.01 | 1.12 | 0.44 | 0.94 | 0.78 | 0.84 |
| SSA/P15 | −4.76 | 0.00 | 1.29 | 3.55 | 1.35 | 3.03 | 2.19 | 1.67 | 1.68 |
| SSA/P16 | −3.85 | 0.15 | 0.56 | 0.64 | −0.09 | −2.61 | 0.78 | 1.05 | 1.08 |
| SSA/P17 | −5.16 | 0.64 | 1.60 | 0.25 | 1.27 | 0.92 | 1.89 | 1.39 | 1.38 |

TABLE 12-continued

Normalized expression levels (median and MAD) obtained by qPCR from 45 independent FFPE samples and the classification result obtained using the summary metric (SM) of the 13 genes molecular signature with different sample normalizations.

| SSA/P18 | −2.23 | −0.14 | −0.69 | 0.25 | 0.70 | 0.50 | 0.57 | 0.44 | 0.46 |
| SSA/P19 | −5.99 | −0.11 | 0.44 | 2.95 | −2.17 | 0.28 | 0.77 | 0.99 | 1.01 |
| SSA/P20 | −2.01 | 0.00 | 0.72 | 0.94 | −1.08 | −1.73 | 0.03 | 0.32 | 0.34 |
| SSA/P21 | −3.25 | 0.37 | 1.44 | 2.57 | 0.89 | −1.07 | 0.81 | 0.79 | 0.83 |

TABLE 13

Raw expression levels of 13 genes in the molecular signature obtained by qPCR from 45 independent FFPE samples.

| sample name | class | SPIRE1 | KIZ | MEGF6 | SLC7A9 | PLA2G16 | NTRK2 |
|---|---|---|---|---|---|---|---|
| HP1 | HP | 16.77 | 14.64 | 16.1 | 19.44 | 16.67 | 15.16 |
| HP2 | HP | 15.94 | 14.87 | 16.94 | 19.44 | 16.06 | 18.01 |
| HP3 | HP | 16.4 | 15.35 | 16.61 | 19.09 | 13.8 | 15.5 |
| HP4 | HP | 11.41 | 9.59 | 14.16 | 16.08 | 12.28 | 11.54 |
| HP5 | HP | 13.33 | 11.37 | 15.59 | 16.81 | 14.55 | 13.71 |
| HP6 | HP | 11.11 | 8.76 | 13.92 | 15.84 | 12.59 | 10.2 |
| HP7 | HP | 13.91 | 10.91 | 16.39 | 18.62 | 13.68 | 11.81 |
| HP8 | HP | 11.69 | 14.27 | 14.81 | 17.75 | 14.8 | 13.85 |
| HP9 | HP | 11.68 | 11.07 | 16.44 | 16.34 | 12.64 | 11.57 |
| HP10 | HP | 13.1 | 11.29 | 16.65 | 18.31 | 13.73 | 13.1 |
| HP11 | HP | 12.75 | 11.74 | 15.62 | 17.42 | 14.79 | 12.51 |
| HP12 | HP | 13.04 | 12.01 | 16.27 | 18.04 | 14.69 | 12.27 |
| HP13 | HP | 12.97 | 11.56 | 16.08 | 18.09 | 14.72 | 13.43 |
| HP14 | HP | 13.05 | 11.01 | 15.41 | 15.55 | 14.81 | 11.82 |
| HP15 | HP | 14.59 | 13.09 | 17.12 | 18.66 | 16.34 | 14.66 |
| HP16 | HP | 12.17 | 11.19 | 16.59 | 17.79 | 14.29 | 10.84 |
| HP17 | HP | 12.72 | 10.98 | 14.66 | 17.58 | 14.41 | 13.17 |
| HP18 | HP | 13 | 10.93 | 16.57 | 17.54 | 13.67 | 11.96 |
| HP19 | HP | 13.75 | 12.89 | 17.9 | 18.91 | 14.35 | 16.6 |
| HP20 | HP | 14.4 | 14.1 | 16.04 | 18.9 | 15.71 | 15.67 |
| HP21 | HP | 15.55 | 13.92 | 17.37 | 18.4 | 16.98 | 17.34 |
| HP22 | HP | 14.2 | 13.96 | 18.14 | 21.68 | 14.12 | 14.3 |
| HP23 | HP | 12.66 | 11.24 | 15.88 | 17.18 | 15.11 | 12.86 |
| HP24 | HP | 14.44 | 12.69 | 16.82 | 18.73 | 16.15 | 16.09 |
| SSA/P1 | SSA/P | 12.28 | 11.25 | 12.19 | 13.72 | 11.39 | 14.76 |
| SSA/P2 | SSA/P | 11.57 | 9.81 | 12.65 | 13.81 | 11.54 | 13.96 |
| SSA/P3 | SSA/P | 12.13 | 10.14 | 12.32 | 15.05 | 11.16 | 14.7 |
| SSA/P4 | SSA/P | 12.83 | 11.32 | 12.71 | 16.12 | 12.57 | 13.55 |
| SSA/P5 | SSA/P | 12.65 | 11.64 | 13.43 | 17.69 | 12.32 | 14.51 |
| SSA/P6 | SSA/P | 12.69 | 11 | 13.97 | 13.57 | 11.96 | 13.55 |
| SSA/P7 | SSA/P | 15.63 | 12.65 | 14.28 | 18.83 | 13.74 | 19.55 |
| SSA/P8 | SSA/P | 15.16 | 13.29 | 13.83 | 17.2 | 13.27 | 18.52 |
| SSA/P9 | SSA/P | 14.75 | 13.13 | 15.74 | 18.57 | 16.05 | 16 |
| SSA/P10 | SSA/P | 15.7 | 13.74 | 15.91 | 18.9 | 16.93 | 16.98 |
| SSA/P11 | SSA/P | 14.09 | 12.84 | 13.75 | 18.61 | 14.07 | 19.67 |
| SSA/P12 | SSA/P | 13.25 | 10.34 | 13.83 | 14.21 | 11.41 | 16.47 |
| SSA/P13 | SSA/P | 15.13 | 13.8 | 16.34 | 19.62 | 16.48 | 15.52 |
| SSA/P14 | SSA/P | 14.22 | 13.29 | 15.66 | 16.38 | 14.29 | 16.53 |
| SSA/P15 | SSA/P | 15.06 | 13.24 | 11.14 | 16.7 | 14.29 | 19.43 |
| SSA/P16 | SSA/P | 14.22 | 13.28 | 12.54 | 16.08 | 13.88 | 17.69 |
| SSA/P17 | SSA/P | 13.19 | 9.94 | 11.2 | 17.09 | 13.06 | 16.62 |
| SSA/P18 | SSA/P | 14.12 | 10.72 | 13.19 | 18.71 | 13.43 | 15.84 |
| SSA/P19 | SSA/P | 13.7 | 14.52 | 14.7 | 18.95 | 15.23 | 17.83 |
| SSA/P20 | SSA/P | 14.13 | 13.17 | 17.25 | 18.7 | 14.45 | 17.01 |
| SSA/P21 | SSA/P | 13.63 | 12.82 | 15.95 | 16.58 | 14.36 | 16.81 |

| sample name | CHFR | CHGA | PTAFR | CLDN1 | TACSTD2 | SEMG1 | SBSPON |
|---|---|---|---|---|---|---|---|
| HP1 | 14.76 | 11.47 | 16.89 | 17.2 | 17.69 | 19.29 | 18.44 |
| HP2 | 15.98 | 13 | 16.03 | 18.13 | 16.25 | 19.37 | 18.43 |
| HP3 | 14.46 | 12.31 | 16.56 | 16.24 | 18.79 | 21.55 | 17.77 |
| HP4 | 11.61 | 7.81 | 12.3 | 11.95 | 14.53 | 15.27 | 16.58 |
| HP5 | 13.16 | 9.71 | 13.3 | 14.13 | 15.28 | 15.03 | 17.59 |
| HP6 | 11.4 | 6.11 | 11.55 | 12.26 | 12.65 | 15.31 | 16.64 |
| HP7 | 12.44 | 8.28 | 13.83 | 16.49 | 15.71 | 15.06 | 18.02 |
| HP8 | 12.84 | 8.74 | 14.07 | 13.72 | 15.81 | 14.29 | 15.59 |
| HP9 | 12.03 | 7.78 | 11.99 | 11.71 | 12.44 | 16.47 | 19.8 |
| HP10 | 12.96 | 9.8 | 13.54 | 14 | 15.58 | 17.4 | 16.95 |
| HP11 | 12.32 | 8.22 | 13.55 | 15.08 | 15.93 | 18.22 | 17.73 |
| HP12 | 12.39 | 9.9 | 14.84 | 13.97 | 15.73 | 17.08 | 21.21 |
| HP13 | 13.01 | 9.07 | 14.65 | 15.94 | 14.04 | 20.29 | 18.94 |

TABLE 13-continued

Raw expression levels of 13 genes in the molecular signature obtained by qPCR from 45 independent FFPE samples.

| | | | | | | | |
|---|---|---|---|---|---|---|---|
| HP14 | 12.14 | 9.01 | 13.62 | 15.92 | 15.83 | 18.36 | 19.06 |
| HP15 | 14.23 | 11.18 | 14.93 | 16.08 | 17.52 | 16.7 | 17.62 |
| HP16 | 12.22 | 9.17 | 13.19 | 12.15 | 15.26 | 15.63 | 18.57 |
| HP17 | 12.74 | 8.7 | 13.95 | 14.74 | 16.74 | 17.1 | 17.13 |
| HP18 | 14 | 9.73 | 13.43 | 12.88 | 16.17 | 15.2 | 16.99 |
| HP19 | 14.71 | 10.52 | 13.26 | 12.69 | 15.38 | 15.09 | 20.07 |
| HP20 | 13.51 | 10.68 | 15.83 | 19.08 | 16.44 | 19.15 | 18.71 |
| HP21 | 15.25 | 11.82 | 16.48 | 17.34 | 18.31 | 20.74 | 17.93 |
| HP22 | 14.29 | 11.89 | 14.41 | 13.58 | 14.42 | 17.96 | 20.61 |
| HP23 | 12.7 | 9.76 | 14.2 | 14.86 | 16.36 | 16.23 | 17.18 |
| HP24 | 13.97 | 9.13 | 15.06 | 17.99 | 16.76 | 18.89 | 17.75 |
| SSA/P1 | 12.97 | 13.29 | 11.76 | 11.73 | 12.07 | 12.76 | 13.64 |
| SSA/P2 | 11.4 | 10.63 | 11.75 | 11.68 | 10.46 | 14.05 | 14.95 |
| SSA/P3 | 11.72 | 10.31 | 11.78 | 11.46 | 9.75 | 12.37 | 14.24 |
| SSA/P4 | 12.26 | 11.79 | 13.51 | 12.59 | 12.84 | 15.84 | 18.66 |
| SSA/P5 | 12.74 | 10.57 | 13.02 | 12.84 | 13.27 | 15.11 | 18.03 |
| SSA/P6 | 13.37 | 11.92 | 11.78 | 11.59 | 11.84 | 11.29 | 17.11 |
| SSA/P7 | 17.41 | 15.29 | 15.71 | 13.41 | 13.11 | 13.96 | 17.86 |
| SSA/P8 | 15.77 | 13.72 | 14.78 | 14.61 | 13.71 | 16.1 | 18.58 |
| SSA/P9 | 15.24 | 13.21 | 15.75 | 14.23 | 14.87 | 15.4 | 19.23 |
| SSA/P10 | 16.11 | 13.58 | 15.72 | 15.24 | 13.91 | 15.7 | 20.37 |
| SSA/P11 | 16.53 | 15.76 | 14.91 | 14.22 | 12.81 | 14.88 | 17.85 |
| SSA/P12 | 14.1 | 14.49 | 13.6 | 13.46 | 12.52 | 12.71 | 11.41 |
| SSA/P13 | 15.91 | 13.74 | 17.05 | 14.86 | 16.7 | 17 | 19.79 |
| SSA/P14 | 15.96 | 14.55 | 15.04 | 13.67 | 13.28 | 16.01 | 17.87 |
| SSA/P15 | 16.64 | 17.43 | 15.92 | 14.31 | 12.62 | 16.66 | 16.15 |
| SSA/P16 | 16.25 | 14.83 | 14.07 | 13.35 | 13.84 | 16.4 | 20.1 |
| SSA/P17 | 15.87 | 17.14 | 14.58 | 13.31 | 15.22 | 16.04 | 17.57 |
| SSA/P18 | 14.14 | 13.56 | 14.71 | 14.95 | 14.58 | 15.97 | 17.34 |
| SSA/P19 | 15.23 | 17.97 | 15.34 | 14.47 | 12.54 | 19.49 | 18.21 |
| SSA/P20 | 15.08 | 13.48 | 14.72 | 13.68 | 14.03 | 17.88 | 19.71 |
| SSA/P21 | 15 | 14.55 | 14.18 | 12.79 | 12.23 | 15.74 | 18.88 |

What is claimed is:

1. A method of detecting a sessile serrated adenoma/polyp (SSA/P) in a subject, the method comprising:
   a. determining the level of expression of nucleic acids in a molecular signature in a biological sample obtained from the subject, wherein the molecular signature consists of CHFR, CHGA, CLDN1, KIZ, MEGF6, NTRK2, PLA2G16, PTAFR, SBSPON, SMEG1, SLC7A9, SPIRE1, and TACTD2, and optionally includes one or more of FOXD1, PIK3R3, PRUNE2, TPD52L1, TRIB2, C4BPA, CPE, DPP10, GRAMD1B, GRIN2D, KLK7, MYNC, TM4SF4 and a one or more nucleic acid used as a normalization control;
   b. comparing the level of expression of each nucleic acid in the molecular signature to a reference value;
   c. detecting a SSA/P in the subject based on the level of expression of each nucleic acid in the molecular signature relative to the reference value, wherein SSA/P is detected when CHFR, CHGA, and NTRK2 are decreased relative to the reference value, and when CLDN1, KIZ, MEGF6, PLA2G16, PTAFR, SBSPON, SMEG1, SLC7A0, SPIRE1, and TACSTD2 are increased relative to the reference value, and the reference value is the level of expression of each nucleic acid in the molecular signature in a non-diseased sample or hyperplastic polyp sample; and
   d. removing the SSA/P by a method selected from polypectomy, endoscopic resection and surgical resection.

2. The method of claim 1, wherein the one or more nucleic acids used as a normalization control are selected from the group consisting of GAPDH, ACTB, B2M, TUBA, G6PD, LDHA, HPRT, ALDOA, PFKP, PGK1, PGAM1, VIM and UBC.

3. The method of claim 1, wherein the method to determine the level of expression of the nucleic acids in the molecular signature is microarray, RNA-seq or real-time qPCR.

4. The method of claim 1, wherein the biological sample is a tissue biopsy.

* * * * *